(12) United States Patent
Robichaud et al.

(10) Patent No.: US 11,993,628 B2
(45) Date of Patent: May 28, 2024

(54) C7, C12, AND C16 SUBSTITUTED NEUROACTIVE STEROIDS AND THEIR METHODS OF USE

(71) Applicant: Sage Therapeutics, Inc., Cambridge, MA (US)

(72) Inventors: Albert Jean Robichaud, Boston, MA (US); Gabriel Martinez Botella, Wayland, MA (US); Boyd L. Harrison, Princeton Junction, NJ (US); Francesco G. Salituro, Marlborough, MA (US); Andrew Griffin, L'Ile Bizard (CA); Maria Jesus Blanco-Pillado, Arlington, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 107 days.

(21) Appl. No.: 17/242,913

(22) Filed: Apr. 28, 2021

(65) Prior Publication Data

US 2022/0002340 A1 Jan. 6, 2022
US 2023/0021308 A9 Jan. 19, 2023

Related U.S. Application Data

(63) Continuation of application No. 17/017,748, filed on Sep. 11, 2020, now abandoned, which is a (Continued)

(51) Int. Cl.
*A61P 25/00* (2006.01)
*A61P 25/08* (2006.01)
(Continued)

(52) U.S. Cl.
CPC ............. *C07J 43/003* (2013.01); *A61P 25/00* (2018.01); *C07J 1/0029* (2013.01); *C07J 7/002* (2013.01);
(Continued)

(58) Field of Classification Search
CPC ........ C07J 43/003; C07J 1/0029; C07J 7/002; C07J 7/003; C07J 7/006; C07J 41/005; C07J 41/0094; A61P 25/00
See application file for complete search history.

(56) References Cited

U.S. PATENT DOCUMENTS 2,856,415 A 10/1958 Mihina
3,169,134 A 2/1965 Klimstra et al.
(Continued)

FOREIGN PATENT DOCUMENTS

CA 2831054 A1 12/2013
CN 1190404 A 8/1998
(Continued)

OTHER PUBLICATIONS

Adams et al., "The estrogenic activity and enzymic oxidation of 17b-estradiol-17a-d1", Steroids, Elsevier Science Publishers, (1965), pp. 75-84.
(Continued)

*Primary Examiner* — John M Mauro
(74) *Attorney, Agent, or Firm* — Honigman LLP; Andrew N. Weber; Jonathan P. O'Brien

(57) ABSTRACT

Described herein are neuroactive steroids of Formula (I), Formula (V), or Formula (IX) or a pharmaceutically acceptable salt thereof; wherein each instance of $R^2$, $R^3$, $R^4$, $R^5$, $R^6$, $R^7$, $R^{11a}$, $R^{11b}$, $R^{12}$, $R^{16}$, $R^{17}$, $R^{19}$, and ===== are as defined herein. Such compounds are envisioned, in certain embodiments, to behave as GABA modulators. Also provided are pharmaceutical compositions comprising a compound described herein and methods of use and treatment, e.g., such as for inducing sedation and/or anesthesia.

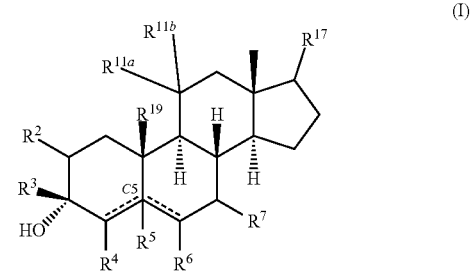

(I)

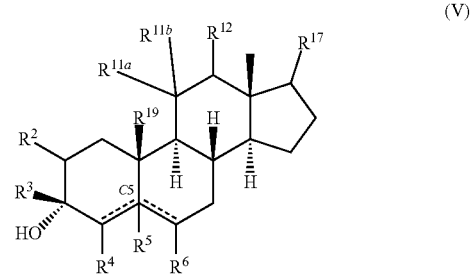

(V)

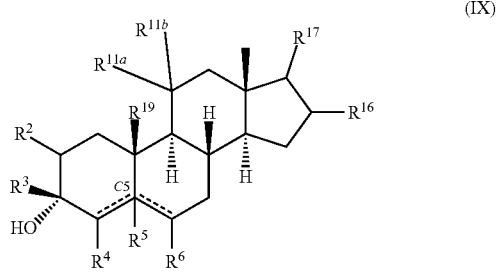

(IX)

39 Claims, No Drawings

Related U.S. Application Data continuation of application No. 16/316,851, filed as application No. PCT/US2017/041605 on Jul. 11, 2017, now abandoned.

(60) Provisional application No. 62/360,887, filed on Jul. 11, 2016, provisional application No. 62/360,876, filed on Jul. 11, 2016, provisional application No. 62/360,884, filed on Jul. 11, 2016.

(51) Int. Cl.

| | | |
|---|---|---|
| *A61P 25/14* | (2006.01) | |
| *A61P 25/20* | (2006.01) | |
| *C07J 1/00* | (2006.01) | |
| *C07J 7/00* | (2006.01) | |
| *C07J 41/00* | (2006.01) | |
| *C07J 43/00* | (2006.01) | |

(52) U.S. Cl.
CPC ............... *C07J 7/003* (2013.01); *C07J 7/006* (2013.01); *C07J 41/005* (2013.01); *C07J 41/0094* (2013.01)

(56) References Cited

U.S. PATENT DOCUMENTS

| | | |
|---|---|---|
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,029,777 A | 6/1977 | Engelfried et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0249120 A1 | 9/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |
| 2018/0071315 A1 | 3/2018 | Cashman et al. |
| 2018/0179247 A1 | 6/2018 | Botella et al. |
| 2019/0160078 A1 | 5/2019 | Masuoka et al. |
| 2019/0177358 A1 | 6/2019 | Martinez Botella et al. |
| 2019/0337975 A1 | 11/2019 | Bryson et al. |

FOREIGN PATENT DOCUMENTS

| | | | |
|---|---|---|---|
| CN | 101412742 A | 4/2009 | |
| CN | 101624414 A | 1/2010 | |
| CN | 104136452 A | 11/2014 | |
| CN | 108727453 A | 11/2018 | |
| DE | 2330342 A1 | 1/1974 | |
| DE | 2526373 A1 | 12/1976 | |
| DE | 2700267 A1 | 7/1977 | |
| DE | 2632677 A1 | 1/1978 | |
| EP | 0104489 A1 | 4/1984 | |
| EP | 0263213 A1 * | 4/1988 | ............ C07J 41/00 |
| EP | 0330253 A1 | 8/1989 | |
| EP | 0656365 A1 | 6/1995 | |
| EP | 1038880 A2 | 9/2000 | |
| FR | 1994 M | 9/1963 | |
| GB | 1380246 A | 1/1975 | |
| GB | 1430942 A | 4/1976 | |
| GB | 1494097 A | 12/1977 | |
| GB | 1538869 A | 1/1979 | |
| GB | 1570394 A | 7/1980 | |
| GB | 1581234 A | 12/1980 | |
| GB | 1581235 A | 12/1980 | |
| RU | 2194712 C2 | 12/2002 | |
| RU | 2243232 C2 | 12/2004 | |
| RU | 2010100334 A | 7/2011 | |
| RU | 2675855 C2 | 12/2018 | |
| WO | 1991016897 A1 | 11/1991 | |
| WO | 9303732 A1 | 3/1993 | |
| WO | 9305786 A1 | 4/1993 | |
| WO | 9318053 A1 | 9/1993 | |
| WO | 9427608 A1 | 12/1994 | |
| WO | 1995021617 A1 | 8/1995 | |
| WO | 1996003421 A1 | 2/1996 | |
| WO | 1996016076 A1 | 5/1996 | |
| WO | 9640043 A2 | 12/1996 | |
| WO | 9805337 A1 | 2/1998 | |
| WO | 0066614 A1 | 11/2000 | |
| WO | 2005051972 A1 | 6/2005 | |
| WO | 2005105822 A2 | 11/2005 | |
| WO | 2006037016 A2 | 4/2006 | |
| WO | 2006131392 A1 | 12/2006 | |
| WO | 2008151745 A1 | 12/2008 | |
| WO | 2008157460 A1 | 12/2008 | |
| WO | 2010003391 A2 | 1/2010 | |
| WO | 2010054158 A2 | 5/2010 | |
| WO | 2010107815 A1 | 9/2010 | |
| WO | 2012013816 A1 | 2/2012 | |
| WO | 2012083090 A2 | 6/2012 | |
| WO | 2012109752 A1 | 8/2012 | |
| WO | 2012110010 A1 | 8/2012 | |
| WO | 2012116290 A2 | 8/2012 | |
| WO | 2013019711 A2 | 2/2013 | |
| WO | 2013036835 A1 | 3/2013 | |
| WO | 2013056181 A1 | 4/2013 | |
| WO | 2013188792 A2 | 12/2013 | |
| WO | 2013192097 A1 | 12/2013 | |
| WO | 2014058736 A1 | 4/2014 | |
| WO | 2014071449 A1 | 5/2014 | |
| WO | 2014100228 A1 | 6/2014 | |
| WO | 2014108808 A2 | 7/2014 | |
| WO | 2014122480 A1 | 8/2014 | |
| WO | 2014169831 A1 | 10/2014 | |
| WO | 2014169832 A1 | 10/2014 | |

(56) References Cited

FOREIGN PATENT DOCUMENTS

| | | |
|---|---|---|
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016036724 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016131414 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018011386 A1 | 1/2018 |
| WO | 2018013613 A1 | 1/2018 |
| WO | 2018013615 A1 | 1/2018 |
| WO | 2018039378 A1 | 3/2018 |
| WO | 2019018119 A1 | 1/2019 |
| WO | 2019045121 A1 | 3/2019 |
| WO | 2019051264 A1 | 3/2019 |
| WO | 2019094724 A1 | 5/2019 |

OTHER PUBLICATIONS

Anderson et al., "Anesthetic Activity of Novel Water-Soluble 2b-Morpholinyl Steroids and Their Modulatory Effects at GABA-A Receptors", Journal ofMedicinal Chemistry., 1997, vol. 40, pp. 1668-1681.

Anderson et al., "Conformationally Constrained Anesthetic Steroids That Modulate GABAA Receptors," Journal of Medicinal Chemistry, 2000, vol. 43, No. 22, pp. 4118-4125.

Anonymous: "Archive History for NCT03000530", Aug. 4, 2017, Retrieved from the Internet: <URL:https://www.clinicaltrials.gov/ct2/his> tory/NCT03000530?VÂ-_6=View#StudyPageTop; [retrieved on Nov. 20, 2018].

Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.

Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.

Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs,"Bioorganic Medicinal Chemistry Letters 20:6680-6684 (2010).

Berge et al., J. Pharmaceutical Sciences, 1977, vol. 66, pp. 1-19.

Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.

Bjorkhem et al., "Steroid hormone metabolism in developing rates", Eur. J.Biochem., 1972, vol. 27, No. 2, pp. 318-326.

Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.

Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.

Caplus Registry No. RN 578728-50-4[Database Registry Chemical Abstracts Service, Columbus, Ohio, Accession Date Sep. 4, 2003; 1p.

CAS Registry No. 1040410-23-8 [Database Registry in STN]; STN Entry Date: Aug. 12, 2008; Chemical Name: 1-((3S,8R,9S,10S,13S,14S,17S)-3-hydroxy-10, 13-dimethyl-2,3,4,5,8,9,10,11,12,13,14, 15, 16, 17-tetradecahydro-1H- cyclopenta[a]phenanthren-17-yl)ethan-1-one.

CAS Registry No. 162882-77-1 [Database Registry in STN]; STN Entry Date: May 11, 1995; Chemical Name: (3a,5b)-3-Hydroxy-3-methyl-19-norpregnan-20-one.

CAS Registry No. 162883-68-3 [Database Registry in STN]; STN Entry Date: May 11, 1995; Chemical Name: 19-Norpregnan-20-one, 3-hydroxy-3-methyl-, (3a,5a)-.

Caspi et al., "Stereochemistry of 19-hydroxy-19alpha-methyl steroids," Chemical Communications, 1966, vol. 7, pp. 209-210.

Cerny et al., "Syntheses of 19-[O-(carboxymethyl)oxime] haptens of epipregnanolone and pregnanolone", Steroids, 2006, vol. 71(2), pp. 120-128.

Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.

Chen et al., "The mechanism investigation in substitution of 21-bromo-3a-hydroxy-3b-methoxymethyl-5a-pregnan-20-one with nucleophiles", Steroids, vol. 71, (2006), pp. 942-948.

Chodounska et al., "Epalons: Synthesis of 3a, 7a-Dihydroxy-5a-Pregnan-20-One", Collection Symposium Series, vol. 63, No. 10, (1998), pp. 1543-1548.

D'hulst et al., "Expression of the GABAergic system in animal models for fragile X syndrome and fragile X associated tremor/ataxia syndrome (FXTAS)", Brain Research, 2008, vol. 1253, pp. 176-183.

Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].

Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].

Database Medline, US National Library of Medicine, Bethesda, MD, 1984, Welling: "Intentions affecting drug absorption", Database accession No. NLM6388952, abstract.

Deluca et al., "Synthesis of 3b-Hydroxy[21-14C]-5b-pregn-8(14)-en-20-one from Chenodeoxycholic Acid", Helvetica Chemica Acta, vol. 69, (1986), pp. 1844-1850.

Deniau et al., "Synthesis of fluorinated analogues of the neurosteroid GABA receptor antagonist, 17-PA", Journal of Fluorine Chemistry, (2008), vol. 129, No. 9, pp. 881-887.

Dorwald, "Side Reactions in Organic Synthesis", 2005, Wiley-VCH, Preface, p. IX.

Duran et al., "Synthesis of 6-thia analogs of the natural neurosteroid allopregnanolone", Tetrahedron, Elsevier Science Publishers, 2006, vol. 62, No. 20, pp. 4762-4768.

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.

Eimon et al., "Brain activity patterns in high-throughput electrophysiology screen predict both drug efficacies and side effects", Nature Communications, (2018) 9:219, pp. 1-14.

Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.

Extended European Search Report for application PCT/CN2014075593 dated Aug. 26, 2016.

Extended European Search Report for application PCT/CN2014075594 dated Aug. 26, 2016.

Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.

Fesik et al., "Geometric Requirements for Membrance Perturbation and Anesthetic Activity", Molecular Pharmacology, 1985, vol. 27, pp. 624-629.

(56) References Cited

OTHER PUBLICATIONS

Galofre et al., "GABAA receptor and cell membrane potential as functional endpoints in cultured neurons to evaluate chemicals for human acute toxicity", Neurotoxicology and Teratology, (2009), vol. 32, pp. 52-61.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Han et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkins et al., "The synthetic neuroactive steroid SGE-516 reduces seizure burden and improves survival in a Dravet syndrome mouse model", Science Reports, (2017), pp. 1-8.
Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids. VII. Preparation of of androstan-3(b)-ol-7-one from from dehydroisoandrosterone", Journal of Biological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela, gamma-ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis, 18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/CN2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for Corresponding International Application No. PCT/US2018/050012 dated Dec. 7, 2018.

(56) References Cited

OTHER PUBLICATIONS

International Search Report and Written Opinion for Corresponding International Application No. PCT/US2018/051048 dated Jan. 11, 2019.
International Search Report and Written Opinion for Corresponding International Application No. PCT/US2018/064546 dated Apr. 9, 2019.
International Search Report and Written Opinion for Corresponding International Application No. PCT/US2019/036848 dated Aug. 22, 2019.
International Search Report and Written Opinion for Corresponding International Application No. PCT/US2019/055926 dated Jan. 14, 2020.
International Search Report and Written Opinion for Corresponding International Application No. PCT/US2019/057195 dated Jan. 22, 2020.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report and Written Opinion for International Application No. PCT/US2018/067277 dated May 24, 2019.
International Search Report and Written Opinion for International Application No. PCT/US2018/067306 dated May 28, 2019.
International Search Report and Written Opinion for International Application No. PCT/US2019/013315 dated Jun. 14, 2019.
International Search Report for International Application No. PCT/US2012/060136 dated Mar. 27, 2013.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-Ã¤atiansÃ¤pure-Derivate. Ã1/4ber GallensÃguren und verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7-dideoxyxestobergsterol A", Chem. Pharm. Bulletin, 2000, vol. 48, No. 10, pp. 1480-1483.
Kanes et al., "A multiple-ascending dose study of the neuroactive steroid Sage-217", Biological Psychiatry, vol. 81, No. 10, 2017, pp S347.
Kanes et al., "A single-ascending dose study of the neuroactive steroid Sage-217", Biological Psychiatry, vol. 81, No. 10, 2017, pp S31.
Kasal et al., "Neurosteroid analogues: synthesis of 6-aza-allopregnanolone", Tetrahedron, Elsevier Science Publishers, 2005, vol. 61, No. 9, pp. 2269-2278.
Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.

Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft, "Sythesis of the C/D/E and A/B RIngs of Xestobergsterol-(A)", The Journal of Organic Chemistry, American Chemical Society etc., vol. 64, No. 7, Mar. 18, 1999, pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lehmann et al., "SchweinegallensÃ¤guren Der Abbau von HyocholsÃ¤gure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
McKim, A. S., "Dimethyl sulfoxide USP, PhEur in approved pharmaceutical products and medical devices." Pharmaceutical Technology 32.5 (2008): 74.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Mohler, "The GABA system in anxiety and depression and its therapeutic potential", Neuropharmacology, (2012) 62; pp. 42-53.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.

(56) References Cited

OTHER PUBLICATIONS

PubChem CID: 70249446, [database online], created Dec. 1, 2012 [retrieved on Mar. 21, 2018]. Retrieved from the National Center for Biotechnology Information, PubChem Compound Database, using internet URL: <https://pubchem.ncbi.nlm.nih.gov/compound/70249446>.

Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.

Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of MedicinalChemistry, 2014, vol. 57, No. 1, pp. 171-190.

Qian et al., "The efficient and enantiospecific total synthesis of cyclopenta[b]phenanthrenes structurally related to neurosteroids", Adv. Syn. Cata., 2010, vol. 352, Nos. 11-12, pp. 2057-2061.

Rogawski et al., "Neuroactive Steroids for the Treatment of Status Epilepticus", Epilepsia (2013), vol. 54, No. 6, pp. 93-98.

Rongone et al., "In vivo metabolism of d-homotestosterone", Steroids, vol. 1, No. 6, 1963, pp. 664-669.

Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.

Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.

Rychnovsky et al., "Synthesis of ent-cholesterol, the unnatural enantiomer", Journal of Organic Chemistry, 1992, vol. 57, No. 9, pp. 2732-2736.

Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fflf35-fc4c-4eb2-9456-3228ec891a59; [retrieved on Dec. 21, 2018].

Santaniello & Caspi, "Reduction of certain steroidal 19-sulfonic esters with metal hydrides", J. of Ster. Biochem, 1976, vol. 7, No. 3, pp. 223-227.

Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.

Sarett., "A new method for the preparation of 17(alpha)-hydroxy-20-ketopregnanes", J. Am. Chem. Soc., 1948, vol. 70, pp. 1454-1458.

Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.

Shen et al., "Microbial aromatization of 19-hydroxymethylepidehydroandrosterone acetate by Corynebacterium simplex", Huaxue Xuebao, 1983, vol. 41, No. 5, pp. 473-474.

Shu et al., "Characteristics of concatemeric GABM receptors containing alpha4/d subunits expressed in Xenopus oocytes" British Journal of Pharmacology (2012) 165, 2228-2243.

Shu et al., "Photodynamic effects of steroid-conjugated fluorophores on gabaa receptors", Molecular Pharmacology, 2009, vol. 76, No. 4, pp. 754-765.

Slavikova, "3.Alpha.-Fluoro Analogues of Allopregnanolone and Their Binding to Gabaareceptors", Collection Symposium Series(XIIIth Symposium on Chmistry of Nucelic Acid Components Spindleruv Mlyn, Czech Republic; Sep. 3-9, 2005); vol. 67, No. 1, Jan. 1, 2002, pp. 30-46.

Slavikova, "Allopregnanalone and Prenanolone Analogues Modified in the C Ring: Synthesis and ACtivity", Journal of Medicinal Chemistry, vol. 56, No. 6, Mar. 28, 2013, pp. 2323-2336.

SlavÃ-kovÃ; et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.

Spiegel et al., "Use of Nonaqueous Solvents in Parenteral Products", Journal of Pharmaceutical Sciences, 1963, vol. 52, No. 10, pp. 917-927.

Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.

Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.

Stastna et al., "Stereoselectivity of sodium borohydride reduction of saturated steroidal ketones utilizing conditions of Luche reduction", Steroids, 2010, vol. 75, No. 10, pp. 721-725.

Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.

Stastna et al., "The use of symmetry in enantioselective synthesis: Four pairs of chrysene enantimers prepared from 19-nortestosterone", Org. Biomol. Chem., 2011, vol. 9, pp. 4685-4694.

Sunol et al., "Activity of b-nor analogues of neurosteroids on the gabaa receptor in primary neuronal cultures", Journal of Medicinal Chemistry, 2006, vol. 49, No. 11, pp. 3225-3234.

Supplemental European Search Report, European Patent Application No. 14826212.4, dated Feb. 16, 2017.

Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.

Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.

Upasani et al., "3a-Hydroxy-3ÃŸ-(phenylethynyl)-5ÃŸ-pregnan-20-ones: Synthesis and Pharmacological Activity of Neuroactive Steroids with High Affinity for GABAA Receptors", J. Med. Chem. (1997) vol. 40, No. 1, pp. 73-84.

Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.

Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.

Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.

Veleiro et al., "Structure-activity relationships of neuroactive steroids acting on the gabaa receptor", Current Medicinal Chemistry, 2009, vol. 16, No. 4, pp. 455-472.

Veleiro et al., "Synthesis and GABAA Receptor Acitivity of a6, 19-Oxido Analogue of Pregnanolone", Bioorganic Medicinal Chemistry Letters, (2003), vol. 13, pp. 343-345.

Welling, "Interactions affecting drug absorption", Clinical Pharmacokinetics, vol. 9, No. 5, Sep. 1984 (Sep. 1984), pp. 404-434.

Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.

Wicha et al., "Transformations of steroidal neopentyl systems. IV. Stereochemistry of Products of Reaction of Methyllithium with

(56) References Cited

OTHER PUBLICATIONS

Steroidal A5-19-aldehydes", Journal of the Chemical Society (Section) C: Organic, 1968, vol. 14, 1740-1746.

Wicha et al., "Transformations of steroidal neopentyl systems. V. Synthesis and proof of the configuration of 19amethyl-19ß-alcohols", Journal of the Chemical Society [Section] C: Organic, 1969, vol. 6, pp. 947-951.

Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.

Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19—oxo-5alpha-analogs", Journal of Organic Chemistry, 1973, vol. 38 No. 7, pp. 1280-1283.

Wu, "A New Classification of Prodrugs: Regulatory Perspectives", Pharmaceuticals, 2009, vol. 2, pp. 77-81.

Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.

Zonana et al., "The Neurobiology of Postpartum Depression", CNS Spectrums, (2005), pp. 792-799, 805.

Zorumski et al., "Enantioselective Modulation of GABAergic Synaptic Transmission by Steroids and Benz[dindenes in Hippocampal Microcultures", Synapse, (1998), vol. 29, pp. 162-171.

Fisher, D. et al., "Effect of renal failure and cirrhosis on the pharmacokinetics and neuromuscular effects of rapacuronium administered by bolus followed by infusion", The Journal of the American Society of Anesthesiologists. 2000, vol. 93(6), pp. 1384-1391.

Salt P. et al., "Inhibition of neuronal uptake of noradrenaline in the isolated perfused rat heart by pancuronium and its homologues, Org. 6368, Org. 7268 and NC 45", British Journal of Anaesthesia. 1980, vol. 52(3), pp. 313-317.

Nakata, Y. et al., "Vecuronium-induced neuromuscular block during xenon or sevoflurane anaesthesia in humans", British Journal of Anaesthesia. 1998, vol. 80(2), pp. 238-240.

\* cited by examiner

C7, C12, AND C16 SUBSTITUTED NEUROACTIVE STEROIDS AND THEIR METHODS OF USE

CROSS-REFERENCE TO RELATED APPLICATIONS

This application is a continuation of U.S. patent application Ser. No. 17/017,748, filed on Sep. 11, 2020, which is a continuation of U.S. patent application Ser. No. 16/316,851, filed on Jan. 10, 2019, which is a national stage entry of PCT Appl. No. PCT/US2017/041605, filed on Jul. 11, 2017. This application claims the benefit of U.S. Provisional Patent Appl. No. 62/360,887, filed Jul. 11, 2016, U.S. Provisional Patent Appl. No. 62/360,884, filed Jul. 11, 2016, and U.S. Provisional Patent Appl. No. 62/360,876, filed Jul. 11, 2016. Each of these documents is hereby incorporated by reference in its entirety.

BACKGROUND

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains at least one distinct site for interaction with neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Compounds as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound as described herein, e.g., a compound of Formula (I), a compound of Formula (V), or a compound of Formula (IX). In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

In an aspect, provided herein is a compound of Formula (I):

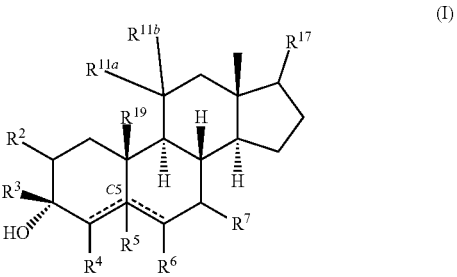

or a pharmaceutically acceptable salt thereof, wherein ⎓⎓⎓⎓⎓ represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{41}$, —$SR^{41}$, —$N(R^{41})_2$, —$NHC(=O)R^{41}$, —$NHC(=O)OR^{41}$, —$S(=O)R^{42}$, —$SO_2R^{42}$, or —$S(=O)_2OR^{41}$, wherein each instance of $R^{41}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; $R^5$ is absent or hydrogen; and ====== represents a single or double bond, wherein when one of ====== at site is a double bond, the other ====== is a single bond; when both of ====== are single bonds, then $R^5$ is hydrogen; and when one of the ====== is a double bond, $R^5$ is absent; $R^{17}$ is alkoxy, cyano, nitro, aryl, heteroaryl, or —C(O)$R^{B1}$, —C(O)CH$_2$R$^{B1}$, or —C(O)CH$_2$CH$_2$R$^{B1}$, wherein $R^{B1}$ is hydrogen, —OH, alkoxy, aryl, or heteroaryl; $R^{19}$ is hydrogen or alkyl; and $R^7$ is halogen, cyano, nitro, alkyl, alkenyl, alkynyl, carbocyclyl, heterocyclyl, aryl, heteroaryl, —OR$^{A1}$, —SR$^{A1}$, —N(R$^{A1}$)$_2$, —NHC(=O)R$^{A1}$, —NHC(=O)OR$^{A1}$, —S(=O)R$^{A2}$, —SO$_2$R$^{A2}$, or —S(=O)$_2$OR$^{A1}$.

In some embodiments, $R^3$ is alkyl.

In some embodiments, the compound of Formula (I) is a compound of Formula (I-a) or (I-b):

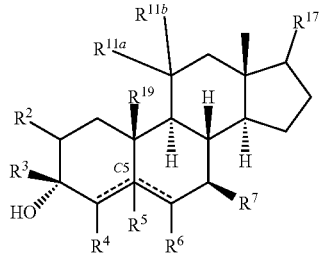

(I-a)

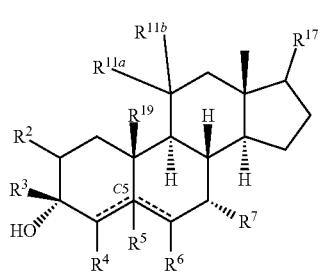

(I-b)

In some embodiments, each of $R^2$, $R^4$, and $R^6$, $R^{11a}$, and $R^{11b}$ is independently hydrogen;

In some embodiments, $R^2$, $R^4$, $R^6$, $R^{11a}$, and $R^{11b}$ are all hydrogen. In some embodiments, each of $R^2$, $R^4$, and $R^6$ is independently halogen, C$_1$-C$_6$ alkyl, C$_1$-C$_6$ alkoxy, or —OH; In some embodiments, $R^3$ is C$_1$-C$_6$ alkyl (e.g. C$_1$-C$_6$ haloalkyl or —CH$_3$).

In some embodiments, the compound of Formula (I) is a compound of Formula (II-a) or (II-b):

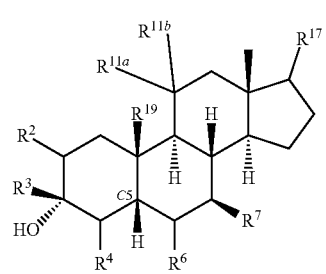

(II-a)

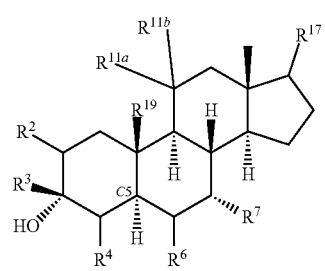

(II-b)

In some embodiments, the compound of Formula (I) is a compound of Formula (II-c) or (II-d):

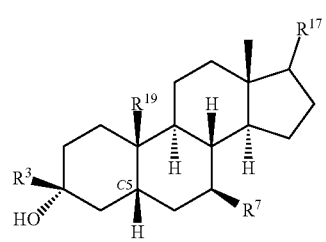

(II-c)

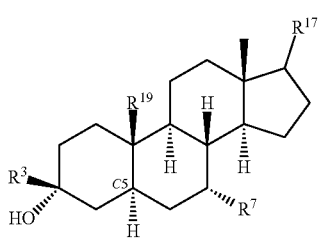

(II-d)

In some embodiments, $R^{19}$ is —CH$_3$. In some embodiments, $R^7$ is alkyl (e.g., unsubstituted alkyl or —CH$_2$OR$^{A1}$) or —OR$^{A1}$. In some embodiments, $R^7$ is —CH$_3$, —CH$_2$CH$_3$, —OH, —OCH$_3$, or —CH$_2$OCH$_3$. In some embodiments, $R^{17}$ is —OCH$_3$, —CN, or —C(O)CH$_3$. In some embodiments, $R^{17}$ is —C(O)CH$_2$R$^{C1}$. In some embodiments, $R^{17}$ is —C(O)CH$_2$R$^{B1}$. In some embodiments, $R^{17}$ is alkoxy, cyano, or —C(O)R$^{B1}$. In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl.

In some embodiments, $R^{B1}$ is

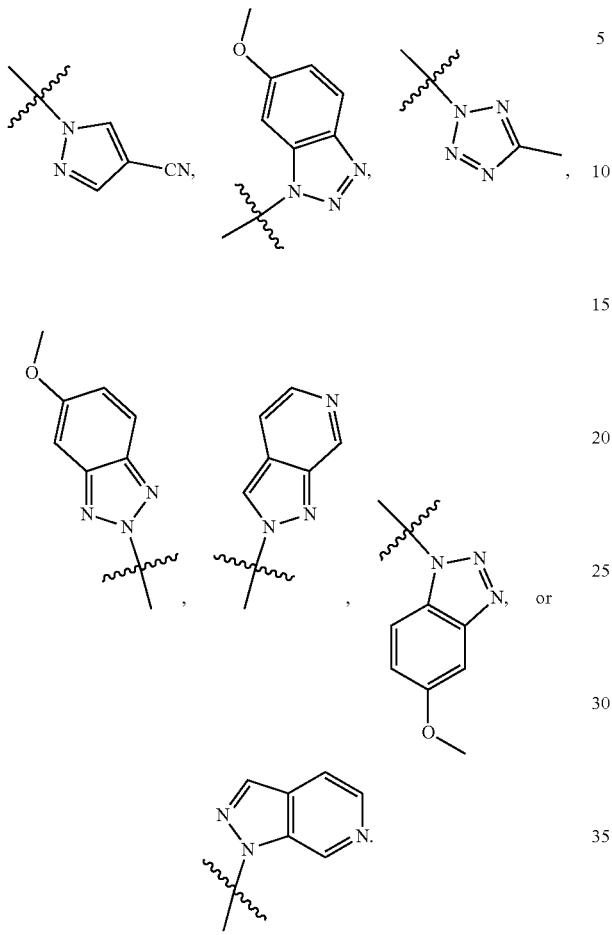

In some embodiments, $R^{B1}$ is

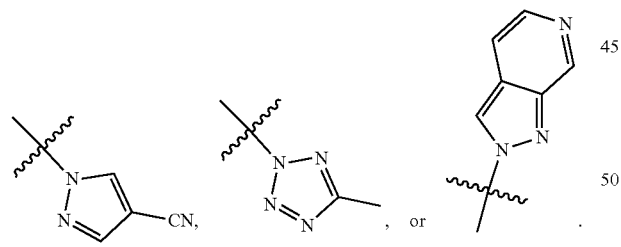

In some embodiments, $R^6$ is halogen. In some embodiments, $R^6$ is fluorine.

In some embodiments, each of $R^{11a}$ and $R^{11b}$ is independently hydrogen, $C_1$-$C_6$ alkyl (e.g. $C_1$-$C_6$ haloalkyl), $C_1$-$C_6$ alkoxy (e.g. $C_1$-$G_6$ alkoxyhalo), or —OH. In some embodiments, $R^{11a}$ and $R^{11b}$ together form oxo. In some embodiments, $R^{17}$ is $C_1$-$G_6$ alkoxy (e.g. —OCH$_3$), cyano, or nitro. In some embodiments, $R^{19}$ is hydrogen or substituted or unsubstituted $C_1$-$G_6$ alkyl (e.g. —CH$_2$OR$^X$, wherein $R^X$ is hydrogen, $C_1$-$G_6$ alkyl, or $C_1$-$G_6$ alkoxy).

In some embodiments, the compound of Formula (I) is a compound of Formula (III-a) or (III-b):

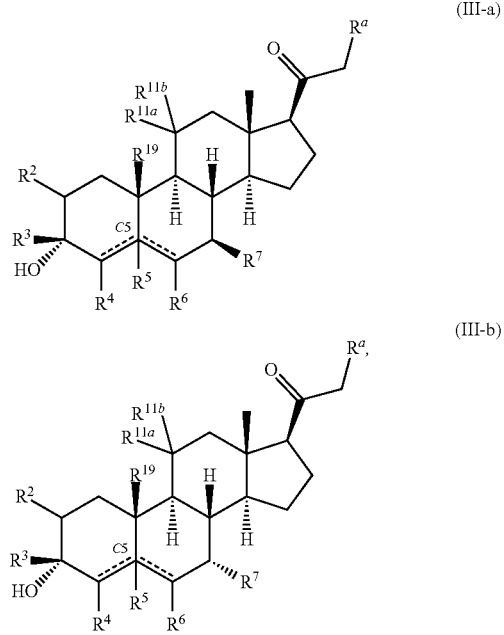

wherein $R^a$ is hydrogen, halogen, $C_1$-$G_6$ alkyl (e.g. —CH$_3$), or —OH. In some embodiments, the compound of Formula (I) is a compound of Formula (IV-a) or (IV-b):

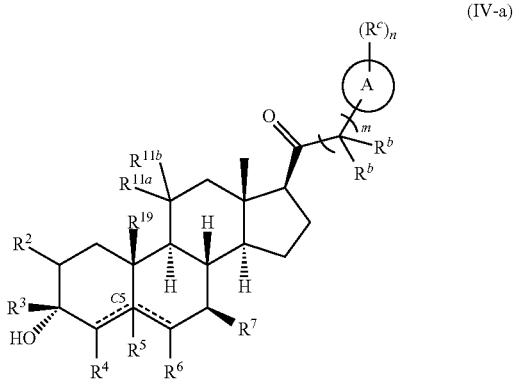

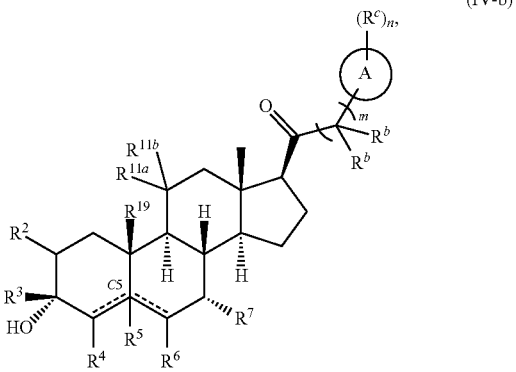

wherein: m is 0, 1, or 2; n is 0, 1, or 2; each $R^b$ is independently hydrogen, halogen, or $C_1$-$G_6$ alkyl; and each $R^c$ is independently halogen, $C_1$-$G_6$ alkyl (e.g. —CH$_3$ or $C_1$-$G_6$ haloalkyl), $C_1$-$G_6$ alkoxy, cyano, or —OH. In some embodiments, A is a 5-10-membered ring. In some embodiments, A is a fused bicyclic ring. In some embodiments, A is monocyclic heteroaryl or bicyclic heteroaryl.

In an aspect, provided is a compound of Formula (V):

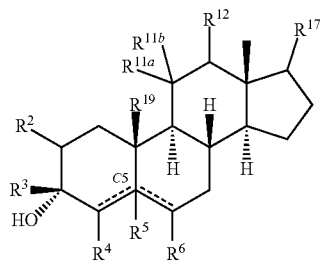

(V)

or a pharmaceutically acceptable salt thereof, wherein ====== represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; $R^5$ is absent or hydrogen; and ====== represents a single or double bond, wherein when one of ====== at site is a double bond, the other ====== is a single bond; when both of ====== are single bonds, then $R^5$ is hydrogen; and when one of ====== the is a double bond, $R^5$ is absent; $R^{17}$ is alkoxy, cyano, nitro, aryl, heteroaryl, —$C(O)R^{B1}$, —$C(O)CH_2R^{B1}$, or —$C(O)CH_2CH_2R^{B1}$, wherein $R^{B1}$ is hydrogen, —OH, alkoxy, aryl, or heteroaryl; $R^{19}$ is hydrogen or alkyl; and $R^{12}$ is halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$.

In some embodiments, $R^3$ is alkyl.

In some embodiments, the compound of Formula (V) is a compound of Formula (V-a) or (V-b):

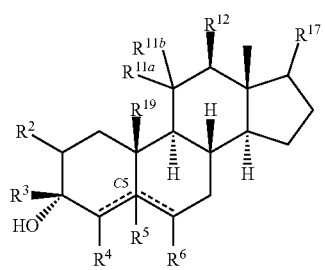

(V-a)

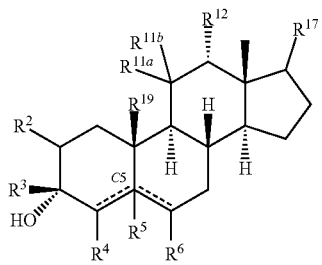

(V-b)

In some embodiments, each of $R^2$, $R^4$, $R^6$, $R^{11a}$, and $R^{11b}$ is independently hydrogen. In some embodiments, $R^2$, $R^4$, $R^6$, $R^{11a}$, and $R^{11b}$ are all hydrogen.

In some embodiments, each of $R^2$, $R^4$, and $R^6$ is independently halogen, $C_1$-$C_6$ alkyl, $C_1$-$C_6$ alkoxy, or —OH.

In some embodiments, $R^3$ is $C_1$-$C_6$ alkyl (e.g. $C_1$-$C_6$ haloalkyl or —$CH_3$).

In some embodiments, the compound of Formula (V) is a compound of Formula (VI-a) or (VI-b):

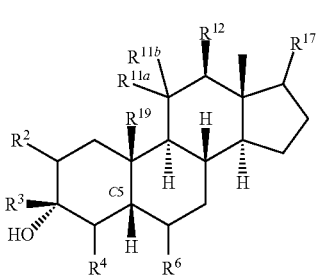

(VI-a)

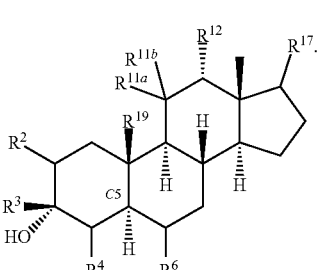

(VI-b)

In some embodiments, the compound of Formula (V) is a compound of Formula (VI-c) or (VI-d):

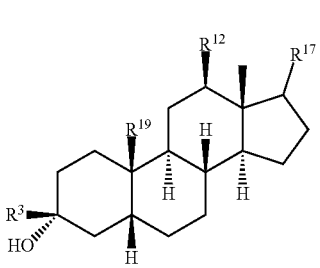

(VI-c)

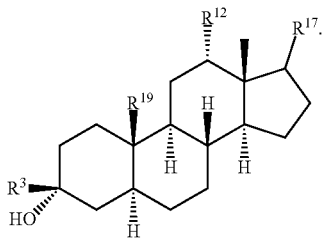

(VI-d)

In some embodiments, $R^{19}$ is —$CH_3$. In some embodiments, $R^{12}$ is —$OR^{A1}$. In some embodiments, $R^{12}$ is —$CH_3$, —$CH_2CH_3$, —OH, —$OCH_3$, or —$CH_2OCH_3$. In some embodiments, $R^{17}$ is —$OCH_3$, —CN, or —$C(O)CH_3$. In some embodiments, $R^{17}$ is —$C(O)CH_2R^{C1}$. In some embodiments, $R^{17}$ is —$C(O)CH_2R^{B1}$. In some embodiments, $R^{17}$ is alkoxy, cyano, or —$C(O)R^{B1}$.

In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl. In some embodiments, $R^{B1}$ is In some embodiments, $R^{B1}$ is

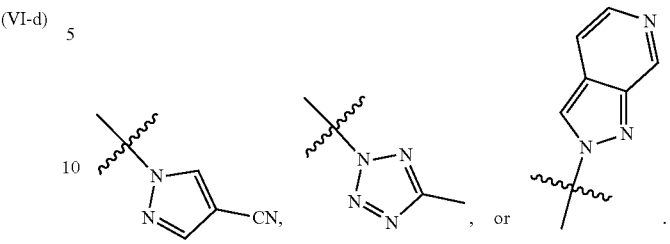

In some embodiments, $R^6$ is halogen. In some embodiments, $R^6$ is fluorine.

In some embodiments, each of $R^{11a}$ and $R^{11b}$ is independently hydrogen, $C_1$-$C_6$ alkyl (e.g. $C_1$-$C_6$ haloalkyl), $C_1$-$C_6$ alkoxy (e.g. $C_1$-$C_6$ haloalkoxy), or —OH. In some embodiments, $R^{11a}$ and $R^{11b}$ together form oxo. In some embodiments, $R^{17}$ is $C_1$-$C_6$ alkoxy (e.g. —$OCH_3$) or cyano. In some embodiments, $R^{19}$ is hydrogen or substituted or unsubstituted $C_1$-$C_6$ alkyl (e.g. —$CH_2OR^X$, wherein $R^X$ is hydrogen, $C_1$-$C_6$ alkyl, or $C_1$-$C_6$ alkoxy). In some embodiments, the compound of Formula (V) is a compound of Formula (VII-a) or (VII-b):

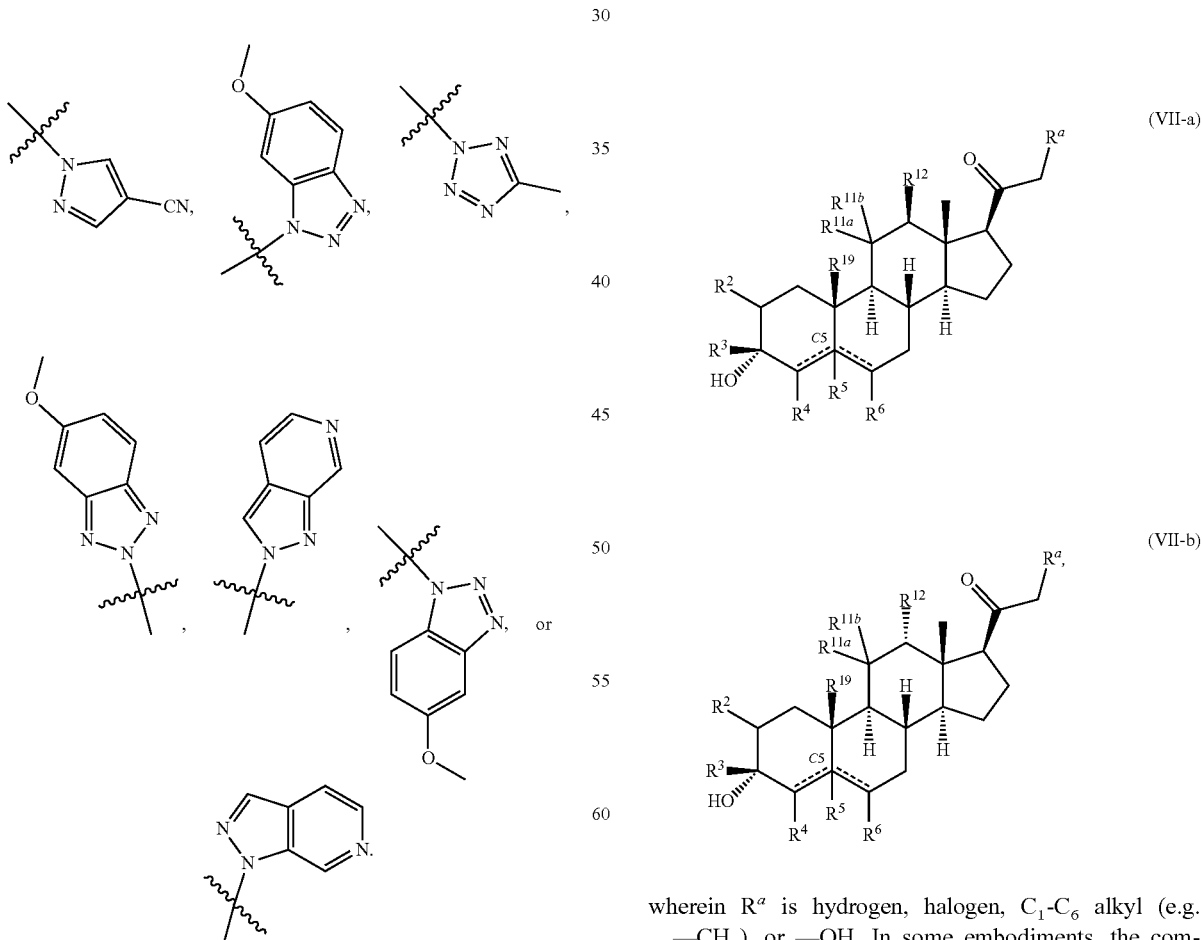

wherein $R^a$ is hydrogen, halogen, $C_1$-$C_6$ alkyl (e.g. —$CH_3$), or —OH. In some embodiments, the compound of Formula (V) is a compound of Formula (VIII-a) or (VIII-b):

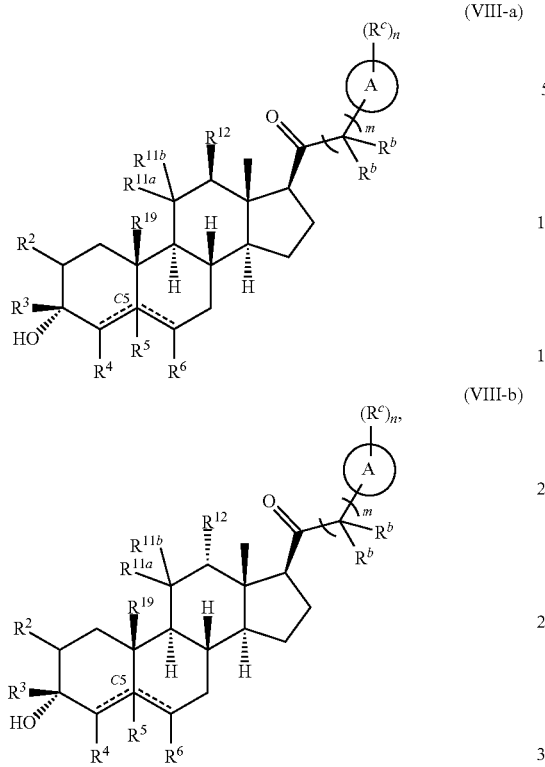

(VIII-a)

(VIII-b)

wherein m is 0, 1, or 2, n is 0, 1, or 2, and each $R^b$ is independently hydrogen, halogen, or $C_1$-$C_6$ alkyl; and each $R^c$ is independently halogen, $C_1$-$C_6$ alkyl (e.g. —$CH_3$ or $C_1$-$C_6$ haloalkyl). $C_1$-$C_6$ alkoxy, cyano, or —OH.

In some embodiments, A is a 5-10-membered ring. In some embodiments, A is a fused bicyclic ring. In some embodiments, A is monocyclic heteroaryl or bicyclic heteroaryl.

In an aspect, provided herein is a compound of Formula (IX):

(IX)

or a pharmaceutically acceptable salt thereof, wherein ====== represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; $R^5$ is absent or hydrogen; and ====== represents a single or double bond, wherein when one of ====== at site is a double bond, the other ====== is a single bond; when both of ====== are single bonds, then $R^5$ is hydrogen; and when one of the ====== is a double bond, $R^5$ is absent; $R^{17}$ is alkoxy, cyano, nitro, aryl, heteroaryl, —$C(O)R^{B1}$, —$C(O)CH_2R^{B1}$, or —$C(O)CH_2CH_2R^{B1}$, wherein $R^{B1}$ is hydrogen, —OH, —$N(R^{A1})_2$, alkoxy, aryl, or heteroaryl; $R^{19}$ is hydrogen or alkyl; and $R^{16}$ is halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$.

In some embodiments, $R^3$ is alkyl.

In some embodiments, the compound of Formula (IX) is a compound of Formula (IX-a) or (IX-b):

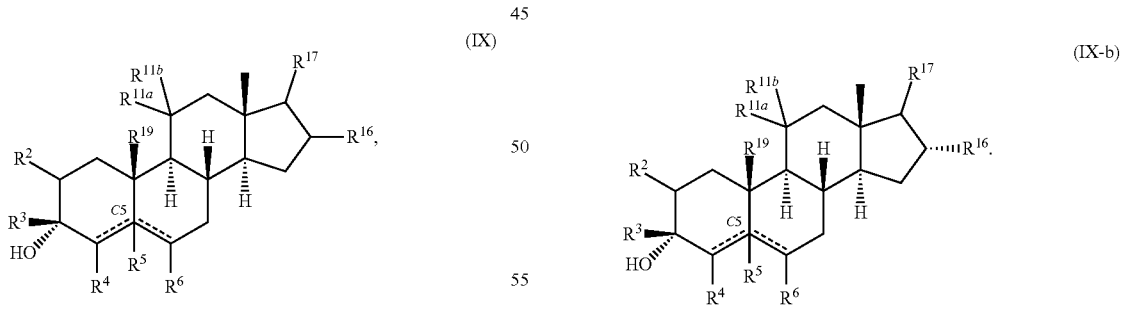

(IX-a)

(IX-b)

In some embodiments, each of $R^2$, $R^4$, and $R^6$, $R^{11a}$, and $R^{11b}$ is independently hydrogen. In some embodiments, $R^2$, $R^4$, and $R^6$, $R^{11a}$, and $R^{11b}$ are all hydrogen. In some embodiments, each of $R^2$, $R^4$, and $R^6$ is independently halogen, $C_1$-$C_6$ alkyl, $C_1$-$C_6$ alkoxy, or —OH.

In some embodiments, $R^3$ is $C_1$-$C_6$ alkyl (e.g. $C_1$-$C_6$ haloalkyl or —$CH_3$).

In some embodiments, the compound of Formula (IX) is a compound of Formula (X-a) or (X-b):

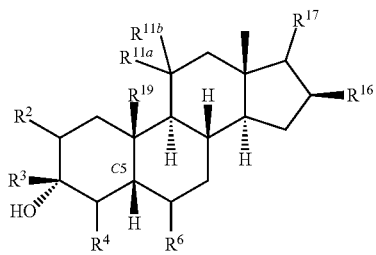

(X-a)

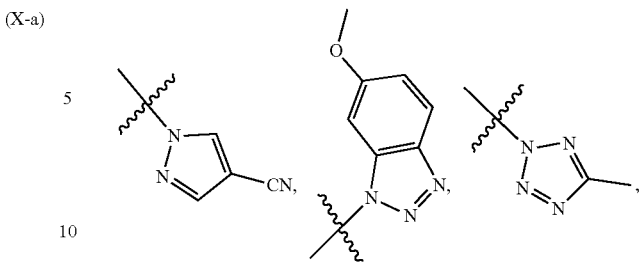

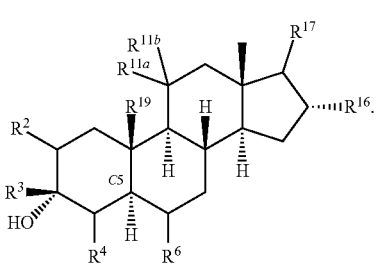

(X-b)

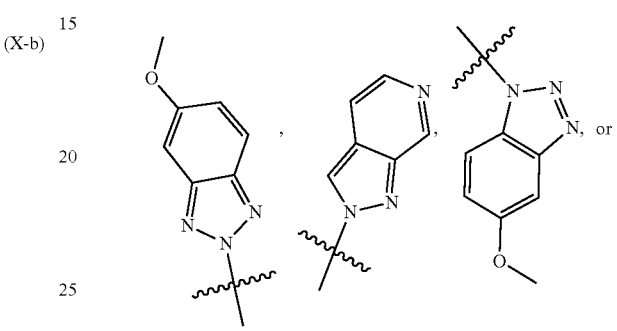

In some embodiments, the compound of Formula (IX) is a compound of Formula (X-c) or (X-d):

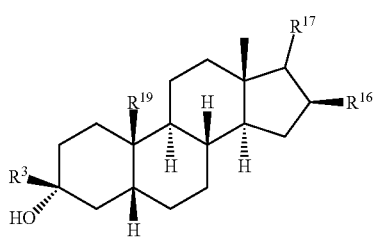

(X-c)

In some embodiments, $R^{B1}$ is

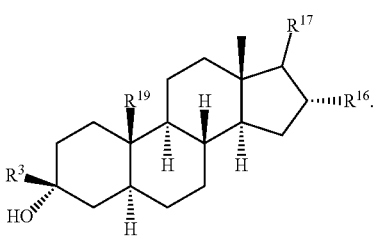

(X-d)

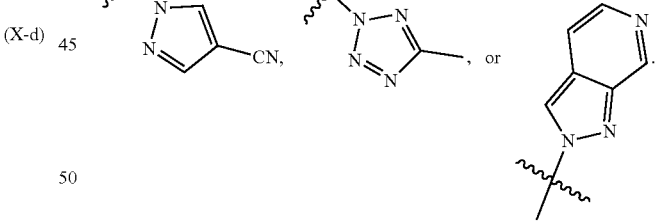

In some embodiments, $R^{19}$ is —$CH_3$. In some embodiments, $R^{16}$ is alkyl or —$OR^{41}$. In some embodiments, $R^{16}$ is —$CH_3$, —$CH_2CH_3$, —OH, —$OCH_3$, or —$CH(CH_3)_2$. In some embodiments, $R^{17}$ is —$OCH_3$, —CN, or —$C(O)CH_3$. In some embodiments, $R^{17}$ is —$C(O)CH_2R^{C1}$. In some embodiments, $R^{17}$ is —$C(O)CH_2R^{B1}$. In some embodiments, $R^{17}$ is alkoxy, cyano, or —$C(O)R^{B1}$. In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl). In some embodiments, $R^{B1}$ In some embodiments, $R^6$ is halogen. In some embodiments, $R^6$ is fluorine.

In some embodiments, each of $R^{11a}$ and $R^{11b}$ is independently hydrogen, $C_1$-$C_6$ alkyl (e.g. $C_1$-$C_6$ haloalkyl), $C_1$-$C_6$ alkoxy (e.g. $C_1$-$C_6$ haloalkoxy), or —OH. In some embodiments, $R^{11a}$ and $R^{11b}$ together form oxo.

In some embodiments, $R^{17}$ is $C_1$-$C_6$ alkoxy (e.g. —$OCH_3$), cyano, or nitro.

In some embodiments, $R^{19}$ is hydrogen or substituted or unsubstituted $C_1$-$C_6$ alkyl (e.g. —$CH_2OR^X$, wherein $R^X$ is hydrogen, $C_1$-$C_6$ alkyl, $C_1$-$C_6$ alkoxy).

In some embodiments, the compound of Formula (IX) is a compound of Formula (X-a1) or (X-b1):

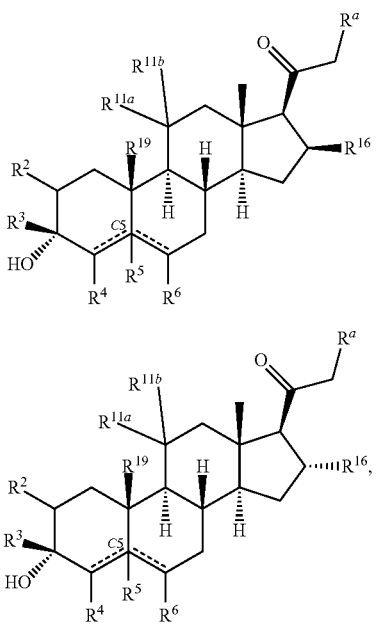

(X-a)

(X-b)

wherein $R^a$ is hydrogen, halogen, $C_{1-6}$ alkyl (e.g. —$CH_3$), or —OH.

In some embodiments, the compound of Formula (IX) is a compound of Formula (XI-a) or (XI-b):

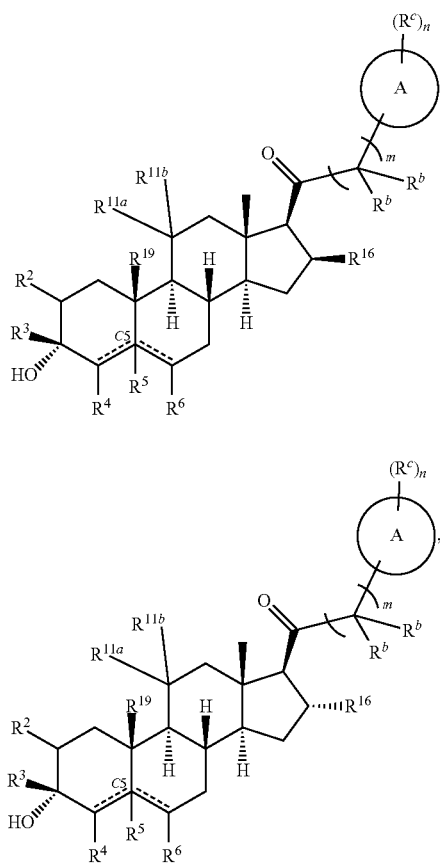

(XI-a)

(XI-b)

wherein m is 0, 1, or 2, n is 0, 1, or 2, each $R^b$ is independently hydrogen, halogen, or $C_1$-$C_6$ alkyl, and each $R^c$ is independently halogen, $C_1$-$C_6$ alkyl (e.g. —$CH_3$ or $C_1$-$C_6$ haloalkyl), $C_1$-$C_6$ alkoxy, cyano, or —OH.

In some embodiments, A is a 5-10-membered ring. In some embodiments, A is a fused bicyclic ring. In some embodiments, A is monocyclic heteroaryl or bicyclic heteroaryl.

In an aspect, also provided herein are compounds described in Table 1 or pharmaceutically acceptable salts thereof.

In an aspect, provided herein is a pharmaceutical composition comprising a compound described herein (e.g., a compound of the Formula (I), Formula (V), or Formula (IX)) and a pharmaceutically acceptable excipient.

In an aspect, provided herein is a method of inducing sedation and/or anesthesia in a subject, comprising administering to the subject an effective amount of a compound described herein (e.g., a compound of the Formula (I), Formula (V), or Formula (IX)), or a pharmaceutically acceptable salt thereof.

In an aspect, provided herein is a method of administering an effective amount of a compound, a pharmaceutically acceptable salt thereof, or pharmaceutical composition of a compound described herein (e.g., a compound of the Formula (I), Formula (V), or Formula (IX)), to a subject in need thereof, wherein the subject experiences sedation and/or anesthesia within two hours of administration. In some embodiments, the subject experiences sedation and/or anesthesia within one hour of administration. In some embodiments, the subject experiences sedation and/or anesthesia instantaneously. In some embodiments, the compound is administered by intravenous administration. In some embodiments, the compound is administered chronically.

In some embodiments, the subject is a mammal. In some embodiments, the subject is a human.

In some embodiments, the compound is administered in combination with another therapeutic agent.

In an aspect, provided herein is a method for treating seizure in a subject, comprising administering to the subject an effective amount of a compound described herein (e.g., a compound of the Formula (I), Formula (V), or Formula (IX).

In an aspect, provided herein is a method for treating epilepsy or status epilepticus in a subject, the method comprising administering to the subject an effective amount of a compound described herein (e.g., a compound of the Formula (I), Formula (V), or Formula (IX)).

In an aspect, provided herein is a method for treating a neuroendocrine disorder or dysfunction in a subject, comprising administering to the subject an effective amount of a compound described herein (e.g., a compound of the Formula (I), Formula (V), or Formula (IX)).

In an aspect, provided herein is a method for treating a neurodegenerative disease or disorder in a subject, comprising administering to the subject an effective amount of a compound described herein (e.g., a compound of the Formula (I), Formula (V), or Formula (IX)).

In an aspect, provided herein is a method for treating a movement disorder or tremor in a subject, comprising administering to the subject an effective amount of a compound described herein (e.g., a compound of the Formula (I), Formula (V), or Formula (IX)).

In an aspect, provided herein is a method for treating a mood disorder or anxiety disorder in a subject, comprising administering to the subject an effective amount of a compound described herein (e.g., a compound of the Formula (I), Formula (V), or Formula (IX)).

In an aspect, provided herein is a method for treating disorders related to GABA function in a subject in need thereof, the method comprising administering to the subject a therapeutically effective amount of a compound, a pharmaceutically acceptable salt thereof, or pharmaceutical composition of a compound described herein (e.g., a compound of the Formula (I), Formula (V), or Formula (IX)).

In an aspect, provided herein is a kit comprising a solid composition comprising a compound described herein (e.g., a compound of the Formula (I), Formula (V), or Formula (IX)) and a sterile diluent.

Thus, in another aspect, provided are methods of treating a CNS-related disorder in a subject in need thereof, comprising administering to the subject an effective amount of a compound as described herein (e.g., a compound of the Formula (I), Formula (V), or Formula (IX)). In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

In some embodiments, the subject is a subject with Rett syndrome, Fragile X syndrome, or Angelman syndrome.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

The absolute configuration of an asymmetric center can be determined using methods known to one skilled in the art. In some embodiments, the absolute configuration of an asymmetric center in a compound can be elucidated from the X-ray single-crystal structure of the compound. In some embodiments, the absolute configuration of an asymmetric center elucidated by the X-ray crystal structure of a compound can be used to infer the absolute configuration of a corresponding asymmetric center in another compound obtained from the same or similar synthetic methodologies. In some embodiments, absolute configuration of an asymmetric center can be determined using nuclear magnetic resonance (NMR) spectroscopy, e.g., through nuclear Overhauser effect (NOE) experiments.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 8 carbon atoms ("$C_{2-8}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

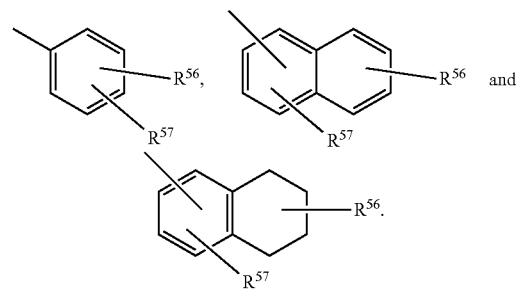

wherein one of $R^{56}$ and $R^{57}$ may be hydrogen and at least one of R and R is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

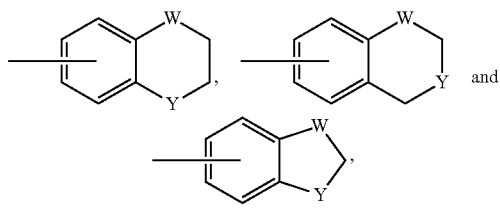

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Hydroxy" or "hydroxyl," independently or as part of another substituent, mean, unless otherwise stated, a —OH group.

Hydroxyalkyl" or "hydroxylalkyl" can include alkyl structures that are substituted with one or more hydroxyl groups.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

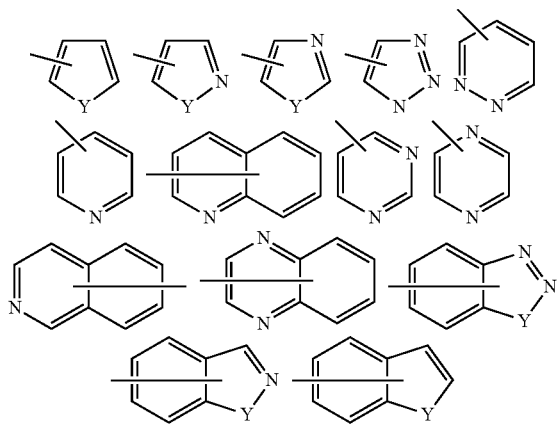

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

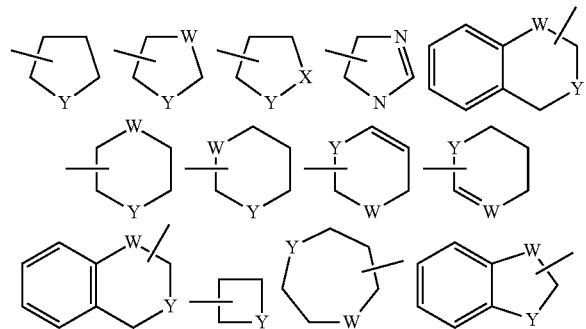

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(═O)CH$_3$), cyclohexylcarbonyl, cyclohexylmethylcarbonyl, benzoyl (—C(═O)Ph), benzylcarbonyl (—C(═O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, $R^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents hydrogen or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, $R^{28}$ is $C_1$-$C_8$ alkyl, substituted with halo or hydroxy; $C_3$-$C_{10}$ cycloalkyl, 4-10-membered heterocyclyl, $C_6$-$C_{10}$ aryl, arylalkyl, 5-10-membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxy, nitro, thioalkoxy, thioaryloxy, thiol, alkyl-S(O)—, aryl-S(O)—, alkyl-S(O)$_2$— and aryl-S(O)$_2$—. Exemplary "substituted alkoxy" groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—(CH$_2$)$_t$($C_6$-$C_{10}$ aryl), —$NR^{39}$—(CH$_2$)$_t$(5-10 membered heteroaryl), —$NR^{39}$—(CH$_2$)$_t$($C_3$-$C_{10}$ cycloalkyl), and —$NR^{39}$—(CH$_2$)$_t$(4-10 membered heterocyclyl), wherein t is an integer from 0 to 4, for instance 1 or 2, each $R^{39}$ independently represents hydrogen or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, and 5-10 membered heteroaryl; or $C_1$-$C_8$ alkyl substituted with halo or hydroxy; or $C_3$-$C_{10}$ cycloalkyl, 4-10 membered heterocyclyl, $C_6$-$C_{10}$ aryl, or 5-10 membered heteroaryl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

"Carboxy" refers to the radical —C(O)OH.

"Cyano" refers to the radical —CN.

"Oxo" refers to =O.

"Nitro" refers to the radical —NO$_2$.

"Ethenyl" refers to substituted or unsubstituted —(C=C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_1$-C$_6$ alkyl)$^+$X$^-$, —NH$_3$$^+$X$^-$, —N(OC$_{1-6}$ alkyl)(C$_1$-C$_6$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_1$-C$_6$ alkyl), —OC(=O)(C$_1$-C$_6$ alkyl), —OCO$_2$(C$_{1-6}$ alkyl), —C(=O)NH$_2$, —C(=O)N(C$_w$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_1$-C$_6$ alkyl), —SO$_2$N(C$_{1-6}$ alkyl)$_2$, —SO$_2$NH(C$_1$-C$_6$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_1$-C$_6$ alkyl), C(=S)NH$_2$, —C(=O)S(C$_1$-C$_6$ alkyl), —C(=S)SC$_{1-6}$ alkyl, —SC(=S)SC$_{1-6}$ alkyl, —P(=O)$_2$(C$_1$-C$_6$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14-membered heteroaryl, or two R$^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{2-10}$ alkenyl, C$_{2-10}$ alkynyl, C$_{3-10}$ carbocyclyl, 3-14-membered heterocyclyl, C$_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, gluco-heptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, trietha-nolamine, N-methylglucamine and the like. Salts further include, by way of example only, sodium, potassium, calcium, magnesium, ammonium, tetraalkylammonium, and the like; and when the compound contains a basic function-ality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exem-plified by sodium, potassium, calcium, magnesium, ammo-nium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional sol-vents include water, ethanol, acetic acid, and the like. The compounds of the invention may be prepared e.g. in crys-talline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative sol-vates include hydrates, ethanolates and methanolates.

"Stereoisomers": It is also to be understood that com-pounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mir-ror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asym-metric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either indi-vidual enantiomer or as a mixture thereof. A mixture con-taining equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, ends and ketones are tautomers because they are rapidly inter-converted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhe-sus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeu-tic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of adminis-tration, and the age, weight, health, and condition of the subject. An effective amount encompasses therapeutic and prophylactic treatment.

As used herein, and unless otherwise specified, a "thera-peutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combi-nation with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "pro-phylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylacti-cally effective amount" can encompass an amount that improves overall prophylaxis or enhances the prophylactic efficacy of another prophylactic agent.

DETAILED DESCRIPTION OF CERTAIN EMBODIMENTS OF THE INVENTION

Provided herein are compounds (e.g., a compound of Formula (I), a compound of Formula (V), or a compound of Formula (IX)), pharmaceutical compositions, and their methods of use to treat a disease or disorder as described herein.

Compounds

Compounds described herein are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In an aspect, provided herein is a compound of Formula (I):

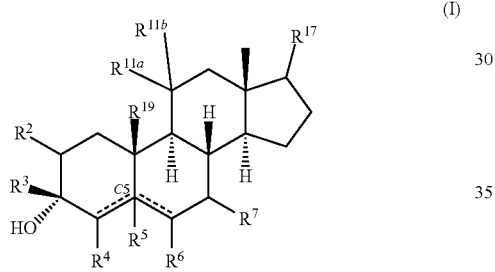

(I)

or a pharmaceutically acceptable salt thereof, wherein ====== represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; $R^5$ is absent or hydrogen; and ====== represents a single or double bond, wherein when one of ====== at site is a double bond, the other ====== is a single bond; when both of ====== are single bonds, then $R^5$ is hydrogen; and when one of the ====== is a double bond, $R^5$ is absent; $R^{17}$ is alkoxy, cyano, nitro, aryl, heteroaryl, or —$C(O)R^{B1}$, —$C(O)CH_2R^{B1}$, or —$C(O)CH_2CH_2R^{B1}$, wherein $R^{B1}$ is hydrogen, —OH, alkoxy, aryl, or heteroaryl; $R^{19}$ is hydrogen or alkyl; and $R^7$ is halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$.

In some embodiments, $R^3$ is alkyl.

In some embodiments, the compound of Formula (I) is a compound of Formula (I-a) or (I-b):

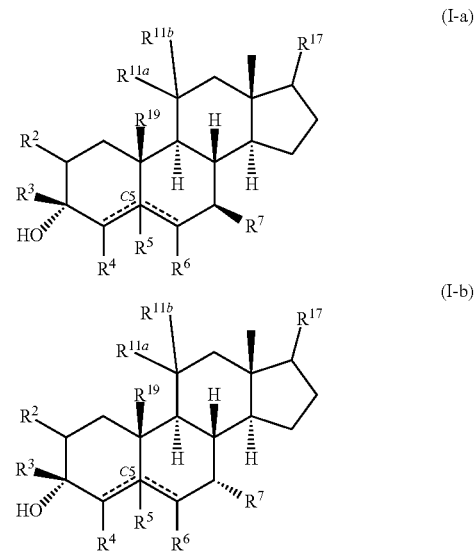

In some embodiments, each of $R^2$, $R^4$, and $R^6$, $R^{11a}$, and $R^{11b}$ is independently hydrogen;

In some embodiments, $R^2$, $R^4$, $R^6$, $R^{11a}$, and $R^{11b}$ are all hydrogen. In some embodiments, each of $R^2$, $R^4$, and $R^6$ is independently halogen, $C_1$-$C_6$ alkyl, $C_1$-$C_6$ alkoxy, or —OH; In some embodiments, $R^3$ is $C_1$-$C_6$ alkyl (e.g. $C_1$-$C_6$ haloalkyl or —$CH_3$).

In some embodiments, the compound of Formula (I) is a compound of Formula (II-a) or (II-b):

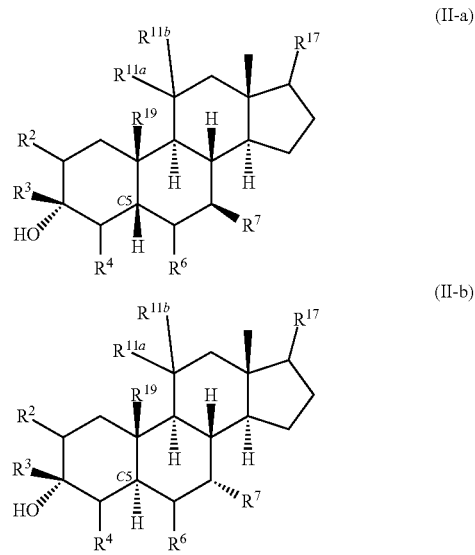

In some embodiments, the compound of Formula (I) is a compound of Formula (II-c) or (II-d):

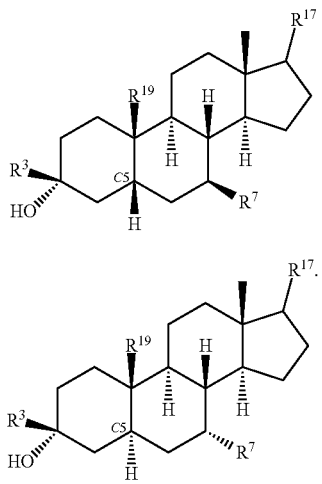

(II-c)

(II-d)

In some embodiments, $R^{19}$ is —$CH_3$. In some embodiments, $R^7$ is alkyl (e.g., unsubstituted alkyl or —$CH_2OR^{A1}$) or —$OR^{A1}$. In some embodiments, $R^7$ is —$CH_3$, —$CH_2CH_3$, —OH, —$OCH_3$, or —$CH_2OCH_3$. In some embodiments, $R^{17}$ is —$OCH_3$, —CN, or —$C(O)CH_3$. In some embodiments, $R^{17}$ is —$C(O)CH_2R^{C1}$. In some embodiments, $R^{17}$ is —$C(O)CH_2R^{B1}$. In some embodiments, $R^{17}$ is alkoxy, cyano, or —$C(O)R^{B1}$. In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl).

In some embodiments, $R^{B1}$ is

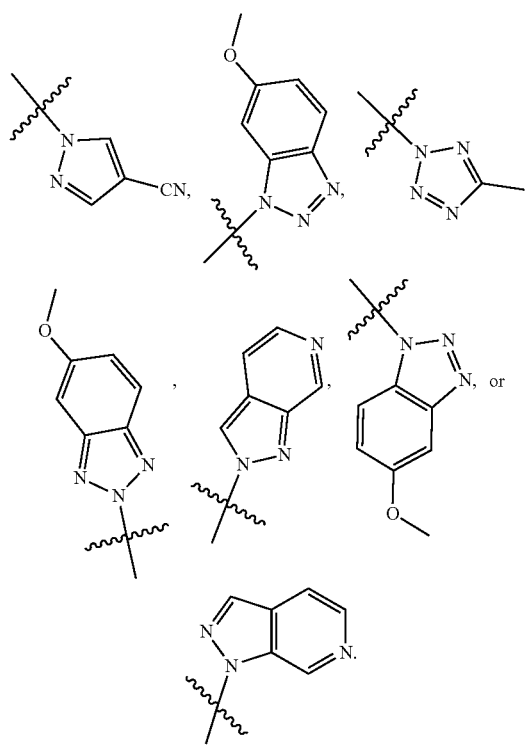

In some embodiments, $R^{B1}$ is

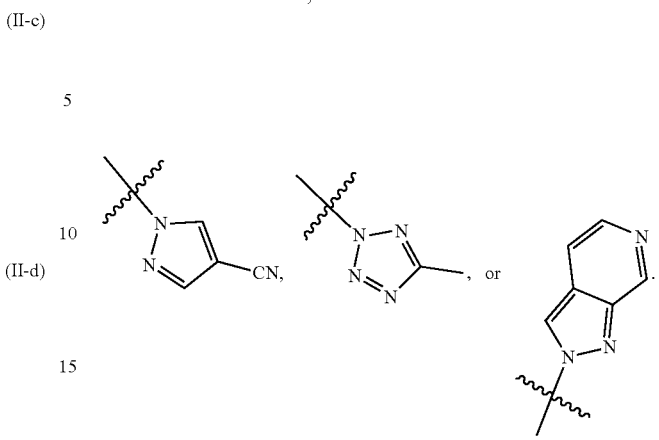

In some embodiments, $R^6$ is halogen. In some embodiments, $R^6$ is fluorine.

In some embodiments, each of $R^{11a}$ and $R^{11b}$ is independently hydrogen, $C_1$-$C_6$ alkyl (e.g. $C_1$-$C_6$ haloalkyl), $C_1$-$C_6$ alkoxy (e.g. $C_1$-$C_6$ alkoxyhalo), or —OH. In some embodiments, $R^{11a}$ and $R^{11b}$ together form oxo. In some embodiments, $R^{17}$ is $C_1$-$C_6$ alkoxy (e.g. —$OCH_3$), cyano, or nitro. In some embodiments, $R^{19}$ is hydrogen or substituted or unsubstituted $C_1$-$C_6$ alkyl (e.g. —$CH_2OR^X$, wherein $R^X$ is hydrogen, $C_1$-$C_6$ alkyl, or $C_1$-$C_6$ alkoxy).

In some embodiments, the compound of Formula (I) is a compound of Formula (III-a) or (III-b):

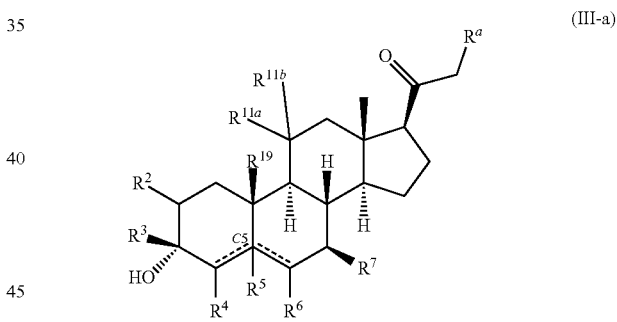

(III-a)

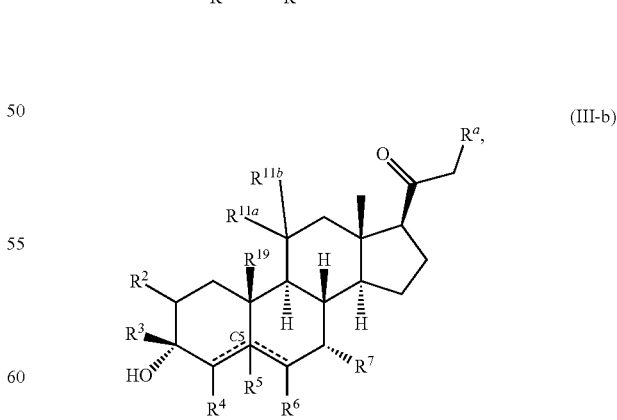

(III-b)

wherein $R^a$ is hydrogen, halogen, $C_1$-$C_6$ alkyl (e.g. —$CH_3$), or —OH. In some embodiments, the compound of Formula (I) is a compound of Formula (IV-a) or (IV-b):

(IV-a)

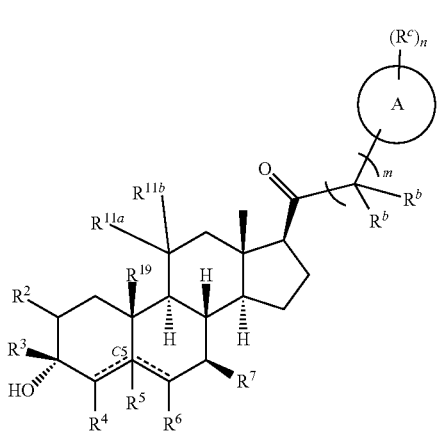

(IV-b)

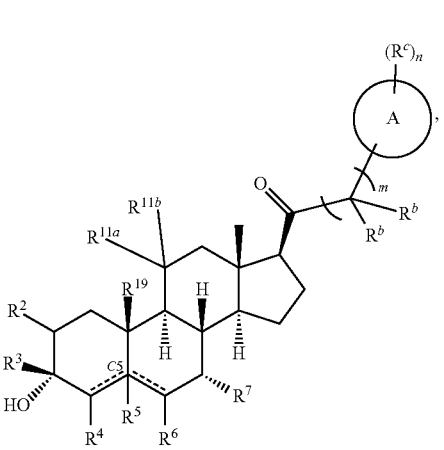

wherein: m is 0, 1, or 2; n is 0, 1, or 2; each $R^b$ is independently hydrogen, halogen, or $C_1$-$C_6$ alkyl; and each $R^c$ is independently halogen, $C_1$-$C_6$ alkyl (e.g. —$CH_3$ or $C_1$-$C_6$ haloalkyl), $C_1$-$C_6$ alkoxy, cyano, or —OH. In some embodiments, A is a 5-10-membered ring. In some embodiments, A is a fused bicyclic ring. In some embodiments, A is monocyclic heteroaryl or bicyclic heteroaryl.

In an aspect, provided is a compound of Formula (V):

(v)

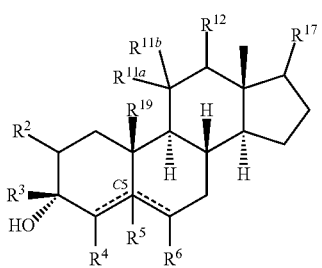

or a pharmaceutically acceptable salt thereof, wherein ====== represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; $R^5$ is absent or hydrogen; and ====== represents a single or double bond, wherein when one of ====== at site is a double bond, the other ====== is a single bond; when both of ====== are single bonds, then $R^5$ is hydrogen; and when one of the ====== is a double bond, $R^5$ is absent; $R^{17}$ is alkoxy, cyano, nitro, aryl, heteroaryl, —$C(O)R^{B1}$, —$C(O)CH_2R^{B1}$, or —$C(O)CH_2CH_2R^{B1}$, wherein $R^{B1}$ is hydrogen, —OH, alkoxy, aryl, or heteroaryl; $R^{19}$ is hydrogen or alkyl; and $R^{12}$ is halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$.

In some embodiments, $R^3$ is alkyl.

In some embodiments, the compound of Formula (V) is a compound of Formula (V-a) or (V-b):

(V-a)

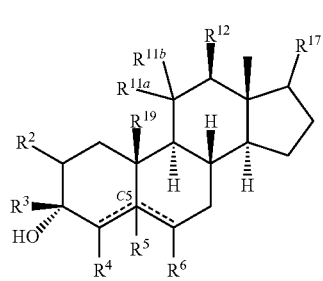

(V-b)

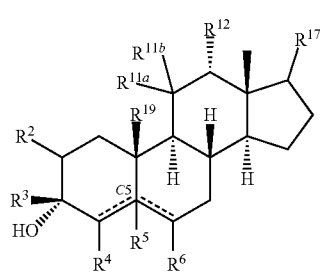

In some embodiments, each of $R^2$, $R^4$, $R^6$, $R^{11a}$, and $R^{11b}$ is independently hydrogen. In some embodiments, $R^2$, $R^4$, $R^6$, $R^{11a}$, and $R^{11b}$ are all hydrogen.

In some embodiments, each of $R^2$, $R^4$, and $R^6$ is independently halogen, $C_1$-$C_6$ alkyl, $C_1$-$C_6$ alkoxy, or —OH.

In some embodiments, $R^3$ is $C_1$-$C_6$ alkyl (e.g. $C_1$-$C_6$ haloalkyl or —$CH_3$).

In some embodiments, the compound of Formula (V) is a compound of Formula (VI-a) or (VI-b):

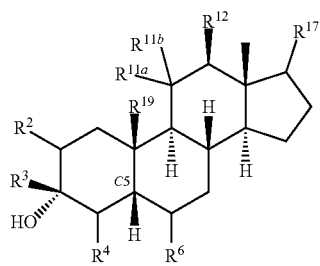

(VI-a)

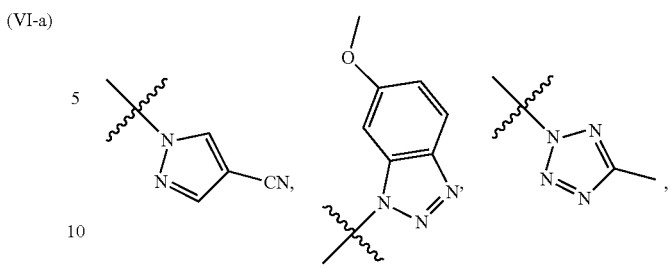


(VI-b)

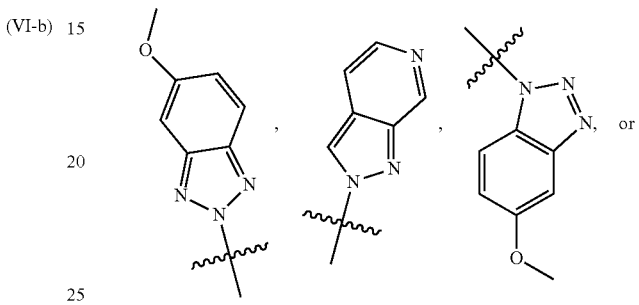

In some embodiments, the compound of Formula (V) is a compound of Formula (VI-c) or (VI-d):

In some embodiments, $R^{B1}$ is

(VI-c)

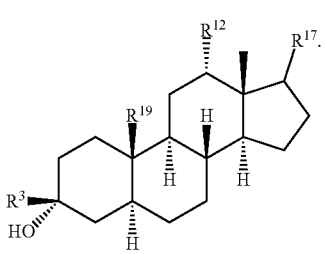

(VI-d)

In some embodiments, $R^{19}$ is —CH$_3$. In some embodiments, $R^{12}$ is —OR$^{A1}$. In some embodiments, $R^{12}$ is —CH$_3$, —CH$_2$CH$_3$, —OH, —OCH$_3$, or —CH$_2$OCH$_3$. In some embodiments, $R^{17}$ is —OCH$_3$, —CN, or —C(O)CH$_3$. In some embodiments, $R^{17}$ is —C(O)CH$_2$R$^{C1}$. In some embodiments, $R^{17}$ is —C(O)CH$_2$R$^{B1}$. In some embodiments, $R^{17}$ is alkoxy, cyano, or —C(O)R$^{B1}$.

In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl. In some embodiments, $R^{B1}$ is In some embodiments, $R^6$ is halogen. In some embodiments, $R^6$ is fluorine.

In some embodiments, each of $R^{11a}$ and $R^{11b}$ is independently hydrogen, C$_1$-C$_6$ alkyl (e.g. C$_1$-C$_6$ haloalkyl), C$_1$-C$_6$ alkoxy (e.g. C$_1$-C$_6$ haloalkoxy), or —OH. In some embodiments, $R^{11a}$ and $R^{11b}$ together form oxo. In some embodiments, $R^{17}$ is C$_1$-C$_6$ alkoxy (e.g. —OCH$_3$) or cyano. In some embodiments, $R^{19}$ is hydrogen or substituted or unsubstituted C$_1$-C$_6$ alkyl (e.g. —CH$_2$OR$^X$, wherein R$^X$ is hydrogen, C$_1$-C$_6$ alkyl, or C$_1$-C$_6$ alkoxy). In some embodiments, the compound of Formula (V) is a compound of Formula (VII-a) or (VII-b):

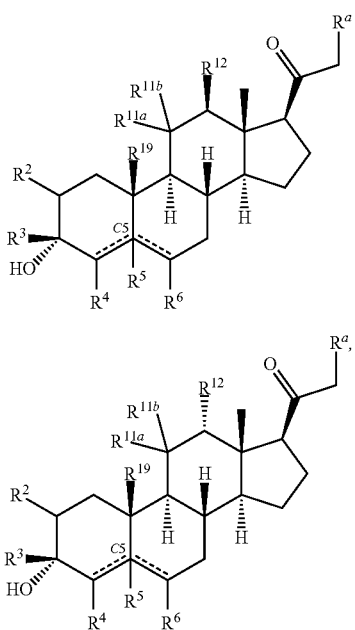

(VII-a)

(VII-b)

wherein $R^a$ is hydrogen, halogen, $C_1$-$C_6$ alkyl (e.g. —$CH_3$), or —OH. In some embodiments, the compound of Formula (V) is a compound of Formula (VIII-a) or (VIII-b):

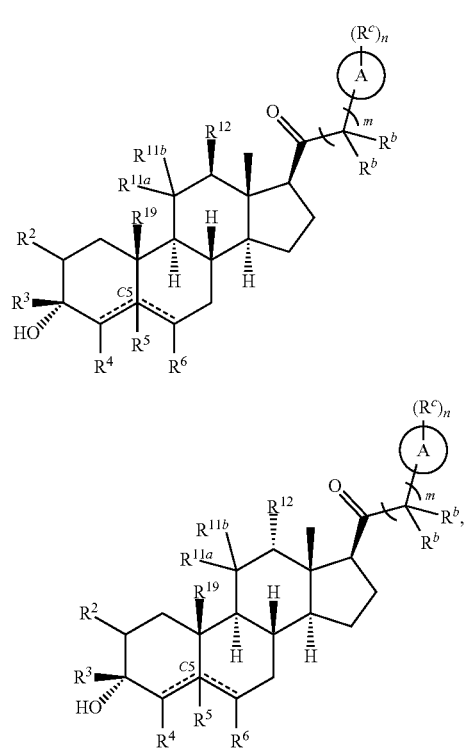

(VIII-a)

(VIII-b)

wherein m is 0, 1, or 2, n is 0, 1, or 2, and each $R^b$ is independently hydrogen, halogen, or $C_1$-$C_6$ alkyl; and each $R^c$ is independently halogen, $C_1$-$C_6$ alkyl (e.g. —$CH_3$ or $C_1$-$C_6$ haloalkyl), $C_1$-$C_6$ alkoxy, cyano, or —OH.

In some embodiments, A is a 5-10-membered ring. In some embodiments, A is a fused bicyclic ring. In some embodiments, A is monocyclic heteroaryl or bicyclic heteroaryl.

In an aspect, provided herein is a compound of Formula (IX):

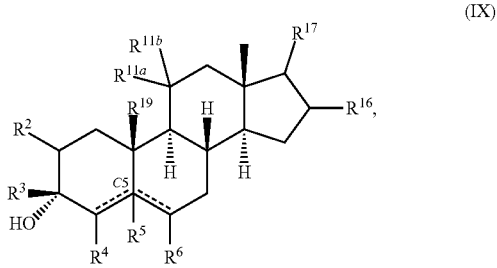

(IX)

or a pharmaceutically acceptable salt thereof, wherein ----- represents a single or double bond as valency permits; each of $R^2$, $R^4$, $R^6$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together form oxo; $R^3$ is hydrogen, alkyl, alkenyl, alkynyl, carbocyclyl, heterocyclyl, aryl, or heteroaryl; R is absent or hydrogen; and ====== represents a single or double bond, wherein when one of ====== at site is a double bond, the other ====== is a single bond; when both of ====== are single bonds, then $R^5$ is hydrogen; and when one of the ====== is a double bond, $R^5$ is absent; $R^{17}$ is alkoxy, cyano, nitro, aryl, heteroaryl, —$C(O)R^{B1}$, —$C(O)CH_2R^{B1}$, or —$C(O)CH_2CH_2R^{B1}$, wherein $R^{B1}$ is hydrogen, —OH, —$N(R^{A1})_2$, alkoxy, aryl, or heteroaryl; $R^{19}$ is hydrogen or alkyl; and $R^{16}$ is halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —$NHC(=O)R^{A1}$, —$NHC(=O)OR^{A1}$, —$S(=O)R^{A2}$, —$SO_2R^{A2}$, or —$S(=O)_2OR^{A1}$.

In some embodiments, $R^3$ is alkyl.

In some embodiments, the compound of Formula (IX) is a compound of Formula (IX-a) or (IX-b):

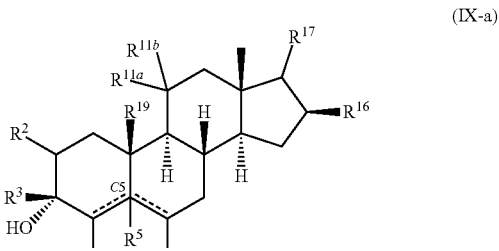

(IX-a)

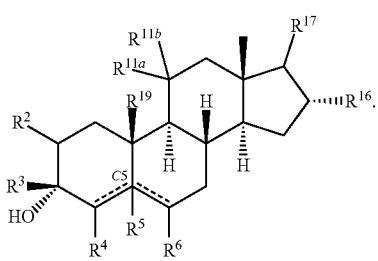

(IX-b)

In some embodiments, each of $R^2$, $R^4$, and $R^6$, $R^{11a}$, and $R^{11b}$ is independently hydrogen. In some embodiments, $R^2$, $R^4$, and $R^6$, $R^{11a}$, and $R^{11b}$ are all hydrogen. In some embodiments, each of $R^2$, $R^4$, and $R^6$ is independently halogen, $C_1$-$C_6$ alkyl, $C_1$-$C_6$ alkoxy, or —OH.

In some embodiments, $R^3$ is $C_1$-$C_6$ alkyl (e.g. $C_1$-$C_6$ haloalkyl or —CH$_3$).

In some embodiments, the compound of Formula (IX) is a compound of Formula (X-a) or (X-b):

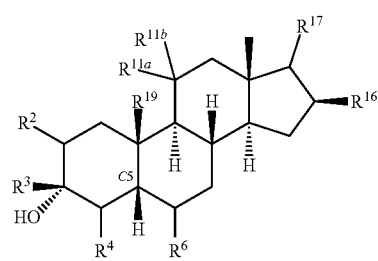

(X-a)

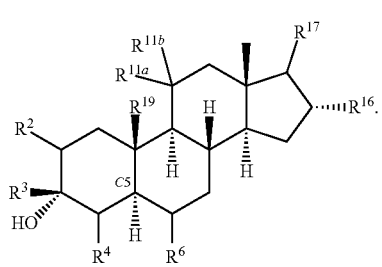

(X-b)

In some embodiments, the compound of Formula (IX) is a compound of Formula (X-c) or (X-d):

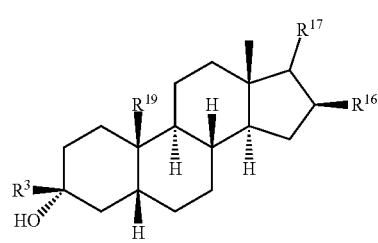

(X-c)

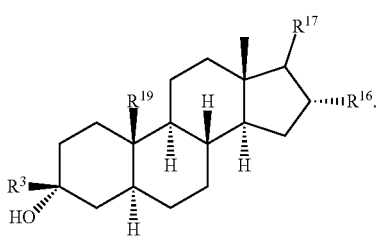

(X-d)

In some embodiments, $R^{19}$ is —CH$_3$. In some embodiments, $R^{16}$ is alkyl. In some embodiments, $R^{16}$ is —CH$_3$, —CH$_2$CH$_3$, —OH, —OCH$_3$, or —CH(CH$_3$)$_2$. In some embodiments, $R^{17}$ is —OCH$_3$, —CN, or —C(O)CH$_3$. In some embodiments, $R^{17}$ is —C(O)CH$_2$R$^{C1}$. In some embodiments, $R^{17}$ is —C(O)CH$_2$R$^{B1}$. In some embodiments, $R^{17}$ is alkoxy, cyano, or —C(O)R$^{B1}$. In some embodiments, $R^{B1}$ is pyrazolyl (e.g., a cyano-substituted pyrazolyl). In some embodiments, $R^{B1}$ is tetrazolyl (e.g., a methyl-substituted tetrazolyl). In some embodiments, $R^{B1}$ is a bicyclic heteroaryl (e.g., a methoxy-substituted bicyclic heteroaryl). In some embodiments, $R^{B1}$ is

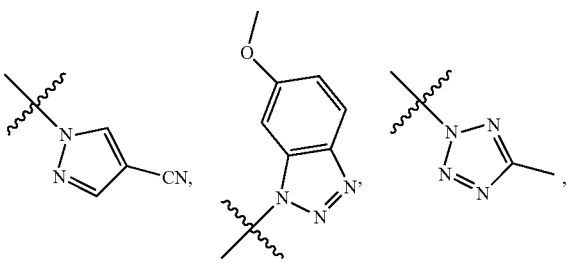

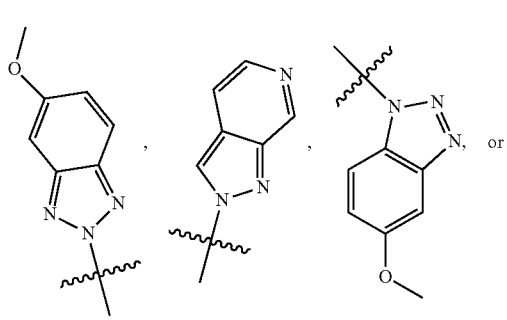

, or

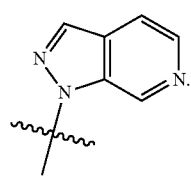

In some embodiments, $R^{B1}$ is

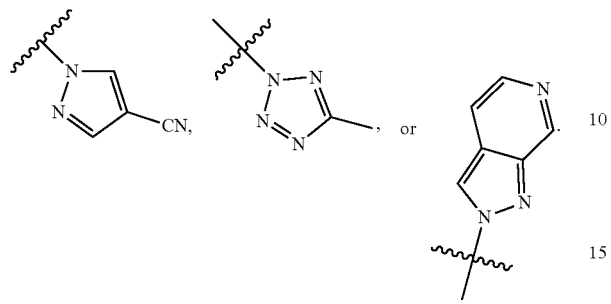

In some embodiments, $R^6$ is halogen. In some embodiments, $R^6$ is fluorine.

In some embodiments, each of $R^{11a}$ and $R^{11b}$ is independently hydrogen, $C_1$-$C_6$ alkyl (e.g. $C_1$-$C_6$ haloalkyl), $C_1$-$C_6$ alkoxy (e.g. $C_1$-$C_6$ haloalkoxy), or —OH. In some embodiments, $R^{11a}$ and $R^{11b}$ together form oxo.

In some embodiments, $R^{17}$ is $C_1$-$C_6$ alkoxy (e.g. —OCH$_3$), cyano, or nitro.

In some embodiments, $R^{19}$ is hydrogen or substituted or unsubstituted $C_1$-$C_6$ alkyl (e.g. —CH$_2$OR$^X$, wherein R$^X$ is hydrogen, $C_1$-$C_6$ alkyl, $C_1$-$C_6$ alkoxy).

In some embodiments, the compound of Formula (IX) is a compound of Formula (X-a1) or (X-b1):

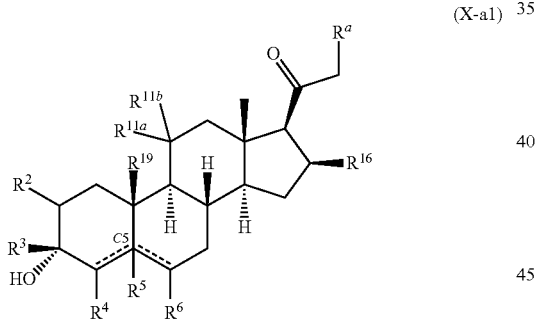
(X-a1)

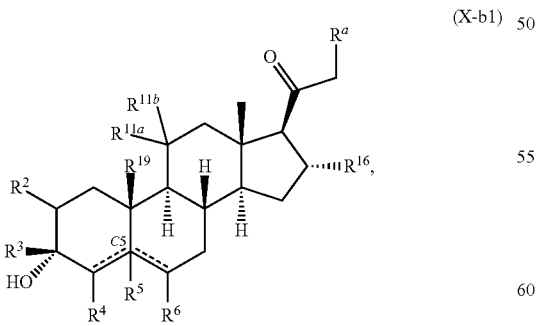
(X-b1)

wherein $R^a$ is hydrogen, halogen, $C_{1-6}$ alkyl (e.g. —CH$_3$), or —OH.

In some embodiments, the compound of Formula (IX) is a compound of Formula (XI-a) or (XI-b):

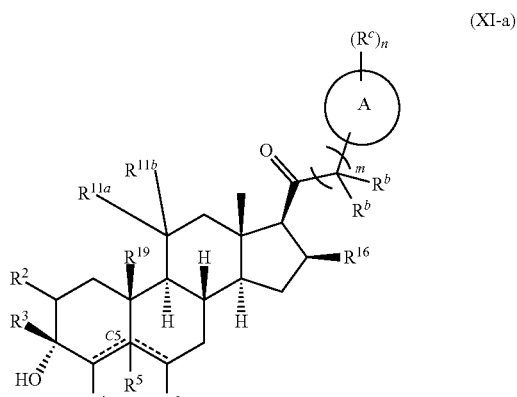
(XI-a)

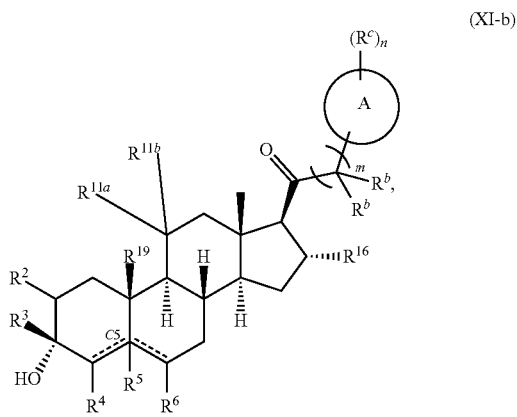
(XI-b)

wherein m is 0, 1, or 2, n is 0, 1, or 2, each $R^b$ is independently hydrogen, halogen, or $C_1$-$C_6$ alkyl, and each $R^c$ is independently halogen, $C_1$-$C_6$ alkyl (e.g. —CH$_3$ or $C_1$-$C_6$ haloalkyl), $C_1$-$C_6$ alkoxy, cyano, or —OH.

In some embodiments, A is a 5-10-membered ring. In some embodiments, A is a fused bicyclic ring. In some embodiments, A is monocyclic heteroaryl or bicyclic heteroaryl.

Also provided herein are compounds described in Table 1 below or pharmaceutically acceptable salts thereof.

TABLE 1

Exemplary Compounds of the Invention

| Compound structure | Compound number |
|---|---|
| 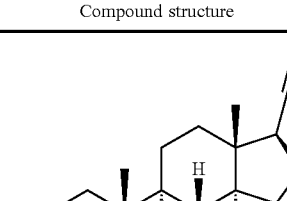 | 1 |

TABLE 1-continued

Exemplary Compounds of the Invention

| Compound structure | Compound number |
|---|---|
| (structure) | 2 |
| (structure) | 3 |
| (structure) | 4 |
| (structure) | 5 |
| (structure) | 6 |
| (structure) | 7 |
| (structure) | 8 |
| (structure) | 9 |
| (structure) | 10 |
| (structure) | 11 |

TABLE 1-continued
Exemplary Compounds of the Invention
| Compound structure | Compound number |
|---|---|
| 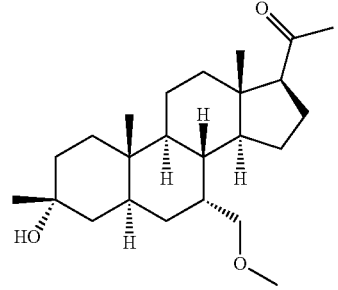 | 12 |
| 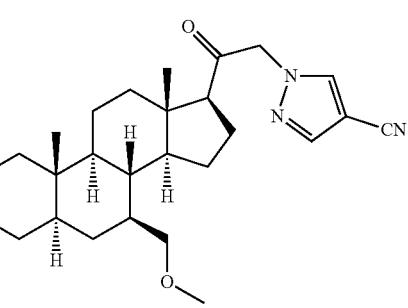 | 13 |
| 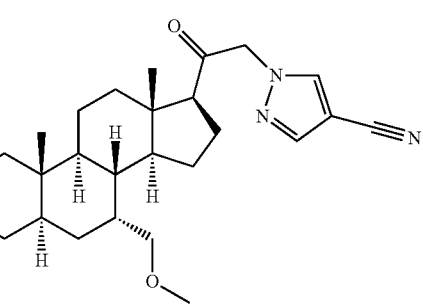 | 14 |
| 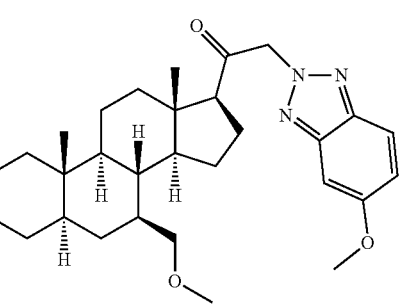 | 15 |
| 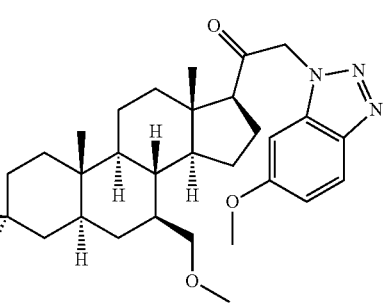 | 16 |
| 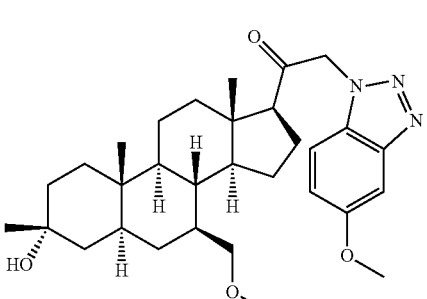 | 17 |
| 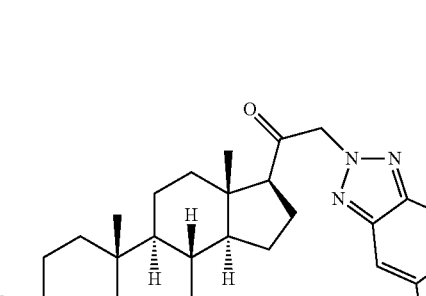 | 18 |
| 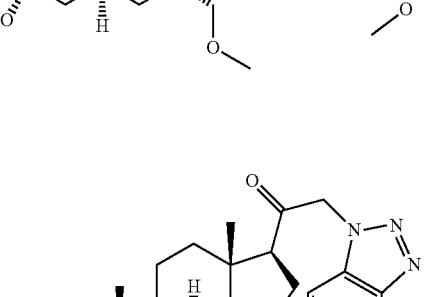 | 19 |
| 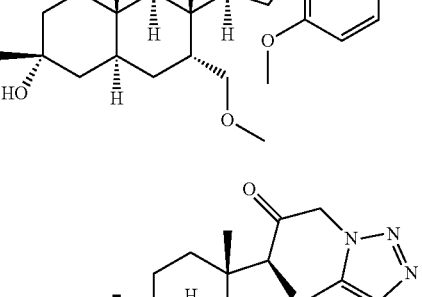 | 20 |

TABLE 1-continued
Exemplary Compounds of the Invention
| Compound structure | Compound number |
|---|---|
| 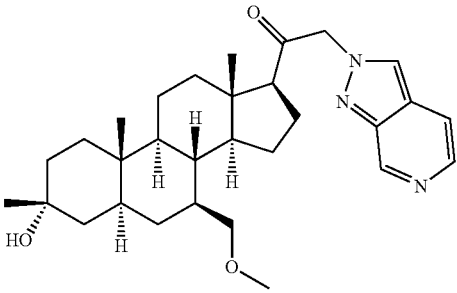 | 21 |
| 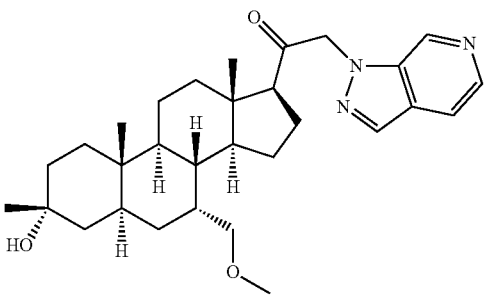 | 23 |
| 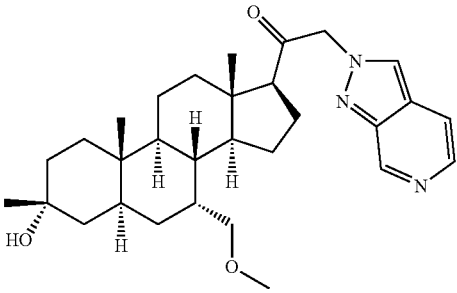 | 24 |
| 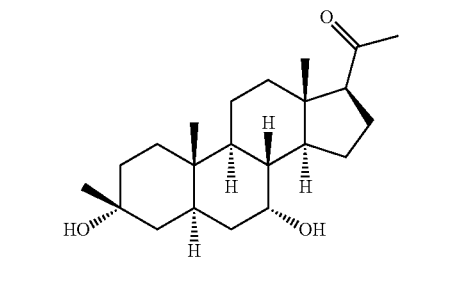 | 25 |
| 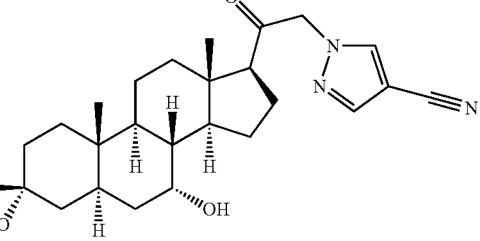 | 26 |
| 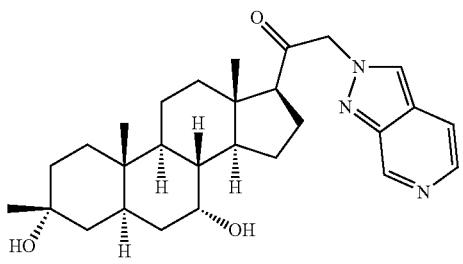 | 27 |
| 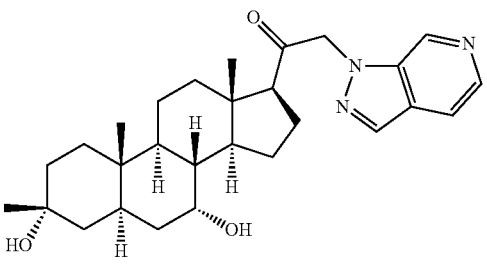 | 28 |
| 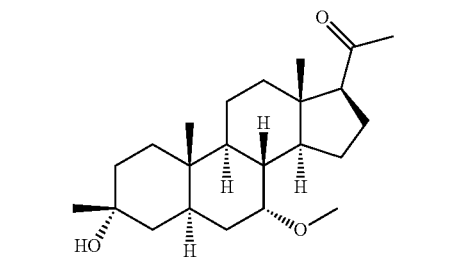 | 29 |
| 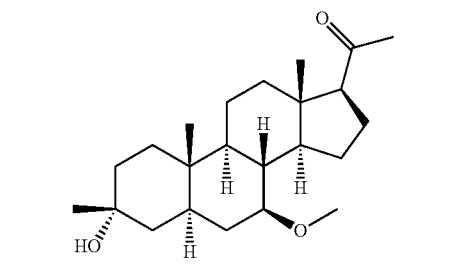 | 30 |
| 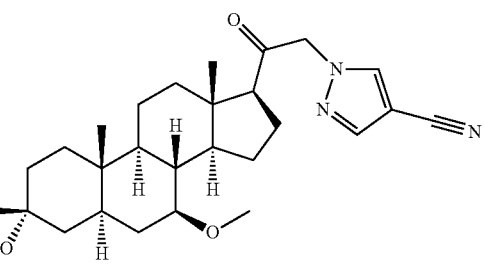 | 31 |

TABLE 1-continued

Exemplary Compounds of the Invention

| Compound structure | Compound number |
|---|---|
| (steroid with 3-OH, 7-methyl, 17-C(O)CH2-tetrazole-methyl) | 34 |
| (steroid with 3-OH, 7-methyl, 17-C(O)CH2-tetrazole-methyl) | 35 |
| (steroid with 3-OH, 7-methyl, 17-C(O)CH2-tetrazole-methyl) | 36 |
| (steroid with 3-OH, 7-methyl, 17-C(O)CH2-tetrazole-methyl) | 37 |
| (steroid with 3-OH, 7-methyl, 17-C(O)CH2-pyrazole-CN) | 38 |
| (steroid with 3-OH, 7-methyl, 17-C(O)CH2-pyrazole-CN) | 39 |
| (steroid with 3-OH, 12-OH, 17-CN) | 40 |
| (steroid with 3-OH, 12-OMe, 17-CN) | 41 |
| (steroid with 3-OH, 12-OMe, 17-OMe) | 42 |
| (steroid with 3-OH, 12-OMe, 17-C(O)CH3) | 43 |

TABLE 1-continued

Exemplary Compounds of the Invention

| Compound structure | Compound number |
|---|---|
| (structure) | 44 |
| (structure) | 45 |
| (structure) | 46 |
| (structure) | 47 |
| (structure) | 48 |
| (structure) | 49 |
| (structure) | 50 |
| (structure) | 51 |
| (structure) | 52 |
| (structure) | 53 |

US 11,993,628 B2
59
TABLE 1-continued
Exemplary Compounds of the Invention
| Compound structure | Compound number |
|---|---|
| 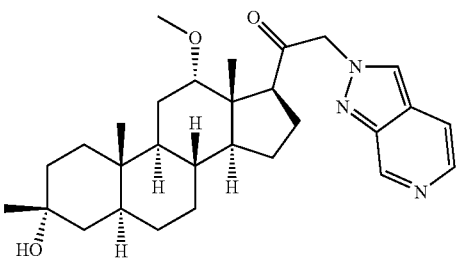 | 54 |
| 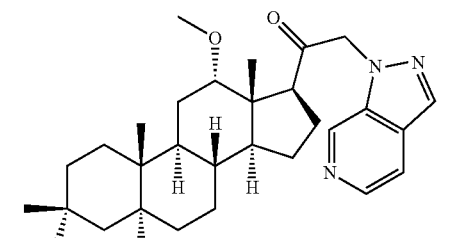 | 55 |
| 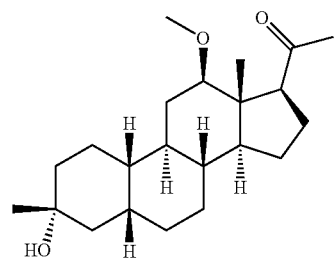 | 56 |
| 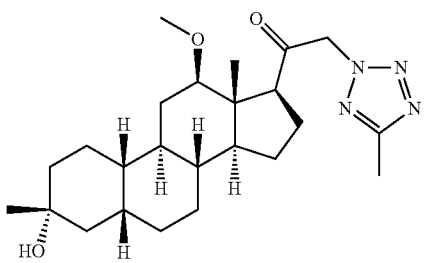 | 58 |
| 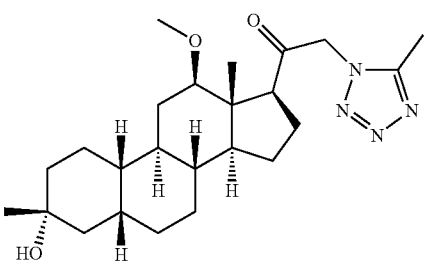 | 59 |
60
TABLE 1-continued
Exemplary Compounds of the Invention
| Compound structure | Compound number |
|---|---|
| 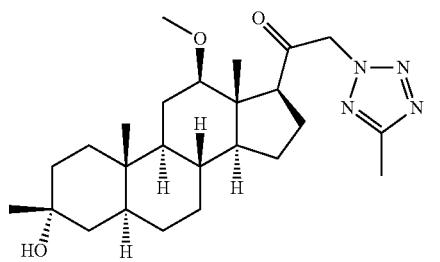 | 60 |
| 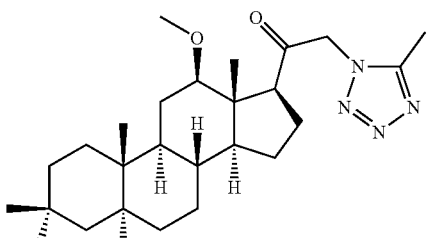 | 61 |
| 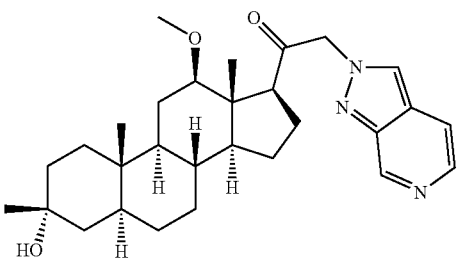 | 62 |
| 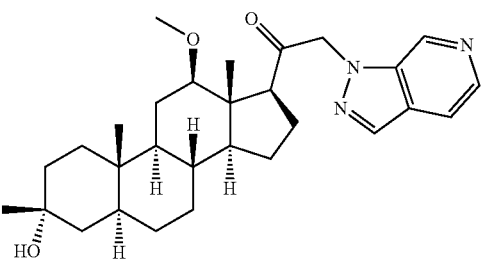 | 63 |
| 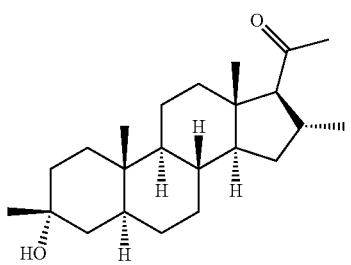 | 64 |

TABLE 1-continued

Exemplary Compounds of the Invention

| Compound structure | Compound number |
| --- | --- |
| (structure) | 65 |
| (structure) | 66 |
| (structure) | 67 |
| (structure) | 68 |
| (structure) | 69 |
| (structure) | 70 |
| (structure) | 71 |
| (structure) | 72 |
| (structure) | 73 |
| (structure) | 74 |

TABLE 1-continued
Exemplary Compounds of the Invention
| Compound structure | Compound number |
|---|---|
| 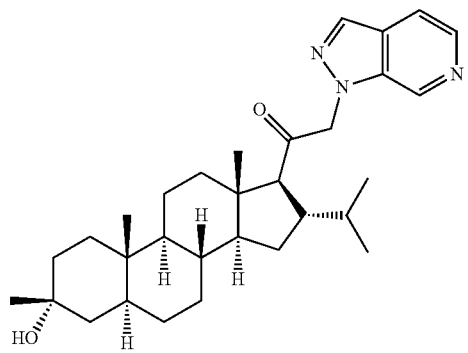 | 75 |
| 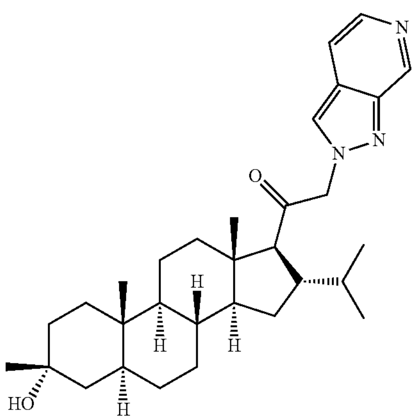 | 76 |
| 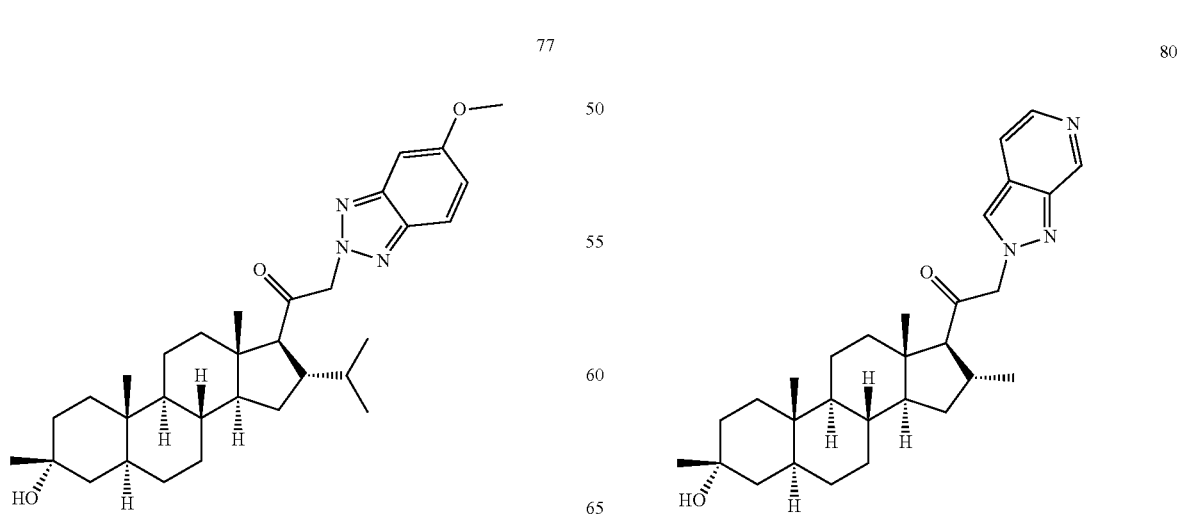 | 77 |
TABLE 1-continued
Exemplary Compounds of the Invention
| Compound structure | Compound number |
|---|---|
| 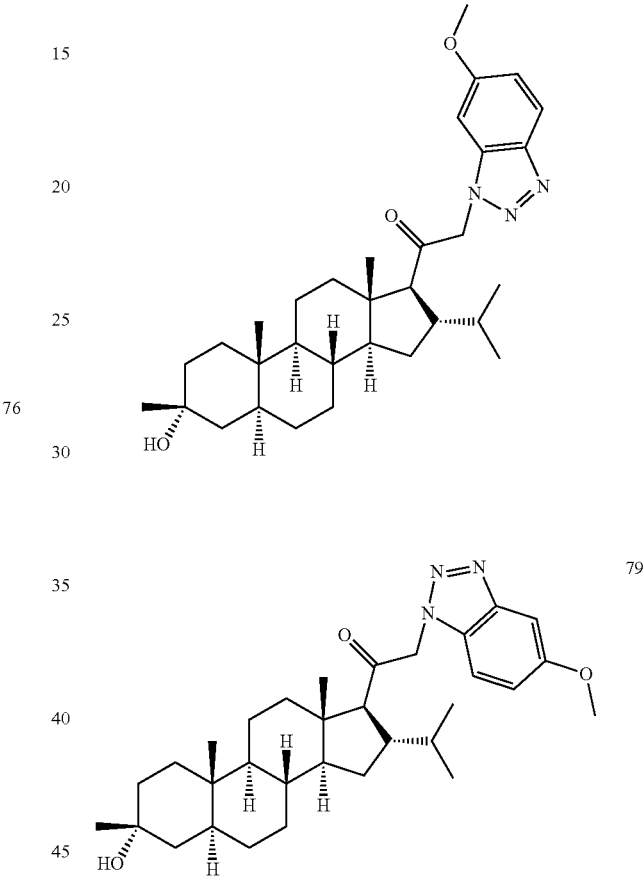 | 78 |
| 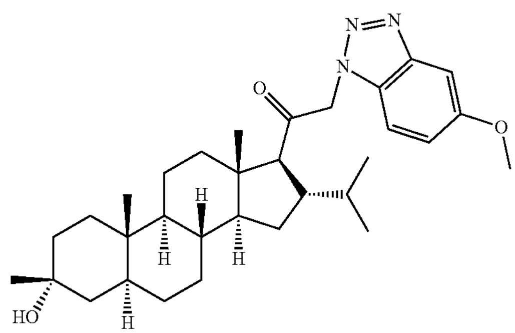 | 79 |
| 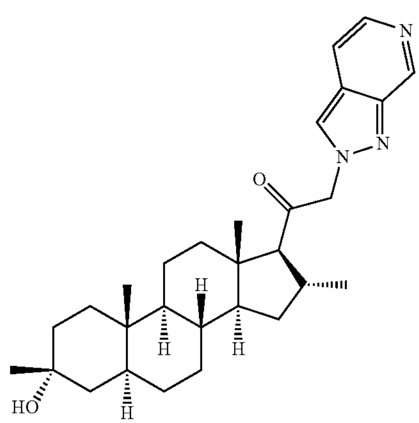 | 80 |

TABLE 1-continued

Exemplary Compounds of the Invention

| Compound structure | Compound number |
|---|---|
| | 81 |
| | 82 |
| | 83 |
| | 84 |
| 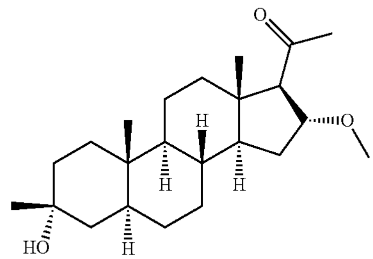 | 85 |
| 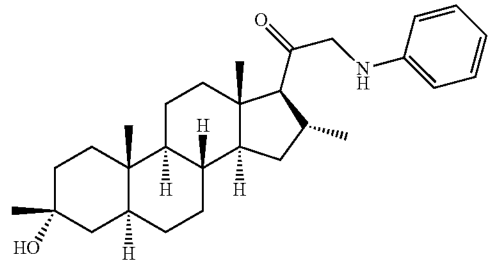 | 86 |
| 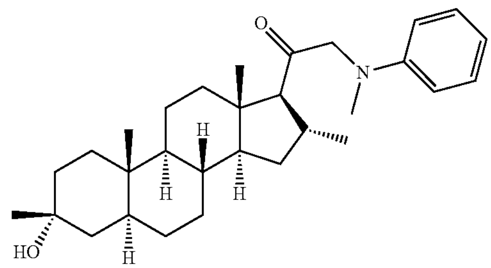 | 87 |
| 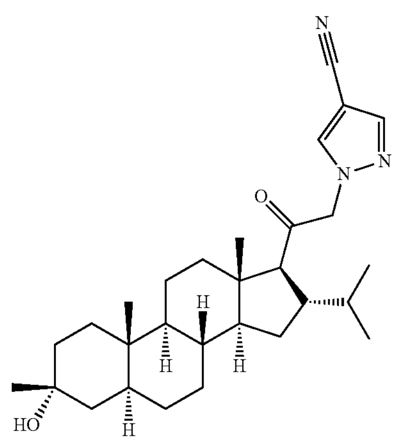 | 88 |
| 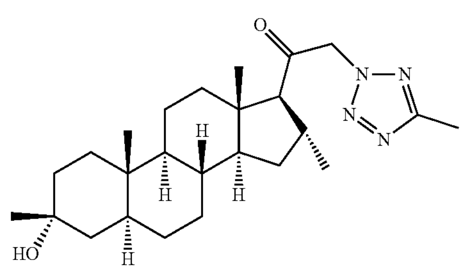 | 89 |

TABLE 1-continued

Exemplary Compounds of the Invention

| Compound structure | Compound number |
| --- | --- |
| (steroid structure with hydroxyl, methyl groups, and methyltetrazole-containing ketone side chain) | 90 |
| (steroid structure with hydroxyl and acetyl side chain) | 91 |
| (steroid structure with hydroxyl and cyanopyrazole-containing ketone side chain) | 92 |

Alternative Embodiments

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences,* Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8□□1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-□-cyclodextrin. In a more particular embodiment, the composition comprises hexapropyl-□-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Methods of Use and Treatment

In an aspect, provided is a method of alleviating or preventing seizure activity in a subject, comprising administering to the subject in need of such treatment an effective amount of a compound of the present invention. In some embodiments, the method alleviates or prevents epileptogenesis.

In some embodiments, such compounds are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, ahention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

Also provided herein are methods for treating a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method provides therapeutic effect (e.g., as measured by reduction in Hamilton Depression Score (HAM-D)) within 4, 3, 2, 1 days; 96, 84, 72, 60, 48, 24, 20, 16, 12, 10, 8 hours or less. In some embodiments, the therapeutic effect is a decrease from baseline in HAM-D score at the end of a treatment period (e.g., 12, 24, 48 hours after administration; 24, 48, 72, 96 hours or more). In some embodiments, the decrease from baseline in HAM-D score is from severe (e.g., HAM-D score of 24 or greater) to symptom-free (e.g., HAM-D score of 7 or lower). In some embodiments, the baseline score is about 10 to 52 (e.g., more than 10, 15, or 20; 10 to 52, 12 to 52, 15 to 52, 17 to 52, 20 to 52, 22 to 52). In some embodiments, the baseline score is at least 10, 15, or 20. In some embodiments, the HAM-D score at the end of the treatment period is about 0 to 10 (e.g., less than 10; 0 to 10, 0 to 6, 0 to 4, 0 to 3, 0 to 2, 1.8). In some embodiments, the HAM-D score at the end of the treatment period is less than 10, 7, 5, or 3. In some embodiments, the decrease in HAM-D score is from a baseline score of about 20 to 30 (e.g., 22 to 28, 23 to 27, 24 to 27, 25 to 27, 26 to 27) to a HAM-D score at the end of the treatment period is about 0 to 10 (e.g., less than 10; 0 to 10, 0 to 6, 0 to 4, 0 to 3, 0 to 2, 1.8). In some embodiments, the decrease in the baseline HAM-D score to HAM-D score at the end of the treatment period is at least 1, 2, 3, 4, 5, 7, 10, 25, 40, 50, or 100 fold). In some embodiments, the percentage decrease in the baseline HAM-D score to HAM-D score at the end of the treatment period is at least 50% (e.g., 60%, 70%, 80%, 90%). In some embodiments, the therapeutic effect is a decrease from baseline in HAM-D score at the end of a treatment period (e.g., 12, 24, 48 hours after administration; 24, 48, 72, 96 hours or more) at least 10, 15, or 20 points. In some embodiments, the therapeutic effect is a decrease from baseline in HAM-D score at the end of a treatment period (e.g., 12, 24, 48 hours after administration; 24, 48, 72, 96 hours or more) at least 5, 7, or 10 points more relative to the therapeutic effect provided by a placebo treatment.

In some embodiments, the method provides therapeutic effect (e.g., as measured by reduction in Montgomery-Åsberg Depression Rating Scale (MADRS)) within 4, 3, 2, 1 days; 96, 84, 72, 60, 48, 24, 20, 16, 12, 10, 8 hours or less. The Montgomery-Åsberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders. 0-6 indicates normal/symptom absent; 7-19 indicates mild depression; 20-34 indicates moderate depression; and >34 indicates severe depression. In some embodiments, the therapeutic effect is a decrease from baseline in MADRS score at the end of a treatment period (e.g., 12, 24, 48 hours after administration; 24, 48, 60, 72, 96 hours or more). In some embodiments, the decrease from baseline in MADRS score is from severe (e.g., MADRS score of 30 or greater) to symptom-free (e.g., MADRS score of 20 or lower). For example, the mean change from baseline in MADRS total score from treatment with a compound described herein is about −15, −20, −25, −30, while the mean change from baseline in MADRS total score from treatment with placebo is about −15, −10, −5.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is a improvement measured by the EPDS.

In some embodiments, the method provides therapeutic effect (e.g., as measured by reduction in Clinical Global Impression-Improvement Scale (CGI)) within 4, 3, 2, 1 days; 24, 20, 16, 12, 10, 8 hours or less. In some embodiments, the therapeutic effect is a CGI score of 2 or less.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, Gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

Epilepsy

The compound of Formula (I), the compound of Formula (V), or the compound of Formula (IX), or pharmaceutically acceptable salt, or a pharmaceutically acceptable composition thereof, can be used in a method described herein, for example in the treatment of a disorder described herein such as epilepsy, status epilepticus, or seizure, for example as described in WO2013/112605 and WO/2014/031792, the contents of which are incorporated herein in their entirety.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The compound of Formula (I), a compound of Formula (V), or a compound of Formula (IX) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example the compound of Formula (I) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

EXAMPLES

In order that the invention described herein may be more fully understood, the following examples are set forth. The synthetic examples described in this application are offered to illustrate the invention provided herein and are not to be construed in any way as limiting its scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Exemplary general method for preparative HPLC: Column: Durashell. Mobile phase: A: water, B: acetonitrile. % B at 0 min: 41%, % B at 8 min: 71%, flow rate: 35 mL/min, detection wavelength: 220 nm.

Exemplary general method for analytical HPLC: Mobile phase: A: water (10 mM NH$_4$HCO$_3$), B: acetonitrile Gradient: 5%-95% B in 1.6 or 2 min, flow rate: 1.8 or 2 mL/min; Column: XBridge C18, 4.6*50 mm, 3.5 Dm at 45 C.

Exemplary general method for SFC: Column: CHIRALPAK® AD (250 mm*30 mm, 5 μm), A=supercritical CO$_2$, B=MeOH (0.1% NH$_3$—H$_2$O), A:B=70:30, flow rate: 60 mL/min, column temperature: 38° C., nozzle pressure: 100 bar, detection wavelength=220 nm.

Exemplary LCMS conditions include:

| 30-90AB_2 MIN_E | |
|---|---|
| Column | Xtimate C18 2.1*30 mm, 3 um |
| Mobile Phase | A: water(4 L) + TFA(1.5 mL) |
| | B: acetonitrile(4 L) + TFA(0.75 mL) |
| | TIME(min)    B % |
| | 0    30 |
| | 0.9    90 |
| | 1.5    90 |
| | 1.51    30 |
| | 2    30 |
| Flow Rate | 1.2 mL/min |
| wavelength | UV 220 nm |
| Oven Temp | 50° C. |
| MS ionization | ESI |
| Detector | PDA, ELSD |

| 10-80AB_2 MIN_E | |
|---|---|
| Column | Xtimate C18 2.1*30 mm, 3 um |
| Mobile Phase | A: water(4 L) + TFA(1.5 mL) |
| | B: acetonitrile(4 L) + TFA(0.75 mL) |
| | TIME(min)    B % |
| | 0    10 |
| | 0.9    80 |
| | 1.5    80 |
| | 1.51    10 |
| | 2    10 |
| Flow Rate | 1.2 mL/min |
| wavelength | UV 220 nm |
| Oven Temp | 50° C. |
| MS ionization | ESI |
| Detector | PDA, ELSD |

| 30-90CD_3 MIN_E | |
|---|---|
| Column | Xbrige Shield RP-18, 5 um, 2.1*50 mm |
| Mobile Phase | A: water(1 L) + NH3H2O(0.5 mL) |
| | B: acetonitrile |
| | TIME(min)    B % |
| | 0    30 |
| | 2    90 |
| | 2.48    90 |
| | 2.49    30 |
| | 3    30 |
| Flow Rate | 1.0 mL/min |
| wavelength | UV 220 nm |
| Oven Temp | 30° C. |
| MS ionization | ESI |
| Detector | PDA, ELSD |

Steroid Inhibition of TBPS Binding

[$^{35}$S]-t-Butylbicyclophosphorothionate (TBPS) binding assays using rat brain cortical membranes in the presence of 5 mM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [$^{35}$S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition ($IC_{50}$) of specific binding and the maximal extent of inhibition ($I_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures. The results of the TBPS binding assays are shown in Table 2.

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2,6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; PE: petroleum ether; MeCN: acetonitrile; MeOH: methanol; Boc: t-butoxycarbonyl; MTBE: methyl tert-butyl ether; EDCI: A-(3-Dimethylaminopropyl)-N'-ethylcarbodiimide hydrochloride; HATU: 1-Bis(dimethylamino)methylene-1H-1,2,3-triazolo[4,5-b]pyridinium 3-oxide hexafluorophosphate.

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2,6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; PE: petroleum ether; MeCN: acetonitrile; MeOH: methanol; Boc: t-butoxycarbonyl; MTBE: methyl tert-butyl ether; EDCI: A-(3-Dimethylaminopropyl)-N'-ethylcarbodiimide hydrochloride; HATU: 1-Bis(dimethylamino)methylene-1H-1,2,3-triazolo[4,5-b]pyridinium 3-oxide hexafluorophosphate.

Example 1. Syntheses of Compounds 1 and 2

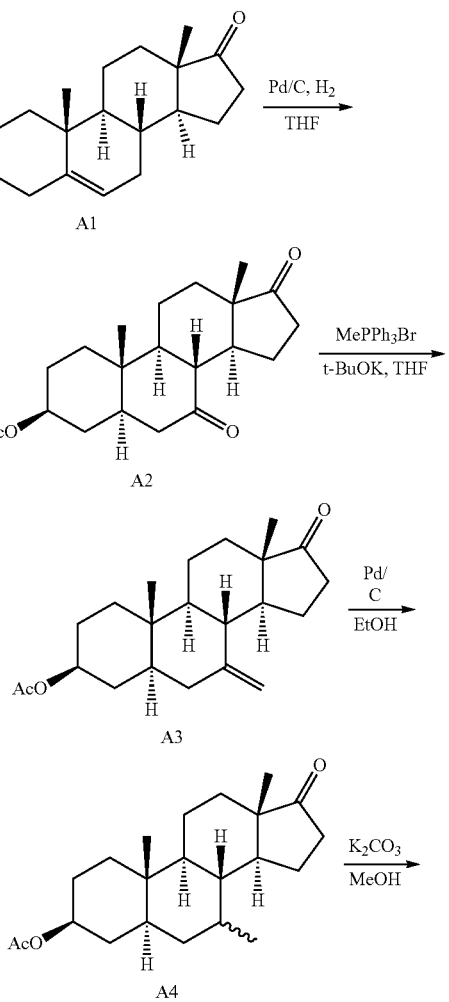

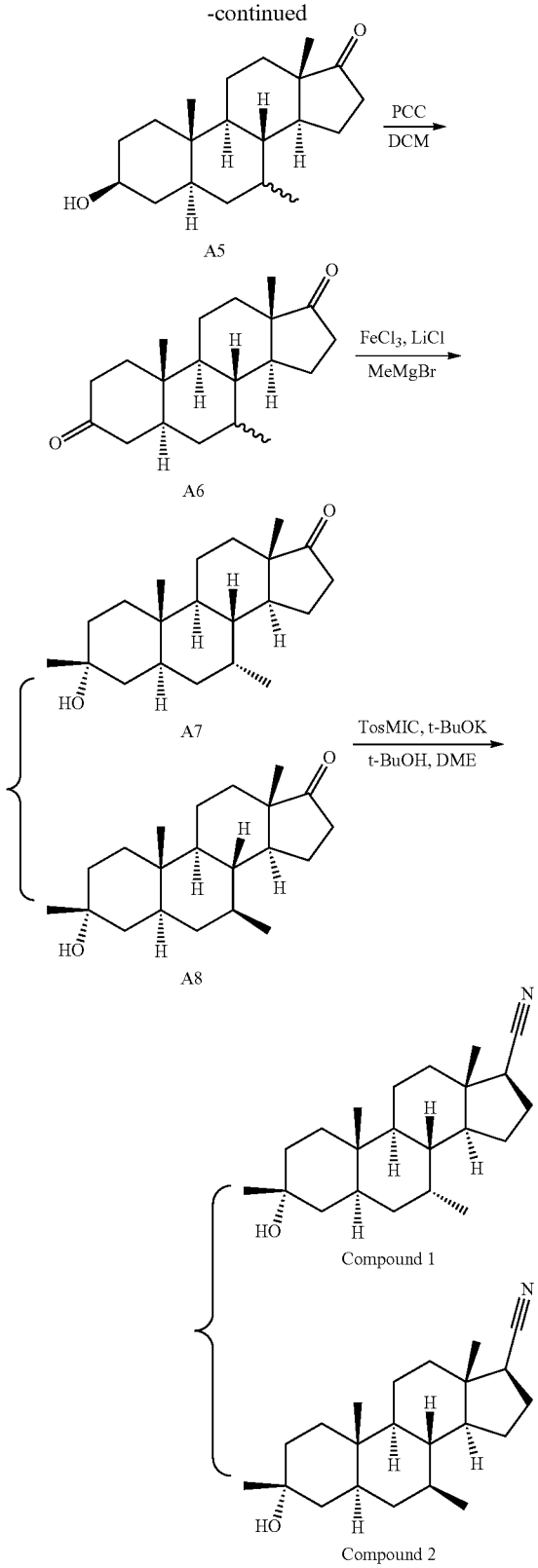

was degassed under vacuum and purged with H₂ for three times. The mixture was stirred under H₂ (15 psi) at 25 C for 48 hours to give a black suspension. The reaction mixture was filtered through a pad of Celite and washed with THF (500 mL). The filtrate was concentrated and to give A2 (98 g, 97%) as a solid.

¹H NMR (400 MHz, CDCl₃) δ 4.73-4.62 (m, 1H), 2.65-2.54 (m, 1H), 2.51-2.32 (m, 3H), 2.20-2.06 (m, 2H), 2.04 (s, 3H), 1.95-1.86 (m, 1H), 1.84-1.67 (m, 5H), 1.67-1.42 (m, 5H), 1.25-1.02 (m, 6H), 0.91-0.81 (m, 3H).

Step 2

To a solution of MePPh₃Br (20.6 g, 57.7 mmol, 1.0 eq) in THF (200 mL) was added t-BuOK (6.47 g, 57.7 mmol, 1.0 eq) at 0° C. After addition, the reaction mixture was heated to 20° C. and stirred for 1 hour. Then the mixture was added to a solution A2 (20 g, 57.7 mmol, 1.0 eq) in THF (200 mL) and the reaction mixture was stirred at 20° C. for 2 h. The mixture was treated with NH₄Cl (100 mL, 10%) and extracted with EtOAc (2×100 mL). The organic phase was separated and concentrated in vacuum to afford product a crude residue. The residue was triturated from MeOH/H₂O (400 ml, 1/1) at 20° C. to give a crude residue. The crude residue was dissolved in DCM (200 mL), washed with saturated brine (2×50 mL), dried over anhydrous Na₂SO₄, filtered and concentrated to give A3 (19 g, 96%) as a solid.

¹H NMR (400 MHz, CDCl₃) δ 4.75 (s, 1H), 4.64 (s, 1H), 2.51-2.44 (m, 1H), 2.35-2.32 (m, 1H), 2.23-2.11 (m, 2H), 2.04 (s, 3H), 1.99-1.93 (m, 1H), 1.86-1.63 (m, 7H), 1.54-1.19 (m, 7H), 1.08-1.01 (m, 1H), 0.99 (s, 3H), 0.90 (s, 3H), 0.89-0.81 (m, 1H).

Step 3

To a solution of A3 (19 g, 55.1 mmol) in ethanol (100 mL) was added Pd—C(dry, 10%, 2 g) under N₂. The suspension was degassed under vacuum and purged with H₂ for three times. The mixture was stirred for 20 hrs at 15° C. under H₂. The reaction mixture was filtered and the filtrate was concentrated in vacuum to give A4 (18 g, 95%) as a solid.

¹H NMR (400 MHz, CDCl₃) δ 4.72-4.67 (m, 1H), 2.46-2.40 (m, 1H), 2.13-2.03 (m, 4H), 1.94-1.91 (m, 1H), 1.80-1.22 (m, 15H), 1.15-1.01 (m, 4H), 0.94-0.75 (m, 8H).

Step 4

To a solution of A4 (18 g, 51.9 mmol) in MeOH (200 mL) was added K₂CO₃ (28.6 g, 207 mmol) in one portion at 15° C. under N₂. The mixture was stirred at 15° C. for 2 h and quenched with water (100 mL). The aqueous phase was extracted with DCM (3×100 mL). The combined organic phase was washed with saturated brine (100 mL), dried over anhydrous Na₂SO₄, filtered and concentrated to afford A5 (15.2 g, 96%) as colourless oil.

¹H NMR (400 MHz, CDCl₃) δ 3.62-3.60 (m, 1H), 2.62-2.40 (m, 1H), 2.11-2.04 (m, 2H), 1.96-1.90 (m, 1H), 1.80-1.02 (m, 20H), 0.90-0.80 (m, 6H), 0.76-0.70 (m, 1H).

Step 5

To a solution of A5 (8 g, 26.2 mmol) in DCM (100 mL) was added silica gel (11.2 g) and PCC (11.2 g, 52.6 mmol) at 25° C. The reaction mixture was stirred at 25° C. for 1 h. The resulting mixture was filtered and the filtrate was concentrated in vacuum. To a solution of the crude product in DCM (20 mL) was added silica gel (20 g) and PE (100

Step 1

To a solution of A1 (100 g, 290 mmol) in THF (500 mL) was added Pd—C(wet, 10%, 10 g) under N₂. The suspension mL). After stirring at 25° C. for 30 mins, the mixture was and filtered and the filtrate was concentrated in vacuum to give A6 (7 g) as a solid.

¹H NMR (400 MHz, CDCl₃) δ 2.42-2.06 (m, 8H), 1.80-1.77 (m, 4H), 1.45-1.22 (m, 8H), 1.05-0.84 (m, 10H).

Step 6

A suspension of LiCl (2.05 g, 48.5 mmol, anhydrous) in THF (200 mL, anhydrous) was stirred at 10° C. for 30 mins under N₂. FeCl₃ (4.11 g, 25.4 mmol, anhydrous) was added at 10° C. After cooling to −30° C., MeMgBr (30.8 mL, 3M in diethyl ether) was added drop-wise at −30° C. After stirring at −30° C. for 10 mins, A6 (7 g, 23.1 mmol) was added at −30° C. The mixture was stirred at −15° C. for 2 hours and quenched with citric acid (200 mL, 10% aq.). The mixture was extracted with EtOAc (2×100 mL). The combined organic phase was washed with saturated brine (300 mL), dried over anhydrous Na₂SO₄, filtered and concentrated in vacuum to give a crude product, which was purified by a silica gel column (PE/EtOAc=0~10/1) to give A7 (1 g, 14%, Rf=0.45 in PE/EtOAc) and A8 (0.8 g, 11%, Rf=0.40 in PE/EtOAc) and a mixture (4 g) as solid.

A7

¹H NMR (400 MHz, CDCl₃) δ 2.48-2.41 (m, 1H), 2.13-2.08 (m, 1H), 1.97-1.90 (m, 1H), 1.84-1.67 (m, 4H), 1.55-1.47 (m, 5H), 1.41-1.25 (m, 5H), 1.23-1.01 (m, 8H), 0.97-0.94 (m, 3H), 0.86 (s, 3H), 0.79 (s, 3H).

The stereochemistry at C7 of A7 was confirmed by NOE.

A8

¹H NMR (400 MHz, CDCl₃) δ 2.48-2.38 (m, 1H), 2.12-2.07 (m, 1H), 1.79-1.73 (m, 2H), 1.56-1.49 (m, 4H), 1.46-1.38 (m, 2H), 1.32-1.19 (m, 12H), 1.03-0.97 (m, 4H), 0.87 (s, 3H), 0.86-0.76 (m, 2H), 0.73 (s, 3H).

The stereochemistry at C7 of A8 was confirmed by NOE.

Step 7a (Compound 1)

Into a over-dried bottom was added t-BuOH (2 mL) and t-BuOK (703 mg, 6.27 mmol). After evaporating and filling with N₂, a solution of A7 (200 mg, 0.627 mmol) in DME (1 mL) was added. After 30 min, a solution of TosMic (243 mg, 1.25 mmol) in DME (1 mL) was added. The mixture became yellow. The resulting mixture was stirred at 25° C. for 16 h and quenched with water. The mixture was extracted with ethyl acetate (3×30 mL). The combined organic layer was washed with brine. The combined organic layer was dried over anhydrous Na₂SO₄ and concentrated. The residue was purified by flash chromatography eluting with (petroleum ether/ethyl acetate=10/1) to give Compound 1 (50 mg, 24%) as a solid.

¹H NMR (400 MHz, CDCl₃) δ2.30-2.24 (m, 1H), 2.16-2.06 (m, 1H), 1.97-1.87 (m, 2H), 1.83-1.71 (m, 3H), 1.67-1.58 (m, 1H), 1.54-1.42 (m, 5H), 1.39-1.24 (m, 4H), 1.20-1.01 (m, 9H), 0.93-0.88 (m, 6H), 0.77 (s, 3H).

LCMS Rt=1.918 min in 3.0 min chromatography, 10-80 AB_3MIN_E.M, purity 100%, MS ESI calcd. for C₂₂H₃₄N [M+H−H₂O]⁺ 312, found 312.

Step 7b (Compound 2)

In an oven-dried round bottom flask was added t-BuOH (2 mL) and t-BuOK (703 mg, 6.27 mmol). The reaction vessel was evaporated and filled with N₂. A8 (200 mg, 0.627 mmol) in DME (1 mL) was added into the suspension. After 30 min, TosMIC (243 mg, 1.25 mmol) in DME (1 mL) was added. The mixture became yellow. The resulting mixture was stirred at 25° C. for 16 h. Water was added and the mixture was stirred. Then it was extracted with ethyl acetate (3×30 mL). The combined organic layer was washed with brine. The combined organic layer was dried over anhydrous Na₂SO₄ and concentrated. The residue was purified by flash chromatography eluting with (petroleum ether:ethyl acetate=4:1) to give Compound 2 (13 mg, 6%) as a solid.

¹H NMR (400 MHz, CDCl₃) δ 2.26-2.17 (m, 1H), 2.14-2.00 (m, 1H), 1.99-1.85 (m, 3H), 1.73-1.67 (m, 1H), 1.56-1.44 (m, 5H), 1.30-1.24 (m, 4H), 1.20 (s, 3H), 1.17-1.09 (m, 4H), 1.04-0.88 (m, 8H), 0.85-0.76 (m, 2H), 0.72 (s, 3H).

LCMS Rt=1.939 min in 3.0 min chromatography, 10-80 AB_3MIN_E.M, purity 100%, MS ESI calcd. for C₂₂H₃₄NO [M+H−H₂O]⁺ 312, found 312.

Example 2. Syntheses of Compounds 3 and 4

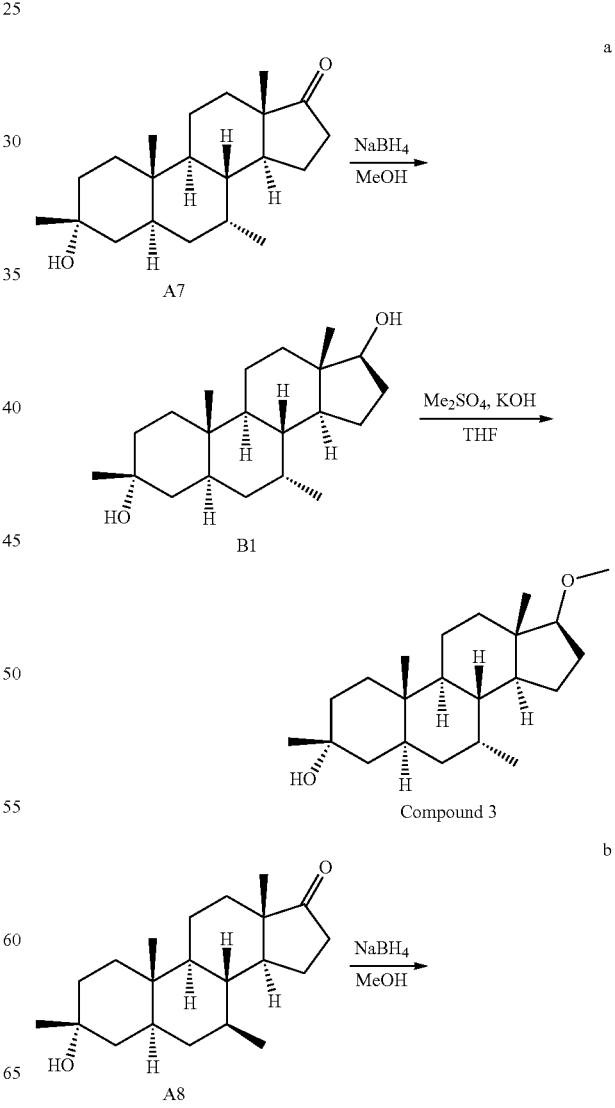

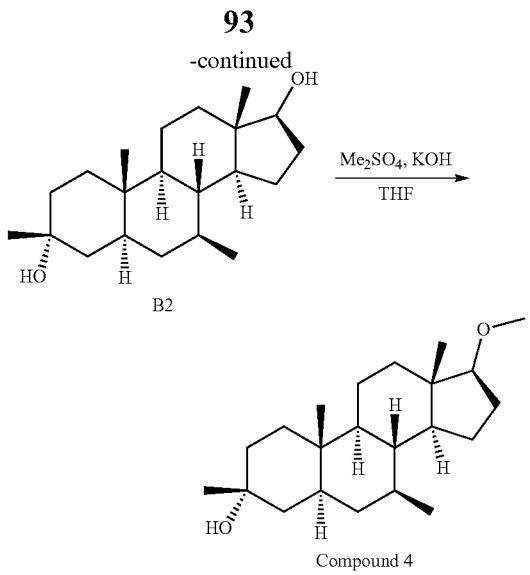

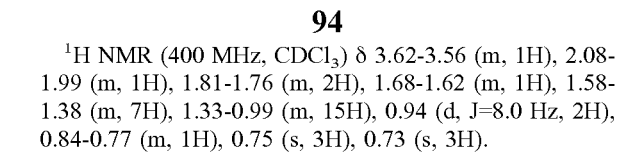

Step 1a (B1)

To a solution of A7 (200 mg, 0.627 mmol) in MeOH (5 mL) was added NaBH$_4$ (47.2 mg, 1.25 mmol) at 25° C. After stirring at 25° C. for 30 mins, the reaction was quenched by adding water (10 mL) and extracted with DCM (2×20 mL). The combined organic layers were dried over Na$_2$SO$_4$, filtered and concentrated in vacuum to give B1 (180 mg, crude) as a solid, which was directly used for next step without further purification.

$^1$H NMR (400 MHz, CDCl$_3$) δ 3.67-3.62 (m, 1H), 2.11-2.02 (m, 1H), 1.82-1.75 (m, 3H), 1.63-1.37 (m, 11H), 1.34-1.20 (m, 8H), 1.14-1.01 (m, 4H), 0.90 (d, J=4.0 Hz, 2H), 0.78 (s, 3H), 0.74 (s, 3H).

Step 2a (Compound 3)

To a solution of B1 (180 mg, 0.561 mmol) in THF (5 mL) was added KOH (94.2 mg, 1.68 mmol) and Me$_2$SO$_4$ (0.282 mg, 0.211 mL, 2.24 mmol) at 0° C. Then the mixture was warmed to 25° C. and stirred at the same temperature for 16 h. The mixture was quenched with 50 mL of water and extracted with EtOAc (2×30 mL). The combined organic layer was dried over Na$_2$SO$_4$, filtered and concentrated in vacuum to give crude product which was purified by a silica gel column (PE/EtOAc=0-10/1) to give Compound 3 (21 mg, 11%) as a solid.

$^1$H NMR (400 MHz, CDCl$_3$) δ 3.34 (s, 3H), 3.22 (t, J=8.0 Hz, 1H), 2.04-1.96 (m, 1H), 1.88-1.71 (m, 3H), 1.63-1.56 (m, 2H), 1.54-1.34 (m, 7H), 1.32-1.17 (m, 8H), 1.16-0.97 (m, 5H), 0.90 (d, J=4.0 Hz, 2H), 0.76 (s, 3H), 0.74 (s, 3H).

LCMS Rt=2.050 min in 3.0 min chromatography, 10-80 AB_3MIN_E.M, purity 100%, MS ESI calcd. for C$_{22}$H$_{37}$O [M+H−H$_2$O]$^+$ 317, found 317.

Step 1b (B2)

To a solution of A8 (200 mg, 0.627 mmol) in MeOH (5 mL) was added NaBH$_4$ (47.2 mg, 1.25 mmol) at 25° C. After stirring at 25° C. for 30 mins, the reaction was quenched by adding water (10 mL) and extracted with DCM (2×20 mL). The combined organic layers were dried over Na$_2$SO$_4$, filtered and concentrated in vacuum to give B2 (170 mg, crude) as a solid, which was directly used for next step without further purification.

$^1$H NMR (400 MHz, CDCl$_3$) δ 3.62-3.56 (m, 1H), 2.08-1.99 (m, 1H), 1.81-1.76 (m, 2H), 1.68-1.62 (m, 1H), 1.58-1.38 (m, 7H), 1.33-0.99 (m, 15H), 0.94 (d, J=8.0 Hz, 2H), 0.84-0.77 (m, 1H), 0.75 (s, 3H), 0.73 (s, 3H).

Step 2b (Compound 4)

To a solution of B2 (170 mg, 0.530 mmol) in THF (5 mL) was added KOH (88.6 mg, 1.58 mmol) and Me$_2$SO$_4$ (0.266 mg, 0.2 mL, 2.11 mmol) at 0° C. Then the mixture was warmed to 25° C. and stirred at the same temperature for 16 h. The mixture was quenched with the addition of 50 mL of water and extracted with EtOAc (2×30 mL). The combined organic layer was dried over Na$_2$SO$_4$, filtered and concentrated in vacuum to give a crude product, which was purified by a silica gel column (PE/EtOAc=0-10/1) to give Compound 4 (21 mg, 11%) as a solid. $^1$H NMR (400 MHz, CDCl$_3$) δ 3.34 (s, 3H), 3.16 (t, J=8.0 Hz, 1H), 2.02-1.93 (m, 1H), 1.88 (dt, J=4.0, 12.0 Hz, 1H), 1.77-1.74 (m, 1H), 1.64-1.39 (m, 9H), 1.33-1.08 (m, 12H), 1.03-0.96 (m, 1H), 0.93 (d, J=8.0 Hz, 2H), 0.80-0.74 (m, 1H), 0.75 (s, 3H), 0.71 (s, 3H).

LCMS Rt=2.079 min in 3.0 min chromatography, 10-80 AB_3MIN_E.M, purity 100%, MS ESI calcd. for C$_{22}$H$_{37}$O [M+H−H$_2$O]$^+$ 317, found 317.

Example 3. Syntheses of Compounds 5 and 6

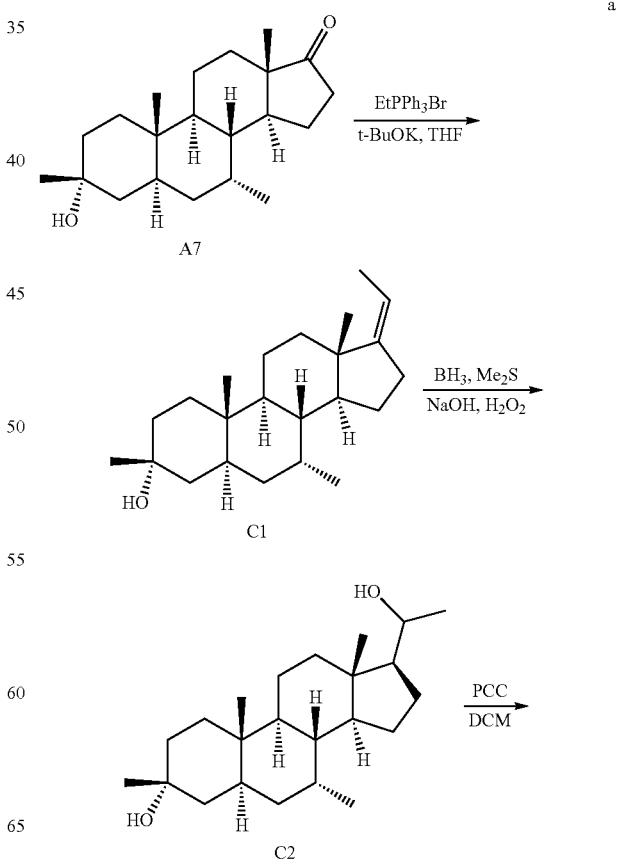

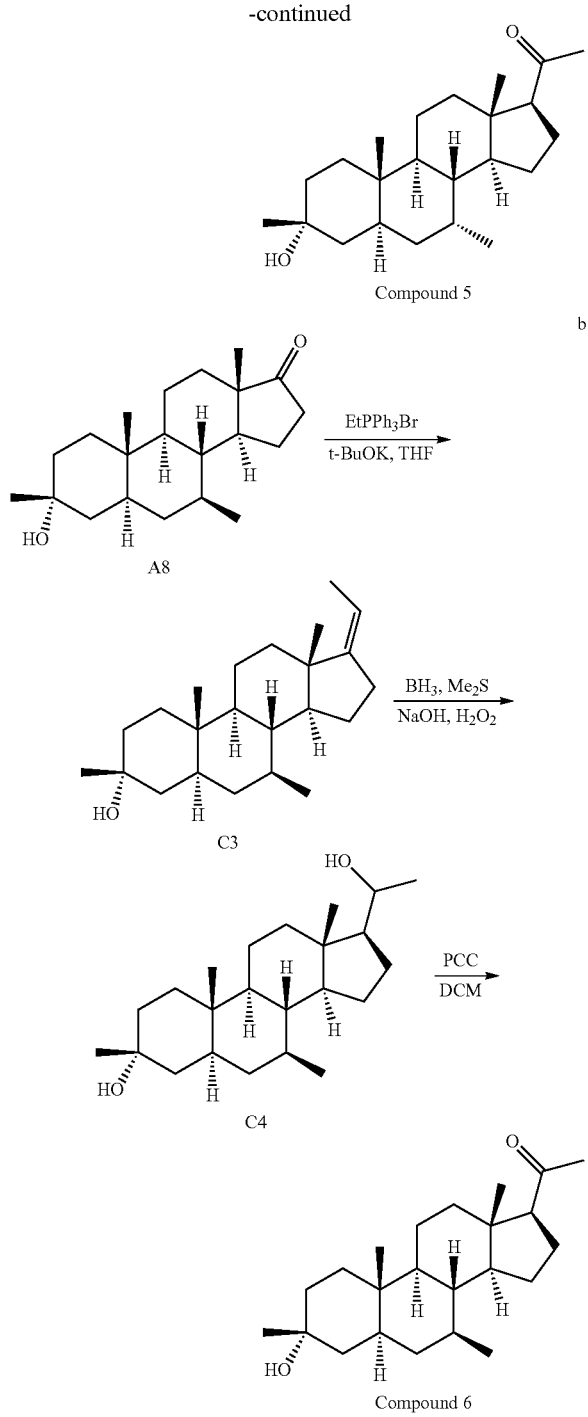

brine (2×20 mL), dried over anhydrous Na$_2$SO$_4$, filtered concentrated and purified by flash column (0~10% of EtOAc in PE) to give C1 (350 mg, 62%) as a solid.

$^1$H NMR (400 MHz, CDCl$_3$) δ 5.14-5.08 (m, 1H), 2.41-2.32 (m, 1H), 2.26-2.12 (m, 2H), 1.87-1.70 (m, 2H), 1.67-1.44 (m, 10H), 1.40-1.08 (m, 11H), 1.07-1.03 (m, 1H), 1.05-0.99 (m, 1H), 0.91 (d, J=6.8 Hz, 3H), 0.86 (s, 3H), 0.77 (s, 3H).

Step 2

To a solution of C1 (200 mg, 0.605 mmol) in THF (3 mL) was added drop-wise a solution of BH$_3$-Me$_2$S (0.605 mL, 6.05 mmol) at 0° C. The solution was stirred at 15° C. for 3 h. After cooling to 0° C., a solution of NaOH solution (3.62 mL, 2 M) was added very slowly. After addition, H$_2$O$_2$ (683 mg, 6.05 mmol, 30% in water) was added slowly and the inner temperature was maintained below 10° C. After stirring at 15° C. for 2 h, the saturated aqueous Na$_2$S$_2$O$_3$ (50 mL) was added until the reaction solution became clear. The mixture was extracted with EtOAc (3×50 mL). The combined organic solution was washed with saturated aqueous Na$_2$S$_2$O$_3$ (2×20 mL), brine (20 mL), dried over Na$_2$SO$_4$ and concentrated in vacuum to give the crude product (180 mg) as a solid, which was used in next step without further purification.

$^1$H NMR (400 MHz, CDCl$_3$) δ 3.77-3.66 (m, 1H), 1.82-1.71 (m, 3H), 1.54-1.42 (m, 8H), 1.32-1.06 (m, 19H), 0.91 (d, J=8.0 Hz, 3H), 0.75 (s, 3H), 0.65 (s, 3H).

Step 3

To a solution of C3 (180 mg, 0.516 mmol) in DCM (5 mL) was added silica gel (222 mg) and PCC (222 mg, 1.03 mmol) at 25° C. The reaction mixture was stirred at 25° C. for 1 h. The resulting mixture was filtered and the filtrate concentrated in vacuum. To a solution of the crude product in DCM (20 mL) was added silica gel (20 g) and PE (100 mL). The mixture was stirred at 25° C. for 30 mins and filtered and the filtrate was concentrated in vacuum to give crude product, which was purified by flash column (0-10% of EtOAc in PE) to give Compound 5 (29 mg, 16%) as a solid.

$^1$H NMR (400 MHz, CDCl$_3$) δ 2.53 (t, J=8.0 Hz, 1H), 2.20-2.14 (m, 1H), 2.11 (s, 3H), 2.01-1.94 (m, 1H), 1.83-1.73 (m, 2H), 1.70-1.59 (m, 3H), 1.55-1.43 (m, 5H), 1.39-1.12 (m, 12H), 1.04-1.01 (m, 1H), 0.92 (d, J=8.0 Hz, 3H), 0.76 (s, 3H), 0.60 (s, 3H).

LCMS Rt=2.150 min in 3.0 min chromatography, 10-80 AB_3MIN_E.M, purity 100%, MS ESI calcd. for C$_{23}$H$_{37}$O [M+H–H$_2$O]$^+$ 329, found 329.

Step 4

To a suspension of PPh$_3$EtBr (1.21 g, 3.27 mmol) in THF (10 mL) was added t-BuOK (0.366 g, 3.27 mmol) at 10° C. The color of the suspension turned dark red. After stirring at 40° C. for 30 min, a solution of A8 (0.35 g, 1.09 mmol) in THF (2 mL) was added at 40° C. and the reaction mixture was stirred at 40° C. for 1 h. The reaction mixture was poured into 20 g of crushed ice and stirred for 15 minutes. The organic layer was separated and the water phase was extracted with EtOAc (2×20 mL). The combined organic phase was washed with saturated brine (2×20 mL), dried over anhydrous Na$_2$SO$_4$, filtered concentrated and purified by flash column (0~10% of EtOAc in PE) to give C3 (140 mg, 39%) as a solid.

Step 1

To a suspension of PPh$_3$EtBr (1.91 g, 5.15 mmol) in THF (10 mL) was added t-BuOK (0.577 g, 5.15 mmol) at 10° C. The color of the suspension turned dark red. After stirring at 40° C. for 30 min, a solution of A7 (0.55 g, 1.72 mmol) in THF (2 mL) was added at 40° C. After stirring at 40° C. for 1 h, the reaction mixture was poured into 20 g of crushed ice and stirred for 15 minutes. The organic layer was separated and the water phase was extracted with EtOAc (2×20 mL). The combined organic phase was washed with saturated ¹H NMR (400 MHz, CDCl₃) δ 5.15-5.12 (m, 1H), 2.31-2.22 (m, 3H), 1.81-1.73 (m, 1H), 1.70-1.61 (m, 4H), 1.56-1.40 (m, 7H), 1.34-1.18 (m, 12H), 0.95 (d, J=4.0 Hz, 3H), 0.89 (s, 3H), 0.87-0.79 (m, 1H), 0.72 (s, 3H).

Step 5

To a solution of C3 (120 mg, 0.363 mmol) in THF (3 mL) was added drop-wise a solution of BH₃-Me₂S (0.363 mL, 3.63 mmol) at 0° C. The solution was stirred at 15° C. for 3 h.

After cooling to 0° C., a solution of NaOH solution (2.17 mL, 2M) was added very slowly. After addition, H₂O₂ (410 mg, 3.63 mmol, 30% in water) was added slowly and the inner temperature was maintained below 10° C. The resulting solution was stirred at 15° C. for 2 h. Then saturated aqueous Na₂S₂O₃ (50 mL) was added until the reaction solution became clear. The mixture was extracted with EtOAc (3×50 mL). The combined organic solution was washed with saturated aqueous Na₂S₂O₃ (2×20 mL), brine (20 mL), dried over Na₂SO₄ and concentrated in vacuum to give the crude product (100 mg) as a solid, which was used in next step without further purification.

¹H NMR (400 MHz, CDCl₃) δ 3.76-3.64 (m, 1H), 1.86-1.79 (m, 3H), 1.54-1.39 (m, 8H), 1.28-1.17 (m, 17H), 0.95 (d, J=6.0 Hz, 3H), 0.82-0.74 (m, 2H), 0.71 (s, 3H), 0.67 (s, 3H).

Step 6

To a solution of C4 (100 mg, 0.286 mmol) in DCM (5 mL) was added silica gel (123 mg) and PCC (123 mg, 0.572 mmol) at 25° C. The reaction mixture was stirred at 25° C. for 1 h. The resulting mixture was filtered and the filtrate concentrated by vacuum. To a solution of the crude product in DCM (20 mL) was added silica gel (20 g) and PE (100 mL). The mixture was stirred at 25° C. for 30 mins and filtered and the filtrate was concentrated in vacuum to give crude product. The crude product was purified by flash column (0-10% of EtOAc in PE) to give Compound 6 (13 mg, 13%) as a solid. ¹H NMR (400 MHz, CDCl₃) δ 2.48 (t, J=9.2 Hz, 1H), 2.16-2.09 (m, 4H), 2.01-1.95 (m, 1H), 1.86-1.82 (m, 1H), 1.73-1.59 (m, 2H), 1.54-1.42 (m, 5H), 1.40-1.14 (m, 13H), 1.05-0.96 (m, 1H), 0.95 (d, J=6.0 Hz, 3H), 0.88-0.80 (m, 1H), 0.71 (s, 3H), 0.62 (s, 3H)

LCMS Rt=2.184 min in 3.0 min chromatography, 10-80 AB_3MIN_E.M, purity 100%, MS ESI calcd. for C₂₃H₃₇O [M+H−H₂O]⁺ 329, found 329.

Example 4. Syntheses of Compounds 7, 8, 9, and 10

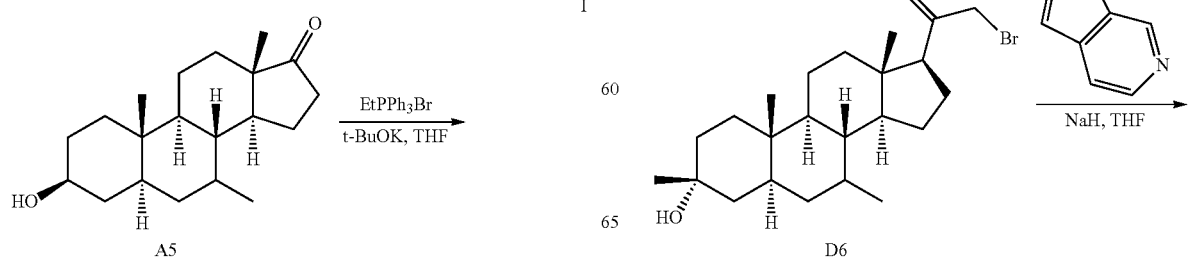

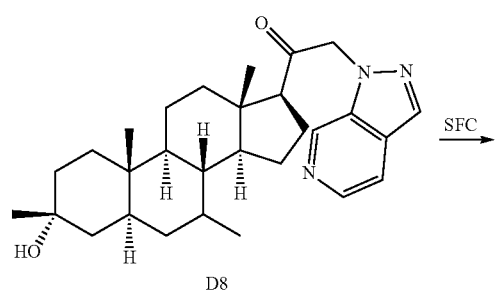

D8

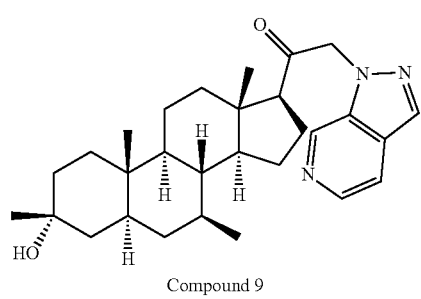

Compound 9

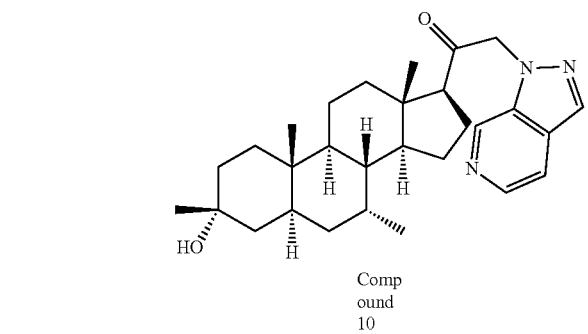

Compound 10

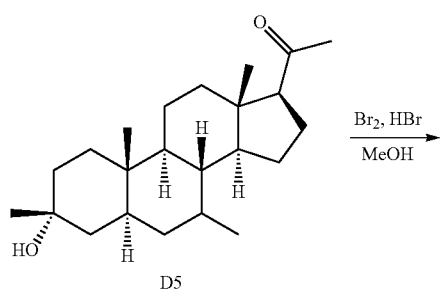

D5

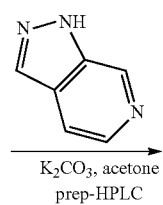

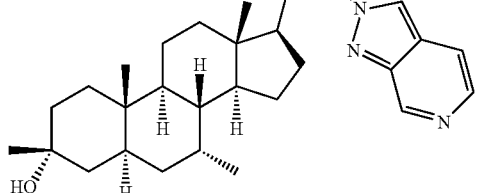

Compound 7

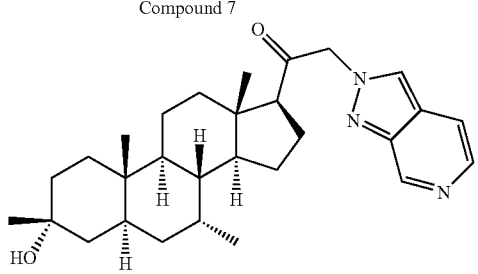

Compound 8

Example 13. Syntheses of Compounds 7 and 8

Part I

Step 1

To a suspension of PPh$_3$EtBr (72.7 g, 196 mmol) in THF (200 mL) was added t-BuOK (21.9 g, 196 mmol) at 10° C. The color of the suspension was turned to dark red. After stirring at 40° C. for 30 min, a solution of A5 (20 g, 65.6 mmol) in THF (20 mL) was added at 40° C. and the reaction mixture was stirred at 40° C. for 1 h. The reaction mixture was poured into 200 g of crashed ice and stirred for 15 minutes. The organic layer was separated and the water phase was extracted with EtOAc (2×200 mL). The combined organic phase was washed with saturated brine (2×200 mL), dried over anhydrous Na$_2$SO$_4$, filtered concentrated and purified by flash column (0~30% of EtOAc in PE) to give D1 (19.5 g, 94%) as a solid.

$^1$H NMR (400 MHz, CDCl$_3$) δ 5.20-5.01 (m, 1H), 3.70-3.50 (m, 1H), 2.48-2.15 (m, 3H), 1.89-1.52 (m, 8H), 1.52-1.09 (m, 7H), 1.09-0.93 (m, 5H), 0.93-0.70 (m, 11H).

Step 2

To a solution of D1 (10 g, 31.5 mmol) in anhydrous DCM (100 mL) was added silica gel (10 g) and PCC (13.5 g, 63.0 mmol). The mixture was stirred at 15° C. for 2 hours. The reaction mixture was filtered, and the filtrate was concentrated. The residue was purified by flash column (0~30% of EtOAc in PE) to give D2 (6.6 g, 67%) as a solid.

$^1$H NMR (400 MHz, CDCl$_3$) δ 5.20-50.8 (m, 1H), 2.49-2.15 (m, 6H), 2.15-1.95 (m, 2H), 1.95-1.72 (m, 2H), 1.72-1.19 (m, 10H), 1.19-0.95 (m, 7H), 0.95-0.75 (m, 6H).

Step 3

Under nitrogen atmosphere, anhydrous THF (100 mL) was cooled to 10° C. and anhydrous LiCl (3.54 g, 83.6 mmol) was added in one portion. The mixture was stirred for 30 min to obtain a clear solution. To this solution was added anhydrous FeCl$_3$ (7.44 g, 45.9 mmol) in one portion. The resulting mixture was stirred for additional 30 mins. The reaction mixture was cooled to −35° C. and methyl magnesium bromide (3 M in diethyl ether, 55.6 mL, 167 mmol) was added dropwise maintaining the internal temperature between −35° C. and −30° C. The above mixture was stirred for 30 min at −30° C. A solution of D2 (6.6 g, 20.9 mmol) in THF (20 mL) was added in one portion. The internal temperature was allowed to −20° C. and held between −15° C. and −20° C. for 2 hrs. The reaction mixture was poured into ice-cooled aqueous HCl (1 M, 200 mL), extracted with EtOAc (2×200 mL). The combined organic layer was washed with water (200 mL), aqueous NaOH (10%, 2×200 mL) and brine (200 mL), dried over anhydrous sodium sulfate, filtered and concentrated. The residue was purified by column chromatography on silica gel (PE/EtOAc=20/1 to 20/1) to give D3 (6.5 g, 94%) as a colorless oil.

$^1$H NMR (400 MHz, CDCl$_3$) δ 5.15-5.05 (m, 1H), 2.42-2.11 (m, 3H), 1.90-1.40 (m, 16H), 1.40-1.10 (m, 5H), 1.10-0.81 (m, 10H), 0.81-0.69 (m, 3H).

Step 4

To a solution of D3 (6 g, 18.1 mmol) in THF (85 mL) was added 9-BBN dimer (13.2 g, 54.3 mmol). The mixture was stirred at 50° C. for 2 hrs. After cooling to 0° C., to the reaction mixture was added ethanol (10.3 mL, 181 mmol) and NaOH (36.1 mL, 5 M, 181 mmol) very slowly. After addition, H$_2$O$_2$ (18.1 mL, 181 mmol, 30%) was added slowly and the inner temperature was maintained below 15° C. The resulting solution was stirred at 75° C. for 1 hrs. The mixture was cooled and added to water (100 mL). The aqueous phase was extracted with EtOAc (3×100 mL). The combined organic phase was washed with saturated brine (100 mL), dried over anhydrous Na$_2$SO$_4$, filtered and concentrated to give D4 (5.9 g, crude) as colourless oil which was used directly for the next step without purification.

Step 5

To a suspension of D4 (5.9 g, 16.9 mmol) in DCM (100 mL) was added silica gel (3 g) and PCC (5.45 g, 25.3 mmol) at 15° C. The mixture was stirred at 15° C. for 2 hrs. The mixture was filtered and the filtrated cake was washed with DCM (50 mL). The combined filtrate was concentrated in vacuum and purified by flash column (0~30% of EtOAc in PE) to afford D5 (4.3 g, impure) as a solid.

Step 6

To a solution of D5 (500 mg, 1.44 mmol) in MeOH (10 ml) was added HBr (57.4 mg, 0.29 mmol, 40% in water) and Br$_2$ (337 mg, 2.15 mmol) at 25° C. The mixture was stirred at 25° C. for 2 hrs. The mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford D6 (480 mg, crude) as light yellow oil, which was used directly for the next step.

$^1$H NMR (400 MHz, CDCl$_3$) δ 3.97-3.86 (m, 2H), 2.86-2.71 (m, 1H), 2.24-1.96 (m, 2H), 1.93-1.68 (m, 6H), 1.54-1.43 (m, 5H), 1.35-1.23 (m, 5H), 1.21-1.15 (m, 5H), 0.96-0.79 (m, 4H), 0.77-0.58 (m, 7H).

Step 7

To a solution of 1H-pyrazolo[3,4-c]pyridine (139 mg, 1.17 mmol) in THF (10 mL) was added NaH (89.5 g, 2.24 mmol, 60%) in portions at 25° C. The mixture was stirred at 60° C. for 10 min. Then D6 (480 mg, 1.12 mmol) in THF (10 mL) was added drop-wise to the solution. The mixture was stirred at 60° C. for 1 h. The mixture was poured into water (50 mL) and extracted with EtOAc (3×20 mL). The combined organic layer was washed with brine (50 mL), dried over with Na$_2$SO$_4$ and concentrated to afford crude product. The residue was purified by silica gel chromatography (100-200 mesh silica gel, Petroleum ether/Ethyl acetate=0/1) to afford the mixture of D7 and D8 (290 mg, crude) as a solid.

Step 8 (Compounds 9 and 10)

D8 (290 mg, 0.62 mmol) was purified by SFC (column: OD (250 mm*30 mm, 10 um)), gradient: 40-40% B (A=0.1% NH$_3$/H$_2$O, B=EtOH), flow rate: 80 mL/min) to give pure Compound 9 (48 mg, 16%) and pure Compound 10 (18 mg, 6%) as a solid.

Compound 9

$^1$H NMR (400 MHz, CDCl$_3$) δ 8.8 (s, 1H), 8.39-8.29 (m, 1H), 8.1 (s, 1H), 7.68-7.61 (d, J=4.8 Hz, 1H), 5.32-5.19 (m, 2H), 2.76-2.62 (m, 1H), 2.27-2.06 (m, 2H), 1.84-1.67 (m, 4H), 1.53-1.26 (m, 11H), 1.23-1.09 (m, 7H), 1.08-1.01 (m, 1H), 0.96-0.89 (d, J=7.2 Hz, 3H), 0.77 (s, 3H), 0.71 (s, 3H).
LCMS Rt=0.885 min in 2 min chromatography, 30-90AB_2MIN_E, purity 100%, MS ESI calcd. for C$_{29}$H$_{42}$N$_3$O$_2$ [M+H]$^+$ 464, found 464.
SFC Rt=1.785 min in 3 min chromatography, OD-H_3UM_3_5_40_4ML_3MIN, purity: 100%.

Compound 10

$^1$H NMR (400 MHz, CDCl$_3$) δ 8.80 (s, 1H), 8.39-8.28 (m, 1H), 8.09 (s, 1H), 7.69-7.61 (d, J=4.8 Hz, 1H), 5.34-5.17 (m, 2H), 2.68-2.57 (m, 1H), 2.24-2.09 (m, 2H), 1.96-1.71 (m, 4H), 1.47-1.13 (m, 15H), 1.07-0.81 (m, 7H), 0.73 (s, 6H).
LCMS Rt=0.908 min in 2 min chromatography, 30-90AB_2MIN_E, purity 98%, MS ESI calcd. for C$_{29}$H$_{42}$N$_3$O$_2$ [M+H]$^+$ 464, found 464.
SFC Rt=2.132 min in 3 min chromatography, OD-H_3UM_3_5_40_4ML_3MIN, purity: 99%.

Part II

Step 1

To a solution of D5 (500 mg, 1.44 mmol) in MeOH (10 ml) was added HBr (57.4 mg, 0.288 mmol, 40% in water) and Br$_2$ (229 mg, 1.46 mmol) at 25° C. The mixture was stirred at 25° C. for 16 hrs. The mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford D6 (500 mg, crude) as a solid used directly for the next step.

Step 2 (Compounds 7 and 8)

To a mixture of D6 (500 mg, 1.17 mmol) and K$_2$CO$_3$ (323 mg, 2.34 mmol) in acetone (3 mL) was added 1H-pyrazolo[3,4-c]pyridine (1.45 mg, 1.22 mmol) at 25° C. The mixture was stirred at 25° C. for 12 h. The mixture was poured into water (50 mL) and extracted with EtOAc (3×20 mL). The combined organic layer was washed with brine (50 mL), dried over with Na$_2$SO$_4$, filtered and concentrated to afford crude product, which was purified by prep-HPLC separation (column: Phenomenex Synergi C18 150*30 mm*4 um)), gradient: 28-58% B (A=0.1% HCl, B=ACN), flow rate: 30 mL/min) and then SFC (column: OJ (250 mm*30 mm, 10 um)), gradient: 35-35% B (A=0.1% NH$_3$H$_2$O, B=ETOH), flow rate: 80 mL/min) to afford Compound 8 (15 mg, yield 75%) as a solid and Compound 7 (5 mg, yield 25%) as a solid.

Compound 7

$^1$H NMR (400 MHz, CDCl$_3$) δ 9.26 (s, 1H), 8.27-8.17 (m, 1H), 7.98 (s, 1H), 7.58-7.49 (m, 1H), 5.32 (d, J=16.0 Hz, 1H), 5.22 (d, J=16.0 Hz, 1H), 2.62 (t, J=8.0 Hz, 1H), 2.24-2.09 (m, 2H), 1.97-1.89 (m, 1H), 1.81-1.72 (m, 2H), 1.52-1.42 (m, 4H), 1.37-1.13 (m, 14H), 1.05-0.98 (m, 1H), 0.96 (d, J=8.0 Hz, 3H), 0.90-0.82 (m, 1H), 0.74-0.71 (m, 6H).

LCMS Rt=2.406 in in 4.0 min chromatography, 10-80AB·1 cm, purity 99.3%, MS ESI calcd. for C$_{29}$H$_{42}$N$_3$O$_2$ [M+H]$^+$ 464, found 464.

Compound 8

$^1$H NMR (400 MHz, CDCl$_3$) δ 9.26 (s, 1H), 8.17 (d, J=8.0 Hz, 1H), 7.98 (s, 1H), 7.52 (dd, J=1.0, 8.0 Hz, 1H), 5.32 (d, J=16.0 Hz, 1H), 5.22 (d, J=16.0 Hz, 1H), 2.67 (t, J=8.0 Hz, 1H), 2.28-2.18 (m, 1H), 2.11-2.08 (m, 1H), 1.85-1.67 (m, 5H), 1.65-1.36 (m, 10H), 1.27-1.12 (m, 7H), 1.04 (br d, J=13.3 Hz, 1H), 0.93 (d, J=8.0 Hz, 3H), 0.77 (s, 3H), 0.71 (s, 3H).

LCMS Rt=2.358 in in 4.0 min chromatography, 10-80AB·1 cm, purity 99.7%, MS ESI calcd. for C$_{29}$H$_{42}$N$_3$O$_2$ [M+H]$^+$ 464, found 464.

Example 5. Synthesis of Compound 11

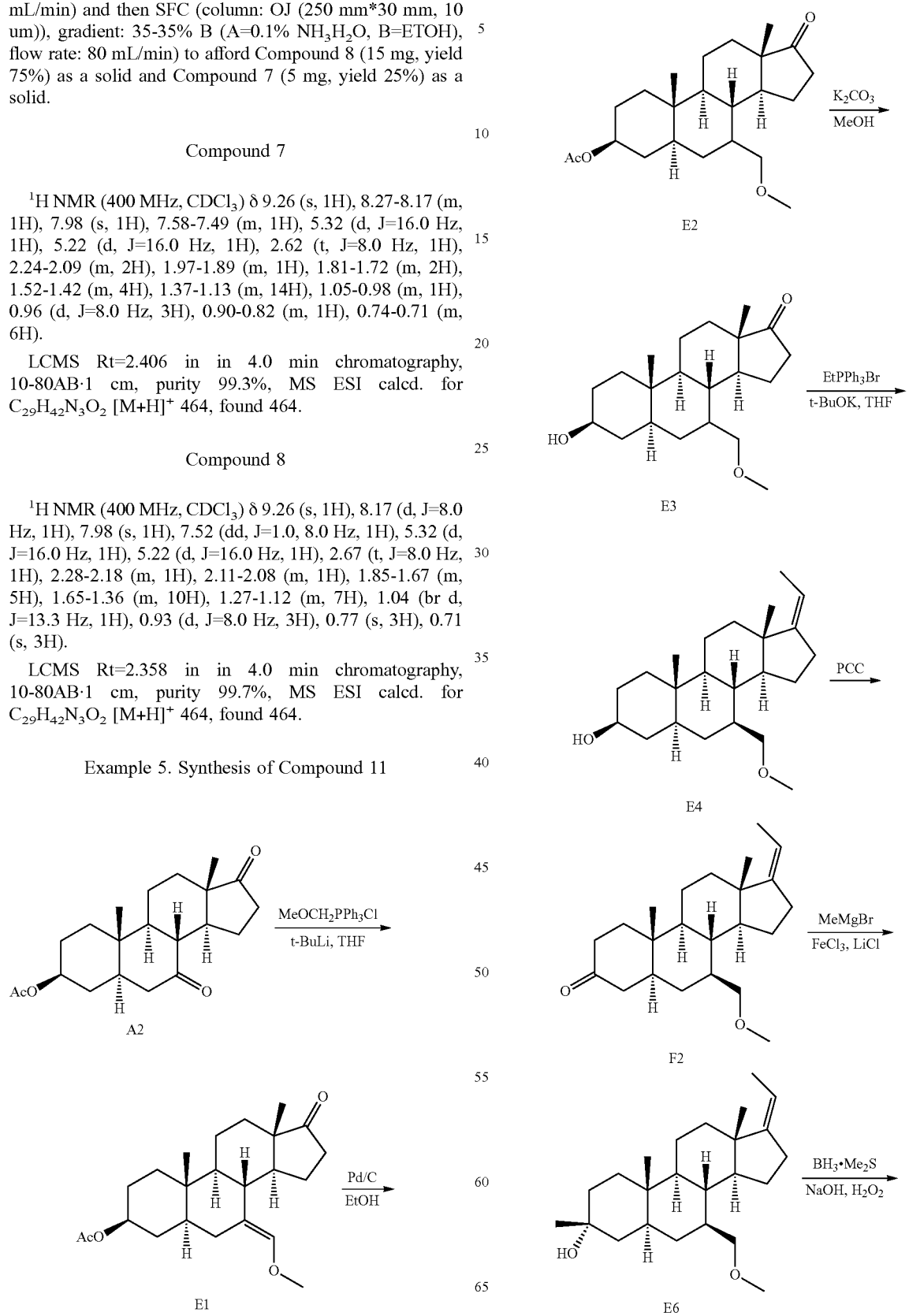

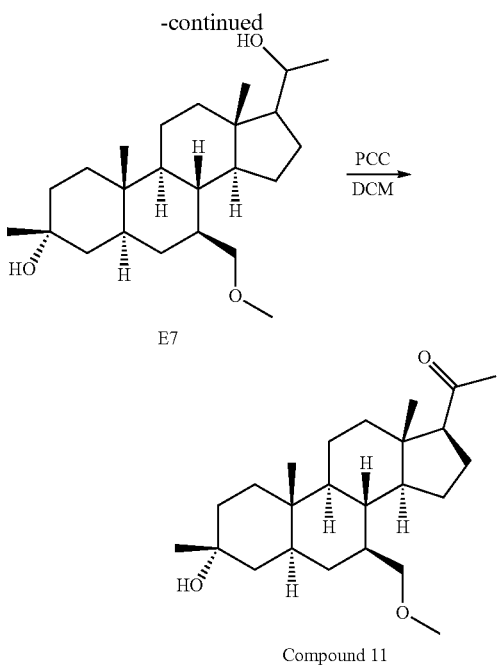

E7

Compound 11

Step 1

To a solution of chloro(methoxymethyl)triphenylphosphorane (19.7 g, 57.7 mmol) in THF (200 mL) was added t-BuLi (44.3 mL, 57.7 mmol, 1.3 M in n-hexane) at −10° C., after addition, the reaction mixture was stirred for 1 hour. Then the mixture was added to A2 (20 g, 57.7 mmol) in THF (200 mL) at 0° C. and the reaction mixture was stirred at 15° C. for 2 h. The mixture was treated with NH$_4$Cl (100 mL, 10%), EtOAc (2×200 mL) was added. The organic phase was separated, concentrated in vacuum to afford crude product. The residue was purified by flash column (0~30% of EtOAc in PE) to give E1 (5 g, 23%) as a solid.

$^1$H NMR (400 MHz, CDCl$_3$) δ 5.77 (s, 1H), 4.75-4.60 (m, 1H), 3.56 (s, 3H), 2.60-2.42 (m, 2H), 2.31-1.98 (m, 8H), 1.80-1.38 (m, 6H), 1.38-1.19 (m, 4H), 1.19-0.80 (m, 9H).

Step 2

To a solution of E1 (5 g, 13.3 mmol) in MeOH (50 mL) was added Pd—C(dry, 10%, 1 g) under N$_2$. The suspension was degassed under vacuum and purged with H$_2$ for three times. The mixture was stirred under H$_2$ (15 psi) at 15° C. for 16 hours to give a black suspension. The reaction mixture was filtered through a pad of Celite and washed with EtOH (3×20 mL). The filtrate was concentrated to E2 (3.8 g, 76%) as a solid.

$^1$H NMR (400 MHz, CDCl$_3$) δ 4.78-4.60 (m, 1H), 3.42-3.35 (m, 1H), 3.35-3.28 (m, 4H), 2.50-2.38 (m, 1H), 2.20-1.95 (m, 5H), 1.85-1.60 (m, 7H), 1.60-1.18 (m, 8H), 1.18-0.91 (m, 2H), 0.91-0.76 (m, 7H).

Step 3

To a solution of E2 (3.8 g, 10.0 mmol) in MeOH (50 mL) was added K$_2$CO$_3$ (5.52 g, 40.0 mmol) in one portion at 15° C. under N$_2$. The mixture was stirred at 15° C. for 2 h. Water (20 mL) was added. The aqueous phase was extracted with DCM (3×20 mL). The combined organic phase was washed with saturated brine (2×20 mL), dried over anhydrous Na$_2$SO$_4$, filtered and concentrated to afford E3 (3 g, 90%) as a solid.

$^1$H NMR (400 MHz, CDCl$_3$) δ 3.68-3.51 (m, 1H), 3.51-3.39 (m, 1H), 3.35-3.28 (m, 4H), 2.50-2.38 (m, 1H), 2.20-2.01 (m, 2H), 1.85-1.70 (m, 5H), 1.70-1.46 (m, 5H), 1.46-1.12 (m, 7H), 1.12-0.91 (m, 1H), 0.91-0.70 (m, 7H).

Step 4

To a suspension of PPh$_3$EtBr (11.5 g, 31.2 mmol) in THF (50 mL) was added t-BuOK (3.5 g, 31.2 mmol) at 10° C. The color of the suspension turned dark red. After stirring at 40° C. for 1 hour, a solution of E3 (3.5 g, 10.4 mmol) in THF (20 mL) was added at 40° C. and the reaction mixture was stirred at 40° C. for 16 h. The mixture was added saturated NH$_4$Cl solution (20 mL) and extracted with EtOAc (2×20 mL). The organic layer was separated and the water phase was extracted with EtOAc (2×10 mL). The combined organic phase was washed with saturated brine (2×20 mL), dried over anhydrous Na$_2$SO$_4$, filtered concentrated and purified by flash column (0~30% of EtOAc in PE) to give E4 (1.5 g, 42%) as a solid.

$^1$H NMR (400 MHz, CDCl$_3$) δ 5.15-5.05 (m, 1H), 3.68-3.55 (m, 1H), 3.51-3.39 (m, 1H), 3.35-3.28 (m, 4H), 2.40-2.31 (m, 1H), 2.22-2.10 (m, 2H), 2.01-1.49 (m, 8H), 1.49-1.11 (m, 6H), 1.11-0.75 (m, 14H).

The stereochemistry at C7 of E4 was confirmed by NOE.

Step 5

To a suspension of E4 (1.5 g, 4.32 mmol) in DCM (30 mL) was added silica gel (2 g) and PCC (1.86 g, 8.64 mmol) at 15° C. The mixture was stirred at 15° C. for 2 hrs. The mixture was filtered and the filtrated cake was washed with DCM (2×20 mL). The combined filtrate was concentrated in vacuum and purified by flash column (0~30% of EtOAc in PE) to give crude product E5 (1.3 g, 87%) as a solid.

$^1$H NMR (400 MHz, CDCl$_3$) δ 5.19-5.10 (m, 1H), 3.52-3.45 (m, 1H), 3.31-3.28 (m, 3H), 3.28-3.19 (m, 1H), 2.45-2.15 (m, 7H), 2.15-2.02 (m, 3H), 1.85-1.75 (m, 1H), 1.75-1.62 (m, 4H), 1.62-1.25 (m, 7H), 0.99 (s, 3H), 0.98-0.80 (m, 5H).

Step 6

Under nitrogen atmosphere, anhydrous THF (20 mL) was cooled to 10° C. and anhydrous LiCl (589 mg, 13.9 mmol) was added in one portion. The mixture was stirred for 30 min to obtain a clear solution. To this solution was added anhydrous FeCl$_3$ (1.24 g, 7.65 mmol) in one portion. The resulting mixture was stirred for additional 30 mins. The reaction mixture was cooled to −35° C. and methyl magnesium bromide (9.26 mL, 27.8 mmol, 3 M in diethyl ether,) was added dropwise maintaining the internal temperature between −35° C. and −30° C. The above mixture was stirred for 30 min at −30° C. E5 (1.2 g, 3.48 mmol) in THF (20 mL) was added in one portion. The internal temperature was allowed to −20° C. and held between −15° C. and −20° C. for 2 hrs. The reaction mixture was poured to ice-cooled aqueous HCl (1 M, 20 mL), extracted with EtOAc (2×20 mL). The combined organic layer was washed with water (20 mL), aqueous NaOH (10%, 2×20 mL) and brine (20 mL), dried over anhydrous sodium sulfate, filtered and concentrated. The residue was purified by column chromatography on silica gel (PE/EtOAc=20/1 to 5/1) to give E6 (1 g, 80%) as a solid.

$^1$H NMR (400 MHz, CDCl$_3$) δ 5.19-5.10 (m, 1H), 3.52-3.45 (m, 1H), 3.29 (s, 3H), 3.20-3.19 (m, 1H), 2.42-2.10 (m, 3H), 1.85-1.76 (m, 1H), 1.76-1.62 (m, 5H), 1.62-1.40 (m, 3H), 1.40-1.11 (m, 13H), 1.01-0.82 (m, 6H), 0.72 (s, 3H).

Step 7

To a solution of E6 (1 g, 2.77 mmol) in THF (15 mL) was added dropwise a solution of BH$_3$-Me$_2$S (2.77 mL, 27.7 mmol, 10M in THF) at 0° C. The solution was stirred at 15° C. for 3 h. After cooling to 0° C., a solution of NaOH solution (16.6 mL, 2M) was added very slowly. After addition, H$_2$O$_2$ (2.76 mL, 27.7 mmol, 30% in water) was added slowly and the inner temperature was maintained below 10° C. The resulting solution was stirred at 15° C. for 2 h. Then saturated aqueous Na$_2$S$_2$O$_3$ (20 mL) was added until the reaction solution became clear. The mixture was extracted with EtOAc (3×20 mL). The combined organic solution was washed with saturated aqueous Na$_2$S$_2$O$_3$ (2×10 mL), brine (20 mL), dried over Na$_2$SO$_4$ and concentrated in vacuum to give E7 (0.9 g, crude) as a solid, which was used in next step without further purification.

Step 8

To a suspension of E7 (0.9 g, 1.37 mmol) in DCM (20 mL) was added silica gel (1 g) and PCC (1.02 g, 4.74 mmol) at 15° C. The mixture was stirred at 15° C. for 2 hrs. The mixture was filtered and the filtrated cake was washed with DCM (2×20 mL). The combined filtrate was concentrated in vacuum, purified by flash column (0-20% of EtOAc in PE) and re-crystallized from DCM/n-hexane (2 mL/20 mL) at 15° C. to give Compound 11 (130 mg, 14%) as solid.

$^1$H NMR (400 MHz, CDCl$_3$) δ 3.45-3.38 (m, 1H), 3.29-3.20 (m, 4H), 2.55-2.45 (m, 1H), 2.19-2.09 (m, 4H), 2.05-1.85 (m, 2H), 1.75-1.55 (m, 2H), 1.55-1.35 (m, 9H), 1.35-1.15 (m, 10H), 0.94-0.82 (m, 1H), 0.72 (s, 3H), 0.63 (s, 3H).

LCMS Rt=1.134 min in 2 min chromatography, 30-90AB_2MIN_E, purity 87%, MS ESI calcd. for C$_{24}$H$_{39}$O$_2$[M+H−H$_2$O]$^+$ 359, found 359.

HPLC Rt=4.54 min in 8 min chromatography, 30-90_AB_1.2 ml_E.met, purity: 100%.

Example 6. Synthesis of Compound 12

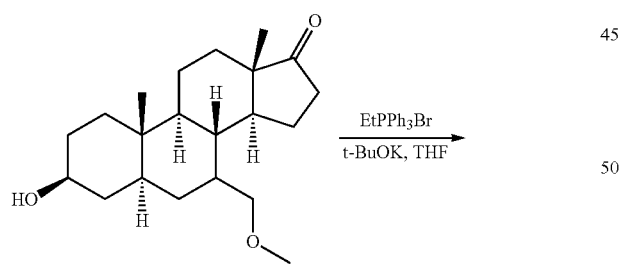

E3

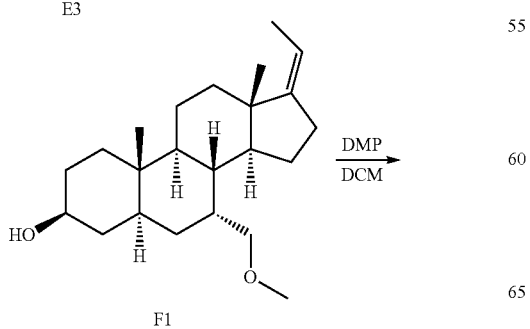

F1

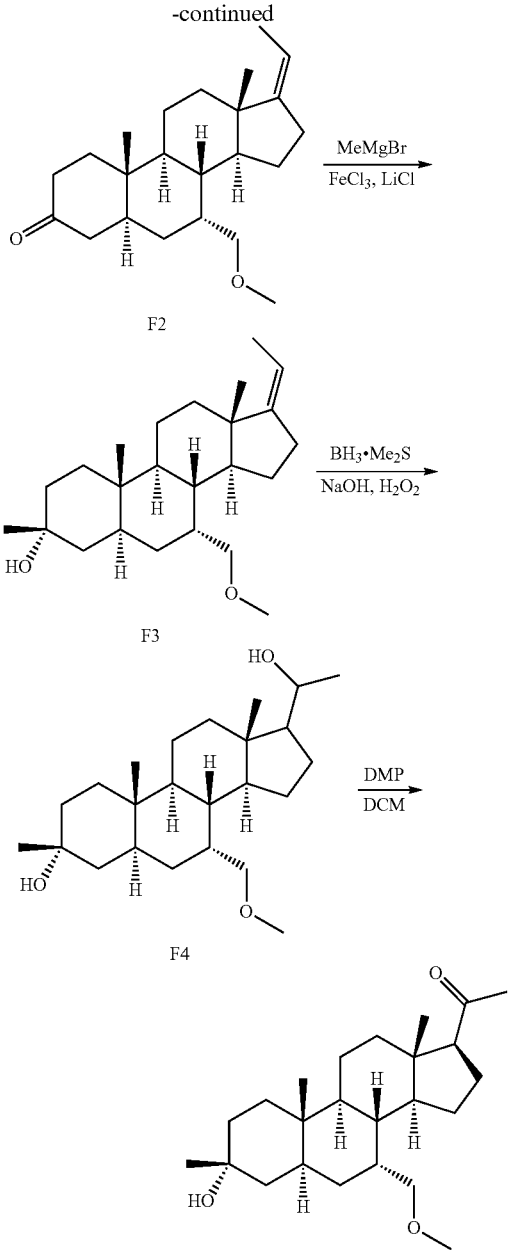

Step 1

To a suspension of PPh$_3$EtBr (26.5 g, 71.6 mmol) in THF (100 mL) was added t-BuOK (8.03 g, 71.6 mmol) at 10° C. The color of the suspension turned dark red. After stirring at 40° C. for 1 hour, a solution of E3 (8 g, 23.9 mmol) in THF (20 mL) was added at 40° C. and the reaction mixture was stirred at 40° C. for 16 h. The mixture was added saturated NH$_4$Cl solution (20 mL) and EtOAc (2×30 mL). The organic layer was separated and the water phase was extracted with EtOAc (2×30 mL). The combined organic phase was washed with saturated brine (2×20 mL), dried over anhydrous Na$_2$SO$_4$, filtered concentrated and purified by flash column (0~20% of EtOAc in PE) to give F1 (2.1 g, 25%) as colorless oil.

$^1$H NMR (400 MHz, CDCl$_3$) δ 5.15-5.05 (m, 1H), 3.68-3.55 (m, 1H), 3.40-3.35 (m, 1H), 3.31 (s, 3H), 2.43-2.32 (m, 1H), 2.22-2.10 (m, 2H), 2.01-1.89 (m, 1H), 1.89-1.50 (m, 8H), 1.50-1.22 (m, 9H), 1.10-0.82 (m, 11H).

The stereochemistry at C7 of F1 was confirmed by NOE.

Step 2

To a solution of F1 (2 g, 5.77 mmol) in DCM (50 mL) was added DMP (4.87 g, 11.5 mmol). After that, the reaction was stirred at 15° C. for 30 min. The reaction mixture was added aqueous saturated NaHCO$_3$ (50 mL) solution, aqueous saturated Na$_2$S$_2$O$_3$ (50 mL) solution, extracted with DCM (2×50 mL). The combined organic layer was washed with aqueous saturated NaHCO$_3$ (2×20 mL) solution and brine (20 mL), dried over Na$_2$SO$_4$, filtered and concentrated in vacuum to give F2 (1.95 g, 98%) as a solid.

$^1$H NMR (400 MHz, CDCl$_3$) δ 5.19-5.10 (m, 1H), 3.50-3.35 (m, 2H), 3.30 (s, 3H), 2.46-2.15 (m, 7H), 2.15-1.98 (m, 3H), 1.78-1.50 (m, 9H), 1.50-1.21 (m, 4H), 1.05-1.12 (m, 4H), 0.89 (s, 3H).

Step 3

Under a nitrogen atmosphere, anhydrous THF (10 mL) was cooled to 10° C. and anhydrous LiCl (958 mg, 22.6 mmol) was added in one portion. The mixture was stirred for 30 min to obtain a clear solution. To this solution was added anhydrous FeCl$_3$ (2.01 mg, 12.4 mmol) in one portion. The resulting mixture was stirred for additional 30 mins. The reaction mixture was cooled to −35° C. and methyl magnesium bromide (15.0 mL, 45.2 mmol, 3 M in diethyl ether,) was added dropwise maintaining the internal temperature between −35° C. and −30° C. The above mixture was stirred for 30 min at −30° C. A solution of F2 (1.95 g, 5.65 mmol) in THF (10 mL) was added in one portion. The internal temperature was allowed to −20° C. and held between −15° C. and −20° C. for 2 hrs. The reaction mixture was poured into ice-cooled aqueous HCl (1 M, 20 mL), extracted with EtOAc (2×20 mL). The combined organic layer was washed with water (20 mL), aqueous NaOH (10%, 2×20 mL) and brine (20 mL), dried over anhydrous sodium sulfate, filtered and concentrated. The residue was purified by flash column (0~30% of EtOAc in PE) to give F3 (1.6 g, 79%) as a solid.

$^1$H NMR (400 MHz, CDCl$_3$) δ 5.19-5.10 (m, 1H), 3.55-3.49 (m, 1H), 3.40-3.35 (m, 1H), 3.31 (s, 3H), 2.42-2.30 (m, 1H), 2.30-2.15 (m, 2H), 1.99-1.90 (m, 1H), 1.80-1.55 (m, 8H), 1.55-1.40 (m, 4H), 1.40-1.20 (m, 9H), 1.20-0.95 (m, 2H), 0.95-0.82 (m, 4H), 0.79 (s, 3H).

Step 3

To a solution of F3 (1.6 g, 4.43 mmol) in THF (25 mL) was added dropwise a solution of BH$_3$-Me$_2$S (4.43 mL, 44.3 mmol, 10M in THF) at 0° C. The solution was stirred at 15° C. for 3 h. After cooling to 0° C., a solution of NaOH solution (26.5 mL, 53.1 mmol, 2M) was added very slowly. After addition, H$_2$O$_2$ (4.42 mL, 44.3 mmol, 30% in water) was added slowly and the inner temperature was maintained below 10° C. The resulting solution was stirred at 15° C. for 2 h. Then saturated aqueous Na$_2$S$_2$O$_3$ (20 mL) was added until the reaction solution became clear. The mixture was extracted with EtOAc (3×20 mL). The combined organic solution was washed with saturated aqueous Na$_2$S$_2$O$_3$ (2×10 mL), brine (20 mL), dried over Na$_2$SO$_4$ and concentrated in vacuum to give F4 (1.66 g, crude) as a solid, which was used in next step without further purification.

Step 4

To a solution of F4 (1.66 g, 4.4 mmol) in DCM (50 mL) was added DMP (3.73 g, 8.80 mmol) at 15° C. The reaction was stirred at 15° C. for 10 min. To the reaction mixture was added aqueous saturated NaHCO$_3$ (50 mL) solution, aqueous saturated Na$_2$S$_2$O$_3$ (50 mL) solution and extracted with DCM (2×20 mL). The combined organic layer was washed with aqueous saturated NaHCO$_3$ (3×20 mL) solution and brine (20 mL), dried over Na$_2$SO$_4$, filtered and concentrated in vacuum and purified by silica gel chromatography (PE/EtOAc=15/1 to 10/1) to give Compound 12 (0.85 g, impure) as a solid. Compound 12 (0.2 g, impure) was re-crystallized from MeCN (15 mL) at 15° C. to give Compound 12 (150 mg, 48%) as a solid.

$^1$H NMR (400 MHz, CDCl$_3$) δ 3.58-3.50 (m, 1H), 3.45-3.35 (m, 1H), 3.32 (s, 3H), 2.55-2.48 (m, 1H), 2.21-2.05 (m, 4H), 2.01-1.85 (m, 2H), 1.85-1.60 (m, 5H), 1.60-1.45 (m, 4H), 1.45-1.20 (m, 12H), 1.10-1.01 (m, 1H), 0.77 (s, 3H), 0.60 (s, 3H).

LCMS Rt=1.126 min in 2 min chromatography, 30-90AB_2MIN_E, purity 100%, MS ESI calcd. for C$_{24}$H$_{39}$O$_2$[M+H−H$_2$O]$^+$ 359, found 359.

Example 7. Synthesis of Compound 13

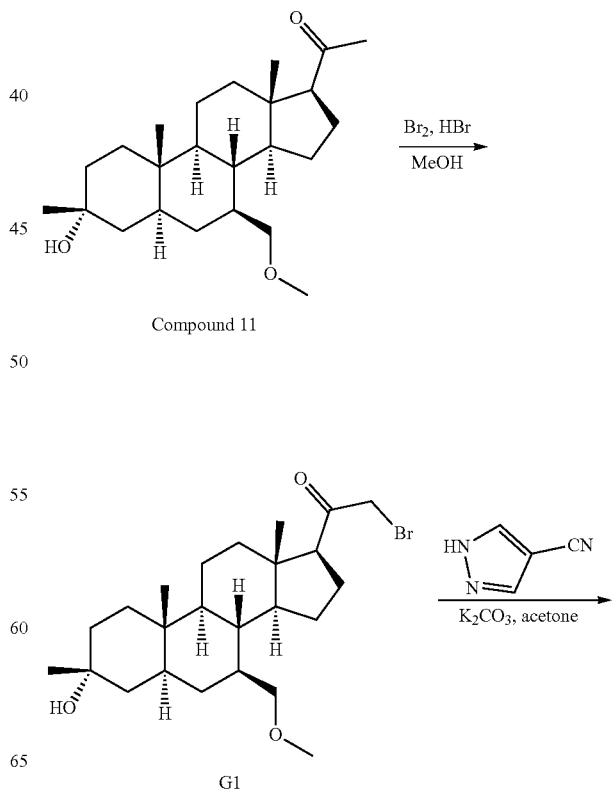

Example 8. Syntheses of Compound 14

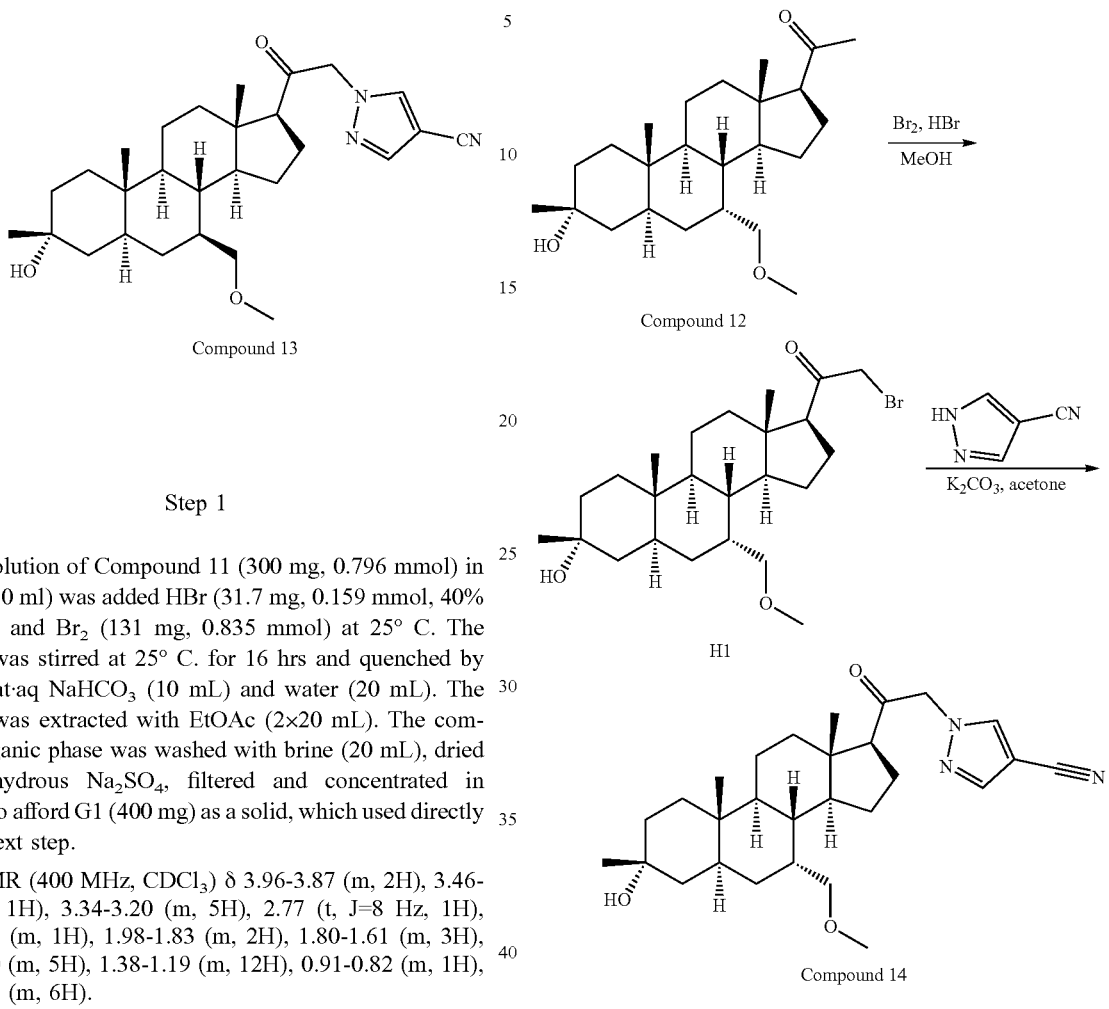

Compound 13

Step 1

To a solution of Compound 11 (300 mg, 0.796 mmol) in MeOH (10 ml) was added HBr (31.7 mg, 0.159 mmol, 40% in water) and Br$_2$ (131 mg, 0.835 mmol) at 25° C. The mixture was stirred at 25° C. for 16 hrs and quenched by adding sat·aq NaHCO$_3$ (10 mL) and water (20 mL). The mixture was extracted with EtOAc (2×20 mL). The combined organic phase was washed with brine (20 mL), dried over anhydrous Na$_2$SO$_4$, filtered and concentrated in vacuum to afford G1 (400 mg) as a solid, which used directly for the next step.

$^1$H NMR (400 MHz, CDCl$_3$) δ 3.96-3.87 (m, 2H), 3.46-3.34 (m, 1H), 3.34-3.20 (m, 5H), 2.77 (t, J=8 Hz, 1H), 2.23-2.06 (m, 1H), 1.98-1.83 (m, 2H), 1.80-1.61 (m, 3H), 1.49-1.40 (m, 5H), 1.38-1.19 (m, 12H), 0.91-0.82 (m, 1H), 0.74-0.64 (m, 6H).

Step 2

To a mixture of G1 (60 mg, 0.131 mmol) and K$_2$CO$_3$ (36.2 mg, 0.2.62 mmol) in acetone (5 mL) was added 1H-pyrazole-4-carbonitrile (18.2 mg, 0.196 mmol) at 25° C. The reaction mixture was stirred at 25° C. for 16 h and treated with H$_2$O (50 mL). The mixture was extracted with EtOAc (3×50 mL). The combined organic solution was washed with brine (20 mL), dried over Na$_2$SO$_4$, filtered and concentrated in vacuum to give the crude product, which was purified by flash column (0~30% of EtOAc in PE) twice to give Compound 13 (15 mg, 25%) as a solid.

$^1$H NMR (400 MHz, CDCl$_3$) δ 7.85 (s, 1H), 7.81 (s, 1H), 5.05-4.87 (m, 2H), 2.54 (m, 1H), 3.40-3.38 (m, 1H), 3.37-3.27 (m, 4H), 2.55 (d, J=8 Hz, 1H), 2.23-2.15 (m, 1H), 2.041.96 (m, 1H), 1.76-1.72 (m, 2H), 1.52-1.49 (m, 8H), 1.32-1.21 (m, 10H), 1.11 (s, 1H), 0.88-0.85 (m, 1H), 0.73 (s, 3H), 0.69 (s, 3H).

LCMS Rt=1.054 in in 2.0 min chromatography, 30-90AB_2MIN_E.M.lcm, purity 100%, MS ESI calcd. for C$_{28}$H$_{42}$N$_3$O$_3$ [M+H]$^+$ 468, found 468.

Step 1

To a solution of Compound 12 (700 mg, 1.85 mmol) in MeOH (10 ml) was added HBr (74 mg, 0.370 mmol, 40% in water) and Br$_2$ (304 mg, 1.94 mmol) at 25° C. After stirring at 25° C. for 16 hrs, the mixture was quenched with sat·aq NaHCO$_3$ (10 mL) and water (20 mL), extracted with EtOAc (2×20 mL). The combined organic phase was washed with brine (20 mL), dried over anhydrous Na$_2$SO$_4$, filtered, concentrated in vacuum to afford H1 (900 mg) as a solid, which was used directly for the next step.

$^1$H NMR (400 MHz, CDCl$_3$) δ 3.92-3.88 (m, 2H), 3.58-3.46 (m, 1H), 3.41 (s, 3H), 3.37-3.27 (m, 3H), 2.84-2.80 (m, 1H), 1.91-1.89 (m, 2H), 1.78-1.65 (m, 3H), 1.54-1.40 (m, 5H), 1.40-1.17 (m, 12H), 0.91 (s, 1H), 0.79-0.75 (m, 3H), 0.62 (s, 3H).

Step 2

To a mixture of H1 (80 mg, 0.175 mmol) and K$_2$CO$_3$ (48.3 mg, 0.350 mmol) in acetone (5 mL) was added 1H-pyrazole-4-carbonitrile (24.3 mg, 0.262 mmol) at 25° C. The reaction mixture was stirred at the 25° C. for 16 h and treated with H₂O (50 mL), extracted with EtOAc (3×50 mL). The combined organic solution was washed with brine (20 mL), dried over Na₂SO₄ and concentrated in vacuum to give the crude product, which was purified by flash column (0~30% of EtOAc in PE) to give Compound 14 (23 mg, 28%) as a solid.

¹H NMR (400 MHz, CDCl₃) δ 7.83 (d, J=18.8 Hz, 2H), 5.04-4.86 (m, 2H), 3.55-3.50 (m, 1H), 3.42-3.41 (m, 1H), 3.32 (s, 3H), 2.59 (t, J=9.2 Hz, 1H), 2.27-2.14 (m, 1H), 2.03-1.98 (m, 1H), 1.95-1.83 (m, 2H), 1.80-1.64 (m, 4H), 1.53-1.47 (m, 3H), 1.45-1.23 (m, 9H), 1.20 (s, 3H), 1.14-1.00 (m, 2H), 0.78 (s, 3H), 0.65 (s, 3H).

LCMS Rt=2.901 in in 4.0 min chromatography, 10-80AB·1 cm, purity 100%, MS ESI calcd. for C₂₈H₄₀N₃O₂ [M−H₂O+H]⁺ 450, found 450.

Example 9. Syntheses of Compounds 15, 16, and 17

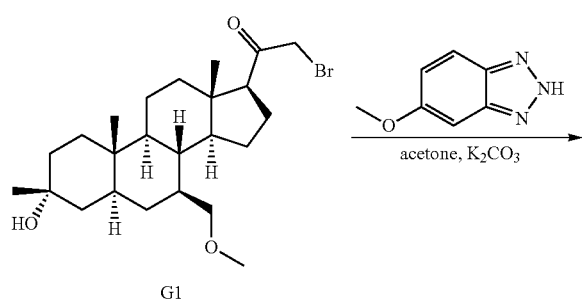

G1

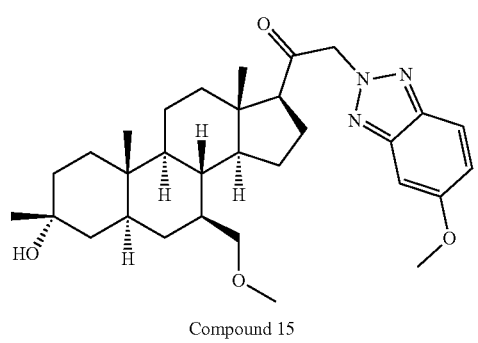

Compound 15

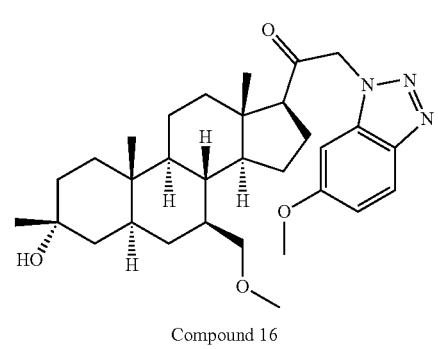

Compound 16

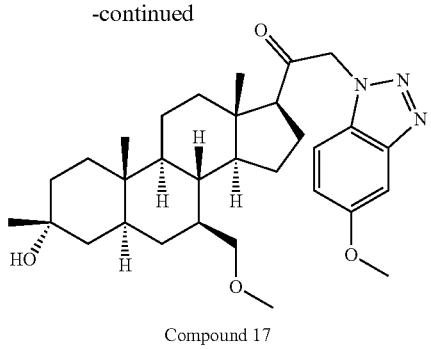

Compound 17

To a solution of G1 (200 mg, 0.439 mmol) in acetone (5 mL) was added 5-methoxy-2H-benzo[d][1,2,3]triazole (98.1 mg, 0.658 mmol), followed by adding K₂CO₃ (121 mg, 0.878 mmol) at 25° C. The resulting reaction mixture was stirred at 25° C. for 16 hrs, treated with water (20 mL) and extracted with EtOAc (3×20 mL). The combined organic solution was washed with brine (20 mL), dried over Na₂SO₄ and concentrated in vacuum to give the crude product, which was purified by flash column (0~30% of EtOAc in PE) to give impure Compound 15 (50 mg). The impure Compound 15 was purified by prep. HPLC separation (column: YMC-Actus Triart C18 150*30 mm*5 um), gradient: 65-95% B (A=water (0.05% HCl)-ACN, B=ACN), flow rate: 25 mL/min) to give Compound 15 (18 mg, 8%) as a solid; and a mixture of Compound 16 and Compound 17 (100 mg, crude). The mixture of Compound 16 and Compound 17 (100 mg, crude) was purified by SFC separation (column: OJ (250 mm*30 mm, 5 um)), gradient: 40-40% B (A=0.1% NH₃H₂O, B=ETOH), flow rate: 60 mL/min) to give Compound 16 (33 mg, 14%) as solid and Compound 17 (16 mg, 7%) as solid.

Compound 15

¹H NMR (400 MHz, CDCl₃) δ 7.73 (d, J=8.0 Hz, 1H), 7.08-7.06 (m, 2H), 5.50-5.39 (m, 2H), 3.88 (s, 3H), 3.41-3.35 (m, 1H), 3.27 (s, 4H), 2.58 (t, J=8.0 Hz, 1H), 2.27-2.07 (m, 2H), 2.01-1.88 (m, 1H), 1.81-1.69 (m, 2H), 1.53-1.47 (m, 5H), 1.46-1.12 (m, 14H), 0.94-0.82 (m, 1H), 0.76 (s, 3H), 0.74 (s, 3H).

LCMS Rt=3.240 min in 4.0 min chromatography, 10-80AB·1 cm, purity 100%, MS ESI calcd. for C₃₁H₄₆N₃O₄ [M+H]⁺ 524, found 524.

Compound 16

¹H NMR (400 MHz, CDCl₃) δ 7.92 (d, J=8.0 Hz, 1H), 7.01 (dd, J=4.0, 8.0 Hz, 1H), 6.60 (d, J=4.0 Hz, 1H), 5.40-5.29 (m, 2H), 3.86 (s, 3H), 3.41-3.35 (m, 1H), 3.30-3.25 (m, 4H), 2.64 (t, J=8.0 Hz, 1H), 2.28-2.09 (m, 2H), 2.00-1.90 (m, 1H), 1.76-1.75 (m, 2H), 1.54-1.43 (m, 7H), 1.42-1.20 (m, 11H), 1.13 (s, 1H), 0.92-0.87 (m, 1H), 0.75 (s, 3H), 0.74 (s, 3H).

LCMS Rt=3.025 min in 4.0 min chromatography, 10-80AB·1 cm, purity 100%, MS ESI calcd. for C₃₁H₄₆N₃O₄ [M+H]⁺ 524, found 524.

Compound 17

¹H NMR (400 MHz, CDCl₃) δ 7.39 (d, J=4.0 Hz, 1H), 7.24-7.13 (m, 2H), 5.43-5.32 (m, 2H), 3.89 (s, 3H), 3.39-3.37 (m, 1H), 3.27 (s, 4H), 2.63 (t, J=12.0 Hz, 1H), 2.25-

2.09 (m, 2H), 1.97-1.95 (m, 1H), 1.83-1.71 (m, 2H), 1.54-1.44 (m, 7H), 1.43-1.20 (m, 11H), 1.12 (s, 1H), 0.91-0.87 (m, 1H), 0.74 (s, 6H)

LCMS Rt=3.033 min in 4.0 min chromatography, 10-80AB·1 cm, purity 100%, MS ESI calcd. for $C_{31}H_{46}N_3O_4$ [M+H]$^+$ 524, found 524.

Example 10. Syntheses of Compounds 18, 19, and 20

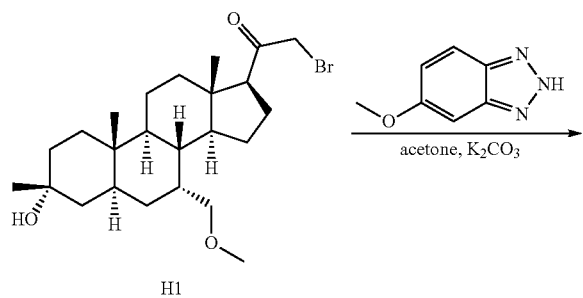

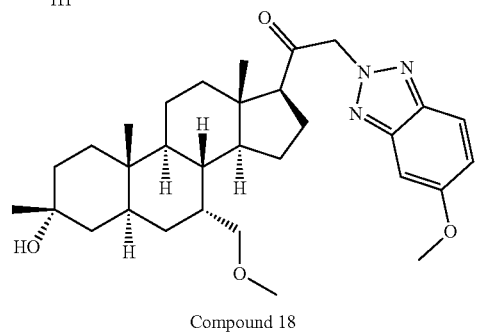

Compound 18

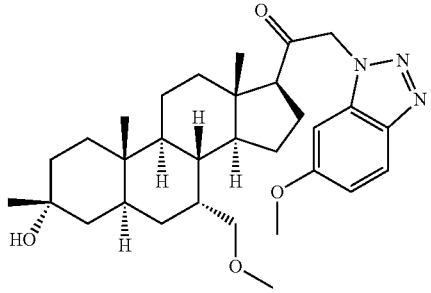

Compound 19

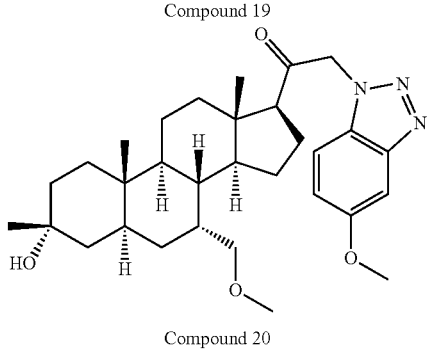

Compound 20

To a solution of H1 (200 mg, 0.439 mmol) in acetone (5 mL) was added 5-methoxy-2H-benzo[d][1,2,3]triazole (98.1 mg, 0.658 mmol), followed by adding K$_2$CO$_3$ (121 mg, 0.878 mmol) at 25° C. The resulting reaction mixture was stirred at 25° C. for 16 hours, treated with water (20 mL), extracted with EtOAc (3×20 mL). The combined organic solution was washed with brine (20 mL), dried over Na$_2$SO$_4$ and concentrated in vacuum to give the crude product, which was purified by flash column (0~30% of EtOAc in PE) to give Compound 18 (10 mg, 4%) as a solid and a mixture of Compound 19 and Compound 20 (100 mg, crude). The mixture of Compound 19 and Compound 20 was purified by SFC separation (column:OD (250 mm*30 mm, 5 um)), gradient: 40-40% B (A=0.1% NH$_3$H$_2$O, B=ETOH), flow rate: 50 mL/min) to give Compound 19 (32 mg, 13%) as a solid and Compound 20 (27 mg, 12%) as a solid.

Compound 18

$^1$H NMR (400 MHz, CDCl$_3$) δ 7.74-7.71 (m, 1H), 7.08-7.06 (m, 2H), 5.48-5.38 (m, 2H), 3.88 (s, 3H), 3.55-3.50 (m, 1H), 3.42-3.38 (m, 1H), 3.32 (s, 3H), 2.64-2.60 (m, 1H), 2.29-2.18 (m, 1H), 2.14-2.06 (m, 1H), 1.92 (m, 1H), 1.68 (m, 5H), 1.53-1.41 (m, 4H), 1.41-1.19 (m, 12H), 1.09-1.02 (m, 1H), 0.79 (s, 3H), 0.73 (s, 3H) LCMS Rt=3.215 min in 4.0 min chromatography, 10-80AB·1 cm, purity 100%, MS ESI calcd. for $C_{31}H_{46}N_3O_4$ [M+H]$^+$ 524, found 524.

Compound 19

$^1$H NMR (400 MHz, CDCl$_3$) δ 7.92 (d, J=8.0 Hz, 1H), 7.01 (m, 1H), 6.61-6.59 (m, 1H), 5.37-5.28 (m, 2H), 3.86 (s, 3H), 3.53 (t, J=8.0 Hz, 1H), 3.43-3.37 (m, 1H), 3.32 (s, 3H), 2.68 (t, J=8.0 Hz, 1H), 2.27-2.17 (m, 1H), 2.13-2.070 (m, 1H), 1.97-1.82 (m, 2H), 1.77-1.68 (m, 3H), 1.55-1.27 (m, 12H), 1.21 (s, 3H), 1.10-1.05 (m, 1H), 0.94 (s, 2H), 0.79 (s, 3H), 0.72 (s, 3H).

LCMS Rt=2.344 min in 3.0 min chromatography, 10-80AB·1 cm, purity 96.15%, MS ESI calcd. for $C_{31}H_{46}N_3O_4$ [M+H]$^+$ 524, found 524.

Compound 20

$^1$H NMR (400 MHz, CDCl$_3$) δ 7.39 (d, J=4.0 Hz, 1H), 7.23-7.11 (m, 2H), 5.36 (s, 2H), 3.89 (s, 3H), 3.53 (t, J=8.0 Hz, 1H), 3.42-3.37 (m, 1H), 3.32 (s, 3H), 2.67 (t, J=8.0 Hz, 1H), 2.26-2.17 (m, 1H), 2.12-2.06 (m, 1H), 1.97-1.81 (m, 2H), 1.77-1.67 (m, 3H), 1.55-1.46 (m, 4H), 1.46-1.22 (m, 9H), 1.21 (s, 3H), 1.12 (s, 1H), 1.09-1.02 (m, 1H), 0.79 (s, 3H), 0.71 (s, 3H).

LCMS Rt=1.095 min in 2.0 min chromatography, 30-90AB_2MIN_E_M, purity 100%, MS ESI calcd. for $C_{31}H_{46}N_3O_4$ [M+H]$^+$ 524, found 524.

Example 11. Syntheses of Compounds 21 and 22

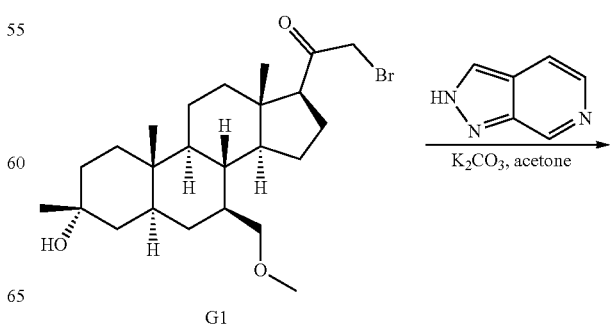

G1

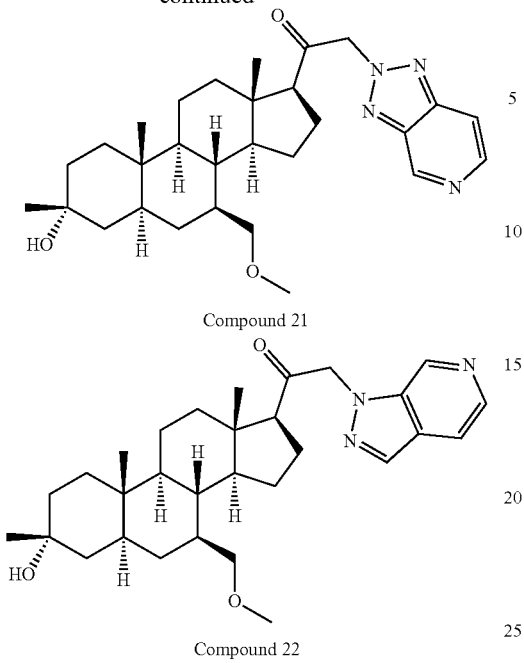

Compound 21

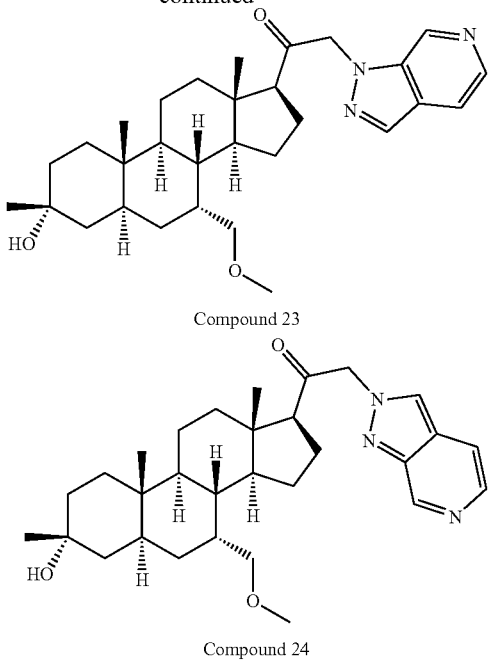

Compound 23

Compound 22

Compound 24

To a solution of the G1 (150 mg, 0.329 mmol) and 1H-pyrazolo[3,4-c]pyridine (41 mg, 0.345 mmol) in acetone (3 mL) was added K$_2$CO$_3$ (26.1 g, 0.658 mmol) at 25° C. After stirring at 25° C. for 10 hrs, the mixture was poured into water (50 mL) and extracted with EtOAc (3×20 mL). The combined organic layer was washed with brine (50 mL), dried over with Na$_2$SO$_4$, filtered and concentrated to afford crude product, which was purified by prep. HPLC (column: YMC-Actus Triart C18 150*30 mm*5 um)), gradient: 30-60% B (A=0.1% HCl, B=ACN), flow rate: 25 mL/min) to afford Compound 22 (3 mg, impure) as a solid and Compound 21 (20 mg, impure). Compound 21 (20 mg, impure) was purified by flash column (0~30% of EtOAc in PE) to give Compound 21 (9 mg, 6%) as a solid.

$^1$H NMR (400 MHz, CDCl$_3$) δ 9.26 (s, 1H), 8.17 (d, J=4.8 Hz, 1H), 7.98 (s, 1H), 7.53 (d, J=6.8 Hz, 1H), 5.36-5.20 (m, 2H), 3.38-3.36 (m, 1H), 3.32-3.31 (m, 1H), 3.27 (s, 3H), 2.70-2.61 (m, 1H), 2.30-2.19 (m, 1H), 2.17-2.13 (m, 1H), 2.04-1.95 (m, 1H), 1.85-1.74 (m, 2H), 1.56-1.49 (m, 6H), 1.45-1.22 (m, 12H), 1.17-1.14 (m, 1H), 0.93-0.88 (m, 1H), 0.73 (s, 6H).

LCMS Rt=1.771 min in 3.0 min chromatography, 10-80AB, purity 100%, MS ESI calcd. For C$_{30}$H$_{44}$N$_3$O$_3$ [M+H]$^+$ 494, found 494.

Example 12. Syntheses of Compounds 23 and 24

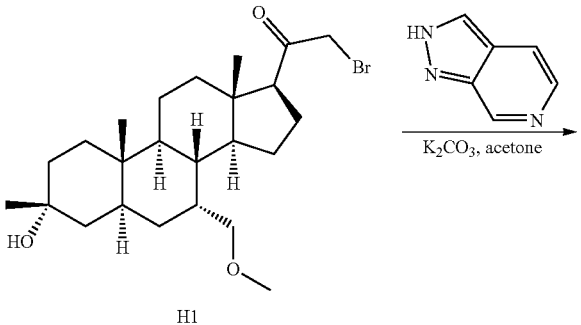

H1

To a mixture of H1 (150 mg, 0.329 mmol) and K$_2$CO$_3$ (90.9 mg, 0.658 mmol) in acetone (3 mL) was added 1H-pyrazolo[3,4-c]pyridine (41 mg, 0.345 mmol) at 25° C. After stirring at 25° C. for 12 h, the mixture was poured into water (50 mL) and extracted with EtOAc (3×20 mL). The combined organic layer was washed with brine (50 mL), dried over with Na$_2$SO$_4$, filtered and concentrated to afford crude product, which was purified by preparative HPLC (column: YMC-Actus Triart C18 150*30 mm*5 um)), gradient: 35-65% B (A=0.1% HCl, B=ACN), flow rate: 25 mL/min) to afford Compound 23 (50 mg, 31%) as a solid and Compound 24 (20 mg, impure). Compound 24 (20 mg, impure) was purified by SFC separation (column: AD (250 mm*30 mm, 10 um)), gradient: 45-45% B (A=0.1% NH$_3$H$_2$O, B=EtOH), flow rate: 80 mL/min) to afford Compound 24 (8 mg, 5%) as a solid.

Compound 23

$^1$H NMR (400 MHz, CDCl$_3$) δ 8.79 (s, 1H), 8.34 (d, J=5.6 Hz, 1H), 8.09 (s, 1H), 7.66-7.63 (m, 1H), 5.23-5.30 (m, 2H), 3.56-3.48 (m, 1H), 3.42-3.37 (m, 1H), 3.33 (s, 3H), 2.69-2.66 (m, 1H), 2.27-2.17 (m, 1H), 2.14-2.07 (m, 1H), 1.97-1.84 (m, 2H), 1.80-1.65 (m, 4H), 1.55-1.28 (m, 13H), 1.21 (s, 3H), 1.10-1.04 (m, 1H), 0.80 (s, 3H), 0.71 (s, 3H).

LCMS Rt=2.290 min in 4.0 min chromatography, 10-80AB, purity 99.1%, MS ESI calcd. For C$_{30}$H$_{44}$N$_3$O$_3$ [M+H]$^+$ 494, found 494.

Compound 24

$^1$H NMR (400 MHz, CDCl$_3$) δ 9.26 (s, 1H), 8.17 (d, J=6.4 Hz, 1H), 7.98 (s, 1H), 7.56-7.50 (m, 1H), 5.35-5.19 (m, 2H), 3.56-3.50 (m, 1H), 3.44-3.39 (m, 1H), 3.33 (s, 3H), 2.66 (t, J=8.8 Hz, 1H), 2.25-2.22 (m, 1H), 2.10-2.07 (m, 1H), 1.97-1.67 (m, 6H), 1.52-1.38 (m, 7H), 1.36-1.25 (m, 6H), 1.21 (s, 3H), 1.15-1.03 (m, 1H), 0.79 (s, 3H), 0.70 (s, 3H).

LCMS Rt=2.155 min in 4.0 min chromatography, 10-80AB, purity 100%, MS ESI calcd. For C$_{30}$H$_{44}$N$_3$O$_3$ [M+H]$^+$ 494, found 494.

Example 13. Synthesis of Compound 25

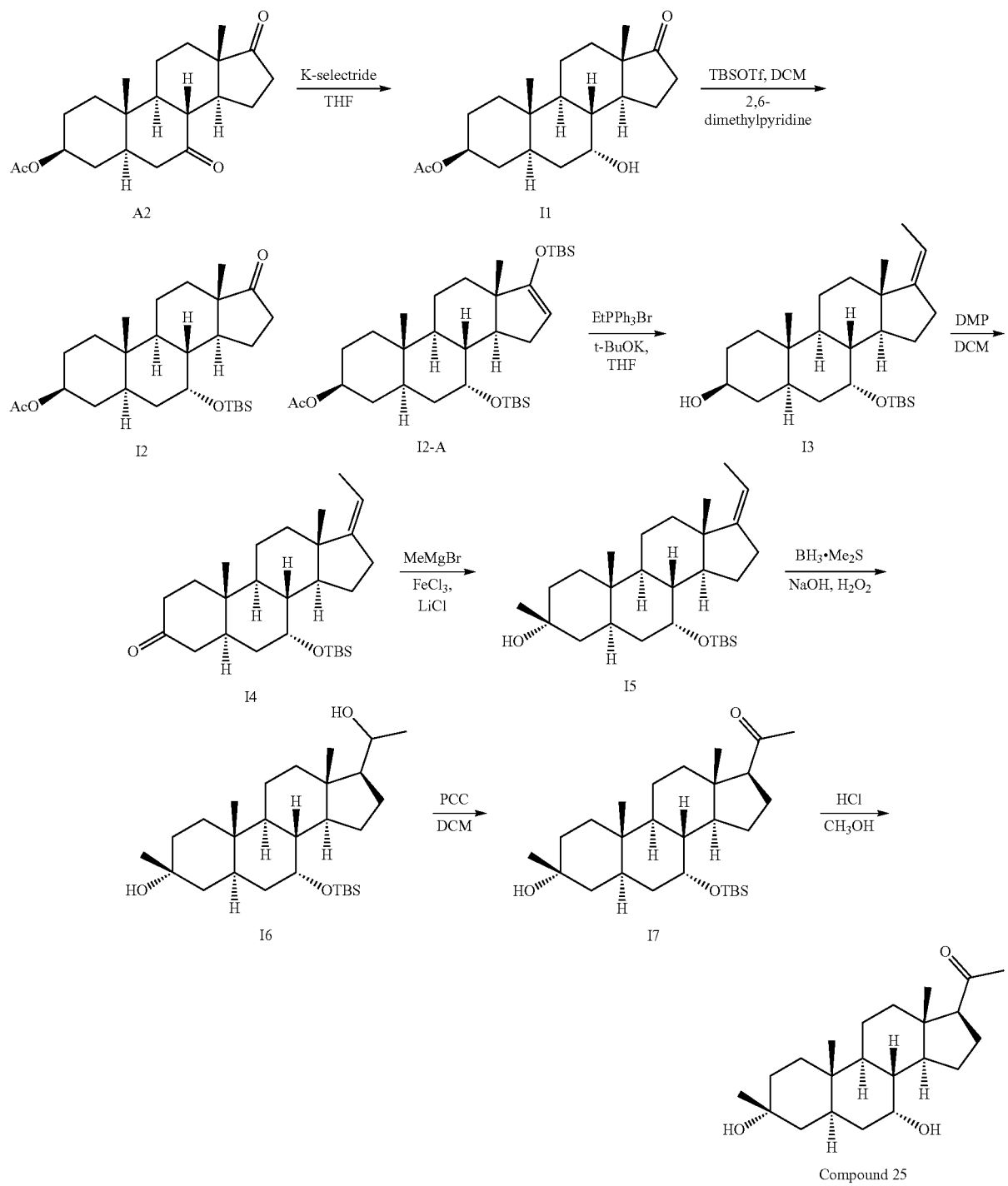

Compound 25

Step 1

To a solution of A2 (20 g, 57.7 mmol) in THF (100 mL) was added dropwise K-selectride (57.7 mL, 57.7 mmol, 1M in THF) at −70° C. The reaction mixture was stirred 2 h at −70° C. The mixture was quenched with sat·NH$_4$Cl (20 mL) at −20° C. and extracted with EtOAc (3×50 mL). The combined organic phase was washed with brine (2×30 mL), dried over Na$_2$SO$_4$, filtered and concentrated and purified by flash column (0~30% of EtOAc in PE) to give I1 (12.5 g, 62%) as a solid.

$^1$H NMR (400 MHz, CDCl$_3$) δ 4.75-4.65 (m, 1H), 4.02-3.90 (m, 1H), 2.51-2.40 (m, 1H), 2.22-2.01 (m, 1H), 1.98-1.40 (m, 15H), 1.40-1.08 (m, 7H), 1.08-0.78 (m, 6H).

Step 2

To a solution of I1 (12 g, 34.4 mmol) in DCM (100 mL) was added TBSOTf (11.8 mL, 51.6 mmol) and 2,6-dimethylpyridine (7.37 g, 68.8 mmol) in one portion at 15° C. The mixture was refluxed at 15° C. for 7 hrs. Then sat·NH$_4$Cl (50 mL) was added to the reaction mixture. The aqueous phase was extracted with DCM (3×50 mL). The combined organic phase was washed with brine (2×50 mL), dried over anhydrous Na$_2$SO$_4$, filtered and concentrated to give residue, which was purified by flash column (0~5% of EtOAc in PE) to afford 12 (8.35 g, crude) combined with another batch of 12-A (7.5 g, crude, 12-A/12=1/1) as an oil, which was used directly for the next step.

Step 3

To a suspension of PPh$_3$EtBr (37.8 g, 102 mmol) in THF (100 mL) was added t-BuOK (11.4 g, 102 mmol) at 10° C. The color of the suspension turned dark red. After stirring at 40° C. for 1 h, a solution of 12 (15.85 g, crude, containing 12-A) in THF (20 mL) was added at 40° C. and the reaction mixture was stirred at 40° C. for 16 h. To the mixture was added saturated NH$_4$Cl solution (20 mL) and EtOAc (60 mL). The organic layer was separated and the aqueous phase was extracted with EtOAc (2×50 mL). The combined organic phase was washed with brine (2×20 mL), dried over anhydrous Na$_2$SO$_4$, filtered, concentrated and purified by flash column (0~20% of EtOAc in PE) to give 13 (10 g, crude) as colorless oil.

Step 4

To a solution of 13 (12 g, 27.7 mmol) in DCM (100 mL) was added DMP (23.4 g, 55.4 mmol) followed by H$_2$O (2.48 mg, 0.138 mmol). The reaction mixture was stirred at 15° C. for 30 min. The reaction mixture was added aqueous saturated NaHCO$_3$ (50 mL) solution, aqueous saturated Na$_2$S$_2$O$_3$ (50 mL) solution, extracted with DCM (2×50 mL). The combined organic layer was washed with aqueous saturated NaHCO$_3$ (2×20 mL) solution and brine (20 mL), dried over Na$_2$SO$_4$, filtered, concentrated in vacuum and purified by flash column (0~10% of EtOAc in PE) to give 14 (6 g, 50%) as a solid.

$^1$H NMR (400 MHz, CDCl$_3$) δ 5.20-5.00 (m, 1H), 3.88 (s, 1H), 2.48-1.97 (m, 10H), 1.80-1.35 (m, 8H), 1.35-1.11 (m, 2H), 1.11-0.80 (m, 18H), 0.02 (s, 6H).

Step 5

Under nitrogen atmosphere, anhydrous THF (20 mL) was cooled to 15° C. and anhydrous LiCl (2.35 g, 55.6 mmol) was added in one portion. The mixture was stirred for 30 min to obtain a clear solution. To the solution was added anhydrous FeCl$_3$ (4.94 g, 30.5 mmol) in one portion. The resulting mixture was stirred for additional 30 mins. The reaction mixture was cooled to −35° C. and methyl magnesium bromide (3 M in diethyl ether, 37.0 mL, 111 mmol) was added dropwise maintaining the internal temperature between −35° C. and −30° C. The above mixture was stirred for 30 min at −30° C. 14 (6 g, 13.9 mmol) in THF (20 mL) was added in one portion. The internal temperature was allowed to 15° C. and the reaction mixture was stirred for 2 hrs. The reaction mixture was poured into ice-cooled aqueous HCl (1 M, 20 mL), extracted with EtOAc (2×20 mL). The combined organic layer was washed with water (20 mL), aqueous NaOH (10%, 2×20 mL) and brine (20 mL), dried over anhydrous sodium sulfate, filtered and concentrated. The residue was purified by flash column (0~5% of EtOAc in PE) to give 15 (3.5 g, 56%) as a solid.

$^1$H NMR (400 MHz, CDCl$_3$) δ 5.15-5.00 (m, 1H), 3.87 (s, 1H), 2.41-2.00 (m, 4H), 1.80-1.49 (m, 7H), 1.49-1.25 (m, 7H), 1.25-1.08 (m, 6H), 1.08-0.81 (m, 14H), 0.81-0.69 (m, 4H), 0.05-0.01 (m, 6H).

Step 6

To a solution of 15 (3.5 g, 7.83 mmol) in THF (20 mL) was added dropwise BH$_3$.Me$_2$S (7.83 mL, 10M, 78.3 mmol) at 0° C. The resulting solution was stirred at 15° C. for 3 h. After cooling to 0° C., a solution of aqueous NaOH (46.9 mL, 93.9 mmol, 2 M) was added very slowly. After the addition, H$_2$O$_2$ (7.84 mL, 78.3 mmol, 30% in water) was added slowly and the inner temperature was maintained below 10° C. The resulting solution was stirred at 15° C. for 1 h. Then saturated aqueous Na$_2$S$_2$O$_3$ (20 mL) was added until the reaction solution became clear. The mixture was extracted with EtOAc (3×20 mL). The combined organic layer was washed with saturated aqueous Na$_2$S$_2$O$_3$ (2×10 mL), brine (20 mL), dried over Na$_2$SO$_4$, filtered and concentrated in vacuum to give 16 (3.4 g, crude) as a solid, which was used in next step without further purification.

Step 7

To a solution of 16 (3.4 g, 7.31 mmol) in DCM (20 mL) was added DMP (6.19 g, 14.6 mmol) followed by H$_2$O (2.62 mg, 0.146 mmol). The reaction mixture was stirred at 15° C. for 30 min. To the reaction mixture was added aqueous saturated NaHCO$_3$ (50 mL) solution and aqueous saturated Na$_2$S$_2$O$_3$ (10 mL) solution. The mixture was extracted with DCM (2×20 mL). The combined organic layer was washed with saturated NaHCO$_3$ (2×20 mL) and brine (20 mL), dried over Na$_2$SO$_4$, filtered, concentrated in vacuum and purified by flash column (0~10% of EtOAc in PE) to give 17 (2.2 g, 65%) as a solid.

$^1$H NMR (400 MHz, CDCl$_3$) δ 3.83-3.80 (m, 1H), 2.59-2.50 (m, 1H), 2.21-1.90 (m, 6H), 1.78-1.49 (m, 9H), 1.49-1.09 (m, 12H), 0.90 (s, 9H), 0.73 (s, 3H), 0.58 (s, 3H), 0.06-0.01 (m, 6H).

Step 8

To a solution of 17 (1.80 g, 3.88 mmol) in CH$_3$OH (50 mL) was added concentrated HCl (0.966 mL, 12 M) 15° C. under N$_2$. The mixture was stirred at 15° C. for 16 hrs. To the mixture was added saturated NaHCO$_3$ (5 mL) and stirred for 20 min. The aqueous phase was extracted with EtOAc (3×50 mL). The combined organic phase was washed with brine (2×50 mL), dried over anhydrous Na$_2$SO$_4$, filtered and concentrated to give a solid, which was purified by flash column (0-70% of EtOAc in PE) to give Compound 25 (1.20 g, impure) as a solid. The impure Compound 25 (600 mg, impure) was triturated with hexane (30 mL) at 68° C. to give Compound 25 (510 mg, 64%) as a solid.

$^1$H NMR (400 MHz, CDCl$_3$) δ 3.85 (brs, 1H), 2.58-2.52 (m, 1H), 2.21-2.06 (m, 4H), 2.03-1.92 (m, 2H), 1.85-1.58 (m, 3H), 1.58-1.45 (m, 4H), 1.45-1.14 (m, 15H), 0.75 (s, 3H), 0.61 (s, 3H).

LCMS Rt=0.893 min in 2.0 min chromatography, 30-90 AB, purity 100%, MS ESI calcd. for C$_{22}$H$_{33}$O [M+H−2H$_2$O]$^+$ 313, found 313.

Example 14. Synthesis of Compound 26

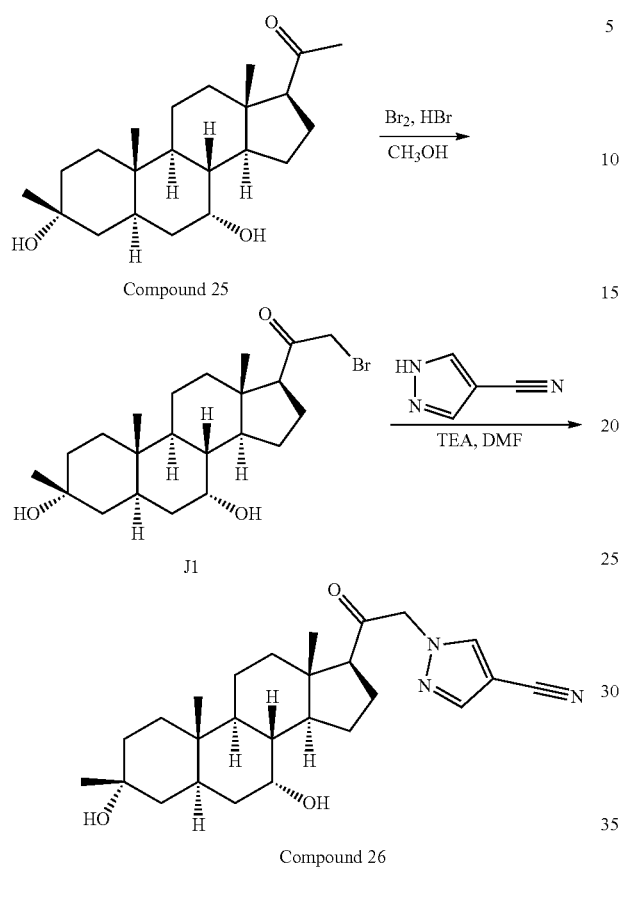

Step 1

To a solution of Compound 25 (497 mg, 1.42 mmol) in MeOH (10 ml) was added HBr (57.2 mg, 0.284 mmol, 40% in water) and Br$_2$ (230 mg, 1.75 mmol) at 15° C. After stirring at 15° C. for 4 hrs, the mixture was quenched by NaHCO$_3$ (10 mL), treated with water (20 mL), extracted with EtOAc (3×20 mL). The combined organic phase was washed with brine (40 mL), dried over anhydrous Na$_2$SO$_4$, filtered, concentrated in vacuum to give J1 (600 mg, crude) as a solid.

$^1$H NMR (400 MHz, CDCl$_3$) δ 3.95-3.86 (m, 2H), 2.86-2.80 (m, 1H), 2.40-2.05 (m, 3H), 2.05-1.57 (m, 6H), 1.55-1.13 (m, 16H), 1.05-0.95 (m, 1H), 0.75 (s, 3H), 0.65-0.55 (m, 3H).

Step 2

To a suspension of TEA (35.2 mg, 0.348 mmol) and 1H-pyrazole-4-carbon (12.9 mg, 0.139 mmol) in DMF (5 mL) was added J1 (50 mg, 0.116 mmol) at 25° C. under N$_2$. The mixture was stirred at 25° C. for 16 h. The mixture was concentrated to give a light yellow solid. The solid was purified by pre-HPLC (Column:YMC-Actus Triart C18 100*30 mm*5 um; Condition: water (0.05% HCl)-ACN; Gradient 53%-83% B; Gradient Time (min):9.5) to afford Compound 26 (22 mg, 43%) as a solid.

$^1$H NMR (400 MHz, CDCl$_3$) δ 7.85 (s, 1H), 7.81 (s, 1H), 5.05-4.87 (m, 2H), 3.88-3.82 (m, 1H), 2.70-2.58 (m, 1H), 2.28-2.15 (m, 1H), 2.05-1.56 (m, 7H), 1.48-1.15 (m, 17H), 0.76 (s, 3H), 0.66 (s, 3H).

LCMS Rt=0.828 min in 1.5 min chromatography, 5-95 AB, purity 100%, MS ESI calcd. for C$_{26}$H$_{34}$N$_3$O [M+H−2H$_2$O]$^+$ 404, found 404.

Example 15. Syntheses of Compounds 27 and 28

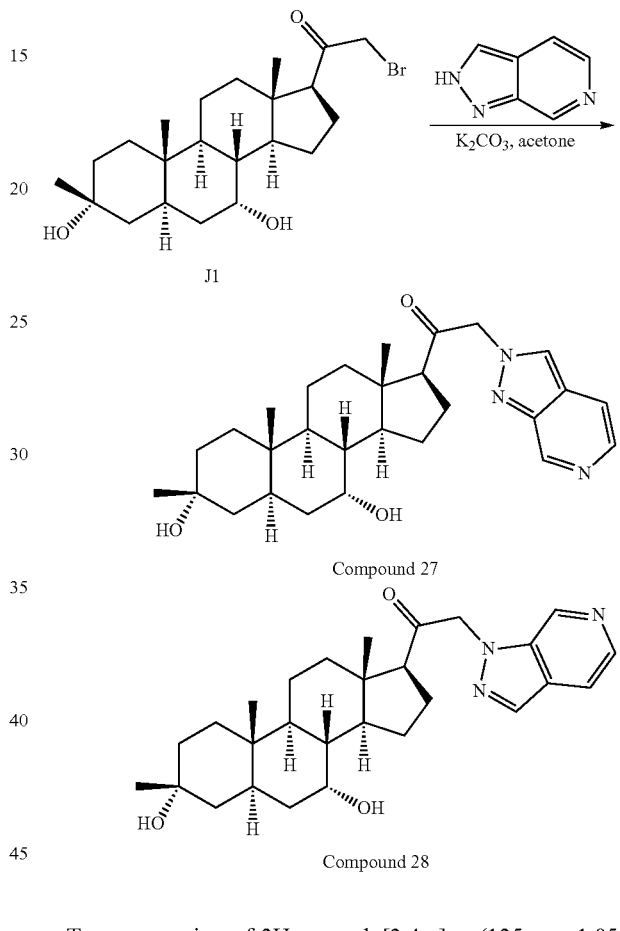

To a suspension of 2H-pyrazolo[3,4-c]py (125 mg, 1.05 mmol) and K$_2$CO$_3$ (193 mg, 1.40 mmol) in acetone (10 mL) was added J1 (300 mg, 0.701 mmol) at 15° C. under N$_2$. The mixture was stirred at 15° C. for 16 hrs. The mixture was filtered and concentrated to give a solid, which was purified by pre-HPLC (Column:Xtimate C18 150*25 mm*5 um; Condition: water (0.05% HCl)-ACN; Gradient 16%-41% B; Gradient Time (min):9.5) to afford Compound 27 (8.00 mg, 2%) as a solid and Compound 28 (6.00 mg, 2%) as a solid.

Compound 27

$^1$H NMR (400 MHz, CDCl3) δ 9.25 (s, 1H), 8.19-8.14 (m, 1H), 7.98 (s, 1H), 7.55-7.50 (m, 1H), 5.36-5.20 (m, 2H), 3.87-3.85 (m, 1H), 2.75-2.70 (m, 1H), 2.33-1.72 (m, 5H), 1.50-1.12 (m, 19H), 0.90-0.77 (m, 4H), 0.71 (s, 3H). LCMS Rt=0.725 min in 1.5 min chromatography, 5-95 AB, purity 100%, MS ESI calcd. for C$_{28}$H$_{40}$N$_3$O$_3$ [M+H]$^+$ 466, found 466.

Compound 28

$^1$H NMR (400 MHz, CDCl3) δ 8.80 (s, 1H), 8.36-8.32 (m, 1H), 8.09 (s, 1H), 7.65-7.60 (m, 1H), 5.32-5.20 (m, 2H), 3.87-3.85 (m, 1H), 2.75-2.68 (m, 1H), 2.33-1.68 (m, 7H), 1.50-1.18 (m, 18H), 0.77 (s, 3H), 0.72 (s, 3H).

LCMS Rt=0.748 min in 1.5 min chromatography, 5-95 AB, purity 100%, MS ESI calcd. for $C_{28}H_{40}N_3O_3$ [M+H]$^+$ 466, found 466.

Example 16. Synthesis of Compound 29

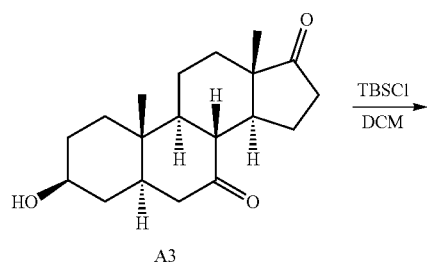

A3

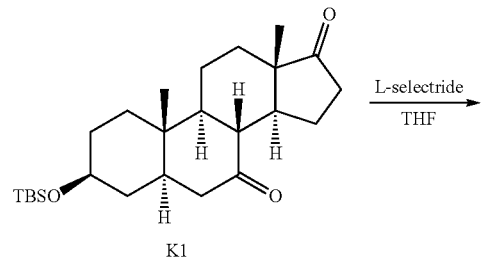

K1

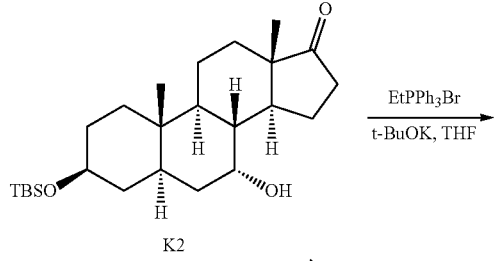

K2

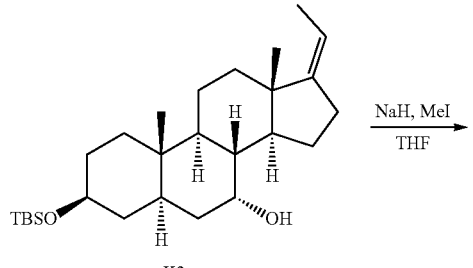

K3

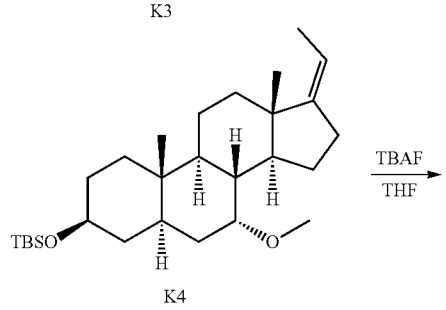

K4

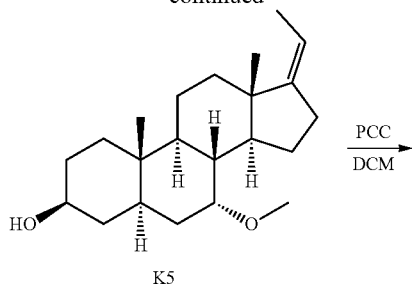

K5

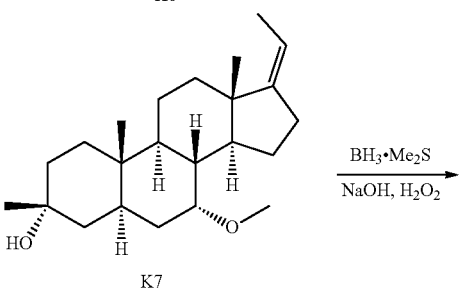

K6

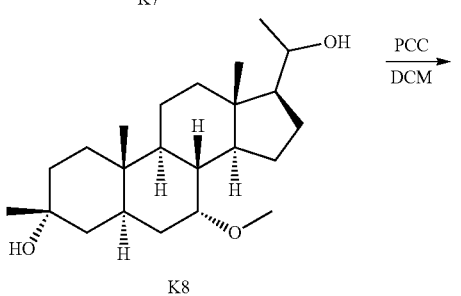

K7

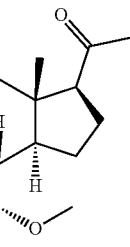

K8

Compound 29

Step 1

To a solution of A3 (82 g, 269 mmol) in DCM (500 mL) was added imidazole (27.4 g, 403 mmol) and TBSCl (60.7 g, 403 mmol) at 25° C. The reaction mixture was stirred at 25° C. for 5 hours. The reaction mixture was concentrated under reduced pressure. The residue was triturated from MeOH (500 mL) to give K1 (102 g, 91%) as a solid.

¹H NMR (400 MHz, CDCl₃) δ 3.62-3.50 (m, 1H), 2.65-2.29 (m, 4H), 2.20-2.01 (m, 2H), 1.85-1.63 (m, 6H), 1.56-1.38 (m, 6H), 1.26-0.93 (m, 5H), 0.92-0.80 (m, 12H), 0.04 (s, 6H).

Step 2

To a solution of K1 (25 g, 59.7 mmol) in THF (50 mL) was added L-selectride (65.6 mL, 1 M in THF, 65.6 mmol) at −70° C. under $N_2$. The reaction mixture was stirred at −70° C. for 5 hours. The reaction mixture was quenched by water (50 mL). The mixture was extracted with EtOAc (3×150 mL). The combined organic phase was washed with saturated brine (2×150 mL), dried over anhydrous $Na_2SO_4$, filtered and concentrated. The residue was purified by silica gel chromatography (PE/EtOAc=30/1 to 3/1) to afford K2 (16 g, crude) as a solid.

¹H NMR (400 MHz, CDCl₃) δ 3.97 (s, 1H), 3.64-3.52 (m, 1H), 2.52-2.38 (m, 1H), 2.18-1.97 (m, 2H), 1.86-1.43 (m, 11H), 1.42-1.13 (m, 6H), 1.08-0.96 (m, 1H), 0.93-0.79 (m, 15H), 0.044 (s, 6H).

Step 5

To a solution of EtPPh₃Br (39.3 g, 106 mmol) in THF (100 mL) was added t-BuOK (11.8 g, 106 mmol) at 25° C. under $N_2$. The reaction mixture was stirred at 25° C. for 0.5 hour. K2 (15 g, 35.6 mmol) was added to the reaction mixture under $N_2$. The reaction mixture was stirred at 50° C. for 5 hours. The reaction mixture was quenched by water (50 mL). The mixture was extracted with EtOAc (3×150 mL). The combined organic phase was washed with brine (2×50 mL), dried over $Na_2SO_4$, filtered and concentrated in vacuum. The residue was purified by silica gel chromatography (PE/EtOAc=30/1 to 10/1) to afford K3 (5.5 g, 36%) and K3 (6 g, crude) as a solid.

¹H NMR (400 MHz, CDCl₃) δ 5.19-5.05 (m, 1H), 3.88 (s, 1H), 3.63-3.52 (m, 1H), 2.45-2.17 (m, 3H), 1.79-1.51 (m, 10H), 1.51-1.23 (m, 10H), 1.10-0.99 (m, 1H), 0.91-0.83 (m, 12H), 0.83-0.78 (m, 3H), 0.07-0.02 (m, 6H).

Step 6

To a solution of K3 (5 g, 11.5 mmol) in THF (50 mL) was added NaH (2.28 g, 60%, 57.4 mmol) at 0° C. The reaction mixture was stirred at 0° C. for 0.5 hour under $N_2$. MeI (44 g, 309 mmol) was added to the reaction mixture at 0° C. The reaction mixture was stirred at 40° C. for 20 hours. The reaction mixture was quenched with ice-water (30 mL) and stirred for 20 mins. The aqueous phase was extracted with EtOAc (3×50 mL). The combined organic phase was washed with brine (2×50 mL), dried over anhydrous $Na_2SO_4$, filtered and concentrated. The residue was purified by silica gel chromatography (PE/EtOAc=50/1 to 10/1) to afford K4 (1.8 g, 35%) as a solid.

¹H NMR (400 MHz, CDCl₃) δ 5.15-5.07 (m, 1H), 3.64-3.54 (m, 1H), 3.28 (s, 3H), 3.26-3.21 (m, 1H), 2.41-2.12 (m, 3H), 1.72-1.51 (m, 10H), 1.49-1.15 (m, 9H), 1.06-0.97 (m, 1H), 0.97-0.77 (m, 15H), 0.05 (s, 6H).

Step 7

To a solution of K4 (1.8 g, 4.02 mmol) in THF (30 mL) was added TBAF (12 mL, 1M in THF, 12.0 mmol) at 25° C., the reaction mixture was stirred at 40° C. for 15 hours. The reaction mixture was quenched with water (20 mL), The aqueous phase was extracted with EtOAc (3×50 mL). The combined organic phase was washed with brine (2×30 mL), dried over anhydrous $Na_2SO_4$, filtered and concentrated. The residue was triturated from water (40 mL) at 80° C. to give K5 (1.6 g, crude) as a solid.

¹H NMR (400 MHz, CDCl₃) δ 5.13-5.03 (m, 1H), 3.64-3.50 (m, 1H), 3.26-3.20 (m, 4H), 2.40-2.10 (m, 3H), 1.84-1.73 (m, 1H), 1.68-1.58 (m, 14H), 1.35-1.14 (m, 5H), 1.11-1.03 (m, 1H), 0.86-0.81 (m, 6H).

Step 8

To a solution of K5 (1.3 g, 3.90 mmol) in DCM (20 mL) was added silica gel (4 g) and PCC (1.68 g, 7.8 mmol) 25° C. The mixture was stirred at 25° C. for 3 hrs. The mixture was filtered though a pad of silica gel and the solid was washed with EtOAc/DCM (30/30 mL). filtered and concentrated under reduced pressure. The residue was purified by silica gel chromatography (PE/EtOAc=10/1 to 1/1) to afford K6 (1 g, 78%) as a solid.

¹H NMR (400 MHz, CDCl₃) δ 5.16-5.07 (m, 1H), 3.32-3.19 (m, 4H), 2.48-2.09 (m, 6H), 2.09-1.87 (m, 3H), 1.78-1.10 (m, 14H), 1.00 (s, 3H), 0.87 (s, 3H).

Step 9

Under nitrogen atmosphere, anhydrous THF (30 mL) was cooled to 10° C. and anhydrous LiCl (508 mg, 12.0 mmol) was added in one portion. The mixture was stirred for 30 inns to obtain a clear solution. To this solution was added anhydrous $FeCl_3$ (1.07 g, 6.64 mmol) in one portion. The resulting mixture was stirred for additional 30 mins. The reaction mixture was cooled to −35° C. and methyl magnesium bromide (8.03 mL, 3 M in ether, 24.1 mmol) was added dropwise maintaining the internal temperature between −35° C. and −30° C. The above mixture was stirred for 30 mins at −30° C. K6 (1 g, 3.02 mmol) in THF (10 mL) was added in one portion. The internal temperature was allowed to −20° C. and held between −15° C. and −20° C. for 2 hrs. The reaction mixture was poured into ice-cooled aqueous HCl (1 M, 50 mL), extracted with EtOAc (2×100 mL). The combined organic layer was washed with water (50 mL), aqueous NaOH (10%, 2×100 mL) and brine (100 mL), dried over anhydrous sodium sulfate, filtered and concentrated. The residue was purified by column chromatography on silica gel (PE/EtOAc=20/1 to 2/1) to give K7 (800 mg, 77%) as a solid.

¹H NMR (400 MHz, CDCl₃) δ 5.17-5.07 (m, 1H), 3.25 (s, 4H), 2.42-2.15 (m, 3H), 1.90-1.80 (m, 1H), 1.67-1.57 (m, 6H), 1.55-1.37 (m, 7H), 1.35-1.14 (m, 10H), 0.84 (s, 3H), 0.76 (s, 3H).

Step 10

To a solution of K7 (0.8 g, 2.3 mmol) in THF (25 mL) was added $BH_3.Me_2S$ (2.3 mL, 10 M in THF, 23 mmol) slowly at 0° C. under $N_2$. The reaction mixture was stirred at 25° C. for 12 hrs. After the mixture was cooled to 0° C., a solution of NaOH (7.66 mL, 3 M in $H_2O$, 23.0 mmol) was added into the mixture very slowly. After the addition was complete, $H_2O_2$ (2.6 g, 30%) was added slowly and the inner temperature was maintained below 10° C. The mixture was stirred at 25° C. for 2 hrs. The resulting solution was extracted with EtOAc (3×150 mL). The combined organic layers were washed with aqueous $Na_2S_2O_3$ (40 mL), brine (50 mL), dried over $Na_2SO_4$. The mixture was filtered. The filtrate was concentrated in vacuum to give K8 (650 mg, crude) as a solid. The crude product was used next step without further purification.

Step 11

To a solution of K8 (0.65 g, 1.78 mmol) in DCM (20 mL) was added silica gel (1.71 g) and PCC (0.765 g, 3.56 mmol) at 25° C. The reaction mixture was stirred at 25° C. for 4 hours. The solution was filtered and the filter cake was washed with EtOAc (10 mL). The solution was filtered and the filter cake was washed with EtOAc (30 mL). The solution was concentrated in vacuo. The residue was purified by silica gel chromatography (PE/EtOAc=50/1 to 1/1) to afford Compound 29 (0.12 g, 19%) as a solid.

$^1$H NMR (400 MHz, CDCl$_3$) δ 3.26 (s, 3H), 3.24-3.19 (m, 1H), 2.62-2.54 (m, 1H), 2.12-2.14 (m, 1H), 2.11 (s, 3H), 2.03-1.84 (m, 2H), 1.74-1.59 (m, 5H), 1.56-1.35 (m, 7H), 1.32-1.11 (m, 9H), 0.75 (s, 3H), 0.59 (s, 3H).

LCMS Rt=0.991 min in 2 min chromatography, 30-90AB_ELSD, purity 97.6.0%, MS ESI calcd. for C$_{22}$H$_{33}$O [M–H$_2$O—CH$_3$OH]$^+$ 313, found 313.

Example 17. Syntheses of Compounds 30 and 31

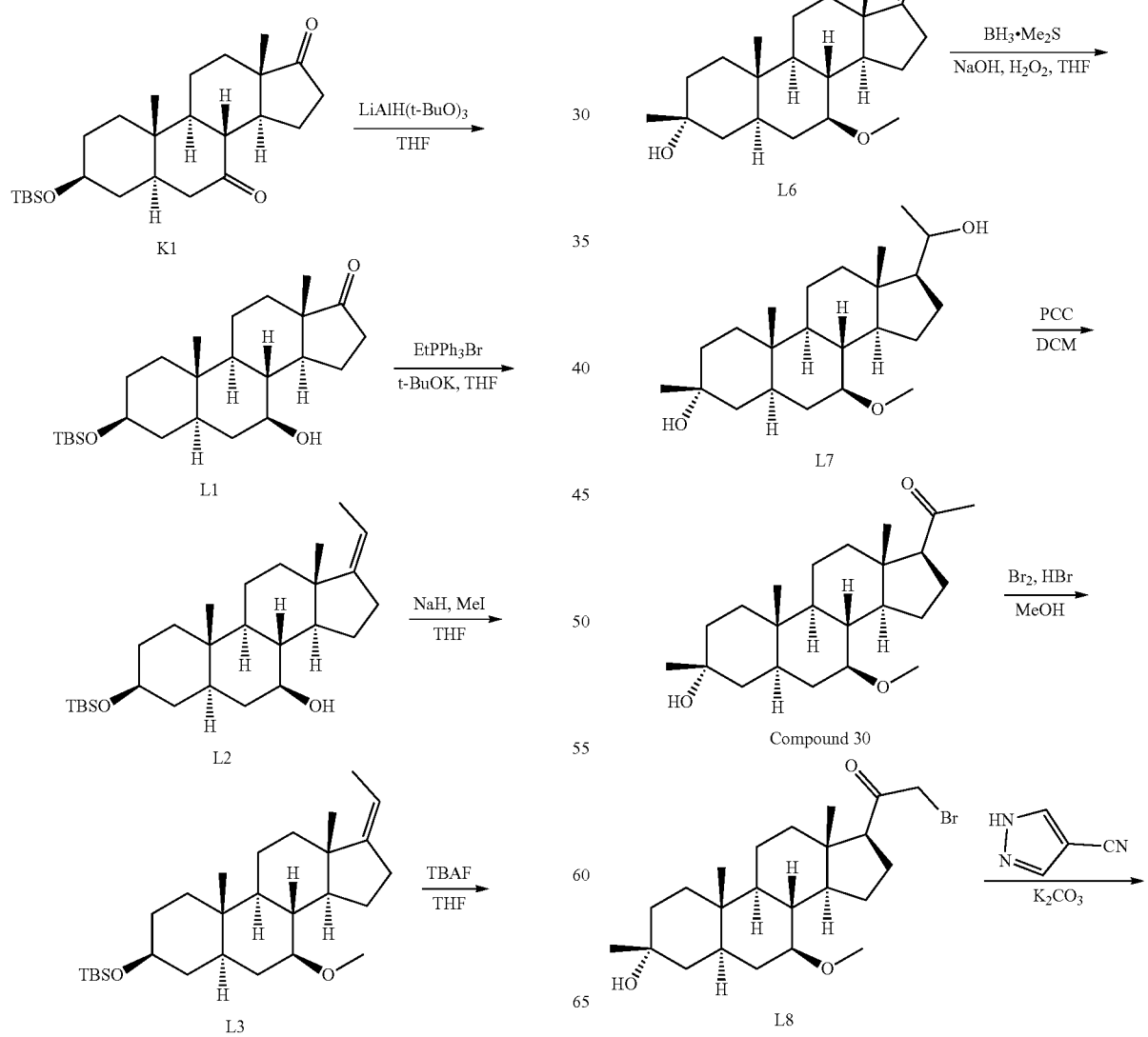

-continued

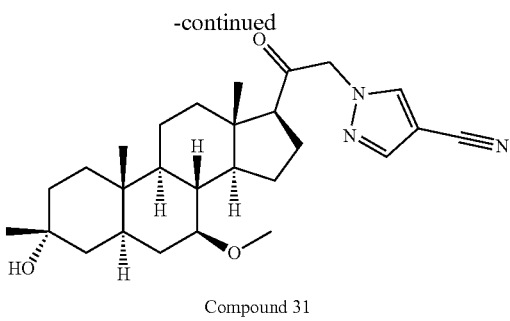

Compound 31

Step 1

To a solution of K1 (15 g, 35.8 mmol) in THF (100 mL) was added LiAlH(t-BuO)₃ (27.2 g, 107 mmol) at −70° C., the reaction mixture was stirred at −70° C. for 5 hours. The reaction mixture was poured into ice-water (50 mL) and stirred for 20 min. The organic layer was separated. The aqueous phase was extracted with EtOAc (2×50 mL). The combined organic phase was washed with saturated brine (2×30 mL), dried over anhydrous $Na_2SO_4$, filtered and concentrated. The residue was purified by flash column (0~10% of EtOAc in PE) to afford L1 (8 g, crude) as a solid.

$^1$H NMR (400 MHz, $CDCl_3$) δ 3.65-3.41 (m, 2H), 2.53-2.38 (m, 1H), 2.30-1.95 (m, 2H), 1.95-1.65 (m, 6H), 1.65-1.38 (m, 8H), 1.38-0.99 (m, 4H), 0.99-0.78 (m, 14H), 0.78-0.65 (m, 1H), 0.046 (m, 6H).

Step 2

To a solution of bromo(ethyl)triphenylphosphorane (28.2 g, 76.0 mmol) in THF (100 mL) was added t-BuOK (8.52 g, 76.0 mmol) at 25° C. The mixture was heated to 60° C. and stirred for 1 h. A solution of L1 (8 g, 19.0 mmol) in THF (20 mL) was added. The mixture was stirred at 60° C. for 16 hrs. The mixture was treated with $NH_4Cl$ (50 mL, sat. aq.). The organic layer was separated. The aqueous phase was extracted with EtOAc (2×50 mL). The combined organic phase was washed with saturated brine (2×50 mL), dried over anhydrous Na2SO4, filtered, concentrated. The residue was purified by flash column (0~5% of EtOAc in PE) to give L2 (5 g, 61%) as a solid.

$^1$H NMR (400 MHz, $CDCl_3$) δ 5.22-5.05 (m, 1H), 3.65-3.49 (m, 1H), 3.49-3.30 (m, 1H), 2.48-2.35 (m, 1H), 2.35-2.19 (m, 2H), 1.98-1.85 (m, 1H), 1.75-1.55 (m, 11H), 1.55-1.25 (m, 9H), 1.25-1.10 (m, 1H), 0.95-0.80 (m, 14H), 0.047 (s, 6H).

Step 3

To a solution of L2 (5 g, 11.5 mmol) in THF (50 mL) was added NaH (2.28 g, 57.4 mmol, 60% in mineral oil) in one portion at 0° C. under $N_2$. After 30 min, MeI (16.1 g, 114 mmol) was added dropwise at 20° C. The reaction mixture was stirred for 6 hours at 40° C. The mixture was quenched with saturated aqueous $NH_4Cl$ (20 mL, sat. aq.) at 0° C. The organic layer was separated. The aqueous phase was extracted with EtOAc (2×20 mL). The combined organic phases was washed with saturated brine (2×20 mL), dried over anhydrous $Na_2SO_4$, filtered and concentrated to afford L3 (5 g, crude) as a solid which used directly for the next step.

$^1$H NMR (400 MHz, $CDCl_3$) δ 5.20-5.10 (m, 1H), 3.60-3.55 (m, 1H), 3.28 (s, 3H), 2.90-2.75 (m, 1H), 2.41-2.05 (m, 3H), 1.85-1.35 (m, 14H), 1.35-1.00 (m, 6H), 1.00-0.65 (m, 15H), 0.05 (m, 6H).

Step 4

To a solution L3 (5 g, 11.1 mmol) in THF (10 mL) was added TBAF (55.5 mL, 55.5 mmol, 1 M in THF). The reaction mixture was stirred at 80° C. for 16 h. The reaction mixture was poured into water (50 mL). The organic layer was separated. The aqueous phase was extracted with EtOAc (2×20 mL). The combined organic phase was washed with saturated brine (2×20 mL), dried over anhydrous $Na_2SO_4$, filtered and concentrated to give L4 (3.6 g, impure) as a solid.

Step 5

To a solution of L4 (3.6 g, 10.8 mmol) in DCM (20 mL) was added silica gel (3 g) and PCC (4.64 g, 21.6 mmol) at 20° C. The mixture was stirred at 20° C. for 2 hrs. The mixture was filtered and the filter cake was washed with DCM (2×10 mL). The combined filtrate was concentrated in vacuum to give L5 (3 g, crude) as a solid.

Step 6

Under $N_2$, anhydrous THF (10 mL) was cooled to 15° C. and anhydrous LiCl (1.53 g, 36.2 mmol) was added in one portion. The mixture was stirred for 30 min to obtain a clear solution. To this solution was added anhydrous $FeCl_3$ (3.22 g, 19.9 mmol) in one portion. The resulting mixture was stirred for additional 30 mins. The reaction mixture was cooled to −35° C. and methyl magnesium bromide (3 M in diethyl ether, 12.0 mL, 36.2 mmol) was added dropwise maintaining the internal temperature between −35° C. and −30° C. The above mixture was stirred for 30 min at −30° C. L5 (3 g, 9.07 mmol) in THF (10 mL) was added in one portion. The internal temperature was allowed to −20° C. and held between −15° C. and −20° C. for 2 hrs. The reaction mixture was poured to ice-cooled aqueous HCl (1 M, 20 mL), extracted with EtOAc (2×20 mL). The organic layer was separated. The combined organic layer was washed with water (20 mL), aqueous NaOH (10%, 2×20 mL) and brine (20 mL), dried over anhydrous sodium sulfate, filtered and concentrated. The residue was purified by flash column (0~10% of EtOAc in PE) to give L6 (2.8 g, 89%) as a solid.

$^1$H NMR (400 MHz, $CDCl_3$) δ 5.20-5.00 (m, 1H), 3.27 (s, 3H), 2.90-2.80 (m, 1H), 2.45-2.10 (m, 4H), 2.90-1.45 (m, 11H), 1.45-1.05 (m, 11H), 0.95-0.72 (m, 7H).

Step 7

To a solution of L6 (2.8 g, 8.07 mmol) in THF (15 mL) was added dropwise a solution of $BH_3.Me_2S$ (8.07 mL, 10M, 80.7 mmol) at 0° C. The solution was stirred at 15° C. for 3 h. After cooling to 0° C., a solution of NaOH solution (48.4 mL, 2M, 96.8 mmol) was added very slowly. After addition, $H_2O_2$ (8.07 mL, 80.7 mmol, 30% in water) was added slowly and the inner temperature was maintained below 10° C. The resulting solution was stirred at 15° C. for 2 h. Then saturated aqueous $Na_2S_2O_3$ (20 mL) was added until the reaction solution became clear. The mixture was extracted with EtOAc (3×20 mL). The combined organic solution was washed with saturated aqueous $Na_2S_2O_3$ (2×10 mL), brine (20 mL), dried over $Na_2SO_4$, filtered and concentrated in vacuum to give L7 (3.1 g, crude) as a solid which was used in next step without further purification.

Step 8

To a solution of L7 (3.1 g, 8.50 mmol) in DCM (20 mL) was added PCC (3.65 g, 17.0 mmol) and silica gel (3 g) at 25° C. The solution was stirred at 25° C. for 3 h. The reaction mixture was filtered and the filter cake was washed with anhydrous DCM (2×20 mL). The combined filtrate was concentrated in vacuum. The residue purified by flash column (0~20% of EtOAc in PE) to give Compound 30 (2 g, impure) as a solid. The residue Compound 30 (2 g, 5.51 mmol) was re-crystallized from MeCN (20 mL) at 65° C. to give Compound 30 (24 mg, 1%, pure) as a solid. The mother liquid was concentrated to give Compound 30 (1776 mg, impure) as a solid.

$^1$H NMR (400 MHz, CDCl$_3$) δ 3.26 (s, 3H), 2.90-2.80 (m, 1H), 2.50-2.41 (m, 1H), 2.20-2.08 (m, 4H), 2.08-1.95 (m, 1H), 1.82-1.70 (m, 2H), 1.70-1.60 (m, 3H), 1.60-1.45 (m, 5H), 1.45-1.20 (m, 9H), 1.20-1.05 (m, 2H), 0.90-0.80 (m, 1H), 0.76 (s, 3H), 0.62 (s, 3H).

LCMS $t_R$=0.905 min in 2 min chromatography, 30-90AB_ELSD, purity 100.0%, MS ESI calcd. for $C_{22}H_{33}O$ [M–H$_2$O—CH$_3$O]$^+$ 313, found 313.

Step 9

To a solution of Compound 30 (200 mg, 551 µmol) in MeOH (10 mL) was added HBr (11.1 mg, 0.0551 mmol, 40% in water) and Br$_2$ (105 mg, 0.661 mmol) at 25° C. The mixture was stirred at 25° C. for 2 hrs. The mixture was quenched by sat·aq NaHCO$_3$ (10 mL), treated with water (20 mL). The mixture was extracted with DCM (2×20 mL). The combined organic phase was washed with brine (20 mL), dried over anhydrous Na$_2$SO$_4$, filtered, concentrated in vacuum to afford L8 (230 mg, crude) as a pale yellow oil, which was used directly in next step without further purification.

Step 10

To a solution of L8 (230 mg, 0.521 mmol) in acetone (5 mL) was added K$_2$CO$_3$ (143 mg, 1.04 mmol) and 1H-pyrazole-4-carbonitrile (58.1 mg, 0.625 mmol) at 25° C. The mixture was stirred at 25° C. for 16 hrs. The mixture was treated with water (20 mL). The mixture was extracted with DCM (2×10 mL). The combined organic phase was washed with brine (10 mL), dried over anhydrous Na$_2$SO$_4$, filtered, concentrated. The residue was purified by flash column (0~50% of EtOAc in PE) to give Compound 31 (63 mg, 27%) as a solid.

$^1$H NMR (400 MHz, CDCl$_3$) δ 7.85 (s, 1H), 7.80 (s, 1H), 5.08-4.85 (m, 2H), 3.27 (s, 3H), 2.85-2.75 (m, 1H), 2.55-2.45 (m, 1H), 2.22-2.12 (m, 1H), 2.12-2.00 (m, 1H), 1.90-1.65 (m, 5H), 1.65-1.1.28 (m, 11H), 1.28-1.20 (m, 3H), 1.20-1.05 (m, 2H), 0.90-0.80 (m, 1H), 0.77 (s, 3H), 0.68 (s, 3H).

LCMS $t_R$=0.912 min in 2 min chromatography, 30-90AB_ELSD, purity 100.0%, MS ESI calcd. for $C_{27}H_{40}N_3O_3$ [M+H]$^+$ 454, found 454.

Example 18. Syntheses of Compounds 32 and 33

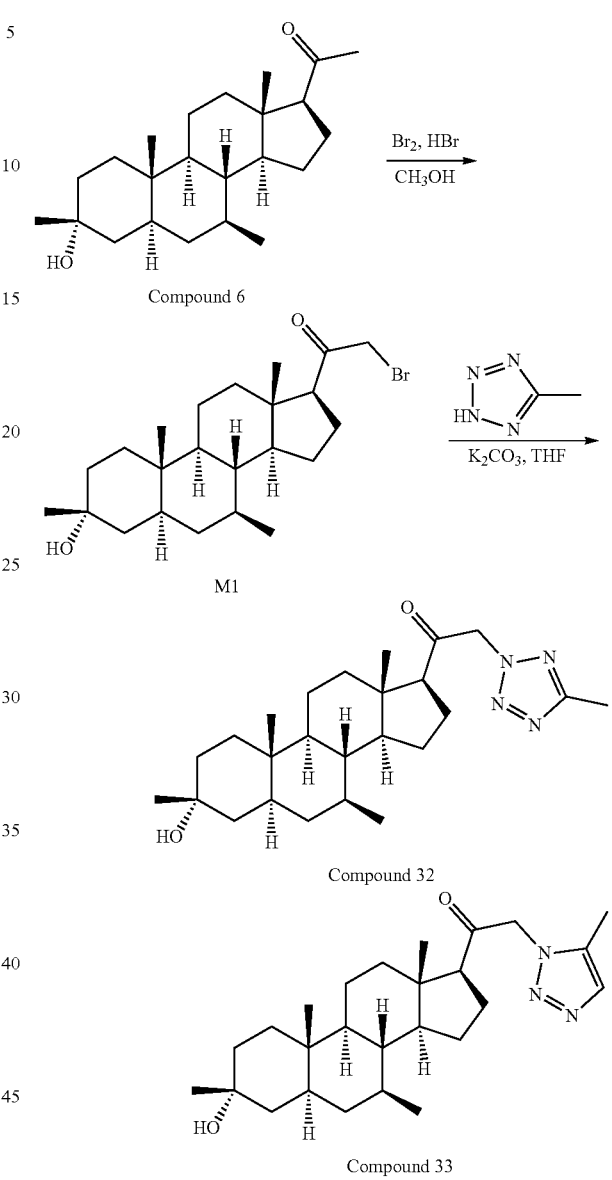

Step 1

To a solution of Compound 6 (1 g, 2.88 mmol) in MeOH (10 ml) was added HBr (0.1 mL, 40% in water) and Br$_2$ (551 mg, 3.45 mmol) at 25° C. The mixture was stirred at 25° C. for 3 hrs. The mixture was quenched with saturated aqueous NaHCO$_3$ (10 mL), treated with water (20 mL) and extracted with EtOAc (2×30 mL). The combined organic phase was washed with Sat Na$_2$S$_2$O$_3$ (50 mL) and brine (50 mL), dried over anhydrous Na$_2$SO$_4$, filtered and concentrated in vacuum. The residue was purified by flash chromatography eluting with (petroleum ether/ethyl acetate=5/1) to give M1 (800 mg, 66%) as a solid.

$^1$H NMR (400 MHz, CDCl$_3$) δ 3.95-3.88 (m, 2H), 2.76 (t, J=8 Hz, 1H), 2.20-2.11 (m, 1H), 1.95-1.84 (m, 2H), 1.78-

1.67 (m, 2H), 1.53-1.43 (m, 4H), 1.42-1.38 (m, 1H), 1.34-1.08 (m, 13H), 1.03-0.93 (m, 4H), 0.87-0.80 (m, 1H), 0.71 (s, 3H), 0.65 (s, 3H).

Step 2

To a solution of M1 (200 mg, 0.47 mmol) in acetone (2 mL) was added $K_2CO_3$ (161 mg, 1.17 mmol) and 5-methyl-2H-tetrazole (59.2 mg, 0.705 mmol). The mixture was stirred at 25° C. for 16 hours. To the mixture was added water (10 mL) and ethyl acetate (20 mL). The organic layer was separated. The aqueous phase was extracted with ethyl acetate (50 mL). The combined organic layers was washed with brine (100 mL), dried over $Na_2SO_4$, filtered and concentrated in vacuum. The residue was purified by flash chromatography eluting with (petroleum ether/ethyl acetate=2/1) to give Compound 32 (56 mg, 28%) and Compound 33 (82 mg, 41%) as a solid.

Compound 33

$^1$HNMR (400 MHz, $CDCl_3$) δ 5.17-5.03 (m, 2H), 2.60 (t, J=8 Hz, 1H), 2.46 (s, 3H), 2.25-2.13 (m, 1H), 2.07-1.87 (m, 1H), 1.83-1.70 (m, 2H), 1.56-1.42 (m, 6H), 1.40-1.11 (m, 13H), 1.05-0.95 (m, 4H), 0.90-0.81 (m, 1H), 0.73 (s, 3H), 0.69 (s, 3H).

LCMS Rt=1.043 min in 2.0 min chromatography, 30-90 AB, purity 100%, MS ESI calcd. For $C_{25}H_{41}N_4O_2$ $[M+H]^+$ 429, found 429.

Example 19. Syntheses of Compounds 34, 35, 36, and 37

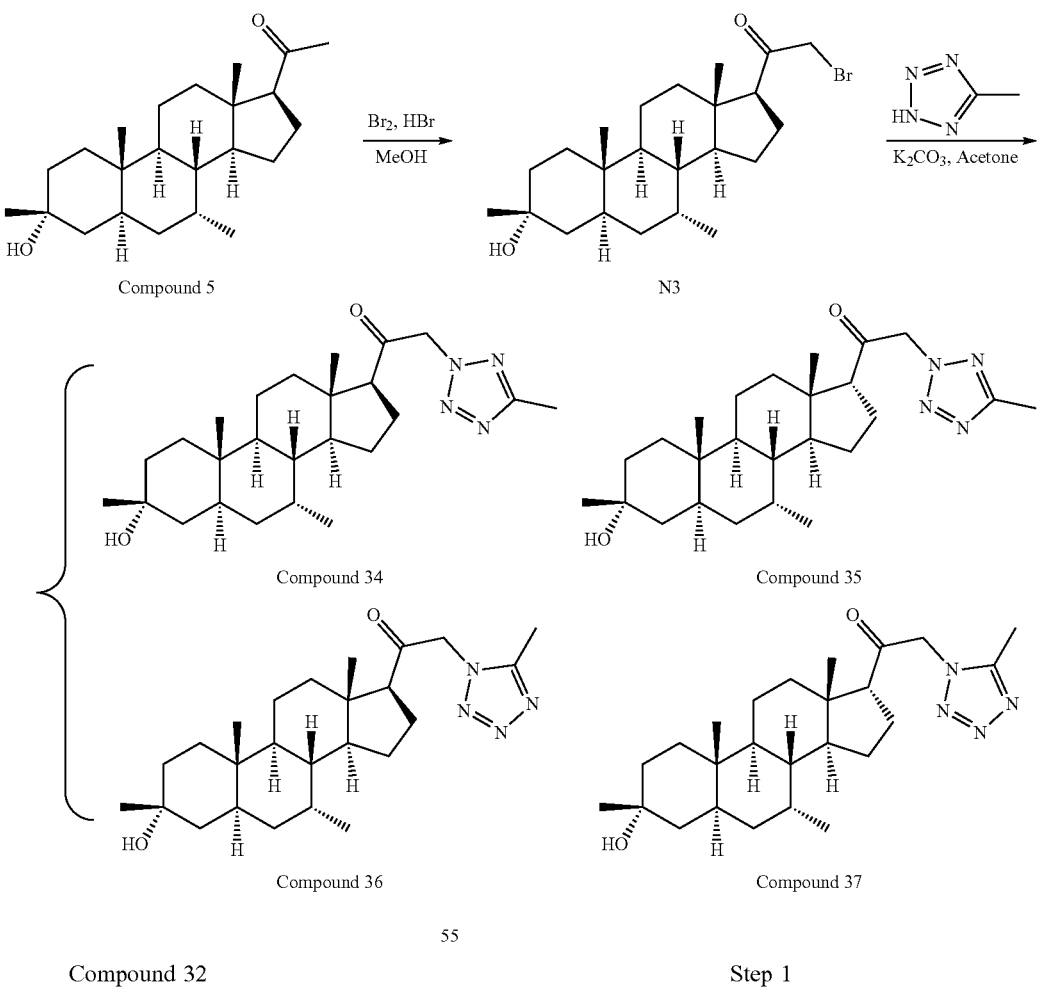

Compound 32

$^1$HNMR (400 MHz, $CDCl_3$) δ 5.40-5.31 (m, 2H), 2.59-2.54 (m, 4H), 2.23-2.13 (m, 1H), 2.10-2.02 (m, 1H), 1.98-1.85 (m, 1H), 1.82-1.68 (m, 2H), 1.54-1.39 (m, 5H), 1.37-1.15 (m, 13H), 1.04-0.94 (m, 4H), 0.90-0.81 (m, 1H), 0.72 (s, 6H).

LCMS Rt=1.103 min in 2.0 min chromatography, 30-90 AB, purity 100%, MS ESI calcd. For $C_{25}H_{41}N_4O_2$ $[M+H]^+$ 429, found 429.

Step 1

To a solution of Compound 5 (1.1 g, 3.17 mmol) in MeOH (20 mL) was added HBr (126 mg, 0.634 mmol, 40% in water) and $Br_2$ (608 mg, 3.80 mmol) at 25° C. The mixture was stirred at 25° C. for 1 h. The mixture was quenched by sat·$NaHCO_3$ (20 mL), and treated with water (20 mL). The mixture was extracted with DCM (2×30 mL). The combined organic phase was washed with brine (2×20 mL), dried over anhydrous $Na_2SO_4$, filtered, concentrated in vacuum to afford N3 (1.2 g, impure) as a solid used directly for the next step.

¹H NMR (400 MHz, CDCl₃) δ 3.95-3.85 (m, 2H), 2.85-2.75 (m, 1H), 2.25-2.10 (m, 1H), 1.95-1.69 (m, 7H), 1.69-1.41 (m, 8H), 1.41-0.98 (m, 12H), 0.98-0.75 (m, 3H), 0.63 (s, 3H).

Step 2

To a solution of N3 (350 mg, 0.822 mmol) in acetone (10 mL) was added K₂CO₃ (226 mg, 1.64 mmol) and 5-methyl-2H-tetrazole (137 mg, 1.64 mmol) at 25° C. The mixture was stirred at 25° C. for 16 hrs. The reaction mixture was treated with water (20 mL). The mixture was extracted with CH₂Cl₂ (2×20 mL). The combined organic phase was washed with brine (20 mL), dried over anhydrous Na₂SO₄, filtered, concentrated in vacuum. The residue was purified by flash column (0~100% of EtOAc in PE) to afford Compound 35 (5 mg, 1%) as a solid, Compound 34 (49 mg, 14%) as a solid, Compound 37 (6 mg, 2%) as a solid and Compound 36 (41 mg, 12%) as a solid.

Compound 34

¹H NMR (400 MHz, CDCl₃) δ 5.40-5.30 (m, 2H), 2.65-2.60 (m, 1H), 2.56 (s, 3H), 2.30-2.15 (m, 1H), 2.09-2.00 (m, 1H), 1.89-1.55 (m, 6H), 1.55-1.01 (m, 17H), 1.01-0.90 (m, 3H), 0.77 (s, 3H), 0.70 (s, 3H).

LCMS Rt=1.084 min in 2 min chromatography, 30-90AB_ELSD, purity 100.0%, MS ESI calcd. for $C_{25}H_{41}N_4O_2$ [M+H]⁺ 429, found 429.

Compound 35

¹H NMR (400 MHz, CDCl₃) δ 5.45-5.25 (m, 2H), 2.80-2.70 (m, 1H), 2.57 (s, 3H), 2.00-1.65 (m, 7H), 1.50-1.40 (m, 5H), 1.40-1.22 (m, 6H), 1.22-1.15 (m, 5H), 1.15-1.00 (m, 2H), 0.94 (s, 3H), 0.94-0.89 (m, 3H), 0.75 (s, 3H).

LCMS Rt=1.094 min in 2 min chromatography, 30-90AB_ELSD, purity 100.0%, MS ESI calcd. for $C_{25}H_{39}N_4O$ [M+H-H2O]⁺ 411, found 411.

Compound 36

¹H NMR (400 MHz, CDCl₃) δ 5.20-5.00 (m, 2H), 2.70-2.60 (m, 1H), 2.47 (s, 3H), 2.25-2.15 (m, 1H), 2.10-2.00 (m, 1H), 1.90-1.65 (m, 5H), 1.65-1.25 (m, 10H), 1.25-1.11 (m, 7H), 1.11-1.05 (m, 1H), 1.05-0.95 (m, 3H), 0.77 (s, 3H), 0.67 (s, 3H).

LCMS Rt=1.007 min in 2 min chromatography, 30-90AB_ELSD, purity 100.0%, MS ESI calcd. for $C_{25}H_{41}N_4O_2$ [M+H]⁺ 429, found 429.

Compound 37

¹H NMR (400 MHz, CDCl₃) δ 5.30-5.20 (m, 1H), δ 5.00-4.90 (m, 1H), 2.90-2.80 (m, 1H), 2.48 (s, 3H), 1.95-1.65 (m, 7H), 1.45-1.40 (m, 3H), 1.40-1.22 (m, 7H), 1.22-1.10 (m, 6H), 1.10-1.06 (m, 2H), 0.97 (s, 3H), 0.96-0.93 (m, 3H), 0.75 (s, 3H).

LCMS Rt=1.021 min in 2 min chromatography, 30-90AB_ELSD, purity 100.0%, MS ESI calcd. for $C_{25}H_{39}N_4O$ [M+H-H2O]⁺ 411, found 411.

Example 20. Syntheses of Compounds 38 and 39

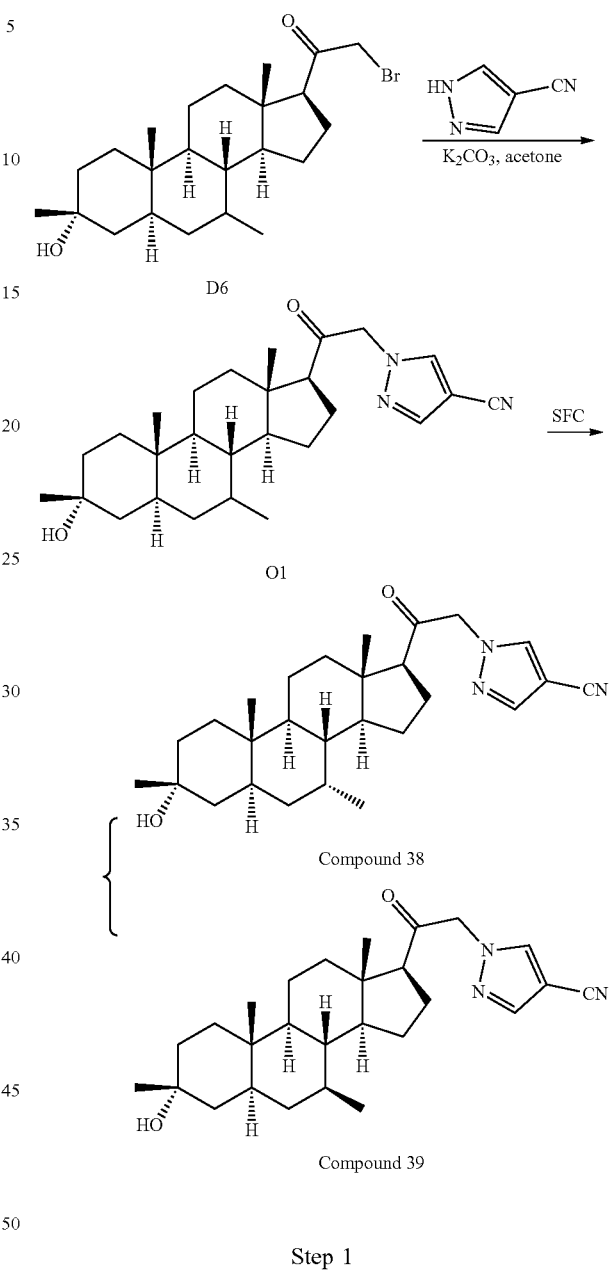

Step 1

To a solution of D6 (500 mg, 1.17 mmol) in acetone (10 mL) was added K₂CO₃ (322 mg, 2.34 mmol) and 1H-pyrazole-4-carbonitrile (162 mg, 1.75 mmol). After stirring at 25° C. for 12 hours, the mixture was poured in to water (50 mL) and extracted with ethyl acetate (3×50 mL). The combined organic layers was washed with brine (150 mL), dried over Na₂SO₄, filtered and concentrated in vacuum. The residue was purified by flash column (0~15% of EtOAc in PE) to afford O1 (340 mg, 60%) as a solid.

¹H NMR (400 MHz, CDCl₃) δ 7.99-7.78 (m, 2H), 5.07-4.84 (m, 2H), 2.67-2.49 (m, 1H), 2.26-2.13 (m, 1H), 2.02-1.81 (m, 2H), 1.64-1.38 (m, 10H), 1.34-0.99 (m, 12H), 0.98-0.91 (m, 3H), 0.76 (s, 2H), 0.72 (s, 1H), 0.69-0.63 (m, 3H).

Step 2

O1 (340 mg, 0.77 mmol) was purified by SFC (column: OD (250 mm*30 mm, 5 um)), gradient: 45-45% B (A=0.1% NH$_3$/H$_2$O, B=EtOH), flow rate: 50 mL/min) to give Compound 38 (145 mg, 43%) and Compound 39 (84 mg, 24%) as a solid.

Compound 38

$^1$H NMR (400 MHz, CDCl$_3$) δ 7.88-7.78 (d, J=19.2 Hz, 2H), 5.06-4.84 (m, 2H), 2.64-2.56 (m, 1H), 2.26-2.15 (m, 1H), 2.04-1.96 (m, 1H), 1.84-1.64 (m, 5H), 1.55-1.24 (m, 11H), 1.22-1.09 (m, 6H), 1.07-0.99 (m, 1H), 0.96-0.89 (m, 3H), 0.76 (s, 3H), 0.66 (s, 3H).

LCMS Rt=1.037 min in 2 min chromatography, 30-90AB_2MIN_E, purity 100%, MS ESI calcd. for C$_{27}$H$_{40}$N$_3$O$_2$ [M+H]$^+$ 438, found 438.

SFC Rt=4.998 min in 10 min chromatography, OD_3_EtOH_DEA_5_40_25ML, purity: 99.8%.

Note: The structure of Compound 38 was confirmed by X-ray.

Compound 39

$^1$H NMR (400 MHz, CDCl$_3$) δ 7.87-7.78 (d, J=17.2 Hz, 2H), 5.07-4.86 (m, 2H), 2.57-2.49 (m, 1H), 2.23-2.13 (m, 1H), 2.06-1.99 (m, 1H), 1.97-1.86 (m, 1H), 1.79-1.67 (m, 2H), 1.55-1.36 (m, 6H), 1.35-1.13 (m, 12H), 1.05-0.92 (m, 4H), 0.89-0.81 (m, 1H), 0.72 (s, 3H), 0.68 (s, 3H).

LCMS Rt=1.051 min in 2 min chromatography, 30-90AB_2MIN_E, purity 100%, MS ESI calcd. for C$_{27}$H$_{39}$N$_3$O$_2$Na [M+Na]$^+$ 460, found 460.

SFC Rt=6.270 min in 10 min chromatography, OD_3_EtOH_DEA_5_40_25ML, purity: 100%.

Example 21. Synthesis of Compound 40

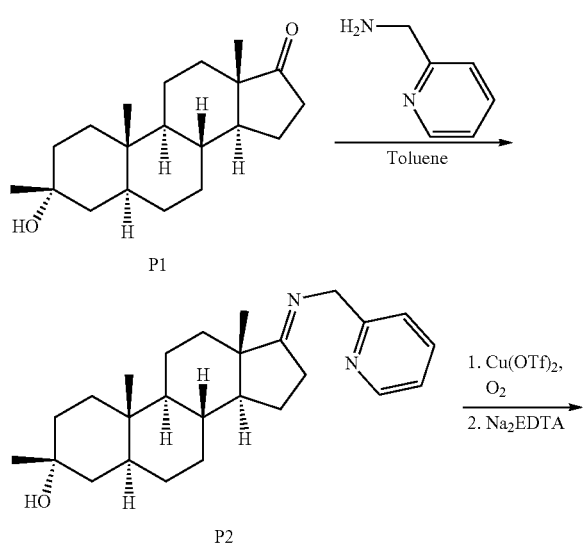

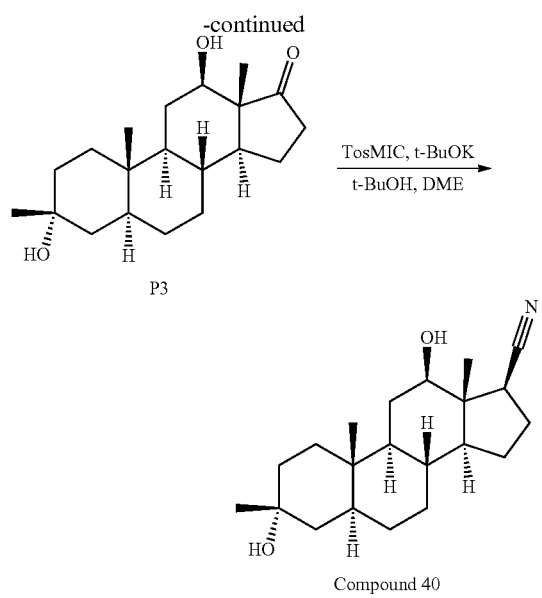

Compound 40

Step 1

To a solution of P1 (2 g, 6.56 mmol) in toluene (20 mL) was added p-toluenesulfonic acid (20 mg, 0.116 mmol) and pyridin-2-ylmethanamine (1.55 g, 14.4 mmol) at 25° C. The reaction mixture was heated to 130° C. in a Dean-Stark apparatus for 16 h. The reaction was cooled to 25° C. and diluted with EtOAc (30 mL). The organic layer was washed sequentially with sat. NH$_4$Cl (2×20 mL), sat. NaHCO$_3$ (20 mL), brine (20 mL) and dried over Na$_2$SO$_4$, then concentrated in vacuum to give crude product P2 (3 g, crude) as yellow oil, which was used directly for the next.

Step 2

P2 (1 g, 2.53 mmol), Cu(OTf)$_2$ (1.18 g, 3.28 mmol) and L-ascorbic acid, sodium salt (1 g, 5.06 mmol) were added to a round-bottom-flask under N$_2$. Acetone (dry, 8 mL) and MeOH (dry, 8 mL) were added at 25° C. and stirred for 5 min (reaction mixture may turn brown). O$_2$ from a balloon was bubbled through the reaction mixture for 5 min (resulting in a blue/green solution). After that, the reaction was heated to 50° C. under an O$_2$ atmosphere for 1.5 h. The reaction mixture was then cooled to 25° C., EtOAc (30 mL) and sat. Na$_4$EDTA (30 mL, pH~10) were added and the reaction mixture was stirred for 1 h. The layers were separated. The aqueous layer was extracted with EtOAc (2×30 mL), dried over Na$_2$SO$_4$ and concentrated in vacuum to give crude product, which was purified by a silica gel column (PE/EtOAc=3/1) to give P3 (230 mg, 28%) as a solid which was triturated with MeCN (5 mL) at 25° C. to give P3 (110 mg, 48% yield) as a solid and P3 (100 mg, impure) as a solid.

$^1$H NMR (400 MHz, CDCl$_3$) δ 3.78-3.73 (m, 1H), 2.98 (d, J=1.4 Hz, 1H), 2.49-2.41 (m, 1H), 2.16-2.03 (m, 1H), 2.02-1.92 (m, 1H), 1.87-1.76 (m, 2H), 1.68-1.56 (m, 1H), 1.55-1.45 (m, 5H), 1.42-1.22 (m, 7H), 1.21 (s, 3H), 1.11 (s, 1H), 1.04-0.86 (m, 5H), 0.78 (s, 3H).

Step 3

Into a over-dried bottom was added t-BuOH (2 mL) and t-BuOK (348 mg, 3.11 mmol). It was degassed and filled with $N_2$. A solution of P3 (100 mg, 0.312 mmol) in DME (2 mL) was added into the suspension. After 30 min, a solution of TosMIC (121 mg, 0.624 mmol) in DME (2 mL) was added. The mixture became yellow. The resulting mixture was stirred at 25° C. for 16 h. Water was added and the mixture was stirred and the mixture was extracted with ethyl acetate (3×30 mL). The combined organic layer was washed with brine. The combined organic layer was dried over anhydrous $Na_2SO_4$ and concentrated. The residue was purified by flash chromatography eluting with (petroleum ether/ethyl acetate=4/1) to give Compound 40 (60 mg, 58% yield) as a pale solid, which was triturated with MeCN (2 mL) to give Compound 40 (30 mg) as a solid.

$^1$H NMR (400 MHz, $CDCl_3$) δ 3.51-3.44 (m, 1H), 2.46-2.37 (m, 1H), 2.23-2.11 (m, 1H), 2.00-1.91 (m, 1H), 1.84-1.74 (m, 2H), 1.70-7.67 (m, 1H), 1.62-1.57 (m, 1H), 1.53-1.31 (m, 8H), 1.30-1.22 (m, 4H), 1.21-1.15 (s, 3H), 1.09 (s, 1H), 1.04-0.84 (m, 6H), 0.77 (s, 3H) LCMS Rt=0.747 min in 2 min chromatography, 30-90 AB, purity 100%, MS ESI calcd. For $C_{21}H_{30}N$ $[M+H-2H_2O]^+$ 296, found 296.

Note: the structure of Compound 40 was confirmed by X-ray.

Example 23. Synthesis of Compound 41

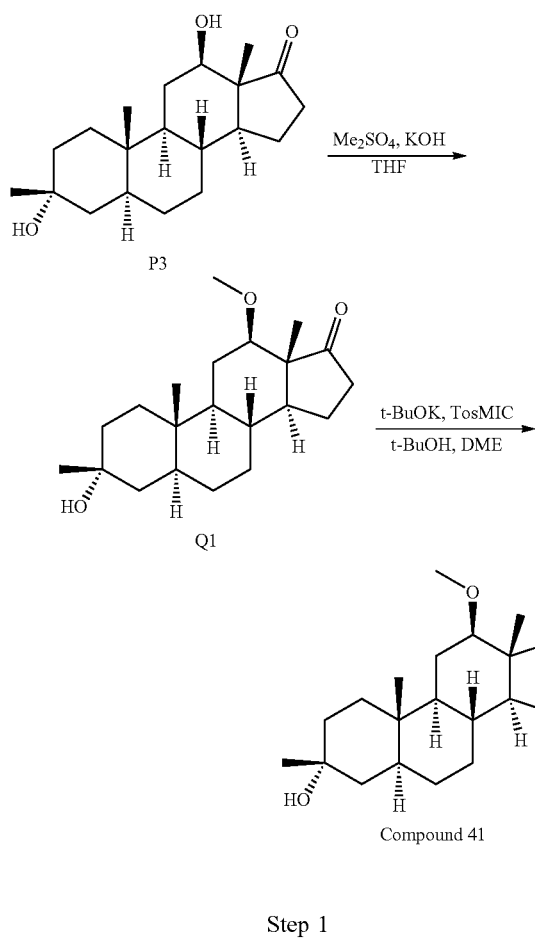

Step 1

To a solution of P3 (1.2 g, 3.74 mmol) in THF (12 mL) was added KOH (632 mg, 11.3 mmol) and $Me_2SO_4$ (966 mg, 0.725 mL, 7.66 mol) at 0° C. Then the mixture was warmed to 25° C. and stirred at the same temperature for 16 h. The mixture was quenched with the addition of 50 mL of water and extracted with EtOAc (2×30 mL). The combined organic layer was dried over $Na_2SO_4$, filtered and concentrated in vacuum to give crude product, which was purified by a silica gel column (PE/EtOAc=10/1-5:1) to give Q1 (600 mg, 48%) as a solid and the starting material P3 (600 mg) as a solid.

$^1$H NMR (400 MHz, $CDCl_3$) δ 3.49 (s, 3H), 3.20-3.15 (m, 1H), 2.48-2.40 (m, 1H), 2.12-1.90 (m, 3H), 1.83-1.75 (m, 1H), 1.59-1.46 (m, 8H), 1.38-1.26 (m, 4H), 1.23-1.15 (m, 5H), 1.01-0.91 (m, 4H), 0.86-0.76 (m, 4H).

Step 2

Into an over-dried bottom was added t-BuOH (2 mL) and t-BuOK (334 mg, 2.98 mmol). It was evaporated and filled with $N_2$. Q1 (100 mg, 0.299 mmol) in DME (1 mL) was added into the suspension. After 30 min, TosMIC (116 mg, 0.598 mmol) in DME (1 mL) was added. The mixture became yellow. The resulting mixture was stirred at 25° C. for 16 h. Water was added and the mixture was stirred. Then it was extracted with ethyl acetate (3×30 mL). The combined organic layer was washed with brine. The combined organic layer was dried over anhydrous $Na_2SO_4$ and concentrated. The residue was purified by flash chromatography eluting with (petroleum ether:ethyl acetate=4/1) to give Compound 41 (25 mg, impure) as a pale yellow oil, which was triturated with MeCN (1 mL) to give Compound 41 (10 mg, 10%) as a solid.

$^1$H NMR (400 MHz, $CDCl_3$) δ 3.41 (s, 3H), 2.92-2.88 (m, 1H), 2.43-2.35 (m, 1H), 2.23-2.09 (m, 1H), 2.02-1.89 (m, 2H), 1.81-1.64 (m, 2H), 1.49-1.32 (m, 5H), 1.27-1.24 (m, 5H), 1.22-1.20 (m, 4H), 1.00-0.85 (m, 7H), 0.83-0.79 (m, 1H), 0.77 (s, 3H).

LCMS Rt=0.903 min in 2 min chromatography, 30-90 AB, purity 100%, MS ESI calcd. For $C_{22}H_{32}N$ $[M+H-2H_2O]^+$ 296, found 296.

Example 24. Synthesis of Compound 42

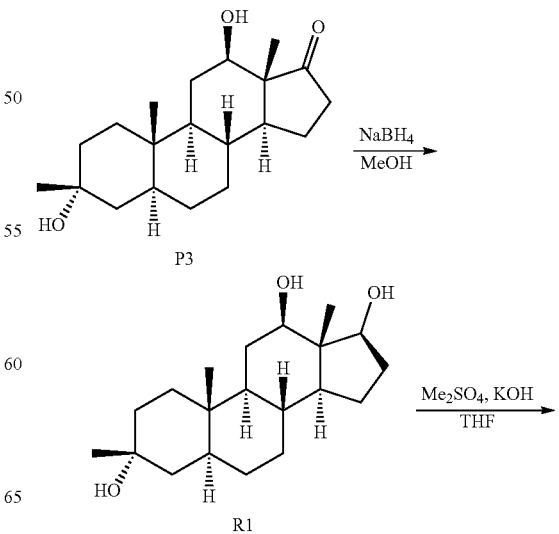

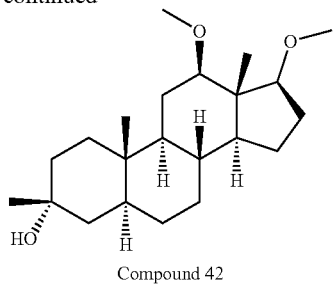

Compound 42

Step 1

To a solution of P3 (200 mg, 0.624 mmol) in MeOH (5 mL) was added NaBH$_4$ (46.9 mg, 1.24 mmol) at 25° C. The reaction was stirred at 25° C. for 30 mins. The reaction was quenched with water (10 mL) and extracted with DCM (2×20 mL). The combined organic layers were dried over Na$_2$SO$_4$, filtered and concentrated in vacuum to give R$^1$ (180 mg, crude) as a colourless oil, which was used directly for next step without further purification.

Step 2

To a solution of R$^1$ (200 mg, 0.620 mmol) in THF (3 mL) was added KOH (211 mg, 3.77 mmol) and Me$_2$SO$_4$ (320 mg, 0.24 mL, 2.54 mmol) at 0° C. Then the mixture was warmed to 25° C. and stirred at the same temperature for 16 h. The mixture was quenched with the addition of 50 mL of water and extracted with EtOAc (2×30 mL). The combined organic layer was dried over Na$_2$SO$_4$, filtered and concentrated in vacuum to give crude product which was purified by a silica gel column (PE/EtOAc=10/1-5:1) to give Compound 42 (30 mg, 14%) as a solid, which was triturated with n-hexane (3 mL) at 25° C. to give Compound 42 (6 mg, 3%) as a solid.

$^1$H NMR (400 MHz, CDCl3) δ 3.39-3.33 (m, 7H), 2.91-2.86 (m, 1H), 2.08-2.02 (m, 1H), 1.91-1.86 (m, 5H), 1.55-1.20 (m, 7H), 1.18-1.14 (m, 8H), 0.92-0.79 (m, 3H), 0.77 (s, 6H).

LCMS Rt=0.952 min in 2 min chromatography, 30-90 AB, purity 99%, MS ESI calcd. For C$_{22}$H$_{38}$O$_3$Na$^+$ [M+Na]$^+$ 373, found 373.

Example 25. Synthesis of Compound 43

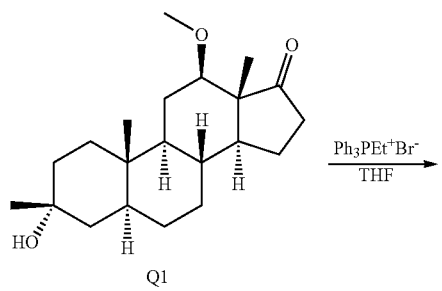

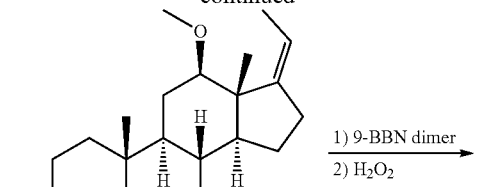

Compound 43

Step 1

To a suspension of EtPPh$_3$Br (3.32 g, 8.95 mmol) in THF (40 mL) was added t-BuOK (1 g, 8.95 mmol) at 25° C. under N$_2$. After stirring at 60° C. for 30 min, a solution of Q1 (600 mg, 1.79 mmol) in THF (10 mL) was added at 60° C. The mixture was stirred at 60° C. for 16 h. The mixture was quenched with NH$_4$Cl (80 mL). The organic layer was separated, dried over Na$_2$SO$_4$, filtered and concentrated in vacuum to give a crude product, which was purified by a silica gel column (PE/EtOAc=10/1-5/1) to give S1 (340 mg, 55%) as a solid.

$^1$H NMR (400 MHz, CDCl$_3$) δ 5.25-5.18 (m, 1H), 3.33 (s, 3H), 3.17-3.12 (m, 1H), 2.42-2.36 (m, 1H), 2.25-2.10 (m, 2H), 1.79-1.76 (m, 6H), 1.75-1.56 (m, 5H), 1.54-1.23 (m, 6H), 1.21-0.98 (m, 5H), 0.90-0.84 (m, 5H), 0.77 (s, 3H).

Step 2

To a solution of S1 (340 mg, 0.981 mmol) in THF (4 mL) was added 9-BBN dimer (597 mg, 2.45 mmol) at 0° C. under N$_2$. The solution was stirred at 60° C. for 16 h. After cooling to 0° C., a solution of EtOH (15 mL) and NaOH (1.96 mL, 5M, 9.81 mmol) was added very slowly. After addition, H$_2$O$_2$ (0.981 ml, 9.81 mmol, 30% in water) was added slowly and the inner temperature was maintained below 10° C. The mixture was stirred at 60° C. under N$_2$ for 1 hour. The mixture was re-cooled to 30° C. Water washed (100 mL) was added to the solution and extracted with EtOAc (2×50 mL). The combined organic layer was dried over Na$_2$SO$_4$, filtered and concentrated in vacuum to give S2 (400 mg, crude) as colorless oil which was directly used for next step.

Step 3

To a solution of S2 (350 mg, 0.960 mmol) in DCM (10 mL) was added PCC (413 mg, 1.92 mmol) and silica gel (454 mg) at 25° C. Then the solution was stirred at 25° C. for 3 h. The reaction mixture was filtered and the residue was washed with anhydrous DCM (2×30 mL). The combined filtrate was concentrated in vacuum to give a crude product, which was purified by a silica gel column (PE/EtOAc=8/1~4/1) to give Compound 43 (270 mg, impure) as pale solid. The solid was triturated with MeCN (5 mL) at 25° C. to give Compound 45 (10 mg, 4%) as a solid for delivery and Compound 43 (250 mg, crude) as pale yellow oil.

$^1$H NMR (400 MHz, CDCl$_3$) δ 3.33 (s, 3H), 3.08-3.03 (m, 1H), 2.71-2.66 (m, 1H), 2.21 (s, 3H), 2.17-1.97 (m, 2H), 1.58-1.55 (m, 3H), 1.54-1.21 (m, 12H), 1.20-1.00 (m, 5H), 0.98-0.75 (m, 5H), 0.65 (s, 3H).

LCMS Rt=0.960 min in 2 min chromatography, 30-90 AB, purity 100%, MS ESI calcd. For C$_{23}$H$_{39}$O$_3$[M+H]$^+$ 363, found 363.

Example 26. Synthesis of Compound 44 and Br$_2$ (439 mg, 0.140 mmol) at 25° C. The mixture was stirred at 25° C. for 16 hrs. The mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford T1 (1.3 g, crude) as light yellow oil which was used directly for the next step.

Step 2

To a mixture of T1 (300 mg, 0.680 mmol) and K$_2$CO$_3$ (186 mg, 1.35 mmol) in acetone (5 mL) was added 1H-pyrazole-4-carbonitrile (94 mg, 1.01 mmol) at 25° C. The reaction mixture was stirred at the 25° C. for 16 h. The reaction mixture was filtered and the filtrate was concentrated in vacuum to give crude product, which was purified by a silica gel column (PE/EtOAc=2/1) to give Compound 44 (37 mg, 12%) as a solid.

$^1$H NMR (400 MHz, CDCl$_3$) δ 7.80 (s, 2H), 5.45 (d, J=17.8 Hz, 1H), 4.93 (d, J=17.8 Hz, 1H), 3.38 (s, 3H), 3.19-3.14 (m, 1H), 2.73-2.67 (m, 1H), 2.20-2.02 (m, 2H), 1.80-1.65 (m, 3H), 1.50-1.32 (m, 5H), 1.31-1.11 (m, 11H), 1.00-0.80 (m, 3H), 0.77 (s, 3H), 0.66 (s, 3H)

LCMS Rt=1.113 min in 2 min chromatography, 30-90 AB, purity 100%, MS ESI calcd. For C$_{27}$H$_{39}$N$_3$O$_3$Na$^+$ [M+Na]$^+$ 476, found 476.

Example 27. Syntheses of Compounds 45 and 46

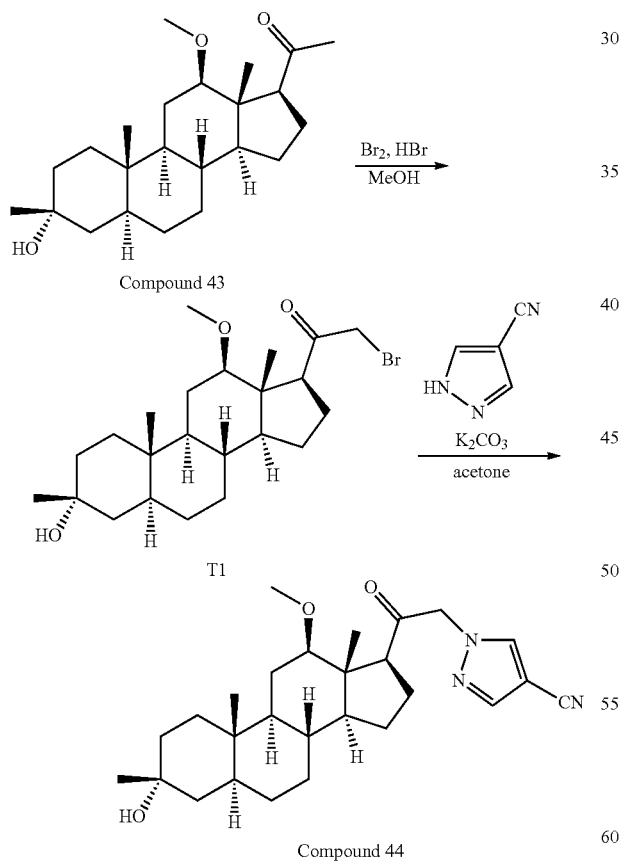

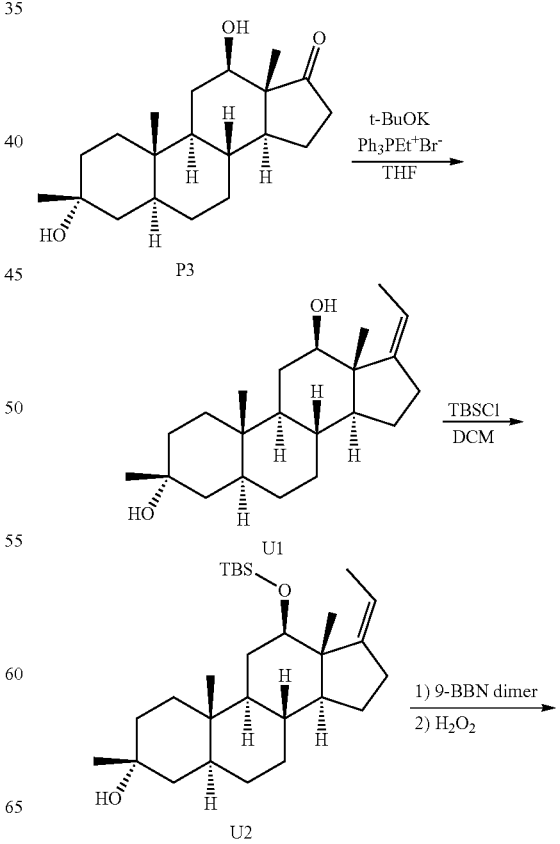

Step 1

To a solution of Compound 43 (1 g, 2.75 mmol) in MeOH (15 ml) was added HBr (44.5 mg, 0.55 mmol, 40% in water)

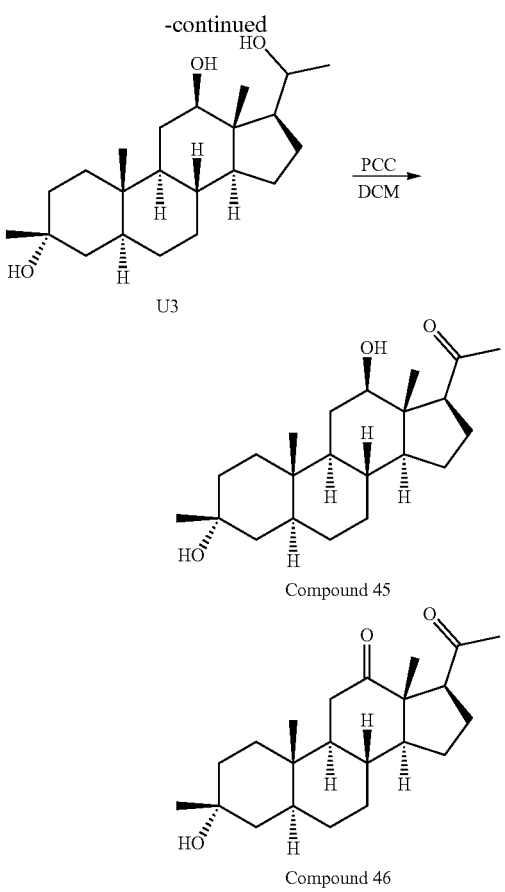

Step 1

To a suspension of EtPPh₃Br (11.5 g, 31.2 mmol) in THF (50 mL) was added t-BuOK (3.50 g, 31.2 mmol) at 25° C. under N₂. After stirring at 60° C. for 30 min, a solution of P3 (2 g, 6.24 mmol) in THF (20 mL) was added at 60° C. The mixture was stirred at 60° C. for 16 h and quenched with NH₄Cl (100 mL). The organic layer was separated, dried over Na₂SO₄, filtered and concentrated in vacuum to give crude product which was purified by a silica gel column (PE/EtOAc=10/1-5/1) to give U1 (1.8 g, 87%) as a solid.

¹H NMR (400 MHz, CDCl₃) δ 5.18-5.14 (m, 1H), 3.68-3.63 (m, 1H), 2.47-2.35 (m, 1H), 2.21-2.09 (m, 1H), 1.89-1.70 (m, 5H), 1.69-1.59 (m, 1H), 1.51-1.45 (m, 4H), 1.41-1.19 (m, 8H), 1.16 (s, 3H), 1.12-0.88 (m, 2H), 1.12-0.88 (m, 1H), 1.12-0.88 (m, 1H), 0.86 (s, 3H), 0.84-0.81 (m, 1H), 0.80 (s, 3H).

Step 2

To a solution of U1 (1.8 g, 5.41 mmol) in DCM (40 mL) was added TBSCl (1.22 g, 8.11 mmol) and 1H-Imidazole (735 mg, 10.8 mmol) at 25° C. The reaction was stirred at 50° C. for 16 h, quenched by water (30 mL) and extracted with DCM (2×20 mL). The combined organic layers were dried over Na₂SO₄, filtered and concentrated in vacuum to give crude product which was purified by a silica gel column (PE/EtOAc=10/1-5/1) to give U2 (1.6 g, 66%) as a solid.

Step 3

To a solution of U2 (1.6 g, 3.58 mmol) in THF (40 mL) was added 9-BBN dimer (4.36 g, 17.9 mmol) at 0° C. under N₂. The solution was stirred at 60° C. for 16 h. After cooling to 0° C., a solution of EtOH (40 mL) and NaOH (7.15 mL, 5M, 35.8 mmol) was added very slowly. After addition, H₂O₂ (3.56 ml, 35.8 mmol, 30% in water) was added slowly and the inner temperature was maintained below 10° C. The mixture was stirred at 60° C. under N₂ for 1 hour. The mixture was re-cooled to 30° C., treated with water (100 mL) and extracted with EtOAc (2×50 mL). The combined organic layer was dried over Na₂SO₄, filtered and concentrated in vacuum to give U3 (2.3 g, crude) as colourless oil, which was directly used for next step.

¹H NMR (400 MHz, CDCl₃) δ 4.15-4.06 (m, 1H), 3.40-3.30 (m, 1H), 1.76-1.68 (m, 3H), 1.56-1.43 (m, 6H), 1.40-1.30 (m, 4H), 1.29-1.15 (m, 13H), 1.04-0.80 (m, 4H), 0.78-0.73 (m, 6H).

Step 4

To a solution of U3 (300 mg, 1.72 mmol) in DCM (15 mL) was added silica gel (404 mg) and PCC (368 mg, 1.71 mmol) at 25° C. The reaction was stirred at 25° C. for 1 h. The mixture was filtered and the filtrate was concentrated in vacuum to give crude product which was purified by a silica gel column (PE/EtOAc=6/1-2/1) to give Compound 46 (10 mg, 3%) and Compound 45 (10 mg, 3%) as a solid.

Compound 45

¹H NMR (400 MHz, CDCl₃) δ 4.86 (s, 1H), 3.45-3.40 (m, 1H), 2.50-2.34 (m, 1H), 2.21-2.05 (m, 4H), 2.03-1.89 (m, 1H), 1.88-1.63 (m, 3H), 1.48-1.22 (m, 9H), 1.21-1.12 (m, 6H), 1.11-0.98 (m, 1H), 0.97-0.80 (m, 3H), 0.75-0.70 (m, 6H). LCMS Rt=0.969 min in 2 min chromatography, 30-90 AB, purity 100%, MS ESI calcd. For C₂₂H₃₅O₂[M+H−H₂O]⁺ 331, found 331.

Compound 46

¹H NMR (400 MHz, CDCl₃) δ 3.35-3.10 (m, 1H), 2.54-2.38 (m, 1H), 2.34-2.09 (m, 5H), 1.89-1.62 (m, 4H), 1.60-1.53 (m, 2H), 1.47-1.24 (m, 9H), 1.21-1.12 (m, 4H), 1.09 (s, 1H), 1.03-0.89 (m, 4H), 0.83 (s, 3H).

LCMS Rt=0.977 min in 2 min chromatography, 30-90 AB, purity 100%, MS ESI calcd. For C₂₂H₃₅O₃[M+H]⁺ 347, found 347.

Example 28. Synthesis of Compound 47

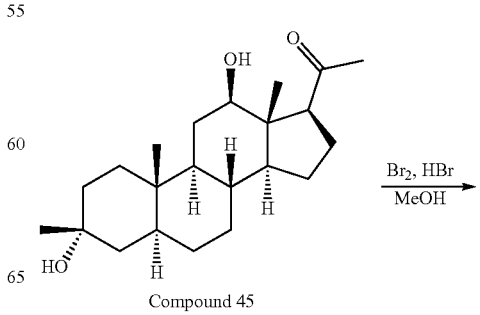

Compound 45

Example 29. Synthesis of Compound 48

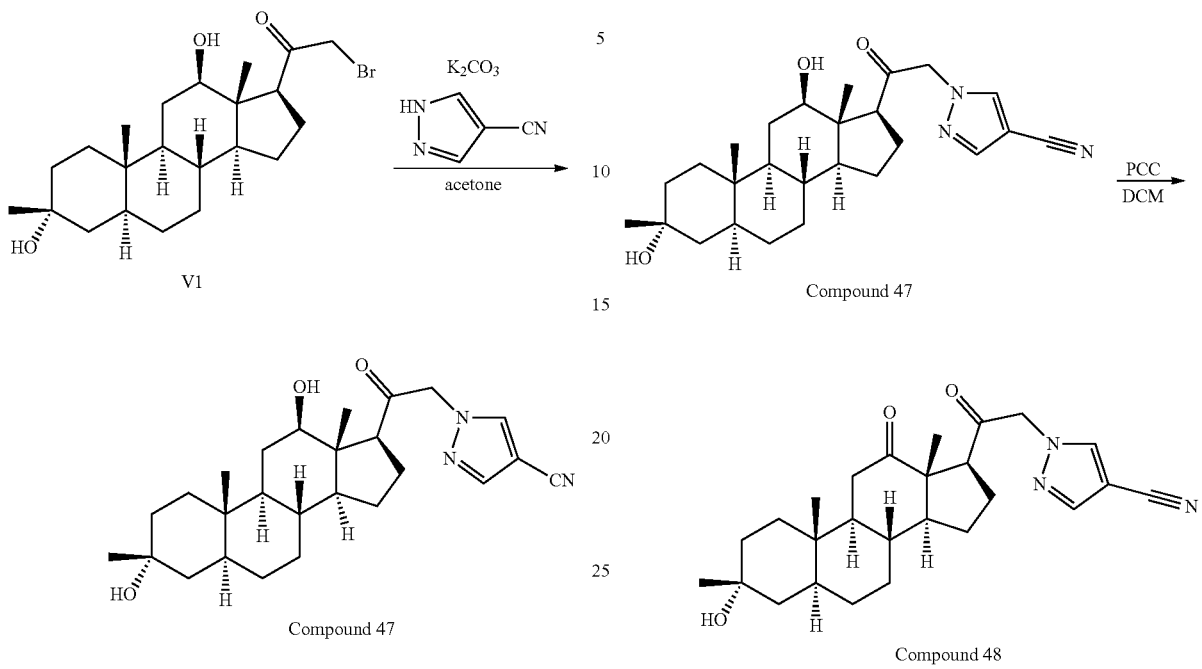

Step 1

To a solution of Compound 45 (560 mg, 1.60 mmol) in MeOH (15 ml) was added HBr (25.9 mg, 0.32 mmol, 40% in water) and Br$_2$ (255 mg, 1.60 mmol) at 25° C. The mixture was stirred at 25° C. for 16 hrs. The mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford VI (700 mg, crude) as light yellow oil which was used directly for the next step.

Step 2

To a mixture of VI (150 mg, 0.351 mmol) and K$_2$CO$_3$ (96.9 mg, 0.702 mmol) in acetone (5 mL) was added 1H-pyrazole-4-carbonitrile (48.9 mg, 0.526 mmol) at 25° C. The reaction mixture was stirred at the 25° C. for 16 h. The reaction mixture was quenched by water (20 mL) and extracted with EtOAc (2×20 mL). The combined organic layer was dried over Na$_2$SO$_4$, filtered and concentrated in vacuum to give crude product (50 mg) which was triturated with MeCN (5 mL) to give Compound 47 (41 mg, 27%) as a solid.

$^1$H NMR (400 MHz, DMSO-d$_6$) δ 8.31 (s, 1H), 8.05 (s, 1H), 5.87 (d, J=18.2 Hz, 1H), 5.22 (d, J=18.2 Hz, 1H), 4.92-4.88 (m, 1H), 3.88 (s, 1H), 3.56-3.49 (m, 1H), 2.86-2.76 (m, 1H), 1.96-1.92 (m, 1H), 1.73-1.58 (m, 4H), 1.57-1.44 (m, 1H), 1.42-1.22 (m, 7H), 1.19-1.11 (m, 5H), 1.07 (s, 3H), 0.92-0.77 (m, 2H), 0.70 (s, 3H), 0.54 (s, 3H)

LCMS Rt=0.980 min in 2 min chromatography, 30-90 AB, purity 100%, MS ESI calcd. For C$_{26}$H$_{37}$N$_3$O$_3$Na$^+$ [M+Na]$^+$ 462, found 462.

To a solution of Compound 47 (50 mg, 0.114 mmol) in DCM (10 mL) was added PCC (98.0 mg, 0.455 mmol) and silica gel (150 mg) at 25° C. Then the solution was stirred at 25° C. for 5 h. The reaction mixture was filtered and the residue was washed with anhydrous DCM (2×30 mL). The combined filtrate was concentrated in vacuum to give a crude product, which was purified by a silica gel column (PE/EtOAc=1/1) to give Compound 48 (13 mg, 26%) as a solid.

$^1$H NMR (400 MHz, CDCl$_3$) δ 7.83-7.79 (m, 2H), 5.55 (d, J=18.4 Hz, 1H), 5.08 (d, J=18.4 Hz, 1H), 3.27 (t, J=9.0 Hz, 1H), 2.52-2.39 (m, 1H), 2.39-2.29 (m, 1H), 2.26-2.14 (m, 1H), 1.89-1.68 (m, 3H), 1.58-1.43 (m, 4H), 1.40-1.23 (m, 9H), 1.21 (s, 3H), 1.07-0.99 (m, 1H), 1.07-0.99 (m, 1H), 0.96 (s, 3H), 0.84 (s, 3H).

LCMS Rt=0.983 min in 2 min chromatography, 30-90 AB, purity 100%, MS ESI calcd. For C$_{26}$H$_{36}$N$_3$O$_3$ [M+H]$^+$ 438, found 438.

Example 30. Syntheses of Compounds 49 and 50

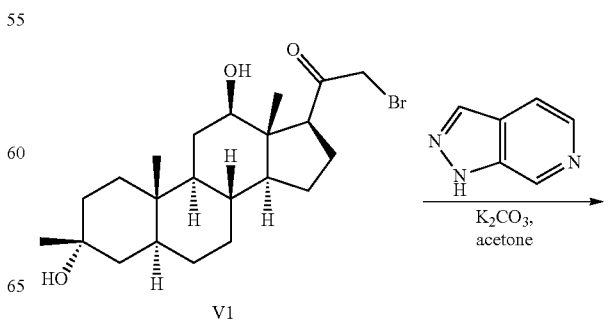

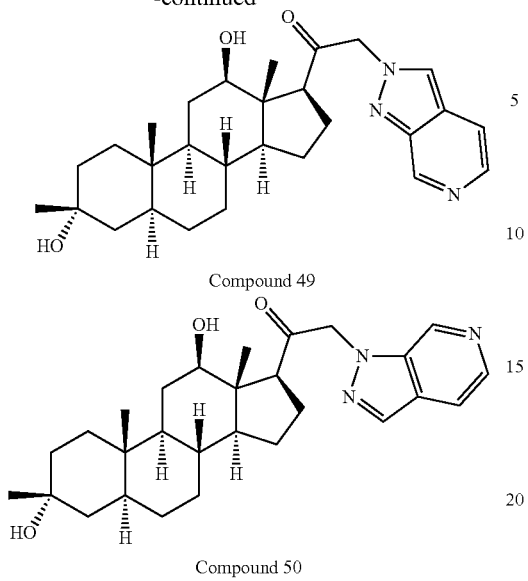

Compound 49

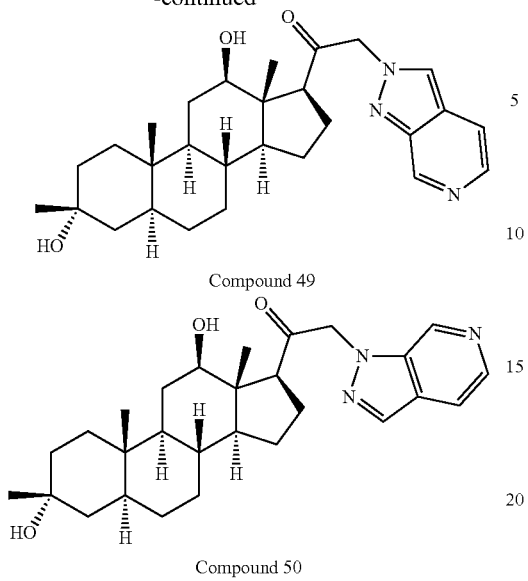

Compound 50

To a mixture of VI (400 mg, 0.936 mmol) and K₂CO₃ (258 mg, 1.87 mmol) in acetone (5 mL) was added 1H-pyrazole-4-carbonitrile (166 mg, 1.40 mmol) at 25° C. The reaction mixture was stirred at the 25° C. for 16 h. The reaction mixture was quenched with water (20 mL) and extracted with EtOAc (2×20 mL). The combined organic layer was dried over Na₂SO₄, filtered and concentrated in vacuum to give crude product, which was purified by prep. HPLC (column: Boston Green ODS 150*30 5u, gradient: 34-44% B (A=0.1% TFA-ACN, B=acetonitrile), flow rate: 30 mL/min) to give mixture of Compound 49 and Compound 50 (120 mg, crude) as yellow oil. The oil was purified by SFC (column: OD (250 mm*30 mm, 5 um); Mobile phase: Supercritical CO₂/MeOH+NH₃H₂O=40/40; Flow rate: 50 ml/min; Wavelength: 220 nm) to give Compound 49 (20 mg, 17%) as a solid and Compound 50 (50 mg, 42%) as a solid.

Compound 49

¹H NMR (400 MHz, CDCl₃) δ 9.28 (s, 1H), 8.17 (d, J=5.6 Hz, 1H), 7.99 (s, 1H), 7.52 (d, J=5.6 Hz, 1H), 5.81 (d, J=17.6 Hz, 1H), 5.37 (d, J=17.6 Hz, 1H), 3.61-3.56 (m, 1H), 2.66-2.60 (m, 2H), 2.21-2.08 (m, 1H), 1.92-1.64 (m, 4H), 1.54-1.44 (m, 4H), 1.42-1.31 (m, 4H), 1.30-1.25 (m, 3H), 1.21 (s, 3H), 1.18-1.05 (m, 3H), 0.97-0.85 (m, 2H), 0.77 (s, 3H), 0.73 (s, 3H).

LCMS Rt=0.655 min in 2 min chromatography, 30-90 AB, purity 100%, MS ESI calcd. For C₂₈H₄₀N₃O₃ [M+H]⁺ 466, found 466.

Compound 50

¹H NMR (400 MHz, CDCl₃) δ 8.92 (s, 1H), 8.33-8.31 (m, 1H), 8.11 (s, 1H), 7.65-7.63 (m, 1H), 5.91 (d, J=18.4 Hz, 1H), 5.35 (d, J=18.4 Hz, 1H), 3.65-3.61 (m, 1H), 2.73-2.67 (m, 1H), 2.62-2.60 (m, 1H), 2.19-2.07 (m, 1H), 1.90-1.64 (m, 4H), 1.54-1.44 (m, 4H), 1.43-1.32 (m, 4H), 1.31-1.22 (m, 4H), 1.21 (s, 3H), 1.19-1.07 (m, 2H), 0.97-0.86 (m, 2H), 0.77 (s, 3H), 0.73 (s, 3H).

LCMS Rt=0.690 min in 2 min chromatography, 30-90 AB, purity 100%, MS ESI calcd. For C₂₈H₄₀N₃O₃ [M+H]⁺ 466, found 466.

Example 31. Syntheses of Compounds 51 and 52

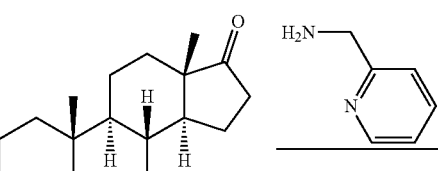

W1

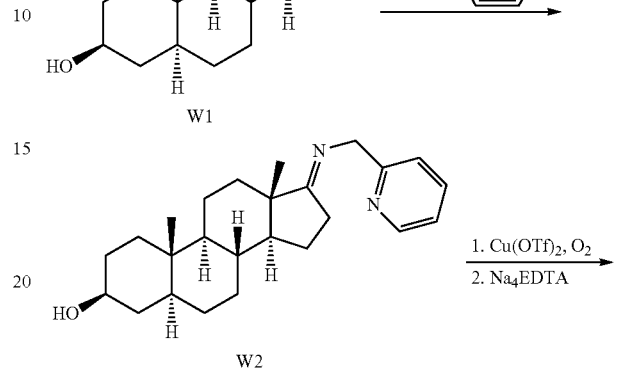

W2

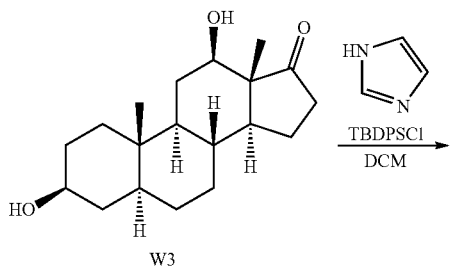

W3

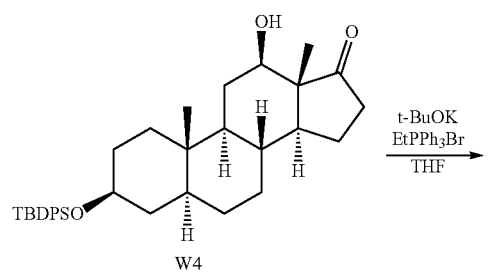

W4

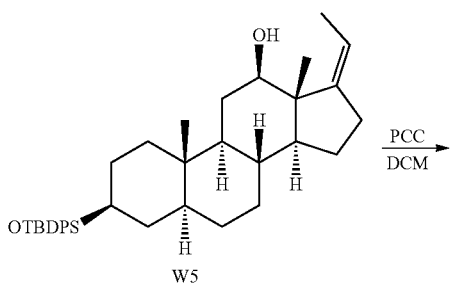

W5

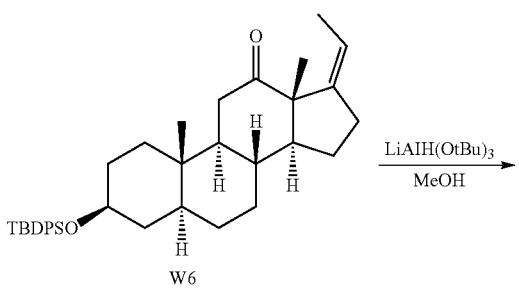

W6

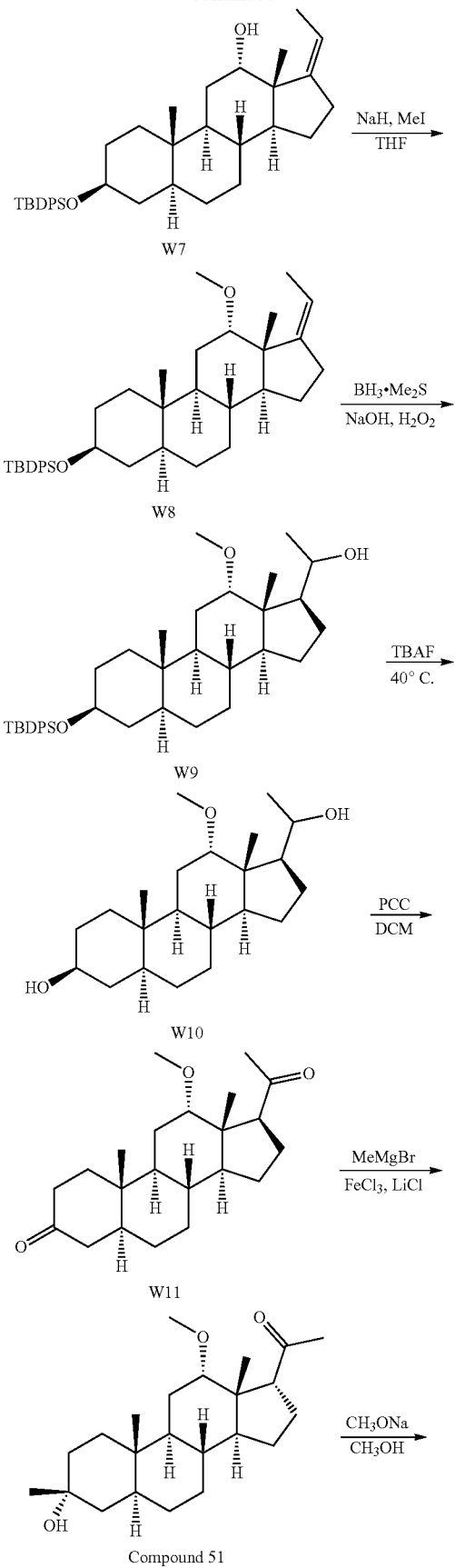

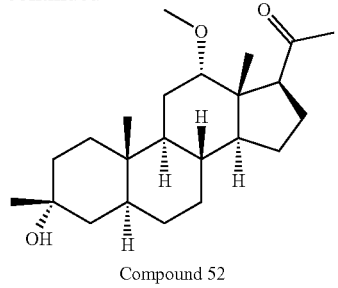

Compound 52

Step 1

To a solution of W1 (50 g, 172 mmol) in toluene (400 mL) was added p-toluenesulfonic acid (532 mg, 3.09 mmol) and pyridin-2-ylmethanamine (40.8 g, 378 mmol) at 25° C. The reaction mixture was heated to 140° C. with a Dean-Stark apparatus for 16 hrs. The reaction mixture was cooled to 25° C. and then diluted with EtOAc (300 mL) and water (200 mL). The combined organic layer was washed sequentially with sat. $NH_4Cl$ (2×200 mL), sat. $NaHCO_3$ (200 mL), brine (200 mL), dried over anhydrous $Na_2SO_4$, filtered and concentrated under reduced pressure to give the crude product, which was triturated from (EtOAc, 200 mL) at 25° C. to give W2 (54 g, 83%) as a pale solid.

$^1$H NMR (400 MHz, $CDCl_3$) δ 8.50-8.43 (m, 1H), 7.60-7.55 (m, 1H), 7.36-7.33 (m, 1H), 7.21-7.06 (m, 1H), 7.18-7.11 (m, 2H), 4.58-4.45 (m, 2H), 3.61-3.40 (m, 1H), 2.40-2.34 (m, 1H), 2.22-2.18 (m, 1H), 1.98-1.95 (m, 2H), 1.93-1.60 (m, 5H), 1.57-1.33 (m, 4H), 1.21-1.17 (m, 3H), 1.05-0.96 (m, 2H), 0.95-0.84 (m, 2H), 0.82 (s, 3H), 0.78 (s, 3H), 0.70-0.65 (s, 1H).

Step 2

W2 (20 g, 52.5 mmol), $Cu(OTf)_2$ (24.6 g, 68.2 mmol) and L-ascorbic acid sodium salt (20.8 g, 105 mmol) were added to a round-bottom-flask under $N_2$. Acetone (160 mL) and MeOH (160 mL) were added at 25° C. and stirred for 5 mins (reaction mixture may turn brown). $O_2$ from a balloon was bubbled through the reaction mixture for 5 mins (resulting in a blue/green solution), after which the reaction was heated to 60° C. under an $O_2$ atmosphere for 18 hrs. The reaction mixture was cooled to 25° C., EtOAc (300 mL) and sat. $Na_4EDTA$ (300 mL, PH~10) were added and the reaction mixture was stirred for 2 hrs. The layer was separated. The aqueous layer was extracted with EtOAc (2×300 mL), dried over $Na_2SO_4$, filtered and concentrated in vacuum to give crude product which was purified by a silica gel column (PE/EtOAc=1/1) to give W3 (12.5 g, 77%) as a solid.

$^1$H NMR (400 MHz, MeOD) δ3.74-3.64 (m, 1H), 3.60-3.47 (m, 1H), 2.48-2.41 (m, 1H), 2.14-2.05 (m, 1H), 2.01-1.91 (m, 1H), 1.89-1.62 (m, 6H), 1.62-1.51 (m, 2H), 1.49-1.28 (m, 7H), 1.22-1.11 (m, 1H), 1.10-0.97 (m, 2H), 0.94 (s, 3H), 0.89 (s, 3H), 0.87-0.80 (m, 1H).

Step 3

To a solution of W3 (10.3 g, 33.6 mmol) in DCM (150 mL) was added TBDPSCl (13.8 g, 50.4 mmol) and imidazole (4.57 g, 67.2 mmol) at 25° C. The reaction was stirred at 25° C. for 16 h. The reaction was quenched with $H_2O$ (100 mL) and extracted with DCM (2×100 mL). The combined organic layer was washed with saturated brine solution (100 mL). The organic phase was then dried over anhydrous Na$_2$SO$_4$, filtered and concentrated in vacuum and the resulting solid was purified by column chromatography (PE/EtOAc=15/1-10/1) to give W4 (6 g, 33%) as a solid.

$^1$H NMR (400 MHz, CDCl$_3$) δ 7.68-7.65 (m, 4H), 7.45-7.33 (m, 6H), 3.70-3.65 (m, 1H), 3.60-3.53 (m, 1H), 2.94 (d, J=0.8 Hz, 1H), 2.46-2.39 (m, 1H), 2.13-2.05 (m, 1H), 2.04-2.01 (m, 2H), 1.98-1.87 (m, 2H), 1.78-1.68 (m, 2H), 1.68-1.57 (m, 2H), 1.54-1.38 (m, 4H), 1.23-1.11 (m, 3H), 1.04 (s, 9H), 0.91 (s, 3H), 0.90-0.84 (m, 1H), 0.82 (s, 3H), 0.79-0.63 (m, 2H).

Step 4

To a suspension of EtPh$_3$PBr (16.7 g, 45.2 mmol) in anhydrous THF (60 mL) under N$_2$ was added t-BuOK (5.07 g, 45.2 mmol) at 25° C. The color of the suspension turned dark red. Then the reaction mixture was heated to 40° C. After stirring at 40° C. for 30 mins, W4 (6.2 g, 11.3 mmol) was added. The reaction mixture was stirred at 40° C. for 1.5 hrs. The reaction mixture was quenched with aq.NH$_4$Cl solution (100 mL) and then extracted with EtOAc (2×100 mL). The combined organic phase was washed with brine (100 mL), dried over Na$_2$SO$_4$, filtered and concentrated in vacuum to get the crude product, which was purified with flash column (0-20% of EtOAc in PE) to give W5 (6 g, 95%) as a solid.

$^1$H NMR (400 MHz, CDCl$_3$) δ 7.71-7.63 (m, 4H), 7.45-7.31 (m, 6H), 5.20-5.14 (m, 1H), 3.71-3.65 (m, 1H), 3.59-3.54 (m, 1H), 2.48-2.34 (m, 1H), 2.16-2.12 (m, 1H), 1.83-1.80 (m, 4H), 1.78-1.70 (m, 1H), 1.69-1.57 (m, 4H), 1.45-1.40 (m, 2H), 1.29-1.21 (m, 3H), 1.20-1.14 (m, 2H), 1.04 (s, 9H), 1.00-0.93 (m, 1H), 0.91-0.85 (m, 2H), 0.83 (s, 3H), 0.80 (s, 3H), 0.79-0.68 (m, 2H), 0.67-0.57 (m, 1H).

Step 5

To a solution of W5 (6 g, 10.7 mmol) in DCM (60 mL) was added silica gel (10 g) and PCC (9.22 g, 42.8 mmol) at 25° C. Then the reaction was stirred at 25° C. for 2 hrs. The reaction mixture was filtered and the residue was washed with DCM (2×80 mL). The combined filtrate was concentrated in vacuum to give crude product which was purified by a silica gel column (PE/EtOAc=10/1) to give W6 (5 g, 84%) as a solid.

$^1$H NMR (400 MHz, CDCl$_3$) δ 7.71-7.61 (m, 4H), 7.46-7.31 (m, 6H), 5.46-5.42 (m, 1H), 3.60-3.54 (m, 1H), 2.57 (t, J=13.2 Hz, 1H), 2.39-2.12 (m, 3H), 1.90-1.71 (m, 2H), 1.71-1.62 (m, 3H), 1.61-1.56 (m, 4H), 1.52-1.33 (m, 6H), 1.32-1.22 (m, 2H), 1.20 (s, 3H), 1.04 (s, 9H), 0.92-0.75 (m, 5H).

Step 6

To a solution of W6 (5 g, 9.01 mmol) in THF (50 mL) was added lithium tri-tert-butoxyaluminum hydride (11.4 g, 45 mmol) in THF (100 mL) was added dropwise at 0° C. The reaction was warmed to 25° C. and stirred at 25° C. for 16 hrs. The reaction was quenched by adding aqueous HCl (1 M, 100 mL) and the mixture was diluted with EtOAc (100 mL). The phases were separated and the organic phase was washed sequentially with water (100 mL) and saturated brine solution (100 mL). The organic phase was then dried over anhydrous Na$_2$SO$_4$ and filtered. The filtrate was concentrated under vacuum to give W7 (5 g, crude) as pale yellow oil.

Step 7

To a solution of W7 (5 g, 8.97 mmol) in THF (50 mL) was added NaH (1.07 g, 26.9 mmol, 60%) in one portion at 0° C. under N$_2$. After 30 mins, MeI (12.7 g, 5.57 mL, 89.7 mmol, actual dosage: 13.6 g) was added dropwise at 25° C. The reaction mixture was stirred for 16 hrs at 40° C. The mixture was quenched with saturated aqueous NH$_4$Cl (100 mL). Then the mixture was extracted with EtOAc (200 mL) and H$_2$O (2×150 mL). The combined organic phases were dried over Na$_2$SO$_4$, and the solvent was evaporated to afford crude product. The crude product was purified by column chromatography on silica gel (PE/EtOAc=20/1-10/1) to give W8 (4.7 g, 92%) as an oil.

$^1$H NMR (400 MHz, CDCl3) δ 7.70-7.65 (m, 4H), 7.45-7.34 (m, 6H), 5.23-5.18 (m, 1H), 3.83-3.77 (m, 1H), 3.63-3.55 (m, 1H), 3.26 (s, 3H), 2.46-2.09 (m, 2H), 1.92-1.85 (m, 1H), 1.76-1.73 (m, 6H), 1.54-1.30 (m, 8H), 1.23-1.09 (m, 6H), 1.05 (m, 9H), 0.86 (s, 3H), 0.80 (s, 3H).

Step 8

To a solution of W8 (4.7 g, 8.23 mmol) in THF (50 mL) was added dropwise a solution of BH$_3$-Me$_2$S (8.22 mL, 82.3 mmol) at 0° C. The solution was stirred at 25° C. for 16 hrs. After cooling to 0° C., a solution of EtOH (4.79 mL, 82.3 mmol) and NaOH solution (39.4 g, 10% in water) was added very slowly. After addition, H$_2$O$_2$ (8.23 mL, 82.3 mmol, 30% in water) was added slowly and the inner temperature was maintained below 10° C. The resulting solution was stirred at 25° C. for 1 h. The mixture was quenched with saturated aqueous Na$_2$S$_2$O$_3$ (50 mL) and extracted with EtOAc (3×50 mL). The combined organic layer was washed with saturated aqueous Na$_2$S$_2$O$_3$ (2×50 mL), brine (50 mL), dried over Na$_2$SO$_4$ and concentrated in vacuum to give W9 (5.1 g, crude) as a solid, which was used directly for next step without further purification.

Step 9

To a solution of W9 (5.1 g, 8.65 mmol) in THF (10 mL) was added TBAF (43.2 mL, 1 M in THF) at 25° C. The reaction was stirred at 40° C. for 48 hrs. The reaction was quenched with water (50 mL) and extracted with EtOAc (2×100 mL). The combined organic layer was dried over Na$_2$SO$_4$, filtered and concentrated in vacuum to give W10 (5 g, crude) as pale yellow oil which was used directly for next step without further purification.

Step 10

To a solution of W10 (5 g, crude) in DCM (50 mL) was added silica gel (13.4 g) and PCC (12.2 g, 56.8 mmol) at 25° C. The reaction was stirred at 25° C. for 4 hrs. The reaction mixture was filtered and the filtrate was concentrated in vacuum to give crude product which was purified by a silica gel column (PE/EtOAc=5/1) to give W11 (1.2 g, impure) as a pale yellow oil.

$^1$H NMR (400 MHz, CDCl$_3$) δ 3.42-3.38 (m, 1H), 3.13 (s, 3H), 2.56-2.52 (dd, J=8.8 Hz, 1H), 2.43-2.21 (m, 4H), 2.05 (s, 3H), 2.04-1.65 (m, 8H), 1.55-1.23 (m, 5H), 1.18-1.01 (m, 3H), 1.00 (s, 3H), 0.94 (s, 3H).

Step 11

A suspension of LiCl (307 mg, 7.26 mmol, anhydrous) in THF (20 mL, anhydrous) was stirred at 10° C. for 30 mins under $N_2$. $FeCl_3$ (616 mg, 3.80 mmol, anhydrous) was added at 10° C. The mixture was cooled to −30° C. To the mixture was added MeMgBr (4.60 mL, 13.8 mmol, 3M in diethyl ether) dropwise at −30° C. The mixture was stirred at −30° C. for 10 mins. W11 (1.2 g, impure) was added at −30° C. The mixture was stirred at −15° C. for 2 hrs. To the mixture was added citric acid (40 mL, 10% aq.). The mixture was extracted with EtOAc (2×60 mL). The combined organic phase was washed with saturated brine (30 mL), dried over anhydrous $Na_2SO_4$, filtered and concentrated in vacuum to give crude product which was purified by a silica gel column (PE/EtOAc=1/10~1/5) to give Compound 51 (650 mg, 52%) as a solid.

$^1$H NMR (400 MHz, $CDCl_3$) δ 3.38-3.36 (m, 1H), 3.11 (s, 3H), 2.53-2.48 (dd, J=8.8 Hz, 1H), 2.04 (s, 3H), 2.01-1.94 (m, 1H), 1.70-1.59 (m, 4H), 1.55-1.46 (m, 4H), 1.42-1.23 (m, 6H), 1.19 (s, 3H), 1.18-0.98 (m, 6H), 0.91 (s, 3H), 0.74 (s, 3H).

LCMS Rt=1.058 min in 2 min chromatography, 30-90 AB, purity 100%, MS ESI calcd. For $C_{23}H_{39}O_3[M+H]^+$ 363, found 363.

The stereochemistry at C17 of Compound 51 was confirmed by NOE.

Step 12

To a solution of Compound 51 (600 mg, 1.65 mmol) in MeOH (6 mL) was added $CH_3ONa$ (891 mg, 16.5 mmol) at 25° C. The reaction was stirred at 50° C. for 16 hrs. The reaction mixture was quenched with HCl (2 mL, 2 M) to adjust the pH to about 7, diluted with water (20 mL) and extracted with DCM (2×20 mL). The combined organic layer was dried over $Na_2SO_4$, filtered and concentrated in vacuum to give crude product which was purified by a silica gel column (PE/EtOAc=5/1-3/1) to give Compound 52 (420 mg, 70%, 10 mg for delivery) as a solid.

$^1$H NMR (400 MHz, CDCl3) δ 3.45-3.42 (m, 1H), 3.35 (s, 3H), 3.27 (t, J=9.2 Hz, 1H), 2.08 (s, 3H), 2.01-1.94 (m, 1H), 1.70-1.59 (m, 4H), 1.55-1.46 (m, 4H), 1.42-1.23 (m, 6H), 1.20 (s, 3H), 1.19-1.17 (m, 3H), 1.16-0.92 (m, 3H), 0.75 (s, 3H), 0.63 (s, 3H).

LCMS Rt=1.033 min in 2 min chromatography, 30-90 AB, purity 100%, MS ESI calcd. For $C_{22}H_{35}O_2[M-CH_3OH+H]^+$ 331, found 331.

The stereochemistry at C17 of Compound 52 was confirmed by NOE during the pilot reaction.

Example 32. Synthesis of Compound 53

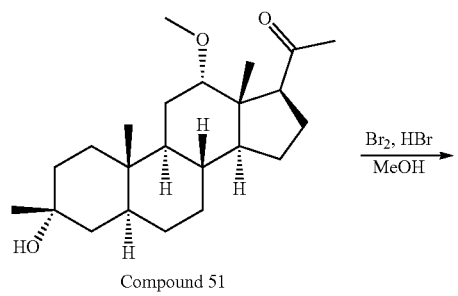

Compound 51

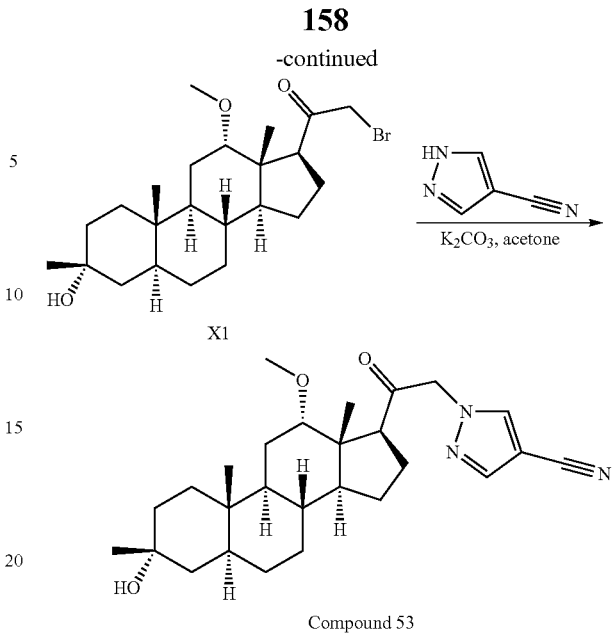

Compound 53

Step 1

To a solution of Compound 51 (400 mg, 1.10 mmol) in MeOH (4 mL) was added HBr (44.5 mg, 0.220 mmol, 40% in water) and the solution of $Br_2$ (0.06 mL, 1.21 mmol) in MeOH (4 mL) at 25° C. The mixture was stirred at 25° C. for 16 hrs. The mixture was quenched by sat·aq $NaHCO_3$ (10 mL) and treated with water (20 mL). The reaction mixture was filtered and the residue was washed with water (10 mL), concentrated in vacuum to give X1 (430 mg, 89%) as a solid.

$^1$H NMR (400 MHz, $CDCl_3$) δ 3.96-3.82 (m, 2H), 3.47 (t, J=8.8 Hz, 1H), 3.38-3.36 (m, 1H), 3.35 (s, 3H), 2.19-1.93 (m, 2H), 1.78-1.60 (m, 4H), 1.53-1.45 (m, 3H), 1.45-1.33 (m, 3H), 1.32-1.22 (m, 5H), 1.20 (s, 3H), 1.15 (s, 1H), 1.13-0.91 (m, 3H), 0.75 (s, 3H), 0.67 (s, 3H).

Step 2

To a solution of 1H-pyrazole-4-carbonitrile (31.6 mg, 0.3397 mmol) and $K_2CO_3$ (78.2 mg, 0.5662 mmol) in acetone (2 mL) was added X1 (100 mg, 0.2265 mmol) at 25° C. The mixture was stirred at 25° C. for 2 h. The mixture was poured into water (10 mL) and extracted with EtOAc (2×10 mL). The combined organic layer was washed with saturated brine (2×10 mL), dried over anhydrous $Na_2SO_4$, filtered and concentrated in vacuum to give Compound 53 (106 mg, crude) as a solid, which was further purified by HPLC (column: Gemini 150*25 5u, gradient: 56-81% B, condition: water (0.05% HCl)-ACN, flow rate: 30 mL/min) to give Compound 53 (57 mg, 54%) as solid.

$^1$H NMR (400 MHz, $CDCl_3$) δ 7.85 (s, 1H), 7.79 (s, 1H), 5.00-4.80 (m, 2H), 3.53-3.50 (m, 1H), 3.41-3.36 (m, 4H), 2.20-2.05 (m, 2H), 1.80-1.65 (m, 4H), 1.60-1.50 (m, 7H), 1.48-0.90 (m, 11H), 0.75 (s, 3H), 0.67 (s, 3H).

LCMS Rt=1.053 min in 2 min chromatography, 30-90AB_2MIN_E, purity 100%, MS ESI calcd. for $C_{27}H_{40}N_3O_3 [M+H]^+$ 454, found 454.

Example 33. Syntheses of Compounds 54 and 55

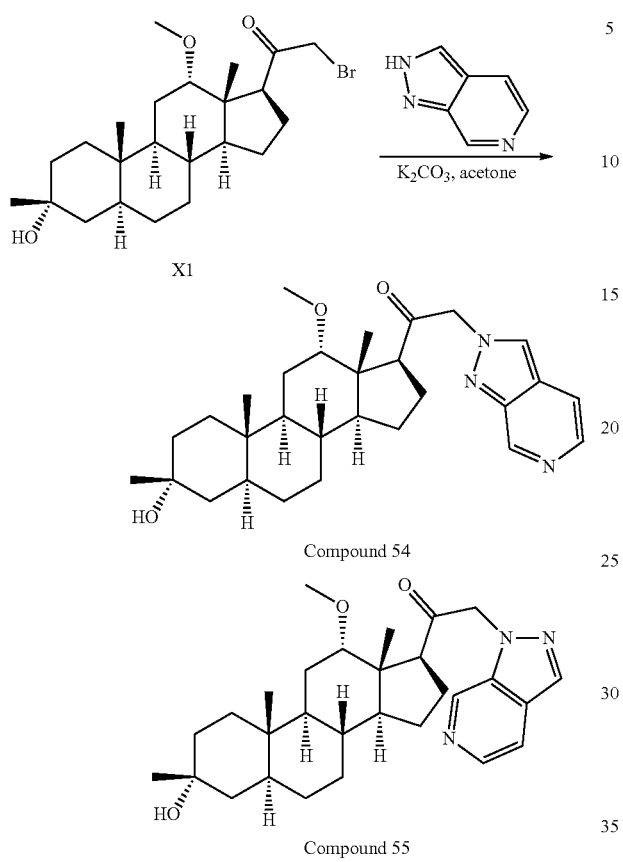

To a solution of X1 (150 mg, 0.339 mmol) in acetone (2 mL) was added 2H-pyrazolo [3,4-c]pyridine (60.5 mg, 0.508 mmol) and K$_2$CO$_3$ (92.8 mg, 0.678 mmol). After stirring at 15° C. for 16 hrs, the reaction mixture was treated with water (5 mL) and extracted with EtOAc (2×10 mL). The combined organic layer was washed with brine (5 mL). The organic layer was dried over Na$_2$SO$_4$, filtered and concentrated. The residue was purified by HPLC (column: Waters Xbridge 150*25 5u), water (10 mM NH4HCO3)-ACN, gradient: 45-65% B, flow rate: 25 mL/min)) to give Compound 55 (20 mg, 12%) as a solid and Compound 54 (15 mg, impure) as a solid, which was combined with another batch prepared from 50 mg of X1. The impure sample was further purified by prep-TLC (PE/EtOAc=1/1) to give Compound 54 (8 mg) as a solid.

Compound 54

$^1$H NMR (400 MHz, CDCl$_3$) δ 9.40-9.20 (m, 1H), 8.25-8.10 (m, 1H), 8.10-8.00 (m, 1H), 7.70-7.55 (m, 1H), 5.39-5.12 (m, 2H), 3.63-3.10 (m, 1H), 3.52-3.48 (m, 1H), 3.42 (s, 3H), 2.34-2.01 (m, 3H), 2.00-1.62 (m, 10H), 1.62-1.48 (m, 5H), 1.48-0.97 (m, 6H), 0.82-0.63 (m, 6H).

LCMS Rt=0.766 min in 2 min chromatography, 30-90AB_2MIN_E, purity 100%, MS ESI calcd. for C$_{29}$H$_{42}$N$_3$O$_3$ [M+H]$^+$ 480 found 480.

Compound 55

$^1$H NMR (400 MHz, CDCl$_3$) δ 8.81-8.78 (m, 1H), 8.36-8.32 (m, 1H), 8.08 (s, 1H), 7.65-7.61 (m, 1H), 5.28-5.12 (m, 2H), 3.70-3.60 (m, 1H), 3.52-3.48 (m, 1H), 3.41 (s, 3H), 2.21-2.01 (m, 2H), 1.84-1.65 (m, 4H), 1.65-1.48 (m, 6H), 1.48-1.19 (m, 10H), 1.19-0.98 (m, 2H), 0.82-0.70 (m, 6H).

LCMS Rt=0.793 min in 2 min chromatography, 30-90AB_2MIN_E, purity 100%, MS ESI calcd. for C$_{29}$H$_{42}$N$_3$O$_3$ [M+H]$^+$ 480 found 480.

Example 34. Syntheses of Compounds 56, 57, 58, and 59

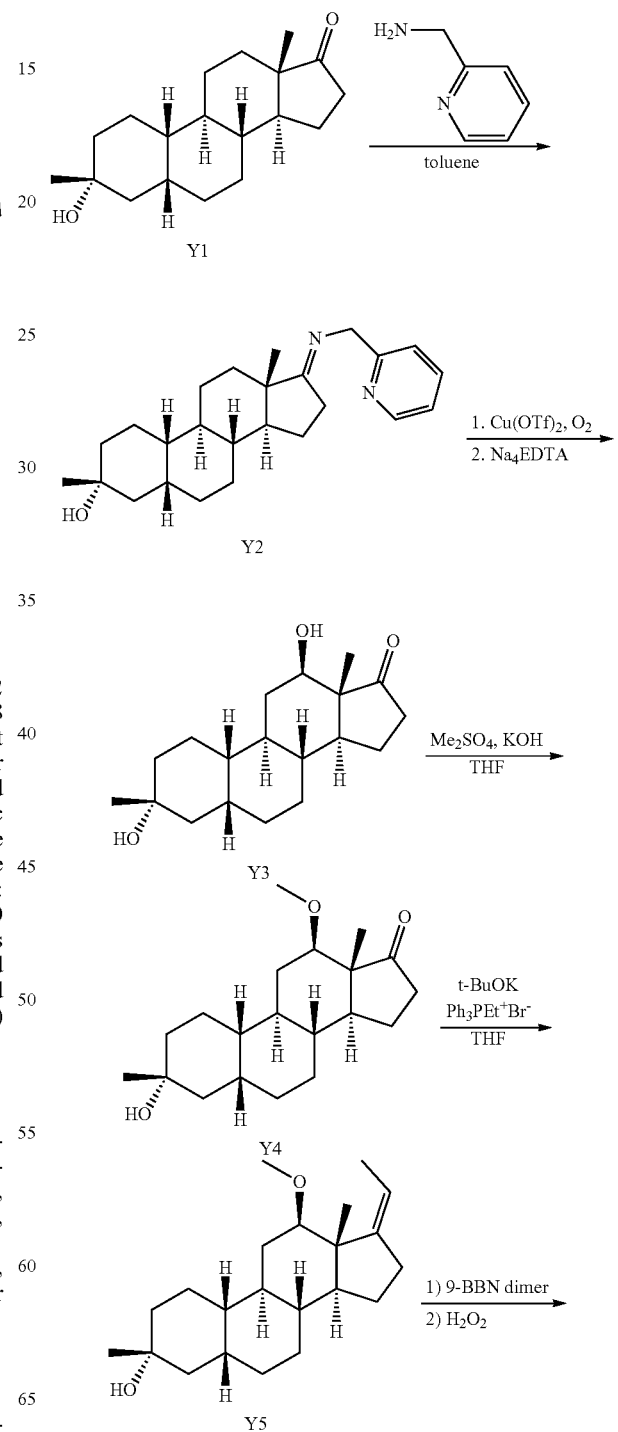

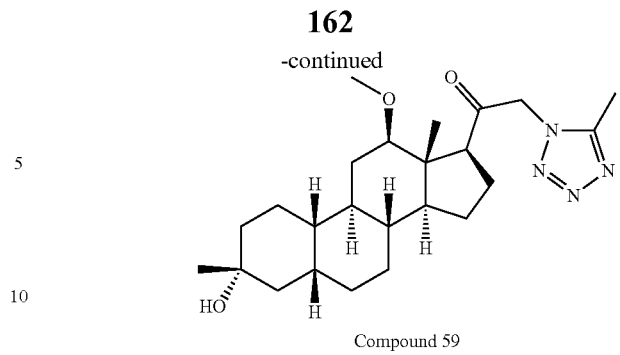

Compound 59

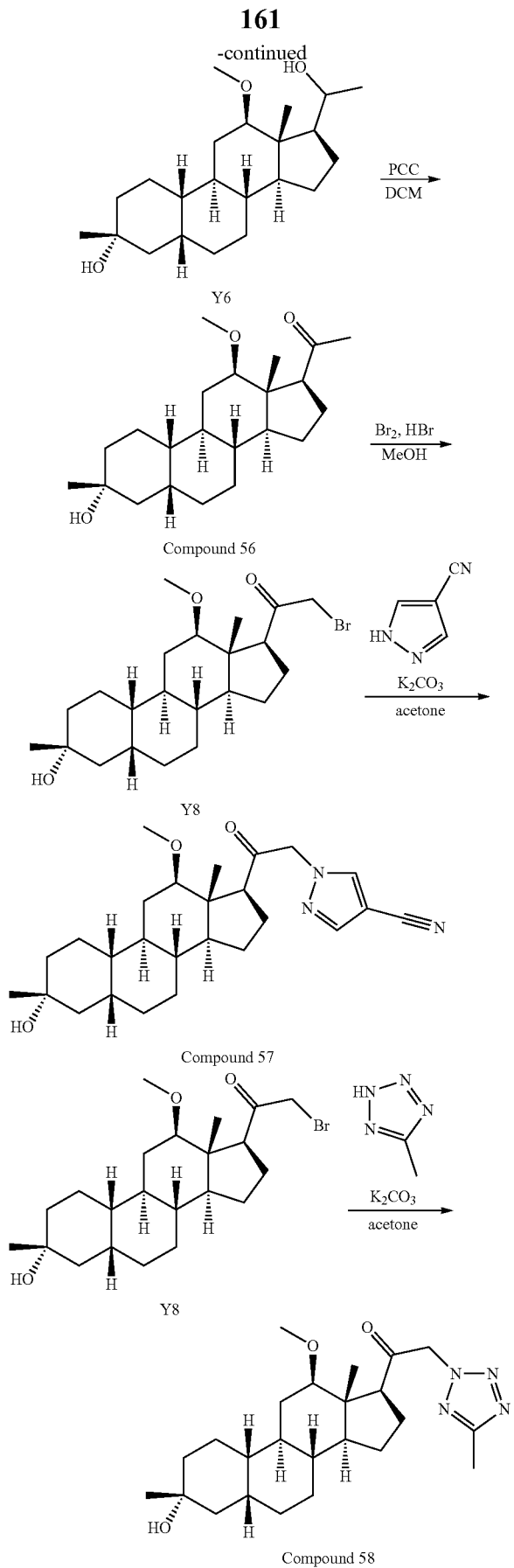

Step 1

To a solution of Y1 (10 g, 34.4 mmol) in toluene (100 mL) was added p-toluenesulfonic acid (106 mg, 0.6 mmol) and pyridin-2-ylmethanamine (8.17 g, 75.6 mmol) at 25° C. The reaction mixture was heated to 140° C. with a Dean-Stark apparatus for 16 hrs. The reaction was cooled to 25° C. and diluted with EtOAc (200 mL). The organic layer was washed sequentially with sat. NH$_4$Cl (2×200 mL), sat. NaHCO$_3$ (200 mL), brine (200 mL), dried over Na$_2$SO$_4$, filtered, and then concentrated in vacuum to give a crude product. The residual was triturated with EtOAc (20 mL) to give Y2 (8.7 g, 66%) as a solid.

$^1$H NMR (400 MHz, CDCl$_3$) δ: 8.57-8.49 (m, 1H), 7.72-7.61 (m, 1H), 7.44-7.38 (m, 1H), 7.17-7.09 (m, 1H), 4.69-4.52 (m, 2H), 2.49-2.22 (m, 2H), 2.06-1.63 (m, 8H), 1.54-1.44 (m, 3H), 1.41 (s, 3H), 1.40-1.32 (m, 3H), 1.30-1.24 (m, 5H), 1.21-1.07 (m, 3H), 0.90 (s, 3H).

Step 2

Y2 (8.7 g, 22.8 mmol), Cu(OTf)$_2$ (10.6 g, 29.6 mmol) and L-ascorbic acid sodium salt (9.03 g, 45.6 mmol) were added to a round-bottom-flask under N$_2$. Acetone (dry, 50 mL) and MeOH (dry, 50 mL) were added at 25° C. and stirred for 5 mins (reaction mixture may turn brown). O$_2$ from a balloon was bubbled through the reaction mixture for 5 min (resulting in a blue/green solution). The reaction mixture was heated at 50° C. under an O$_2$ atmosphere for 24 hrs. The reaction mixture was then cooled to 25° C. EtOAc (100 mL) and sat. Na$_4$ETDA (200 mL, pH~10) were added and the reaction mixture was stirred for 1 h. The layers were separated. The aqueous layer was extracted with EtOAc (2×200 mL), dried over Na$_2$SO$_4$, filtered and concentrated in vacuum to give crude product, which was purified by flash column (0~40% of EtOAc in PE) to give Y3 (4 g, 57%) as a solid.

$^1$H NMR (400 MHz, CDCl$_3$) δ: 3.82-3.74 (m, 1H), 2.98 (brs, 1H), 2.49-2.40 (m, 1H), 2.17-2.03 (m, 1H), 2.01-1.71 (m, 5H), 1.67-1.29 (m, 12H), 1.26 (s, 3H), 1.23-1.01 (m, 3H), 0.93 (s, 3H).

Step 3

To a solution of Y3 (2 g, 6.52 mmol) in THF (20 mL) was added KOH (2.21 g, 39.6 mmol) and Me$_2$SO$_4$ (1.85 g, 14.6 mmol) at 0° C. Then the mixture was warmed to 25° C. and stirred at the same temperature for 16 hrs. Me$_2$SO$_4$ (4.08 g, 32.4 mmol) was added at 0° C. and the mixture was stirred at 40° C. for 16 hrs. The mixture was quenched with the addition of 50 mL of water and extracted with EtOAc (2×30 mL). The combined organic layer was dried over Na$_2$SO$_4$, filtered and concentrated in vacuum to give crude product, which was purified by a silica gel column (PE/EtOAc=10/1-5/1) to give Y4 (1.2 g, 58%) as a solid.

$^1$H NMR (400 MHz, CDCl$_3$) δ: 3.50 (m, 1H), 3.19 (dd, J=6.8 Hz, J=4.8 Hz, 1H), 2.48-2.40 (m, 1H), 2.12-2.00 (m, 2H), 1.98-1.51 (m, 7H), 1.48-1.28 (m, 10H), 1.27 (s, 3H), 1.23-1.01 (m, 4H), 0.93 (s, 3H).

Step 4

To a suspension of EtPPh$_3$Br (4.15 g, 11.2 mmol) in THF (20 mL) was added t-BuOK (1.25 g, 11.2 mmol) at 25° C. under N$_2$. The mixture was stirred at 50° C. for 30 mins. To the mixture was added Y4 (1.2 g, 3.74 mmol) in THF (12 mL) at 50° C. The mixture was stirred at 50° C. for 16 hrs. The mixture was quenched with sat·NH$_4$Cl solution (50 mL) and extracted with EtOAc (2×100 mL). The combined organic layer was dried over Na$_2$SO$_4$, filtered and concentrated in vacuum to give crude product which was purified by a silica gel column (PE/EtOAc=5/1-3/1) to give Y5 (1.1 g, 89%) as colourless oil.

$^1$H NMR (400 MHz, CDCl$_3$) δ 5.26-5.18 (m, 1H), 3.34 (s, 3H), 3.16 (dd, J=10.6 Hz, J=5.0 Hz, 1H), 2.44-2.39 (m, 1H), 2.20-2.15 (m, 4H), 1.80-1.76 (m, 5H), 1.75-1.23 (m, 9H), 1.27 (s, 3H), 1.25-0.95 (m, 6H), 0.86 (s, 3H).

Step 5

To a solution of Y5 (1.1 g, 3.30 mmol) in THF (30 mL) was added 9-BBN dimer (2.01 g, 8.25 mmol) at 25° C. under N$_2$. The solution was stirred at 50° C. for 16 hrs. After cooling to 0° C., a solution of EtOH (30 mL) and NaOH (6.60 mL, 5M in H$_2$O, 33.0 mmol) was added very slowly. After the addition, H$_2$O$_2$ (3.30 mL, 33.0 mmol, 30% in water) was added slowly and the inner temperature was maintained below 10° C. The mixture was stirred at 50° C. under N$_2$ for 1 h. The mixture was re-cooled to 30° C. Water (100 mL) was added to the solution and extracted with EtOAc (2×100 mL). The combined organic layer was washed sat. Na$_2$S$_2$O$_3$ (100 mL), dried over Na$_2$SO$_4$, filtered and concentrated in vacuum to give Y6 (3 g, crude) as colorless oil, which was used directly for the next step.

Step 6

To a solution of Y6 (3 g, 8.55 mmol) in DCM (30 mL) was added silica gel (6.1 g) and PCC (5.51 g, 25.6 mmol) at 25° C. The reaction was stirred at 25° C. for 2 hrs. The reaction mixture was filtered and the filtrate was concentrated in vacuum to give crude product, which was purified by a silica gel column (PE/EtOAc=5/1) to give Compound 56 (1.2 g, impure) as colourless oil. Compound 56 (1.2 g, impure) was purified by combi-flash (DCM/acetone=30/1-20/1) to give Compound 56 (250 mg, pure) as a solid and Compound 56 (420 mg, impure) as a solid. Compound 56 (250 mg, 0.717 mmol) was triturated with (PE/EtOAc=3/1, 120 mL) to afford Compound 56 (240 mg, 96%) as a solid.

$^1$H NMR (400 MHz, CDCl$_3$) δ 3.34 (m, 1H), 3.08 (dd, J=10.8 Hz, J=4.4 Hz, 1H), 2.69 (t, J=8.8 Hz, 1H), 2.22 (s, 3H), 2.11-2.05 (m, 2H), 1.80-1.55 (m, 8H), 1.53-1.29 (m, 5H), 1.28 (s, 3H), 1.19-0.85 (m, 9H), 0.66 (s, 3H).

LCMS Rt=0.924 min in 2 min chromatography, 30-90 AB, purity 100%, MS ESI calcd. For C$_{22}$H$_{37}$O$_3$[M+H]$^+$ 349, found 349.

Step 7

To a solution of Compound 56 (420 mg, 1.20 mmol) in MeOH (8 ml) was added HBr (48.5 mg, 0.240 mmol, 40% in water) and Br$_2$ (210 mg, 1.32 mmol) in MeOH (8 mL) at 25° C. The mixture was stirred at 25° C. for 16 hrs. The mixture was quenched by sat·NaHCO$_3$ (10 mL) and water (20 mL), extracted with EtOAc (2×20 mL). The combined organic phase was washed with brine (20 mL), dried over anhydrous Na$_2$SO$_4$, filtered and concentrated in vacuum to afford Y8 (500 mg, 98%) as light yellow oil, which was used directly for the next step.

$^1$H NMR (400 MHz, CDCl$_3$) δ 4.15-3.99 (m, 2H), 3.34 (s, 3H), 3.11 (dd, J=11.0 Hz, J=4.6 Hz, 1H), 3.01 (t, J=9.2 Hz, 1H), 2.58 (s, 1H), 2.19-2.05 (m, 3H), 1.90-1.59 (m, 6H), 1.51-1.32 (m, 7H), 1.28 (s, 3H), 1.13-1.01 (m, 3H), 0.94-0.82 (m, 2H), 0.65 (s, 3H).

Step 8

To a mixture of Y8 (250 mg, 0.585 mmol) and K$_2$CO$_3$ (160 mg, 1.16 mmol) in acetone (4 mL) was added 1H-pyrazole-4-carbonitrile (81.6 mg, 0.877 mmol) at 25° C. The reaction mixture was stirred at the 25° C. for 16 hrs. The reaction mixture was filtered and the filtrate was concentrated in vacuum to give crude product, which was purified by a silica gel column (PE/EtOAc=2/1-1/1) to give Compound 57 (125 mg, 49%) as a solid.

$^1$H NMR (400 MHz, CDCl$_3$) δ 7.81 (s, 2H), 5.45 (d, J=17.6 Hz, 1H), 4.94 (d, J=17.6 Hz, 1H), 3.40 (s, 3H), 3.19 (dd, J=11 Hz, J=4.6 Hz, 1H), 2.75-2.65 (m, 1H), 2.22-2.07 (m, 2H), 1.92-1.59 (m, 6H), 1.52-1.41 (m, 7H), 1.40-1.30 (m, 3H), 1.29 (s, 3H), 1.15-1.04 (m, 2H), 0.99-0.82 (m, 2H), 0.67 (s, 3H).

LCMS Rt=0.981 min in 2 min chromatography, 30-90 AB, purity 100%, MS ESI calcd. For C$_{26}$H$_{37}$N$_3$O$_3$Na [M+Na]$^+$ 462, found 462.

Step 9

To a solution of Y8 (250 mg, 0.585 mmol) in acetone (5 mL) was added 5-methyl-2H-tetrazole (73.7 mg, 0.877 mmol), followed by K$_2$CO$_3$ (160 mg, 1.16 mmol). The resulting reaction mixture was stirred at 25° C. for 16 hrs. The mixture was filtered and the filtrate was concentrated in vacuum to give crude product, which was purified by a silica gel column (PE/EtOAc=3/1-1/1) to give Compound 58 (60 mg, impure) as a solid and Compound 59 (54 mg, 22%) as a solid. Compound 58 (60 mg, impure) was re-purified by combi-flash (EtOAc in PE, 40%-50%) to afford Compound 58 (45 mg, 75%) as a solid.

Compound 58

$^1$H NMR (400 MHz, CDCl$_3$) δ 5.89 (d, J=16.8 Hz, 1H), 5.35 (d, J=17.2 Hz, 1H), 3.45 (s, 3H), 3.18 (dd, J=11 Hz, J=4.2 Hz, 1H), 2.74-2.64 (m, 1H), 2.56 (s, 3H), 2.23-2.06 (m, 2H), 1.91-1.67 (m, 6H), 1.53-1.36 (m, 8H), 1.37-1.29 (m, 3H), 1.28 (s, 3H), 1.15-1.02 (m, 2H), 0.99-0.87 (m, 1H), 0.69 (s, 3H).

LCMS Rt=0.951 min in 2 min chromatography, 30-90 AB, purity 99.42%, MS ESI calcd. For C$_{23}$H$_{33}$N$_4$O [M+H–CH$_3$OH—H$_2$O]$^+$ 381, found 381.

Compound 59

$^1$H NMR (400 MHz, CDCl$_3$) δ 5.62 (d, J=18.0 Hz, 1H), 5.24 (d, J=18.4 Hz, 1H), 3.42 (s, 3H), 3.24 (dd, J=11.2 Hz, J=4.4 Hz, 1H), 2.84-2.72 (m, 1H), 2.45 (s, 3H), 2.22-2.06

(m, 2H), 1.91-1.72 (m, 5H), 1.52-1.37 (m, 7H), 1.38-1.30 (m, 3H), 1.29 (s, 3H), 1.17-1.03 (m, 3H), 1.01-0.83 (m, 2H), 0.69 (s, 3H).

LCMS Rt=0.912 min in 2 min chromatography, 30-90 AB, purity 100%, MS ESI calcd. For $C_{24}H_{39}N_4O_3$ [M+H]$^+$ 431, found 431.

Example 35. Syntheses of Compounds 60 and 61

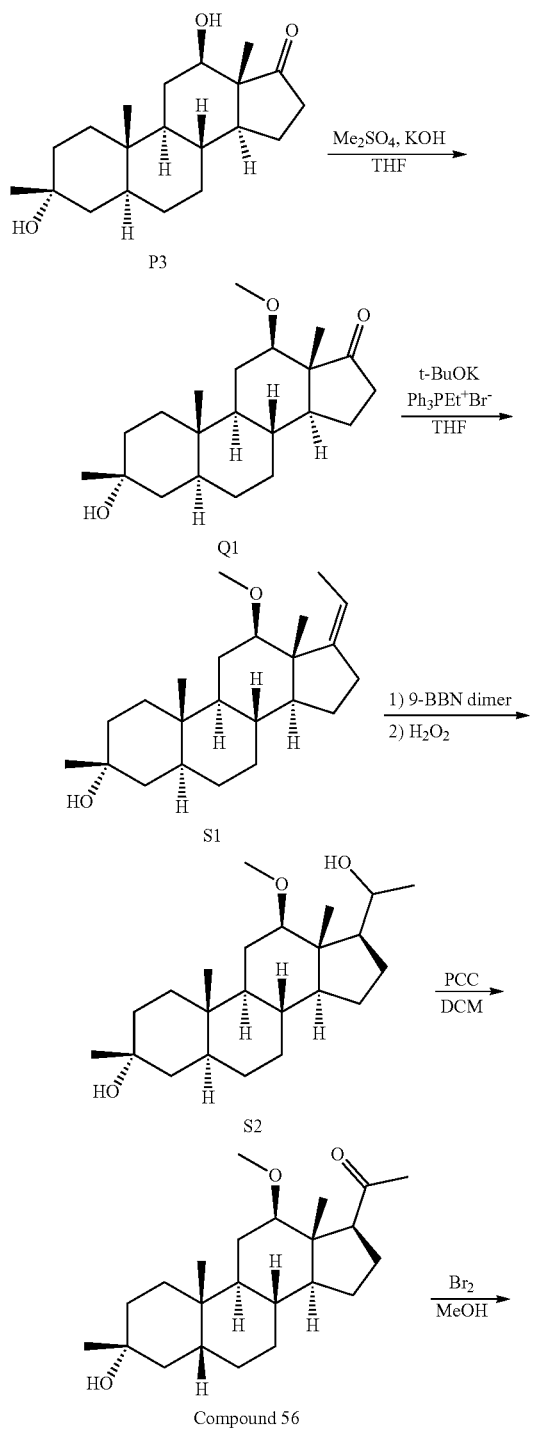

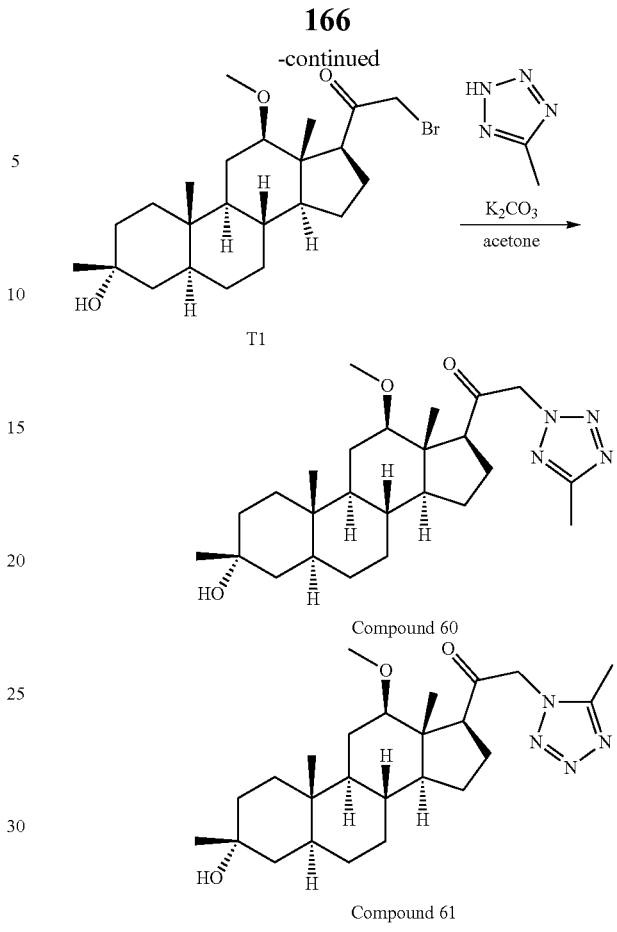

Step 1

To a solution of P3 (2 g, 6.24 mmol) in THF (20 mL) was added KOH (1.05 g, 18.9 mmol) and Me$_2$SO$_4$ (1.60 g, 1.20 mL, 12.7 mmol) at 0° C. Then the mixture was warmed to 25° C. and stirred at this temperature for 16 hrs. Me$_2$SO$_4$ (1.60 g, 1.20 mL, 12.7 mmol) at 0° C. was added and the mixture was stirred at 25° C. for 16 hrs. The mixture was quenched with 50 mL of water and extracted with EtOAc (2×30 mL). The combined organic layer was dried over Na$_2$SO$_4$, filtered and concentrated in vacuum to give crude product, which was purified by a silica gel column (PE/EtOAc=10/1-5/1) to give Q1 (1.7 g, 82%) as a solid.

$^1$H NMR (400 MHz, CDCl$_3$) δ 3.49 (s, 3H), 3.17 (dd, J=11.2 Hz, J=4.8 Hz, 1H), 2.48-2.39 (m, 1H), 2.12-1.88 (m, 3H), 1.84-1.74 (m, 1H), 1.54-1.49 (m, 3H), 1.42-1.33 (m, 2H), 1.32-1.22 (m, 6H), 1.21 (s, 3H), 1.14-1.11 (m, 2H), 1.13 (s, 1H), 1.02-0.94 (m, 1H), 0.93 (s, 3H), 0.87-0.79 (m, 1H), 0.77 (s, 3H).

Step 2

To a suspension of EtPPh$_3$Br (5.64 g, 15.2 mmol) in THF (60 mL) was added t-BuOK (1.70 g, 15.2 mmol) at 25° C. under N$_2$. The mixture was stirred at 50° C. for 30 mins. To the mixture was added Q1 (1.7 g, 5.08 mmol) in THF (20 mL) at 50° C. The mixture was stirred at 50° C. for 16 hrs. The reaction was cooled to 25° C. and the mixture was quenched with sat·NH$_4$Cl (100 mL) and extracted with EtOAc (2×100 mL). The combined organic layer was dried over Na$_2$SO$_4$, filtered and concentrated in vacuum to give crude product, which was purified by a silica gel column (PE/EtOAc=5/1-3/1) to give S1 (1.6 g, 91%) as a solid.

$^1$H NMR (400 MHz, CDCl$_3$) δ 5.27-5.16 (m, 1H), 3.33 (s, 3H), 3.14 (dd, J=10.4 Hz, J=4.8 Hz, 1H), 2.46-2.33 (m, 1H), 2.26-2.06 (m, 2H), 1.80-1.75 (m, 3H), 1.73-1.70 (m, 1H), 1.55-1.51 (m, 2H), 1.42-1.32 (m, 3H), 1.28-1.22 (m, 5H), 1.20 (s, 3H), 1.19-1.16 (m, 2H), 1.15-1.02 (m, 2H), 0.97-0.87 (m, 1H), 0.86 (s, 3H), 0.82-0.78 (m, 1H), 0.82-0.78 (m, 1H), 0.77 (s, 3H).

Step 3

To a solution of S1 (1.6 g, 4.61 mmol) in THF (20 mL) was added 9-BBN dimer (2.80 g, 11.5 mmol) at 0° C. under N$_2$. The solution was stirred at 50° C. for 16 hrs. After cooling to 0° C., a solution of EtOH (30 mL) and NaOH (9.22 mL, 5M in H$_2$O, 46.1 mmol) was added in sequence very slowly. After the addition, H$_2$O$_2$ (4.60 mL, 46.1 mmol, 30% in water) was added slowly and the inner temperature was maintained below 10° C. The mixture was stirred at 50° C. under N$_2$ for 1 h. The mixture was cooled to 30° C., diluted with water (100 mL) and extracted with EtOAc (2×100 mL). The combined organic layer was washed with sat. Na$_2$S$_2$O$_3$ (50 mL), dried over Na$_2$SO$_4$, filtered and concentrated in vacuum to give S2 (3.5 g, crude) as colorless oil, which was directly used in next step without further purification.

Step 4

To a solution of S2 (3.5 g, 9.60 mmol) in DCM (35 mL) was added silica gel (5.6 g) and PCC (5.15 g, 23.9 mmol) at 25° C. The reaction was stirred at 25° C. for 2 hrs. The reaction mixture was filtered and the filtrate was concentrated in vacuum to give crude product which was purified by a silica gel column (PE/EtOAc=5/1) to give Compound 56 (950 mg, 27%) as a solid.

$^1$H NMR (400 MHz, CDCl$_3$) δ 3.33 (s, 3H), 3.06 (dd, J=10.8 Hz, J=4.4 Hz, 1H), 2.68 (t, J=9.0 Hz, 1H), 2.21 (s, 3H), 2.11-1.95 (m, 2H), 1.74-1.62 (m, 3H), 1.54-1.43 (m, 3H), 1.42-1.22 (m, 7H), 1.21 (s, 3H), 1.18-1.02 (m, 4H), 0.96-0.78 (m, 2H), 0.76 (s, 3H), 0.65 (s, 3H).

Step 5

To a solution of Compound 56 (200 mg, 0.552 mmol) in MeOH (4 ml) was added HBr (22.3 mg, 0.11 mmol, 40% in water) and Br$_2$ (96.9 mg, 0.607 mmol) in MeOH (4 mL) at 25° C. The mixture was stirred at 25° C. for 16 hrs. The mixture was quenched by sat·NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford T1 (230 mg, crude) as light yellow oil, which was used directly for the next step.

$^1$H NMR (400 MHz, CDCl$_3$) δ 4.18-4.09 (m, 1H), 4.06-3.97 (m, 1H), 3.32 (s, 3H), 3.08 (dd, J=10.8 Hz, J=4.4 Hz, 1H), 3.03-2.96 (m, 1H), 2.15-1.97 (m, 4H), 1.79-1.64 (m, 6H), 1.54-1.49 (m, 5H), 1.21 (s, 3H), 1.19-1.01 (m, 6H), 0.76 (s, 3H), 0.64 (s, 3H).

Step 6

To a solution of T1 (230 mg, 0.521 mmol) in acetone (5 mL) was added 5-methyl-2H-tetrazole (65.7 mg, 0.782 mmol), followed by K$_2$CO$_3$ (143 mg, 1.04 mmol). The resulting reaction mixture was stirred at 25° C. for 16 hrs.

The mixture was filtered and the filtrate was concentrated in vacuum to give crude product which was purified by a silica gel column (PE/EtOAc=3/1-1/1) to give Compound 60 (70 mg, 30%, impure) as colourless oil and Compound 61 (45 mg, 19%, impure) as colourless oil. Compound 60 (70 mg, impure) was purified by a silica gel column (PE/EtOAc=3/1) to give Compound 61 (54 mg, 77%) as a solid. Compound 61 (45 mg, impure) was purified by a silica gel column (PE/EtOAc=2/1-1/1) to give Compound 61 (28 mg, 62%) as a solid.

Compound 60

$^1$H NMR (400 MHz, CDCl$_3$) δ 5.92-5.86 (m, 1H), 5.37-5.32 (m, 1H), 3.44 (s, 3H), 3.16 (dd, J=10.8 Hz, J=4.4 Hz, 1H), 2.68 (t, J=8.8 Hz, 1H), 2.56 (s, 3H), 2.23-2.03 (m, 2H), 2.01 (s, 1H), 1.74-1.66 (m, 3H), 1.54-1.49 (m, 3H), 1.39-1.24 (m, 6H), 1.21 (s, 3H), 1.19-1.09 (m, 3H), 0.98-0.80 (m, 3H), 0.77 (s, 3H), 0.68 (s, 3H).

LCMS Rt=1.030 min in 2 min chromatography, 30-90 AB, purity 100%, MS ESI calcd. For C$_{24}$H$_{37}$N$_4$O$_2$ [M+H–CH3OH]$^+$ 413, found 413.

Compound 61

$^1$H NMR (400 MHz, CDCl$_3$) δ 5.65-5.59 (m, 1H), 5.26-5.20 (m, 1H), 3.41 (s, 3H), 3.22 (dd, J=11.2 Hz, J=4.4 Hz, 1H), 2.76 (t, J=8.4 Hz, 1H), 2.44 (s, 3H), 2.20-2.04 (m, 2H), 1.84-1.65 (m, 3H), 1.54-1.50 (m, 2H), 1.46-1.24 (m, 8H), 1.22 (s, 3H), 1.20-1.07 (m, 3H), 1.00-0.81 (m, 3H), 0.78 (s, 3H), 0.68 (s, 3H).

LCMS Rt=0.983 min in 2 min chromatography, 30-90 AB, purity 100%, MS ESI calcd. For C$_{25}$H$_{41}$N$_4$O$_3$ [M+H]$^+$ 445, found 445.

Example 52. Syntheses of Compounds 62 and 63

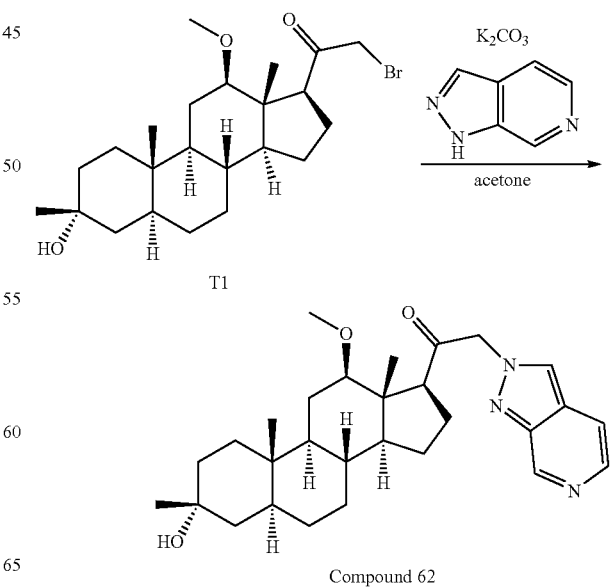

Compound 62

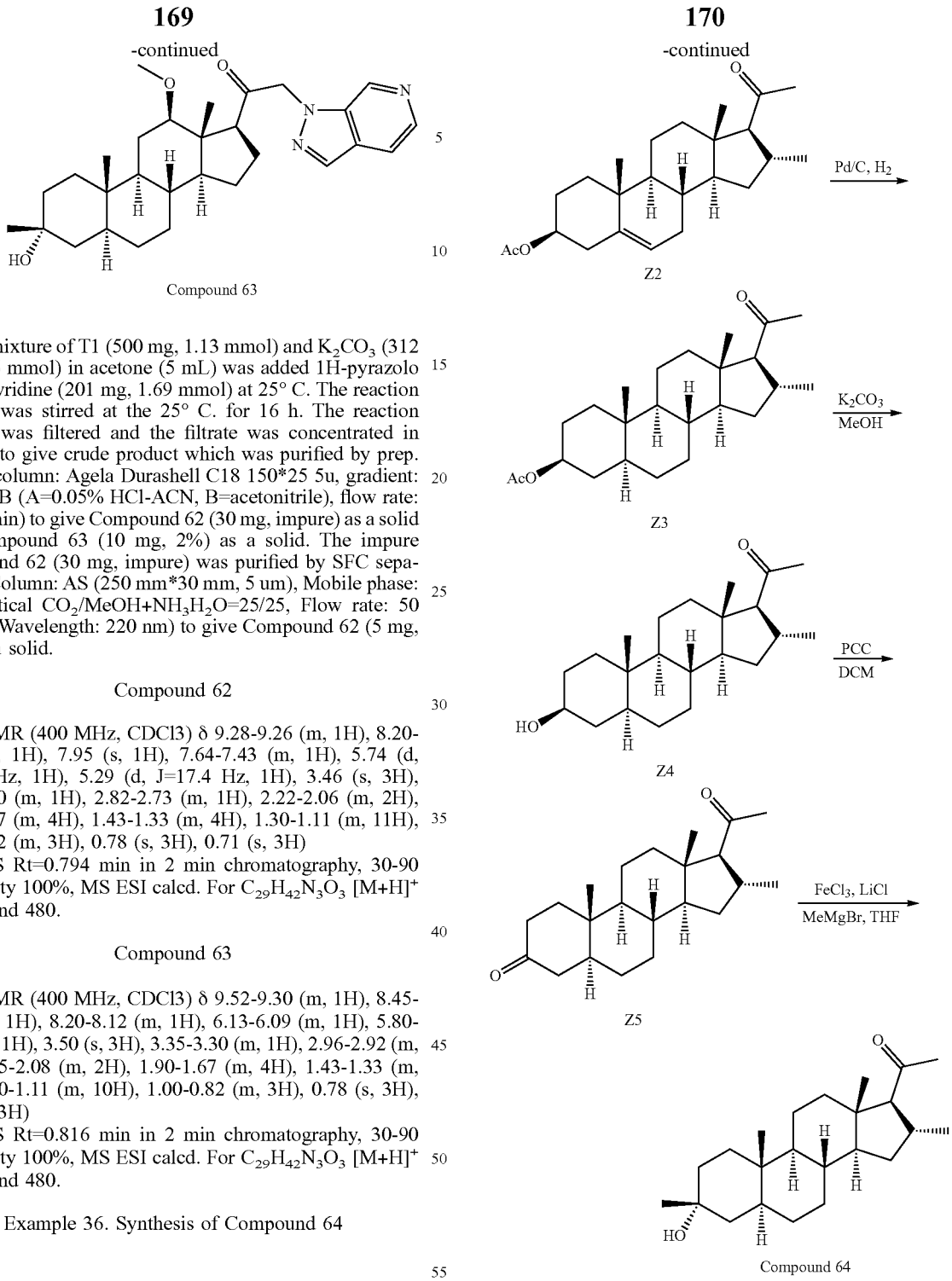

Compound 63

To a mixture of T1 (500 mg, 1.13 mmol) and $K_2CO_3$ (312 mg, 2.26 mmol) in acetone (5 mL) was added 1H-pyrazolo[3,4-b]pyridine (201 mg, 1.69 mmol) at 25° C. The reaction mixture was stirred at the 25° C. for 16 h. The reaction mixture was filtered and the filtrate was concentrated in vacuum to give crude product which was purified by prep. HPLC (column: Agela Durashell C18 150*25 5u, gradient: 30-60% B (A=0.05% HCl-ACN, B=acetonitrile), flow rate: 30 mL/min) to give Compound 62 (30 mg, impure) as a solid and Compound 63 (10 mg, 2%) as a solid. The impure Compound 62 (30 mg, impure) was purified by SFC separation (Column: AS (250 mm*30 mm, 5 um), Mobile phase: Supercritical $CO_2$/MeOH+$NH_3H_2O$=25/25, Flow rate: 50 ml/min, Wavelength: 220 nm) to give Compound 62 (5 mg, 1%) as a solid.

Compound 62

$^1$H NMR (400 MHz, CDCl3) δ 9.28-9.26 (m, 1H), 8.20-8.14 (m, 1H), 7.95 (s, 1H), 7.64-7.43 (m, 1H), 5.74 (d, J=17.4 Hz, 1H), 5.29 (d, J=17.4 Hz, 1H), 3.46 (s, 3H), 3.25-3.20 (m, 1H), 2.82-2.73 (m, 1H), 2.22-2.06 (m, 2H), 1.80-1.67 (m, 4H), 1.43-1.33 (m, 4H), 1.30-1.11 (m, 11H), 1.00-0.82 (m, 3H), 0.78 (s, 3H), 0.71 (s, 3H)

LCMS Rt=0.794 min in 2 min chromatography, 30-90 AB, purity 100%, MS ESI calcd. For $C_{29}H_{42}N_3O_3$ [M+H]$^+$ 480, found 480.

Compound 63

$^1$H NMR (400 MHz, CDCl3) δ 9.52-9.30 (m, 1H), 8.45-8.32 (m, 1H), 8.20-8.12 (m, 1H), 6.13-6.09 (m, 1H), 5.80-5.60 (m, 1H), 3.50 (s, 3H), 3.35-3.30 (m, 1H), 2.96-2.92 (m, 1H), 2.15-2.08 (m, 2H), 1.90-1.67 (m, 4H), 1.43-1.33 (m, 6H), 1.30-1.11 (m, 10H), 1.00-0.82 (m, 3H), 0.78 (s, 3H), 0.71 (s, 3H)

LCMS Rt=0.816 min in 2 min chromatography, 30-90 AB, purity 100%, MS ESI calcd. For $C_{29}H_{42}N_3O_3$ [M+H]$^+$ 480, found 480.

Example 36. Synthesis of Compound 64

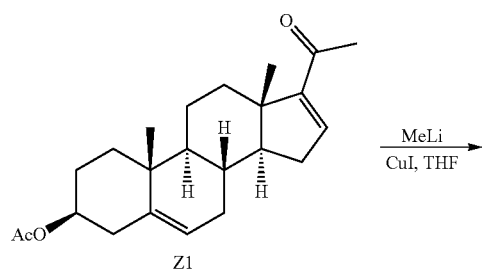

Step 1

To a stirred slurry of CuI (13.7 g, 72.2 mmol) in dry THF (90 mL) at 0° C. was added a solution of MeLi (87 mL, 1.6 M in ether) in ether until the initially formed yellow precipitate just redissolved to give a dear solution. Then a solution of Z1 (10 g. 27.8 mmol) in dry THF (200 mL) was added at 0° C., during which a bright yellow precipitate formed in the solution. The mixture was stirred at 0° C. for 30 mins and quenched with $NH_4Cl$ (300 mL). The aqueous phase was extracted with EtOAc (3×400 mL). The combined organic phase was washed with saturated brine (2×400 mL), dried over anhydrous Na$_2$SO$_4$, filtered and concentrated. The residue was purified by flash column (0~30% of EtOAc in PE) to give Z2 (7.1 g, 68%) as a solid.

$^1$H NMR (CDCl$_3$, 400 MHz) δ 5.38-5.36 (m, 1H), 4.62-4.58 (m, 1H), 2.68-2.66 (m, 1H), 2.33-2.27 (m, 2H), 2.12 (s, 4H), 2.03 (s, 3H), 2.00-1.95 (m, 2H), 1.96-1.85 (m, 2H), 1.65-1.50 (m, 2H), 1.50-1.45 (m, 5H), 1.47-1.35 (m, 4H), 1.01 (s, 3H), 0.93 (t, J=7.2 Hz, 3H), 0.65 (s, 3H).

The stereochemistry at C16 of Z2 was confirmed by NOE.

Step 2

To a solution of Z2 (7 g, 18.7 mmol) in MeOH (50 mL) and THF (50 mL) was added dry Pd/C (2 g) under N$_2$. The mixture was degassed under vacuum and purged with H$_2$ several times. The mixture was stirred for 20 hrs at 25° C. under 30 psi of H$_2$. The reaction mixture was filtered and the filtrate was concentrated in vacuum to give Z3 (6.5 g, 92%) as a solid.

$^1$H NMR (CDCl$_3$, 400 MHz) δ 4.77-4.64 (m, 1H), 2.65-2.60 (m, 1H), 2.11-2.10 (m, 4H), 2.00 (s, 3H), 1.95-1.70 (m, 4H), 1.69-1.48 (m, 9H), 1.40-1.10 (m, 8H), 1.10-0.95 (m, 5H), 0.61 (s, 3H).

Step 3

To a solution of Z3 (6.5 g, 17.3 mmol) in MeOH (50 mL) was added K$_2$CO$_3$ (4.77 g, 34.6 mmol) at 20° C. under N$_2$. The mixture was stirred at 20° C. for 2 hrs and quenched with water (40 mL). The aqueous phase was extracted with DCM (3×60 mL). The combined organic phase was washed with saturated brine (2×60 mL), dried over anhydrous Na$_2$SO$_4$, filtered and concentrated to give Z4 (4.7 g, crude) as a solid.

$^1$H NMR (CDCl$_3$, 400 MHz) δ 3.65-3.55 (m, 1H), 2.65-2.62 (m, 1H), 2.14-2.11 (m, 4H), 1.93-1.90 (m, 1H), 1.85-1.80 (m, 1H), 1.70-1.55 (m, 1H), 1.50-1.45 (m, 4H), 1.43-1.30 (m, 3H), 1.20-1.19 (m, 7H), 1.15-1.05 (m, 1H), 1.05-1.00 (m, 1H), 1.00-0.80 (m, 4H), 0.82 (s, 3H), 0.64 (m, 4H).

Step 4

To a solution of Z4 (4.7 g, 14.1 mmol) in DCM (70 mL) was added silica gel (7.2 g) and PCC (6.07 g, 28.2 mmol) at 20° C. After stirring at 20° C. for 1 h, the resulting mixture was filtered and the filtrate concentrated by vacuum. The crude product was re-dissolved in DCM (80 mL) and treated with silica gel (20 g) and PE (80 mL). The mixture was stirred at 20° C. for 30 mins and filtered. The filtrate was concentrated in vacuum to give Z5 (3.4 g, crude) as a solid.

$^1$H NMR (CDCl$_3$, 400 MHz) δ 2.65-2.62 (m, 1H), 2.45-2.20 (m, 3H), 2.15-2.10 (m, 5H), 2.10-1.90 (m, 2H), 1.70-1.15 (m, 12H), 1.00 (s, 3H), 0.94-0.92 (m, 4H), 0.80-0.70 (m, 1H), 0.65 (s, 3H).

Step 5

Under nitrogen atmosphere, anhydrous THF (40 mL) was cooled to 10° C. and anhydrous LiCl (907 mg, 21.4 mmol) was added in one portion. The mixture was stirred for 30 min after which a clear solution was obtained. To this mixture was added anhydrous FeCl$_3$ (1.81 g, 11.2 mmol) in one portion. The resulting mixture was stirred for additional 30 min. The reaction mixture was cooled to −35° C. and methyl magnesium bromide (3 M in diethyl ether, 13.6 mL, 40.8 mmol) was added dropwise maintaining the internal temperature between −35° C. and −30° C. The above mixture was stirred for 30 min at −30° C. Z5 (3.4 g, 10.2 mmol) was added in one portion. The internal temperature was allowed to −20° C. and held between −15° C. and −20° C. for 2 hours. TLC showed the reaction was completed. The reaction mixture was quenched with aqueous HCl (2 M, 20 mL), extracted with CH$_2$Cl$_2$ (2×50 mL). The combined organic layer was washed with aqueous NaOH (10%, 2×30 mL) and brine (30 mL), dried over anhydrous sodium sulfate, filtered and concentrated. The residue was purified by flash column (0-20% of EtOAc in PE) to give Compound 64 (0.56 g, 13%) as a solid and 2.5 g impure product. The 2.5 g impure product was purified by flash column (5%-20% of EtOAc in PE) to give Compound 64 (2.4 g, 56%) as a solid.

$^1$H NMR (CDCl$_3$, 400 MHz) δ 2.64-2.62 (m, 1H), 2.27-2.10 (m, 4H), 1.93-1.89 (m, 1H), 1.70-1.60 (m, 3H), 1.59-1.30 (m, 6H), 1.30-1.10 (m, 12H), 0.94-0.92 (m, 4H), 0.80-0.75 (m, 1H), 0.74 (m, 3H), 0.62 (m, 3H).

LCMS Rt=1.263 min in 2 min chromatography, 30-90 AB, purity 98%, MS ESI calcd. For C$_{23}$H$_{37}$O [M+H−H$_2$O]$^+$ 329, found 329.

Example 37. Synthesis of Compound 65

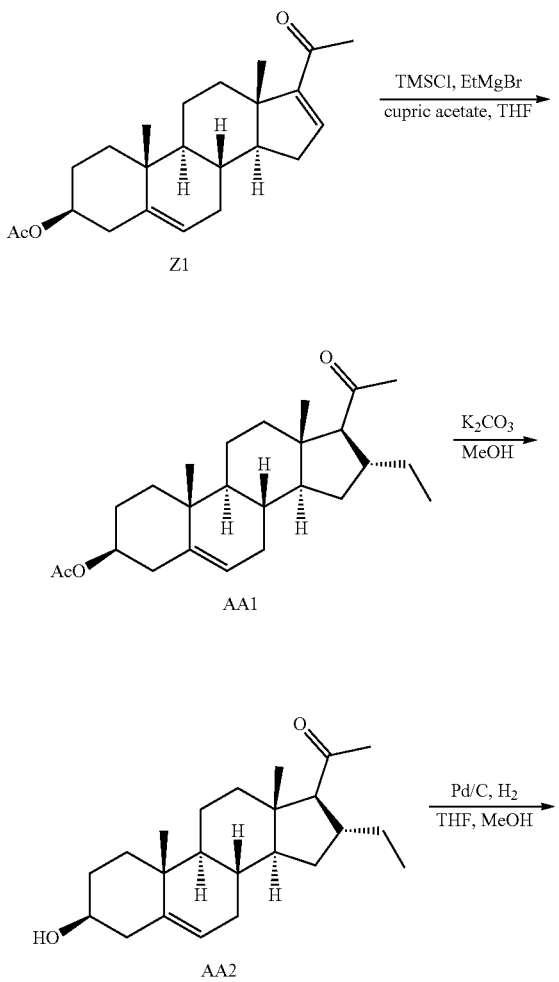

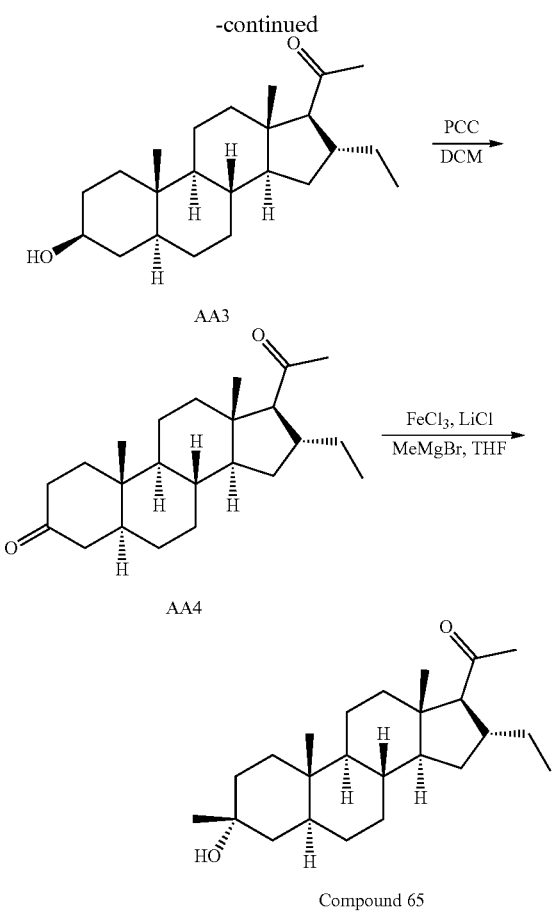

$^1$H NMR (CDCl$_3$, 400 MHz) δ 5.36-5.34 (m, 1H), 3.53-3.51 (m, 1H), 2.60-2.45 (m, 1H), 2.30-2.20 (m, 3H), 2.12 (s, 3H), 1.97-1.95 (m, 2H), 1.87-1.83 (m, 2H), 1.60-1.30 (m, 9H), 1.25-1.10 (m, 4H), 1.05-0.95 (m, 4H), 0.83-0.79 (m, 3H), 0.65 (s, 3H).

Step 3

To a solution of AA2 (3.6 g, 10.4 mmol) in MeOH (100 mL) and THF (100 mL) was added dry Pd/C (1 g) under N$_2$. The mixture was degassed under vacuum and purged with H$_2$ several times. The mixture was stirred for 20 hrs at 30° C. under 30 psi of H$_2$. The reaction mixture was filtered and the filtrate was concentrated in vacuum to give AA3 (3.5 g, 96%) as a solid.

$^1$H NMR (methanol-d4, 400 MHz) δ 3.54-3.52 (m, 1H), 2.47-2.46 (m, 1H), 2.34-2.33 (m, 1H), 2.14 (s, 3H), 1.98-1.94 (m, 1H), 1.80-1.65 (m, 4H), 1.60-1.20 (m, 14H), 1.10-0.90 (m, 3H), 0.85-0.70 (m, 7H), 0.65 (s, 3H).

Step 4

To a solution of AA3 (3.5 g, 10.5 mmol) in DCM (50 mL) was added silica gel (5 g) and PCC (4.52 g, 21 mmol) at 20° C. After stirring at 20° C. for 1 h, the resulting mixture was filtered and the filtrate concentrated by vacuum. The crude product was re-dissolved in DCM (50 mL) and treated with silica gel (30 g) and PE (50 mL). The mixture was stirred at 20° C. for 30 mins and filtered. The filtrate was concentrated in vacuum to give AA4 (2.89 g, 83%) as a solid.

$^1$H NMR (CDCl$_3$, 400 MHz) δ 2.55-2.20 (m, 5H), 2.12 (s, 3H), 2.00-2.93 (m, 3H), 1.65-1.55 (m, 2H), 1.50-1.20 (m, 12H), 1.00 (s, 3H), 0.98-0.85 (m, 1H), 0.82-0.78 (m, 4H), 0.65 (s, 3H).

Step 1

A solution of copper(II) acetate (503 mg, 2.78 mmol) in anhydrous THF (350 mL) was cooled to 0° C. After adding ethyl magnesium bromide (27 mL, 8.10 mmol) dropwise, a solution of Z1 (10 g, 27.8 mmol) together with chlorotrimethyl silane (15 g, 139 mmol) in THF (50 mL) was added dropwise, keeping the temperature below 10° C. After an hour at 0° C., ethyl magnesium bromide (10 mL, 30 mmol) was added and the reaction was stirred for 30 mins. The reaction was quenched by the addition of NH$_4$Cl (300 mL). extracted with EtOAc (3×400 mL). The combined organic phase was washed with saturated brine (2×800 mL), dried over anhydrous Na$_2$SO$_4$, filtered and concentrated. The residue was purified by flash column (0-25% of EtOAc in PE) to give AA1 (4.8 g, 44%) as a solid.

$^1$H NMR (CDCl$_3$, 400 MHz) δ 5.36-5.34 (m, 1H), 4.60-4.56 (m, 1H), 2.50-2.48 (m, 1H), 2.31-2.28 (m, 2H), 2.21-2.20 (m, 1H), 2.01 (s, 3H), 2.00-1.83 (m, 6H), 1.56-1.50 (m, 7H), 1.47-1.45 (m, 3H), 1.30-1.10 (m, 3H), 1.05-0.95 (m, 4H), 0.79 (t, J=6.8 Hz, 3H), 0.63 (s, 3H).

Step 2

To a solution of AA1 (4.8 g, 12.8 mmol) in MeOH (80 mL) was added K$_2$CO$_3$ (3.52 mg, 25.6 mmol) at 20° C. under N$_2$. The mixture was stirred at 20° C. for 2 hrs and quenched with water (40 mL). The aqueous phase was extracted with DCM (3×60 mL). The combined organic phase was washed with saturated brine (2×60 mL), dried over anhydrous Na$_2$SO$_4$, filtered and concentrated to give AA2 (3.6 g, 84%) as a solid.

Step 5

Under nitrogen atmosphere, anhydrous THF (40 mL) was cooled to 10° C. and anhydrous LiCl (741 mg, 17.5 mmol) was added in one portion. The mixture was stirred for 30 min after which a clear solution was obtained. To this mixture was added anhydrous FeCl$_3$ (1.49 g, 9.21 mmol) in one portion. The resulting mixture was stirred for an additional 30 min. The reaction mixture was cooled to −35° C. and methyl magnesium bromide (3 M in diethyl ether, 11.1 mL, 33.5 mmol) was added dropwise maintaining the internal temperature between −35° C. and −30° C. The above mixture was stirred for 30 min at −30° C. AA4 (2.89 g, 8.38 mmol) was added in one portion. The internal temperature was allowed to −20° C. and held between −15° C. and −20° C. for 2 hours. The reaction mixture was quenched with aqueous HCl (2 M, 20 mL), extracted with CH$_2$Cl$_2$ (2×50 mL). The combined organic layer was washed with aqueous NaOH (10%, 2×30 mL) and brine (30 mL), dried over anhydrous sodium sulfate, filtered and concentrated. The residue was triturated from EtOAc to give Compound 65 (0.25 g, 8%) as a solid, and 2 g of impure product.

$^1$H NMR (CDCl$_3$, 400 MHz) δ 2.51-2.44 (m, 1H), 2.21-2.18 (m, 1H), 2.11 (s, 3H), 1.91-1.88 (m, 1H), 1.70-1.60 (m, 3H), 1.60-1.78 (m, 4H), 1.75-1.65 (m, 5H), 1.60-1.05 (m, 11H), 1.00-1.80 (m, 1H), 0.79-0.75 (m, 4H), 0.73 (s, 3H), 0.62 (s, 3H).

LCMS Rt=1.315 min in 2 min chromatography, 30-90 AB, purity 100%, MS ESI calcd. For C$_{24}$H$_{39}$O [M+H−H$_2$O]$^+$ 343, found 343.

The stereochemistry at C16 of Compound 65 was confirmed by NOE.

Example 38. Synthesis of Compound 66

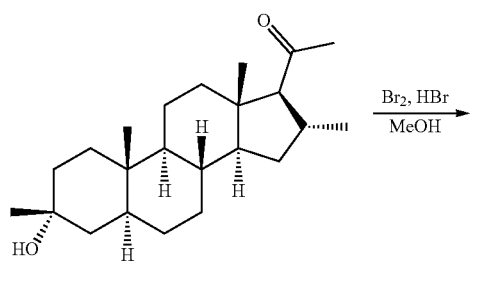

Compound 64

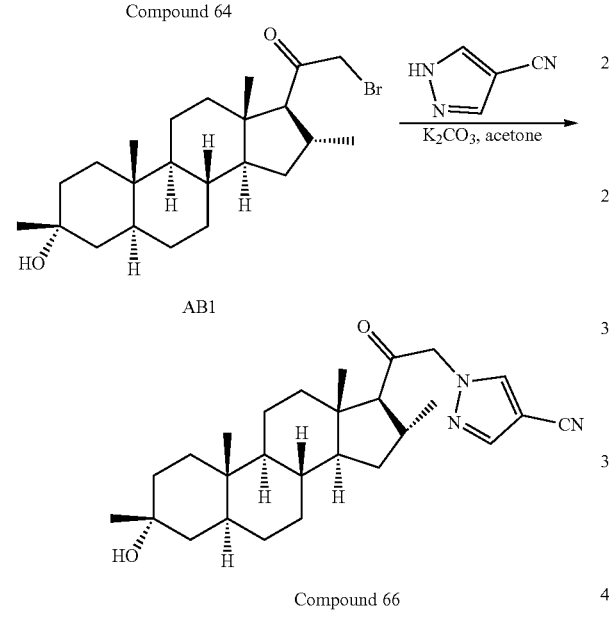

Step 1

To a solution of Compound 64 (900 mg, 2.59 mmol) in MeOH (10 ml) was added HBr (103 mg, 0.518 mmol, 40% in water) and Br$_2$ (406 mg, 2.59 mmol) at 25° C. After stirring at 25° C. for 16 hrs, the mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford AB1 (1.2 g) as a solid used directly for the next step.

$^1$H NMR (400 MHz, CDCl$_3$) δ 3.89 (d, J=12.0 Hz, 1H), 3.85 (d, J=12.0 Hz, 1H) 2.68-2.67 (m, 1H), 2.46 (d, J=12 Hz, 1H), 1.82-1.80 (m, 1H), 1.66-1.59 (m, 2H), 1.52-1.44 (m, 5H), 1.37-1.18 (m, 14H), 0.96 (d, J=8.0 Hz, 4H), 0.84-0.77 (m, 1H), 0.74 (s, 3H), 0.65 (s, 3H)

Step 2

To a mixture of AB1 (100 mg, 0.235 mmol) and K$_2$CO$_3$ (64.9 mg, 0.47 mmol) in acetone (5 mL) was added 1H-pyrazole-4-carbonitrile (32.7 mg, 0.352 mmol) at 25° C. The reaction mixture was stirred at the 25° C. for 16 h. Then saturated aqueous H$_2$O (50 mL) was added. The mixture was extracted with EtOAc (3×50 mL). The combined organic solution was washed with brine (20 mL), dried over Na$_2$SO$_4$ and concentrated in vacuum to give the crude product. The crude product was purified by flash column (0~30% of EtOAc in PE) to give Compound 66 (38 mg, 37%) as a solid.

$^1$H NMR (400 MHz, CDCl$_3$) δ 7.86 (s, 1H), 7.81 (s, 1H), 5.00 (d, J=16.0 Hz, 1H), 4.85 (d, J=16.0 Hz, 1H), 2.71-2.68 (m, 1H), 2.18-2.09 (m, 1H), 1.98-1.96 (m, 1H), 1.65-1.53 (m, 2H), 1.52-1.50 (m, 5H), 1.37-1.14 (m, 14H), 0.97 (d, J=8 Hz, 4H), 0.85-0.81 (m, 1H), 0.75 (s, 3H), 0.68 (s, 3H).

LCMS Rt=2.594 min in 4.0 min chromatography, 30-90AB_220&254.lcm, purity 100%, MS ESI calcd. for C$_{27}$H$_{38}$N$_3$O [M+H−H$_2$O]$^+$ 420, found 420.

Example 39. Syntheses of Compounds 67, 68, and 69

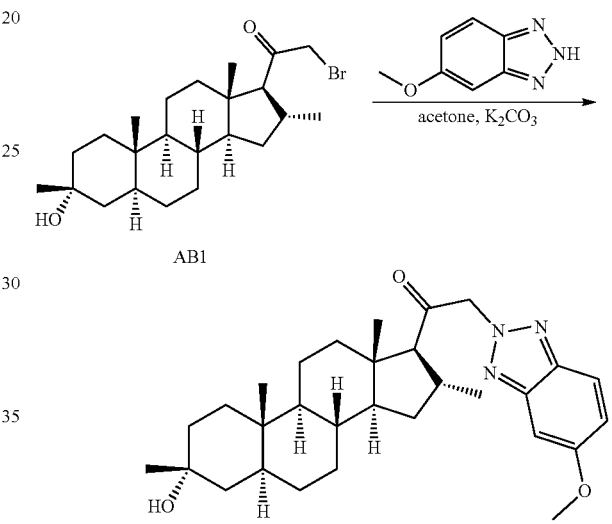

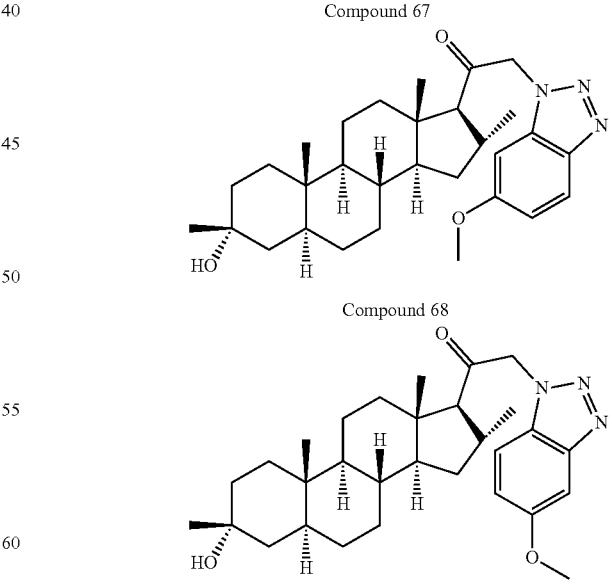

To a solution of AB1 (200 mg, 0.47 mmol) in acetone (2 mL) was added 5-methoxy-2H-benzo[d][1,2,3]triazole (105 mg, 0.705 mmol), followed by K$_2$CO$_3$ (129 mg, 0.940 mmol) at 25° C. The resulting reaction mixture was stirred at 25° C. for 16 hours. To the mixture was added water (20 mL) and then extracted with EtOAc (3×20 mL). The combined organic solution was washed with brine (20 mL), dried over Na$_2$SO$_4$ and concentrated in vacuum to give the crude product. The crude product was purified by per-HPLC separation (column: DYA-5 C18 150*25 mm*5 um, gradient: 60-100% B (A=0.05% HCl-ACN, B=acetonitrile), flow rate: 25 mL/min) to give impure Compound 67 and a mixture of Compound 68 and Compound 69. The impure Compound 67 was purified by flash column (0~30% of EtOAc in PE) to give Compound 67 (23 mg, 10%) as a solid. The mixture of Compound 68 and Compound 69, which were purified by SFC separation (column:AD (250 mm*30 mm, 10 um), gradient: 40-40% B (A=0.1% NH$_3$H$_2$O, B=ETOH), flow rate: 80 mL/min) to give Compound 68 (23 mg, 10%) as solid and Compound 69 (18 mg, 8%) as solid.

Compound 67

$^1$H NMR (400 MHz, CDCl$_3$) δ 7.73 (d, J=8.0 Hz, 1H), 7.07 (d, J=8.0 Hz, 2H), 5.41 (d, J=16 Hz, 2H), 3.88 (s, 3H), 2.76-2.78 (m, 1H), 2.22 (d, J=8.0 Hz, 1H), 2.09-2.06 (m, 1H), 1.66-1.62 (m, 2H), 1.52-1.48 (m, 5H), 1.37-1.21 (m, 14H), 0.98 (d, J=8.0 Hz, 3H), 0.99-0.97 (m, 2H), 0.76 (s, 6H).

LCMS Rt=2.963 min in 4.0 min chromatography, 30-90AB·1 cm, purity 96.89%, MS ESI calcd. for C$_{30}$H$_{44}$N$_3$O$_3$ [M+H]$^+$ 494, found 494.

Compound 68

$^1$H NMR (400 MHz, CDCl$_3$) δ 7.92 (d, J=8.0 Hz, 1H), 7.01 (dd, J=2.0, 8.0 Hz, 1H), 6.58 (d, J=2.0 Hz, 1H), 5.30 (s, 2H), 3.86 (s, 3H), 2.72-2.69 (m, 1H), 2.29 (d, J=8.0 Hz, 1H), 2.08-2.05 (m, 1H), 1.67-1.57 (m, 2H), 1.54-1.51 (m, 5H), 1.37-1.21 (m, 14H), 0.94 (d, J=8 Hz, 4H), 0.88-0.80 (m, 1H), 0.76 (s, 3H), 0.75 (s, 3H).

LCMS Rt=2.718 min in 4.0 min chromatography, 30-90AB·1 cm, purity 100%, MS ESI calcd. for C$_{30}$H$_{44}$N$_3$O$_3$ [M+H]$^+$ 494, found 494.

Compound 69

$^1$H NMR (400 MHz, CDCl$_3$) δ 7.39 (d, J=2.0 Hz, 1H), 7.18-7.16 (m, 2H), 5.33 (s, 2H), 3.89 (s, 3H), 2.74-2.68 (m, 1H), 2.28 (d, J=8.0 Hz, 1H), 2.10-2.01 (m, 1H), 1.67-1.53 (m, 2H), 1.52-1.51 (m, 5H), 1.37-1.21 (m, 14H), 0.94 (d, J=8 Hz, 4H), 0.88-0.80 (m, 1H), 0.76 (s, 3H), 0.76 (s, 3H).

LCMS Rt=2.732 min in 4.0 min chromatography, 30-90AB·1 cm, purity 100%, MS ESI calcd. for C$_{30}$H$_{44}$N$_3$O$_3$ [M+H]$^+$ 494, found 494.

Example 40. Syntheses of Compounds 70, 71, and 72

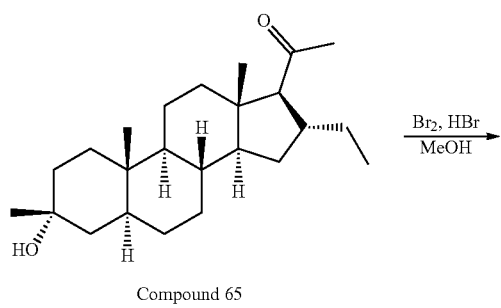

Compound 65

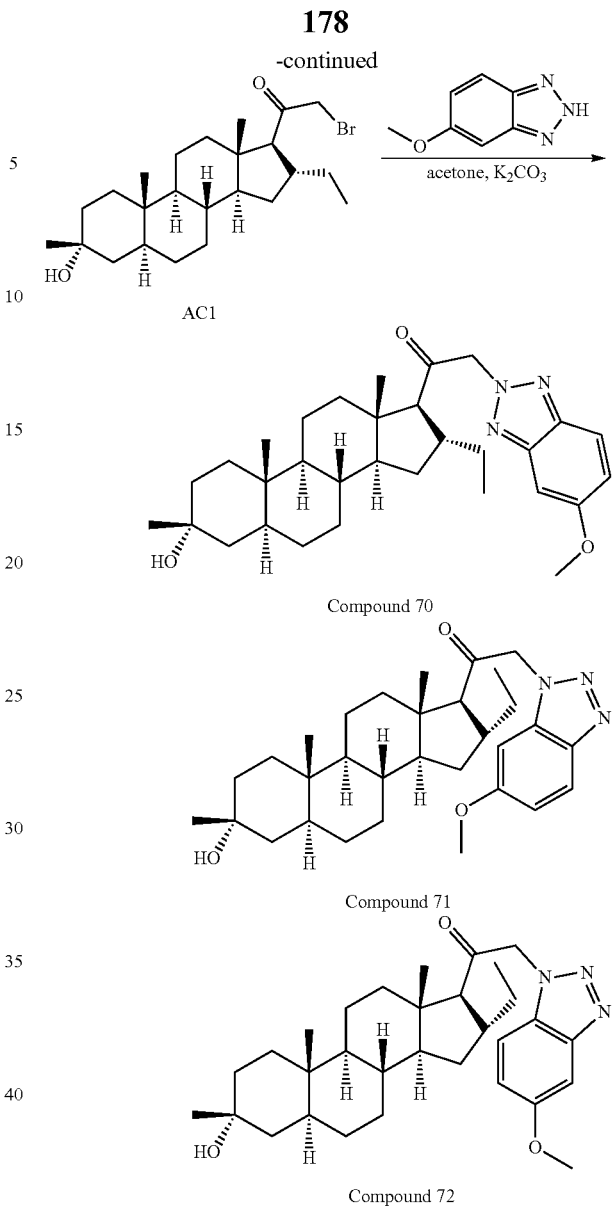

Step 1

To a solution of Compound 65 (1 g, 2.77 mmol) in MeOH (10 ml) was added HBr (110 mg, 0.554 mmol, 40% in water) and Br$_2$ (442 mg, 2.82 mmol) at 25° C. The mixture was stirred at 25° C. for 16 hrs. The mixture was quenched by sat·aq NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuum to afford AC1 (1.2 g) as a solid used directly for the next step.

Step 2

To a solution of AC1 (200 mg, 0.486 mmol) in acetone (2 mL) was added 5-methoxy-2H-benzo[d][1,2,3]triazole (108 mg, 0.729 mmol), followed by K$_2$CO$_3$ (134 mg, 0.972 mmol) at 25° C. The resulting reaction mixture was stirred at 25° C. for 16 hours. To the mixture was added water (20 mL) and then extracted with EtOAc (3×20 mL). The combined organic solution was washed with brine (20 mL), dried over Na$_2$SO$_4$ and concentrated in vacuum to give the crude product, which was purified by flash column (0~30% of EtOAc in PE) to give Compound 70 (33 mg, 7%) as a solid; and 100 mg of a mixture of Compound 71 and Compound 72. The mixture was purified by SFC (column: OD (250 mm*30 mm, 5 um)), gradient: 45-45% B (A=0.1% NH$_3$H$_2$O, B=ETOH), flow rate: 50 mL/min) to give Compound 72 (46 mg, 9%) as a solid and Compound 72 (32 mg, 7%) as a solid.

Compound 70

$^1$H NMR (400 MHz, CDCl$_3$) δ 7.73 (d, J=8.0 Hz, 1H), 7.07 (d, J=8.0 Hz, 2H), 5.41 (d, J=12 Hz, 2H), 3.87 (s, 3H), 2.56-2.54 (m, 1H), 2.28 (d, J=8.0 Hz, 1H), 2.09-2.06 (m, 1H), 1.66-1.62 (m, 2H), 1.52-1.48 (m, 5H), 1.37-1.21 (m, 16H), 1.00-0.92 (m, 1H) 0.83 (d, J=8.0 Hz, 4H), 0.76 (s, 3H), 0.75 (s, 3H).

LCMS Rt=3.059 in in 4.0 min chromatography, 30-90AB·1 cm, purity 96.49%, MS ESI calcd. for C$_{31}$H$_{46}$N$_3$O$_3$ [M+H]$^+$ 508, found 508.

Compound 71

$^1$H NMR (400 MHz, CDCl$_3$) δ 7.39 (d, J=4.0 Hz, 1H), 7.20-7.13 (m, 2H), 5.41-5.30 (m, 2H), 3.89 (s, 3H), 2.56-2.54 (m, 1H), 2.35 (d, J=8.0 Hz, 1H), 2.09-2.06 (m, 1H), 1.69-1.62 (m, 2H), 1.52-1.48 (m, 5H), 1.37-1.21 (m, 16H), 1.00-0.92 (m, 1H) 0.85-0.79 (m, 4H), 0.76 (s, 3H), 0.73 (s, 3H).

LCMS Rt=2.822 in in 4.0 min chromatography, 30-90AB·1 cm, purity 100%, MS ESI calcd. for C$_{31}$H$_{46}$N$_3$O$_3$ [M+H]$^+$ 508, found 508.

Compound 72

$^1$H NMR (400 MHz, CDCl$_3$) δ 7.92 (d, J=8.0 Hz, 1H), 7.01 (dd, J=4, 8.0 Hz, 1H), 6.57 (d, J=4 Hz, 1H), 5.38-5.27 (d, J=12 Hz, 2H), 3.85 (s, 3H), 2.60-2.53 (m, 1H), 2.37 (d, J=8.0 Hz, 1H), 2.13-2.06 (m, 1H), 1.73-1.65 (m, 2H), 1.56-1.51 (m, 5H), 1.37-1.21 (m, 16H), 0.83-0.80 (m, 1H), 0.82 (d, J=8.0 Hz, 4H), 0.76 (s, 3H), 0.74 (s, 3H).

LCMS Rt=2.795 in in 4.0 min chromatography, 30-90AB·1 cm, purity 100%, MS ESI calcd. for C$_{31}$H$_{46}$N$_3$O$_3$ [M+H]$^+$ 508, found 508.

Example 41. Synthesis of Compound 73

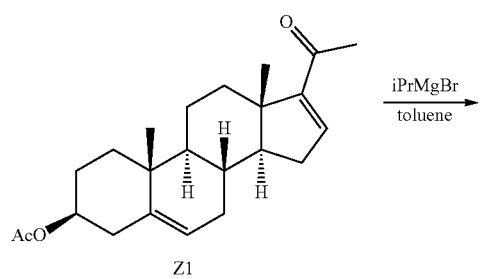

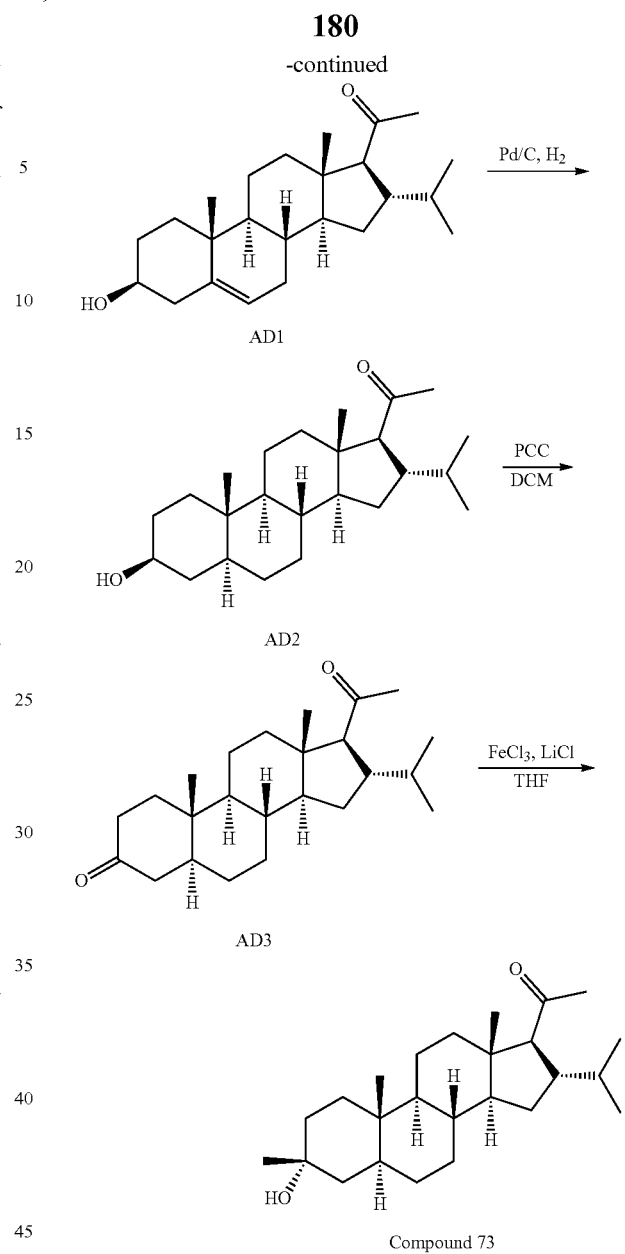

Step 1

To a solution of iPrMgCl (420 mL, 2 M in THF) in THF (100 mL) was added a solution of Z1 (20 g, 56.1 mmol) in toluene (400 mL) at 20° C. After stirring at this temperature for 30 mins, the suspension was allowed to heat at 40° C. for 18 hrs. The reaction mixture was quenched with aqueous NH$_4$Cl (500 mL), extracted with EtOAc (2×600 mL). The combined organic layer was washed with brine (500 mL), dried over anhydrous Na$_2$SO$_4$, filtered and concentrated. The residue was purified by flash column (0-20% of EtOAc in PE) to give AD1 (7 g, 31%) as a solid.

$^1$H NMR (CDCl$_3$, 400 MHz) δ 5.35-5.34 (m, 1H), 3.52 (s, 1H), 2.48-2.20 (m, 4H), 2.13 (s, 3H), 2.00-1.75 (m, 4H), 1.70-1.25 (m, 11H), 1.20-1.05 (m, 2H), 1.00 (s, 3H), 0.95-0.80 (m, 1H), 0.85-0.83 (m, 3H), 0.76-0.73 (m, 3H), 0.64 (s, 2H).

181

Step 2

To a solution of AD1 (4 g, 1.87 mmol) in MeOH (100 mL) and THF (100 mL) was added dry Pd(OH)$_2$/C (1 g) under N$_2$. The mixture was degassed under vacuum and purged with H$_2$ several times. The mixture was stirred for 20 hrs at 30° C. under 30 psi of H$_2$. The reaction mixture was filtered and the filtrate was concentrated in vacuum to give AD2 (3.8 g, 95%) as a solid.

$^1$H NMR (CDCl$_3$, 400 MHz) δ 3.58 (s, 1H), 2.45-2.30 (m, 2H), 2.11 (s, 4H), 1.90-1.50 (m, 8H), 1.45-1.25 (m, 5H), 1.25-1.30 (m, 3H), 1.15-1.00 (m, 2H), 0.95-0.85 (m, 3H), 0.84-0.75 (m, 6H), 0.74-0.65 (m, 3H), 0.61 (s, 3H).

Step 3

To a solution of AD2 (3.8 g, 1.8 mmol) in DCM (15 mL) was added silica gel (1.03 g) and PCC (775 mg, 3.6 mmol) at 25° C. After stirring at 25° C. for 1 h, the resulting mixture was filtered and the filtrate concentrated by vacuum. The crude product was re-dissolved in DCM (20 mL) and treated with silica gel (20 g) and PE (30 mL). The mixture was stirred at 25° C. for 30 mins and filtered. The filtrate was concentrated in vacuum to give AD3 (3.4 g, crude) as a solid.

$^1$H NMR (CDCl$_3$, 400 MHz) δ 2.45-2.25 (m, 5H), 2.13 (s, 3H), 2.10-2.00 (m, 2H), 1.90-1.73 (m, 1H), 1.75-1.65 (m, 2H), 1.60-1.55 (m, 1H), 1.64 (m, 1H), 1.59-1.25 (m, 6H), 1.25-1.10 (m, 4H), 1.00 (s, 3H), 0.95-0.90 (m, 1H), 0.85-0.83 (m, 3H), 0.75-0.73 (m, 3H), 0.64 (s, 3H).

Step 4

Under nitrogen atmosphere, anhydrous THF (40 mL) was cooled to 10° C. and anhydrous LiCl (491 mg, 11.6 mmol) was added in one portion. The mixture was stirred for 30 min, after which a clear solution was obtained. To this mixture was added anhydrous FeCl$_3$ (992 mg, 6.12 mmol) in one portion. The resulting mixture was stirred for additional 30 min. The reaction mixture was cooled to −35° C. and methyl magnesium bromide (3 M in diethyl ether, 11.1 mL, 33.5 mmol) was added dropwise maintaining the internal temperature between −35° C. and −30° C. The above mixture was stirred for 30 min at −30° C. AD3 (2 g, 5.57 mmol) was added in one portion. The internal temperature was allowed to −20° C. and held between −15° C. and −20° C. for 2 hours. The reaction mixture was quenched with aqueous NH$_4$Cl (50 mL), extracted with EtOAc (3×100 mL). The combined organic layer was washed with brine (50 mL), dried over anhydrous sodium sulfate, filtered and concentrated. The residue was purified by flash column (0-20% of EtOAc in PE) to give Compound 73 (310 mg) as a yellow oil, which was lyophilized to give Compound 73 (300 mg, 14%) as white powder.

$^1$H NMR (CDCl$_3$, 400 MHz) δ 2.35 (s, 2H), 2.12 (s, 3H), 1.90-1.86 (m, 1H), 1.70-1.60 (m, 2H), 1.54-1.45 (m, 6H), 1.45-1.25 (m, 7H), 1.20-1.15 (m, 3H), 0.94-0.85 (m, 4H), 0.85-0.82 (m, 4H), 0.80-0.70 (m, 7H), 0.62 (s, 3H).

LCMS Rt=1.318 min in 2 min chromatography, 30-90 CD, purity 100%, MS ESI calcd. For C$_{25}$H$_{41}$O$^+$ [M+H-H$_2$O]$^+$ 357, found 357.

182

Example 42. Synthesis of Compound 74

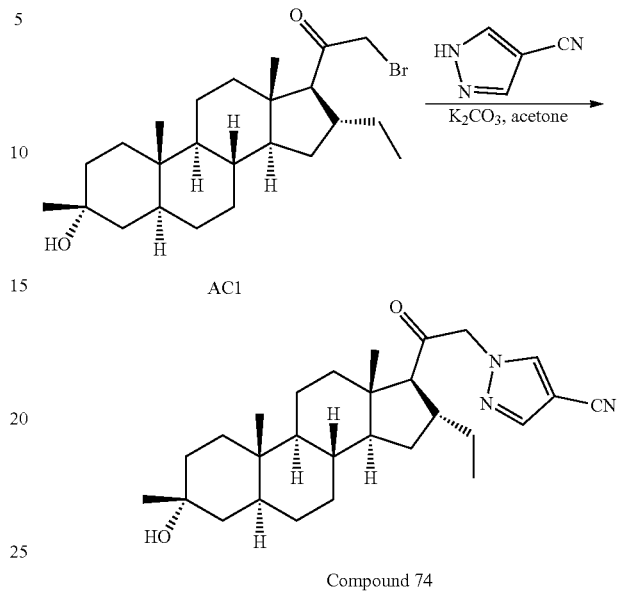

AC1

Compound 74

To a mixture of AC1 (80 mg, 0.182 mmol) and K$_2$CO$_3$ (50.3 mg, 0.364 mmol) in acetone (5 mL) was added 1H-pyrazole-4-carbonitrile (25.4 mg, 0.273 mmol) at 25° C. The reaction mixture was stirred at the 25° C. for 16 h and treated with H$_2$O (50 mL). The mixture was extracted with EtOAc (3×50 mL). The combined organic solution was washed with brine (20 mL), dried over Na$_2$SO$_4$, filtered and concentrated in vacuum to give the crude product, which was purified by flash column (0~30% of EtOAc in PE) to give an impure solid (50 mg). The impure product was purified by flash column (0~30% of EtOAc in PE) to give Compound 74 (32 mg, 39%) as a solid.

$^1$H NMR (400 MHz, CDCl$_3$) δ 7.85 (s, 1H), 7.81 (s, 1H), 5.00 (d, J=16 Hz, 1H), 4.87 (d, J=16 Hz, 1H), 2.54 (m, 1H), 2.25 (d, J=8.0 Hz, 1H), 1.96 (m, 1H), 1.65 (m, 2H), 1.53-1.47 (m, 5H), 1.38-1.12 (m, 16H), 1.01-0.92 (m, 1H), 0.81 (t, J=8.0 Hz, 4H), 0.75 (s, 3H), 0.68 (s, 3H).

LCMS Rt=2.682 in in 4.0 min chromatography, 30-90AB·1 cm, purity 100%, MS ESI calcd. for C$_{28}$H$_{40}$N$_3$O [M−H$_2$O+H]$^+$ 434, found 434.

Example 44. Syntheses of Compounds 78 and 79

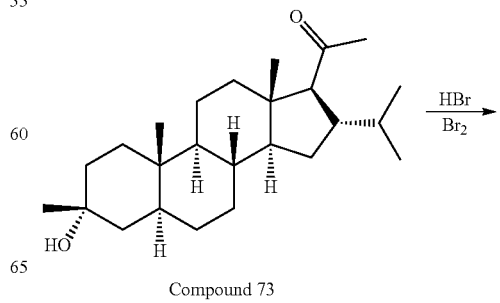

Compound 73

1.32 (m, 8H), 1.29-1.23 (m, 4H), 1.21-1.18 (m, 4H), 1.17-1.12 (m, 2H), 1.02-0.83 (m, 6H), 0.81-0.71 (m, 8H), 0.67-0.61 (m, 3H).

Step 2

To a solution of AE1 (150 mg, 0.33 mmol) in acetone (5 mL) was added K₂CO₃ (91 mg, 0.66 mmol) and 1H-pyrazolo[3,4-c]pyridine (39.3 mg, 0.33 mmol). The mixture was stirred at 15° C. for 12 hrs. Second batch of K₂CO₃ (45.5 mg, 0.33 mmol) and 1H-pyrazolo[3,4-c]pyridine (7.86 mg, 0.06 mmol) was added at 15° C. The mixture was stirred at 15° C. for another 8 hrs and poured in to water (10 mL), extracted with ethyl acetate (3×10 mL). The combined organic layer was washed with brine (20 mL), dried over Na₂SO₄, filtered and concentrated in vacuum. The residue was purified by flash column (0-80% of EtOAc in PE) to afford Compound 78 (70 mg, impure) as a solid and Compound 79 (31 mg, 19%) as a solid. The impure Compound 78 (70 mg, 0.14 mmol) was purified by SFC (column: AS (250 mm*30 mm, 5 um)), gradient: 35-35% B (A=0.1% NH₃/H₂O, B=EtOH), flow rate: 50 mL/min) to give a solid, which was further purified by re-crystallized from MeCN (3 mL) to give Compound 78 (36 mg, 22%) as a solid.

Compound 78

¹H NMR (400 MHz, CDCl₃) δ 8.77 (s, 1H), 8.38-8.29 (m, 1H), 8.09 (s, 1H), 7.66-7.61 (m, 1H), 5.33-5.21 (m, 2H), 2.53-2.42 (m, 2H), 2.13-2.04 (m, 1H), 1.75-1.65 (m, 2H), 1.56-1.23 (m, 15H), 1.21 (s, 3H), 1.21-1.14 (m, 2H), 1.03-0.91 (m, 1H), 0.88-0.79 (m, 7H), 0.76 (s, 3H), 0.71 (s, 3H).

LCMS Rt=0.968 min in 2 min chromatography, 30-90AB_2MIN_E, purity 100%, MS ESI calcd. for C₃₁H₄₆N₃O₂ [M+H]⁺ 492, found 492.

Compound 79

¹H NMR (400 MHz, CDCl₃) δ 9.26 (s, 1H), 8.18-8.14 (d, J=6 Hz, 1H), 7.96 (s, 1H), 7.54-7.49 (m, 1H), 5.37-5.18 (m, 2H), 2.53-2.44 (m, 2H), 2.12-2.03 (m, 1H), 1.74-1.66 (m, 2H), 1.52-1.28 (m, 12H), 1.26-1.13 (m, 8H), 1.03-0.92 (m, 1H), 0.87-0.82 (m, 4H), 0.81-0.75 (m, 6H), 0.71 (s, 3H).

LCMS Rt=0.917 min in 2 min chromatography, 30-90AB, purity 100%, MS ESI calcd. for C₃₁H₄₆N₃O₂ [M+H]⁺ 492, found 492.

Example 44. Syntheses of Compounds 80, 81, and 82

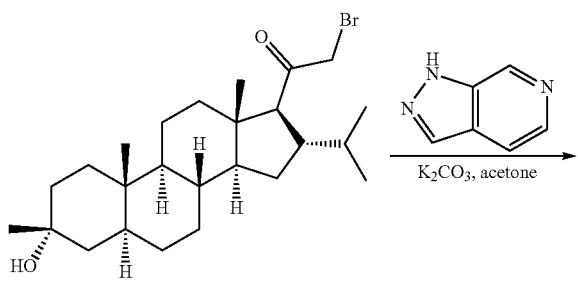

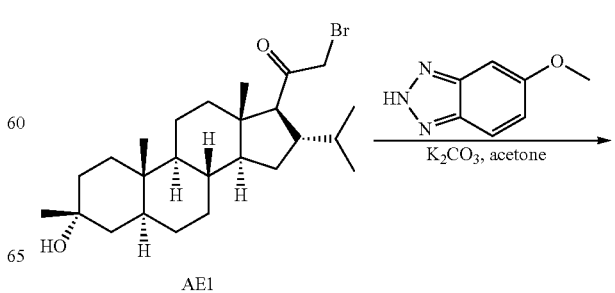

Step 1

To a solution of compound 73 (750 mg, 2 mmol) in MeOH (10 mL) was added HBr (80.7 mg, 0.4 mmol, 40% in water) and Br₂ (326 mg, 2.04 mmol) at 15° C. After stirring at 15° C. for 16 hrs, the mixture was quenched by sat·aq NaHCO₃ (10 mL) and water (20 mL), extracted with EtOAc (3×20 mL). The combined organic phase was washed with brine (40 mL), dried over anhydrous Na₂SO₄, filtered and concentrated in vacuum. The residue was purified by flash column (0-30% of EtOAc in PE) to give AE1 (660 mg, 69%) as a solid.

¹H NMR (400 MHz, CDCl₃) δ 3.99-3.86 (m, 2H), 2.68-2.63 (m, 1H), 1.86-1.76 (m, 1H), 1.72-1.59 (m, 2H), 1.53-

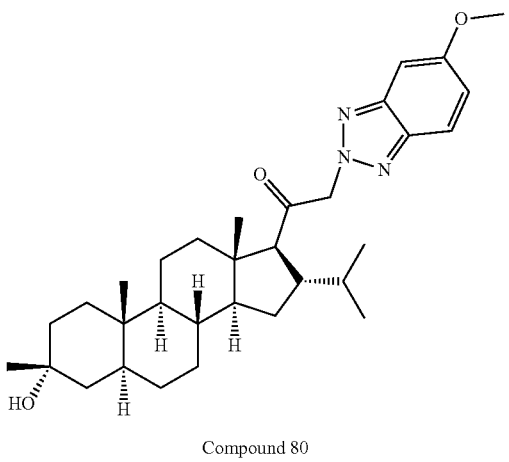

Compound 80

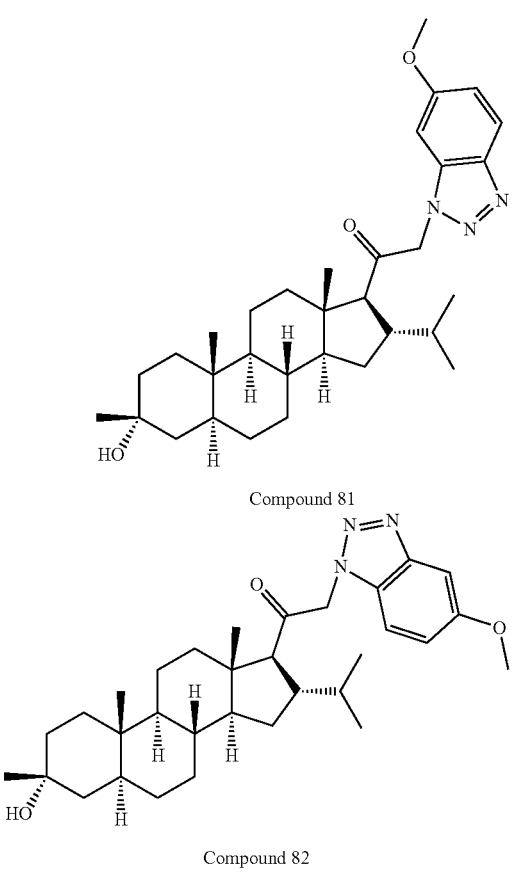

Compound 81

Compound 82

To a solution of AE1 (250 mg, 0.55 mmol) in acetone (10 mL) was added K$_2$CO$_3$ (151 mg, 1.1 mmol) and 5-methoxy-2H-benzo[d][1,2,3]triazole (123 mg, 0.83 mmol) and the mixture was stirred at 15° C. for 12 hours. A second batch of K$_2$CO$_3$ (75.5 mg, 0.55 mmol) and 5-methoxy-2H-benzo[d][1,2,3]triazole (61.5 mg, 0.41 mmol) was added at 15° C. and the mixture was stirred at 15° C. for 8 hours. The mixture was poured in to water (20 mL) and extracted with ethyl acetate (3×20 mL). The combined organic layers was washed with brine (50 mL), dried over Na$_2$SO$_4$, filtered and concentrated in vacuum. The residue was purified by flash column (0~45% of EtOAc in PE) to afford Compound 80 (44 mg, 15%) as a solid and a mixture of Compound 81 and Compound 82 (200 mg, 69%) as a light yellow oil.

The mixture of Compound 81 and Compound 82 (200 mg, 0.05 mmol) was purified by SFC (column: OD (250 mm*30 mm, 10 um)), gradient: 40-40% B (A=0.1% NH3/H2O, B=MEOH), flow rate: 80 mL/min) to give Compound 81 (43 mg, 21%) as a solid and Compound 82 (26 mg, 13%) as a solid.

Compound 80

$^1$H NMR (400 MHz, CDCl$_3$) δ 7.78-7.69 (m, 1H), 7.11-7.03 (m, 2H), 5.49-5.37 (m, 2H), 3.87 (s, 3H), 2.54-2.41 (m, 2H), 2.14-2.05 (m, 1H), 1.73-1.64 (m, 2H), 1.57-1.23 (m, 17H), 1.21 (s, 3H), 1.19-1.07 (m, 2H), 0.86-0.79 (m, 6H), 0.78-0.71 (m, 6H).

LCMS Rt=1.348 min in 2 min chromatography, 30-90AB_2MIN_E, purity 100%, MS ESI calcd. for C$_{32}$H$_{48}$N$_3$O$_3$ [M+H]$^+$ 522, found 522.

Compound 81

$^1$H NMR (400 MHz, CDCl$_3$) δ 7.94-7.89 (d, J=9.6 Hz, 1H), 7.03-6.97 (m, 1H), 6.58-6.54 (m, 1H), 5.46-5.27 (m, 2H), 3.83 (s, 3H), 2.56-2.44 (m, 2H), 2.13-2.05 (m, 1H), 1.75-1.66 (m, 2H), 1.61-1.23 (m, 16H), 1.21 (s, 3H), 1.15 (s, 1H), 1.03-0.91 (m, 1H), 0.89-0.79 (m, 7H), 0.76 (s, 3H), 0.72 (s, 3H).

LCMS Rt=1.273 min in 2 min chromatography, 30-90AB_2MIN_E, purity 100%, MS ESI calcd. for C$_{32}$H$_{48}$N$_3$O$_3$ [M+H]$^+$ 522, found 522.

Compound 82

$^1$H NMR (400 MHz, CDCl$_3$) δ 7.41-7.37 (d, J=1.2 Hz, 1H), 7.19-7.11 (m, 2H), 5.45-5.31 (m, 2H), 3.89 (s, 3H), 2.53-2.43 (m, 2H), 2.12-2.04 (m, 1H), 1.75-1.65 (m, 2H), 1.61-1.23 (m, 15H), 1.21 (s, 3H), 1.19-0.91 (m, 3H), 0.88-0.78 (m, 7H), 0.76 (s, 3H), 0.71 (s, 3H).

LCMS Rt=1.277 min in 2 min chromatography, 30-90AB_2MIN_E, purity 100%, MS ESI calcd. for C$_{32}$H$_{48}$N$_3$O$_3$ [M+H]$^+$ 522, found 522.

Example 45. Syntheses of Compounds 83, 84, and 85

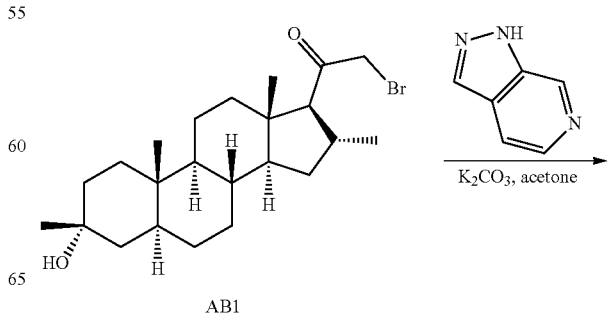

AB1

Compound 83

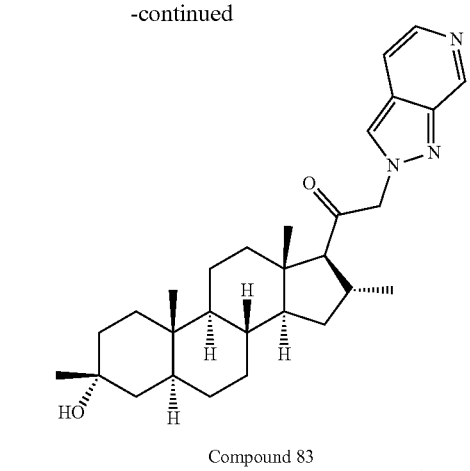

Compound 83

¹H NMR (400 MHz, CDCl₃) δ 9.26 (s, 1H), 8.17 (d, J=4.8 Hz, 1H), 7.98 (s, 1H), 7.53 (d, J=6.0 Hz, 1H), 5.34-5.16 (m, 2H), 2.78-2.70 (m, 1H), 2.27 (d, J=8.4 Hz, 1H), 2.07-2.01 (m, 1H), 1.73-1.59 (m, 3H), 1.54-1.45 (m, 5H), 1.42-1.24 (m, 11H), 1.21 (s, 3H), 0.98 (d, J=6.8 Hz, 3H), 0.86-0.80 (m, 1H), 0.76 (s, 3H), 0.73 (s, 3H).

LCMS Rt=2.405 min in 4 min chromatography, 10-80AB, purity 99%, MS ESI calcd. For $C_{29}H_{42}N_3O_2$ [M+H]⁺ 464, found 464.

Compound 84

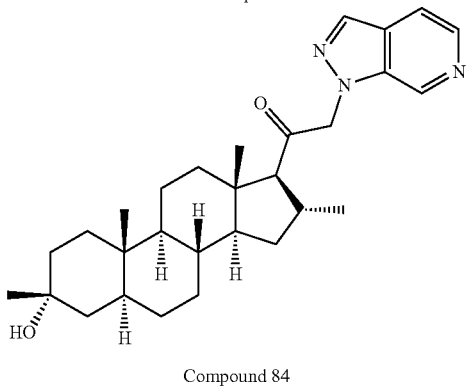

Compound 84

¹H NMR (400 MHz, CDCl₃) δ 8.78 (s, 1H), 8.34 (d, J=5.6 Hz, 1H), 8.10 (s, 1H), 7.65-7.63 (m, 1H), 5.28-5.17 (m, 2H), 2.76-2.65 (m, 1H), 2.29-2.26 (m, 1H), 2.10-2.02 (m, 1H), 1.72-1.60 (m, 3H), 1.55-1.48 (m, 5H), 1.42-1.34 (m, 4H), 1.32-1.19 (m, 10H), 0.96 (d, J=7.2 Hz, 3H), 0.88-0.82 (m, 1H), 0.77 (s, 3H), 0.74 (s, 3H).

LCMS Rt=2.014 min in 3 min chromatography, 10-80AB, purity 100%, MS ESI calcd. For $C_{29}H_{42}N_3O_2$ [M+H]⁺ 464, found 464.

Compound 85

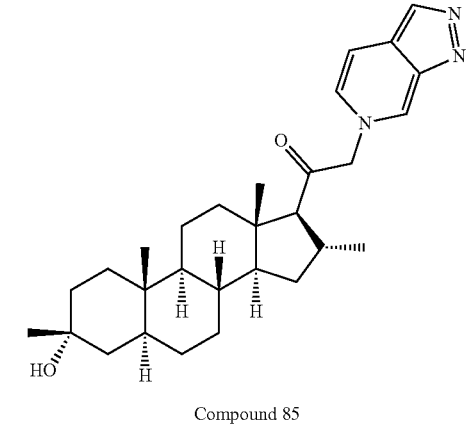

Compound 85

¹H NMR (400 MHz, CDCl₃) δ 9.03 (s, 1H), 8.56 (s, 1H), 7.87 (d, J=6.8 Hz, 1H), 7.18 (d, J=8.0 Hz, 1H), 5.32-5.18 (m, 2H), 3.80-2.74 (m, 1H), 2.35-2.32 (m, 1H), 2.01-1.98 (m, 1H), 1.71-1.51 (m, 6H), 1.45-1.24 (m, 13H), 1.22 (s, 3H), 1.03 (d, J=7.2 Hz, 3H), 0.91-0.86 (m, 1H), 0.77 (s, 3H), 0.74 (s, 3H).

LCMS Rt=2.388 min in 4 min chromatography, 10-80AB, purity 98.7%, MS ESI calcd. For $C_{29}H_{42}N_3O_2$ [M+H]⁺ 464, found 464.

To a solution of AB1 (150 mg, 0.352 mmol) and 1H-pyrazolo[3,4-c]pyridine (43.9 mg, 0.369 mmol) in acetone (3 mL) was added K₂CO₃ (97.2 g, 0.704 mmol) at 25° C. After stirring at 25° C. for 10 hrs, the mixture was poured into water (50 mL) and extracted with EtOAc (3×20 mL). The combined organic layer was washed with brine (50 mL), dried over Na₂SO₄, filtered and concentrated to afford crude product (100 mg), which was purified by preparative HPLC (column: YMC-Actus Triart C18 150*30 mm*5 um)), gradient: 40-70% B (A=0.1% HCl, B=ACN), flow rate: 25 mL/min) to afford Compound 85 (15 mg, 9%) as a solid, Compound 84 (17 mg, 10%) as a solid and Compound 83 (20 mg, impure). Compound 83 (20 mg, impure) was purified by SFC separation (column: AD (250 mm*30 mm, 10 um)), gradient: 50-50% B (A=0.1% NH₃H₂O, B=EtOH), flow rate: 80 mL/min) to afford Compound 83 (3 mg, yield 15%) as a solid.

Example 46. Syntheses of Compounds 86 and 87

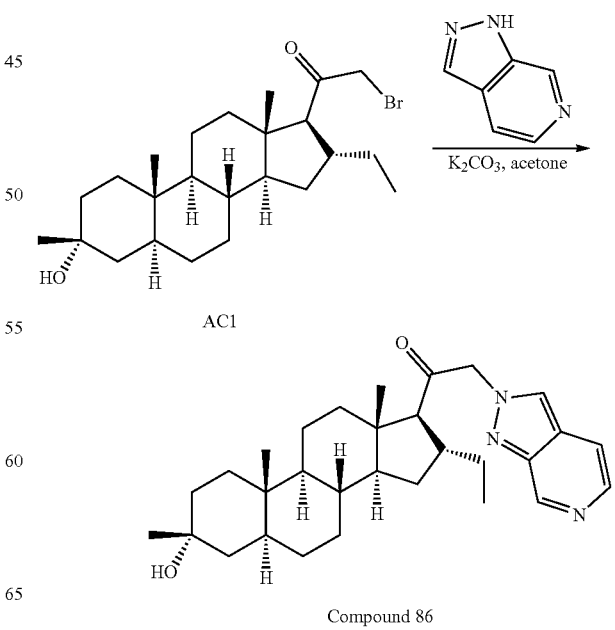

Compound 86

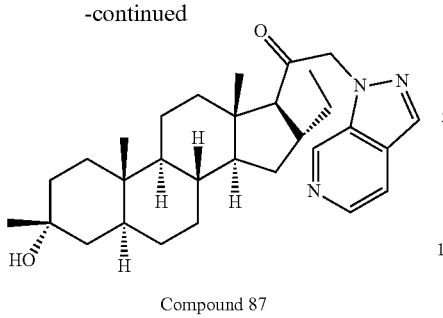

Compound 87

To a mixture of AC1 (150 mg, 0.341 mmol) and $K_2CO_3$ (94.2 mg, 0.682 mmol) in acetone (3 mL) was added 1H-pyrazolo[3,4-c]pyridine (42.6 mg, 0.358 mmol) at 25° C. After stirring at 25° C. for 12 hrs, the mixture was poured into water (50 mL) and extracted with EtOAc (3×20 mL). The combined organic layer was washed with brine (50 mL), dried over with $Na_2SO_4$, filtered and concentrated to afford crude product, which was purified by prep-HPLC separation (column: YMC-Actus Triart C18 150*30 mm*5 um)), gradient: 45-75% B (A=0.1% HCl, B=ACN), flow rate: 25 mL/min) to afford Compound 87 (36 mg, 22%) as a solid and Compound 86 (20 mg, impure). The crude Compound 86 was purified by SFC separation (column: AD (250 mm*30 mm, 10 um)), gradient: 45-45% B (A=0.1% $NH_3H_2O$, B=ETOH), flow rate: 80 mL/min) to afford Compound 86 (11 mg, 7%) as a solid.

Compound 86

$^1$H NMR (400 MHz, $CDCl_3$) δ 9.28 (s, 1H), 8.25-8.1 (m, 1H), 8.02 (s, 1H), 7.65-7.55 (m, 1H), 5.37-5.19 (m, 2H), 2.58-2.5 (m, 1H), 2.33 (d, J=12 Hz, 1H), 2.10-2.05 (m, 1H), 1.72-1.65 (m, 2H), 1.53-1.45 (m, 5H), 1.42-1.23 (m, 12H), 1.21 (s, 3H), 1.16 (s, 1H), 1.01-0.93 (m, 1H), 0.83 (t, J=8.0 Hz, 4H), 0.77 (s, 3H), 0.73 (s, 3H).

LCMS Rt=2.502 min in 4.0 min chromatography, 10-80AB·1 cm, purity 100%, MS ESI calcd. for $C_{30}H_{44}N_3O_2$ [M+H]$^+$ 478, found 478.

Compound 87

$^1$H NMR (400 MHz, $CDCl_3$) δ 9.26 (s, 1H), 8.17 (d, J=4.0 Hz, 1H), 7.97 (s, 1H), 7.54-7.50 (m, 1H), 5.35-5.17 (m, 2H), 2.60-2.52 (m, 1H), 2.35-2.30 (m, 1H), 2.10-2.04 (m, 1H), 1.69-1.62 (m, 4H), 1.52-1.46 (m, 5H), 1.39-1.26 (m, 11H), 1.21 (s, 3H), 1.12-0.98 (m, 1H), 0.83 (t, J=8.0 Hz, 4H), 0.76 (s, 3H), 0.73 (s, 3H)

LCMS Rt=1.750 min in 3.0 min chromatography, 10-80AB_3MIN_E.M, purity 100%, MS ESI calcd. for $C_{30}H_{44}N_3O_2$ [M+H]$^+$ 478, found 478.

Example 47. Synthesis of Compound 88

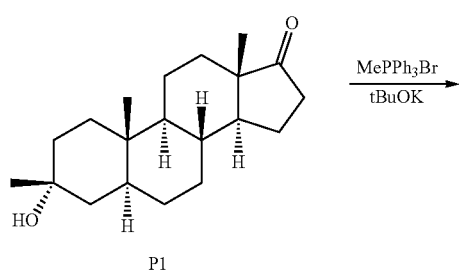

P1

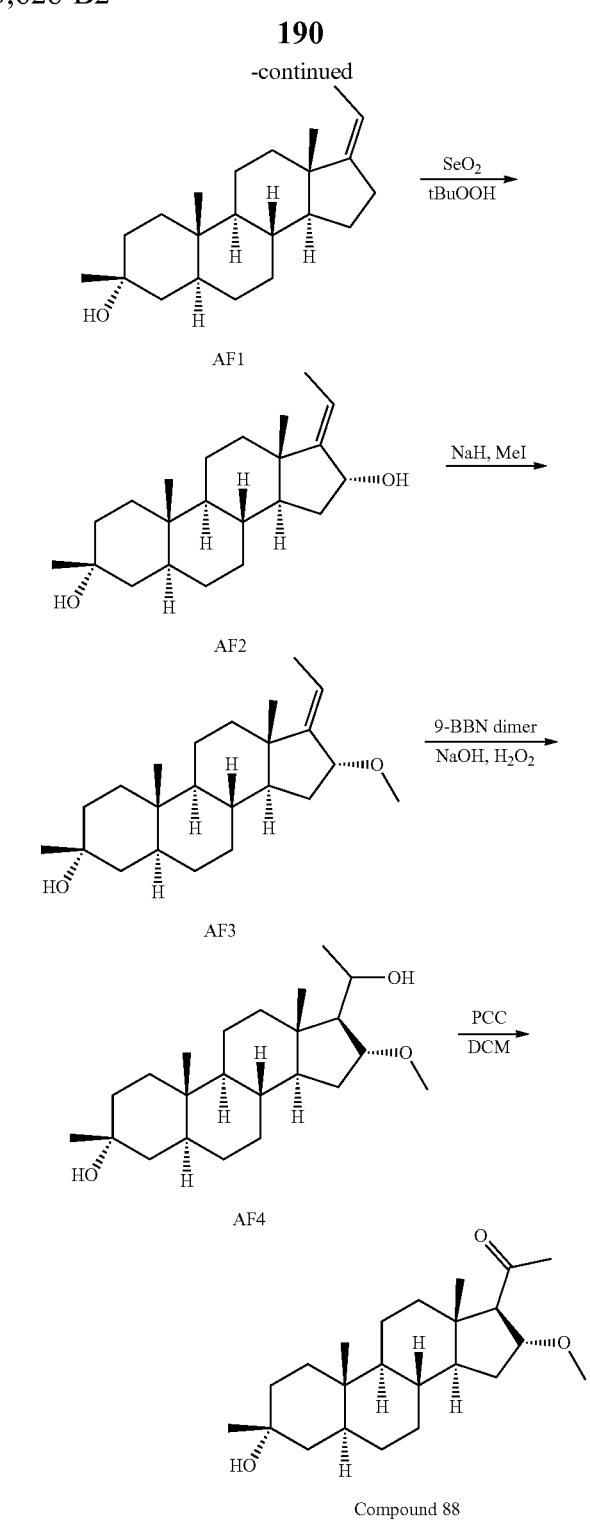

The synthesis of P1 is disclosed in WO2016/61527.

Step 1

To a suspension of MePPh$_3$Br (14.5 g, 39.3 mol) in THF (300 mL) was added t-BuOK (4.4 g, 39.3 mmol) at 15° C. under $N_2$. After stirring at 50° C. for 30 min, P1 (10 g, 32.8 mmol) was added in portions below 65° C. The mixture was stirred at 50° C. for 1 h and treated with $NH_4Cl$ (300 mL). The organic layer was separated, concentrated in vacuum to give a cured which was triturated from MeOH/water (150 L, 1:1) at 50° C. The mixture was filtered after cooled and the solid was washed with MeOH/water (2×150 mL, 1:1), dried in vacuum to give AF1 (8 g, 77%) as a solid.

$^1$H NMR (400 MHz, CDCl$_3$) δ 5.15-5.05 (m, 1H), 2.40-2.10 (m, 3H), 1.80-1.55 (m, 5H), 1.54-1.40 (m, 6H), 1.39-1.25 (m, 4H), 1.24-1.10 (m, 10H), 0.77 (s, 3H), 076-0.70 (m, 4H).

Step 2

To a suspension of selenium dioxide (854 mg, 7.70 mmol) in DCM (40 mL) was added dropwise tert-butyl hydro peroxide (3.13 mL, 23.1 mmol 70% solution in water) to give a nearly homogeneous solution after stirring at 0° C. for 1 h. Then a solution of AF1 (4.9 g, 15.4 mmol) in DCM (10 mL) was added dropwise to give a clear solution. The resulting mixture was stirred 20° C. for 18 h. The reaction mixture was diluted with PE (100 mL) and a lot of white precipitate appeared. The precipitate was collected by filtration and dried in air to give the product AF2 (4.9 g, crude) as a solid.

$^1$H NMR (400 MHz, CDCl$_3$) δ 5.55-5.50 (m, 1H), 4.45-4.40 (m, 1H), 2.30-2.20 (m, 1H), 1.75-1.55 (m, 8H), 1.54-1.15 (m, 17H), 1.10-1.00 (m, 1H), 0.90-0.80 (m, 4H), 0.75 (s, 3H).

Step 3

To a solution of AF2 (2.2 g, 6.61 mmol) in dry THF (60 mL) was slowly added to a stirred suspension NaH (791 mg, 19.8 mmol) in dry THF (20 mL) at −5° C. Then MeI (10.2 mL, 165 mmol) was added to reaction mixture and stirred for 24 h at 35° C. The reaction mixture was quenched by water (80 mL) and extracted with DCM (2×80 mL). The combined organic layer was washed by brine and dried over anhydrous Na$_2$SO$_4$, filtered and concentrated in vacuum to give a residue (2.5 g). The residue was purified by silica gel chromatography eluted with PE:EtOAc=5:1 to give AF3 (1.56 g, 68%) as a solid.

$^1$H NMR (400 MHz, CDCl$_3$) δ 5.60-5.50 (m, 1H), 4.00-3.90 (m, 1H), 3.30 (m, 3H), 2.30-2.20 (m, 1H), 1.75-1.60 (m, 6H), 1.59-1.15 (m, 18H), 1.05-0.95 (m, 1H), 0.85 (s, 3H), 0.80-0.79 (m, 1H), 0.75 (s, 3H).

Step 4

To a solution of AF3 (500 mg, 1.44 mmol) in dry THF (5 mL) was added borane-tetrahydrofuran complex (2.88 mL of 1.0 M solution in THF) and the reaction mixture was stirred at 20° C. for 1 hour. NaOH (4.76 mL, 14.3 mmol, 3 M in water) was slowly added. The mixture was cooled in ice (0° C.) and 30 percent aqueous solution of H$_2$O$_2$ (1.62 g, 14.3 mmol) was slowly added. The mixture was stirred at ambient temperature for 1 hour and then extracted with DCM (3×50 mL). The combined DCM extracts were washed with 10 percent aqueous Na$_2$S$_2$O$_3$ (100 mL), brine (100 mL), dried over Na$_2$SO$_4$, filtered, and concentrated in vacuum to afford compound AF4 (500 mg, crude) as a solid, which was used in next step without further purification.

Step 5

To a solution To a solution of AF4 (500 mg, 1.37 mmol) in DCM (40 mL) was added PCC (590 mg, 2.74 mmol) and silica gel (1 g) at 25° C. Then the solution was stirred at 25° C. for 3 h. The reaction mixture was filtered and the residue was washed with anhydrous DCM (2×30 mL). The combined filtrate was concentrated in vacuum to give Compound 88 (200 mg, crude) as a solid, which was purified by silica gel column (PE/EtOAc=1/1) and lyophilization to afford Compound 88 (20 mg, 10%) as a solid.

$^1$H NMR (400 MHz, CDCl$_3$) δ 4.40-4.30 (m, 1H), 3.20 (s, 3H), 2.55-2.50 (m, 1H), 2.16 (s, 3H), 1.95-1.90 (m, 1H), 1.70-1.55 (m, 4H), 1.50-1.40 (m, 5H), 1.39-1.15 (m, 12H), 1.05-0.95 (m, 1H), 0.90-0.85 (m, 1H), 0.74 (s, 3H), 0.60 (s, 3H).

HPLC Rt=4.28 min in 8.0 min chromatography, 30-90 AB, purity 100%.

LCMS Rt=1.061 min in 2.0 min chromatography, 30-90 AB, purity 92%, MS ESI calcd. for C$_{23}$H$_{39}$O$_3$[M+H]$^+$ 363, found 363.

The stereochemistry at C16 of Compound 88 was confirmed by NOE.

Example 48. Syntheses of Compounds 89 and 90

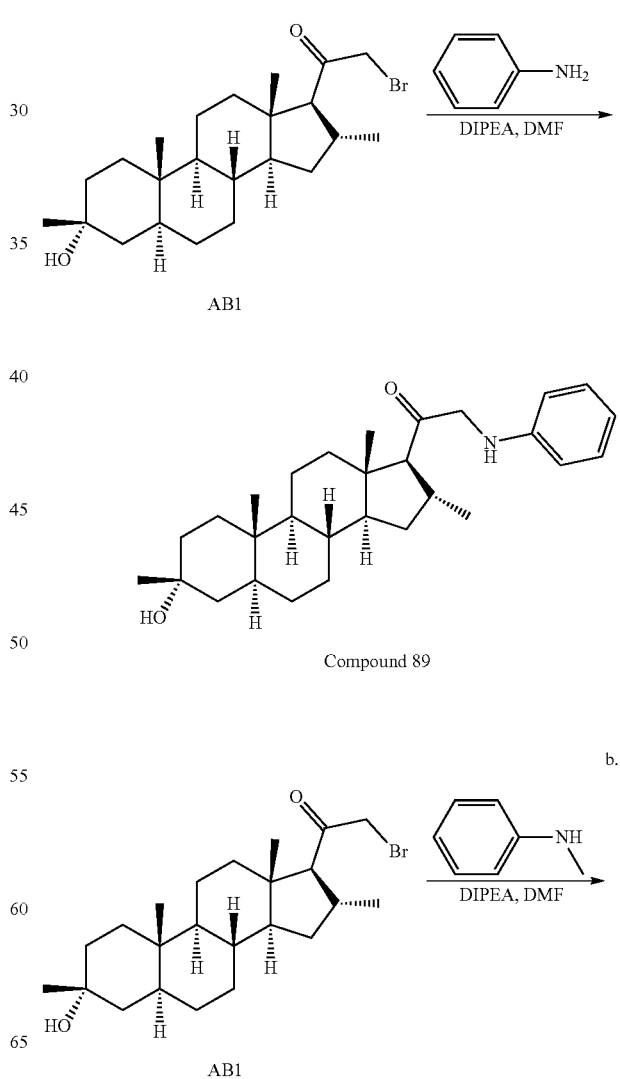

a.

AB1

Compound 89 b.

AB1

-continued

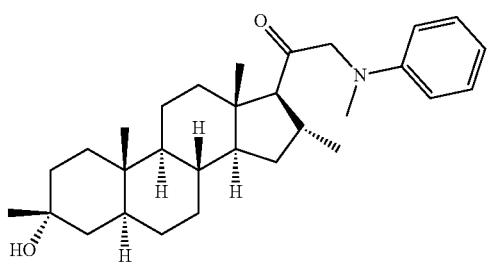

Compound 90

Step 1a (Compound 89)

To a solution of AB1 (80 mg, 0.188 mmol), DIEA (60.6 mg, 0.47 mmol) in DMF (2 mL) was added aniline (26.2 mg, 0.282 mmol) at 25° C. The mixture was stirred at 60° C. for 16 hours. The mixture was poured into water (10 mL) and extracted with EtOAc (2×20 mL). The combined organic layers was washed with brine (20 mL), dried over $Na_2SO_4$, filtered and concentrated in vacuum. The residue was purified by HPLC separation (column: Phenomenex Gemini C18 250*50 mm*10 um, gradient: 87-97% B, Condition: (water (0.05% ammonia hydroxide v/v)-ACN), flow rate: 30 mL/min) to give Compound 89 (12 mg, impure) as a solid. The Compound 89 (12 mg, impure) was purified by a silica gel column (PE/EtOAc=5/1) to give Compound 89 (5 mg, 6%) as a solid.

$^1$HNMR (400 MHz, CDCl3) δ 7.19 (t, J=8 Hz, 2H), 6.72 (t, J=8 Hz, 1H), 6.60 (d, J=8 Hz, 2H), 4.73-4.69 (m, 1H), 4.01-3.85 (m, 2H), 2.79-2.66 (m, 1H), 2.19 (d, J=12 Hz, 1H), 1.89-1.82 (m, 1H), 1.70-1.58 (m, 3H), 1.51-1.34 (m, 6H), 1.31-1.15 (m, 11H), 1.01-0.92 (m, 4H), 0.88-0.78 (m, 2H), 0.74 (s, 3H), 0.67 (s, 3H).

LCMS Rt=4.893 min in 7.0 min chromatography, 30-90 CD, purity 100%, MS ESI calcd. For $C_{29}H_{44}NO_2$ $[M+H]^+$ 438, found 438.

Step 1b (Compound 90)

To a solution of AB1 (80 mg, 0.188 mmol), DIEA (60.6 mg, 0.47 mmol) in DMF (2 mL) was added N-methylaniline (30.2 mg, 0.282 mmol) at 25° C. The mixture was stirred at 60° C. for 16 hours. The mixture was poured into water (10 mL) and extracted with EtOAc (2×20 mL). The combined organic layers was washed with brine (20 mL), dried over $Na_2SO_4$, filtered and concentrated in vacuum. The residue was purified by HPLC separation (column: Phenomenex Gemini C18 250*50 mm*10 um, gradient: 90-100% B, Condition: (water (0.05% ammonia hydroxide v/v)-ACN), flow rate: 30 mL/min) to give Compound 90 (10 mg, impure) as a solid. The Compound 90 (10 mg, impure) was purified by a silica gel column (PE/EtOAc=5/1) to give Compound 90 (3 mg, 4%) as a solid.

$^1$HNMR (400 MHz, CDCl3) δ 7.20 (t, J=8 Hz, 2H), 6.71 (t, J=8 Hz, 1H), 6.61 (d, J=8 Hz, 2H), 4.73-4.69 (m, 1H), 4.06-3.95 (m, 2H), 3.01 (s, 3H), 2.75-2.63 (m, 1H), 2.24 (d, J=8 Hz, 1H), 1.91-1.61 (m, 2H), 1.52-1.38 (m, 5H), 1.36-1.15 (m, 13H), 1.01-0.88 (m, 4H), 0.86-0.78 (m, 2H), 0.75 (s, 3H), 0.68 (s, 3H).

LCMS Rt=5.041 min in 7.0 min chromatography, 30-90 CD, purity 100%, MS ESI calcd. For $C_{30}H_{46}NO_2$ $[M+H]^+$ 452, found 452.

Example 49. Synthesis of Compound 91

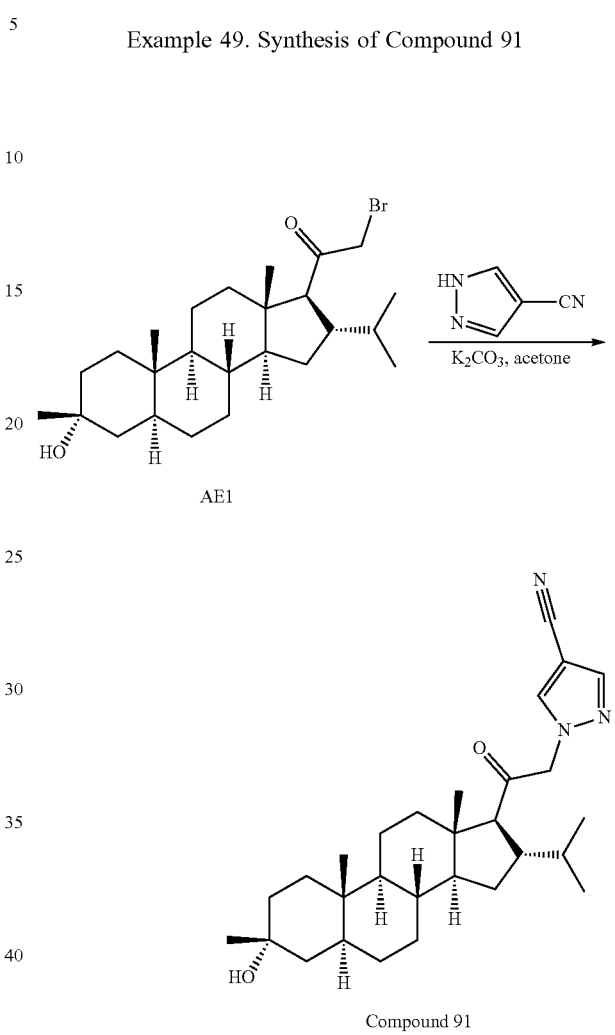

Compound 91

To a solution of AE1 (100 mg, 0.22 mmol) in acetone (3 mL) was added $K_2CO_3$ (60.7 mg, 0.44 mmol) and 1H-pyrazole-4-carbonitrile (30.7 mg, 0.33 mmol). The mixture was stirred at 15° C. for 12 hours. The mixture was poured in to water (10 mL) and extracted with ethyl acetate (3×10 mL). The combined organic layers was washed with brine (150 mL), dried over $Na_2SO_4$, filtered and concentrated in vacuum. The residue was purified by flash column (0~30% of EtOAc in PE) to afford Compound 91 (90 mg, 88%, impure) as a solid, which was purified by SFC (column: OD (250 mm*30 mm, 10 um)), gradient: 40-40% B (A=0.1% $NH_3/H_2O$, B=EtOH), flow rate: 50 mL/min) to give Compound 91 (44 mg, 48%) as a solid.

$^1$H NMR (400 MHz, CDCl$_3$) δ 7.86-7.79 (d, J=14 Hz, 2H), 5.04-4.85 (m, 2H), 2.52-2.36 (m, 2H), 1.99-1.92 (m, 1H), 1.73-1.63 (m, 2H), 1.57-1.22 (m, 16H), 1.205 (s, 3H), 1.19-1.13 (m, 2H), 1.02-0.89 (m, 1H), 0.86-0.83 (m, 3H), 0.79-0.73 (m, 6H), 0.66 (s, 3H).

LCMS Rt=1.227 min in 2 min chromatography, 30-90AB_2MIN_E, purity 100%, MS ESI calcd. for $C_{29}H_{44}N_3O_2$ $[M+H]^+$ 466, found 466.

Example 50. Syntheses of Compounds 92 and 93

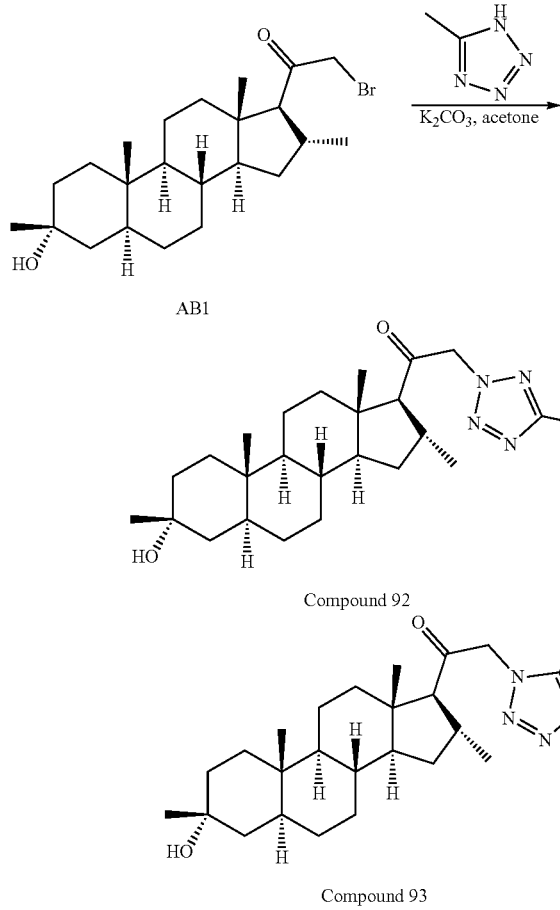

To a solution of AB1 (550 mg, 1.29 mmol) in acetone (10 mL) was added K$_2$CO$_3$ (356 mg, 2.58 mmol) and 5-methyl-1H-tetrazole (162 mg, 1.93 mmol) at 25° C. The mixture was stirred at 25° C. for 16 hours. To the mixture was added water (50 mL) and ethyl acetate (50 mL). The organic layer was separated. The mixture was extracted with ethyl acetate (2×50 mL). The combined organic layers was washed with brine (200 mL), dried over Na$_2$SO$_4$, filtered and concentrated in vacuum. The residue was purified by column chromatography on silica gel with PE:EtOAc=0:1-1:1 to give Compound 93 (233 mg, 42%) and Compound 92 (112 mg, 20%) as solid.

Compound 92

$^1$HNMR (400 MHz, CDCl$_3$) δ 5.37-5.26 (m, 2H), 2.74-2.66 (m, 1H), 2.46 (s, 3H), 2.27-2.25 (m, 1H), 2.02-1.98 (m, 1H), 1.70-1.57 (m, 4H), 1.56-1.46 (m, 5H), 1.42-1.16 (m, 13H), 0.98 (m, 3H), 0.86-0.79 (m, 1H), 0.74 (m, 6H).

LCMS Rt=1.108 min in 2 min chromatography, 30-90AB_2MIN_E, purity 100%, MS ESI calcd. for C$_{25}$H$_{41}$N$_4$O$_2$ [M+H]$^+$ 429, found 429.

Compound 93

$^1$HNMR (400 MHz, CDCl$_3$) δ 5.16-4.97 (m, 2H), 2.74-2.68 (m, 1H), 2.46 (s, 3H), 2.27-2.25 (m, 1H), 2.00-1.97 (m, 1H), 1.72-1.63 (m, 2H), 1.60 (s, 1H), 1.54-1.41 (m, 4H), 1.41-1.15 (m, 14H), 1.0-0.90 (m, 4H), 0.87-0.81 (m, 1H), 0.76-0.70 (m, 6H).

LCMS Rt=1.043 min in 2 min chromatography, 30-90AB_2MIN_E, purity 100%, MS ESI calcd. for C$_{25}$H$_{41}$N$_4$O$_2$ [M+H]$^+$ 429, found 429.

Example 51. Syntheses of Compounds 94 and 95

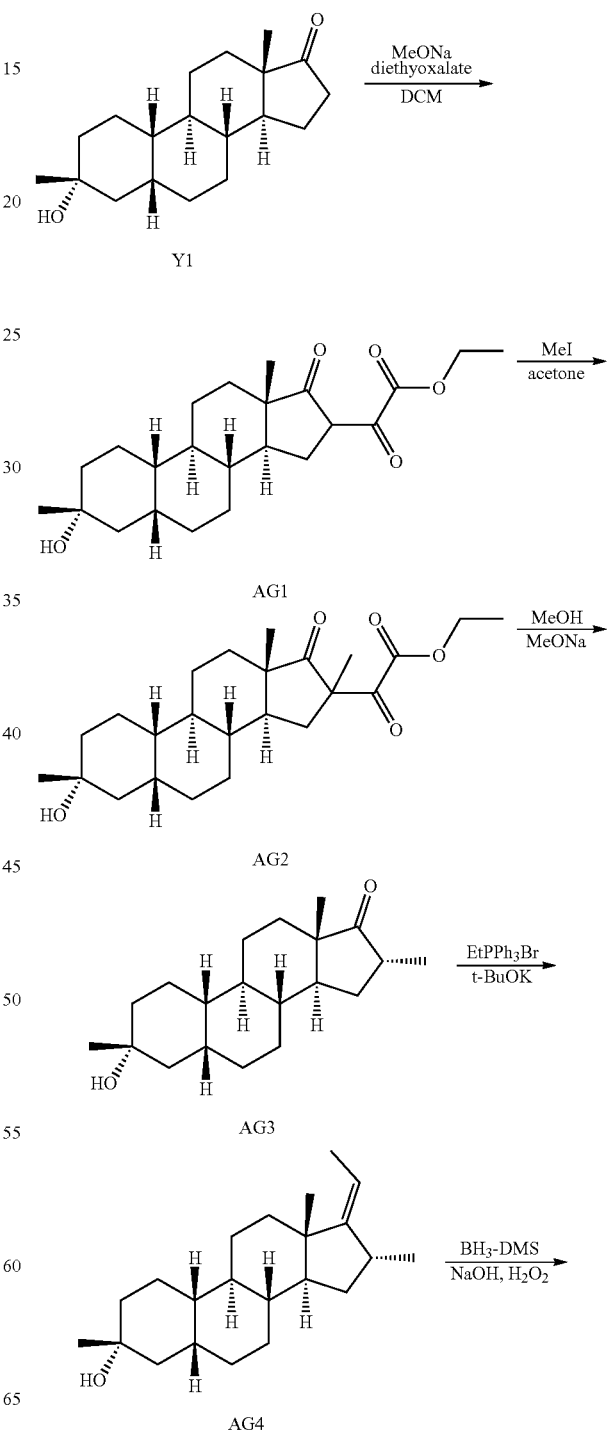

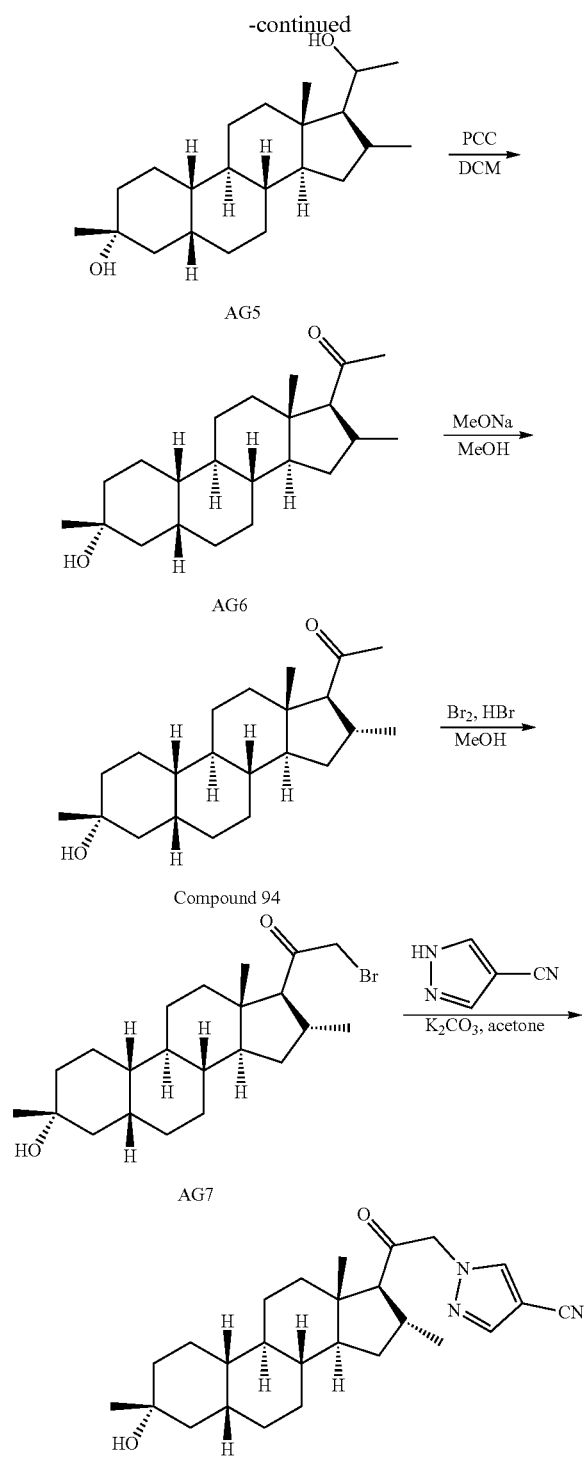

C. for 10 min and then concentrated in vacuum to give a crude product AG1 (10 g, crude) as a solid which was used for the next step directly.

Step 2

To a solution of AG1 (10 g, crude) in acetone (150 mL) was added MeI (32.6 g, 230 mmol) at 20° C. The mixture was warmed to 60° C. and stirred at 60° C. for 18 hours. The mixture was concentrated in vacuum to give a crude product (13 g, crude) as yellow oil, which was used directly for the next step.

Step 3

To a solution of AG2 (13 g, crude) in MeOH (100 mL) was added MeONa (1.73 g, 32.1 mmol) at 0° C. The mixture was warmed to 15° C. and stirred at 15° C. for 18 hours. The reaction was treat with water (30 mL) and EtOAc (20 mL). The mixture was extracted with EtOAc (2×30 mL). The combined organic phase was washed with brine (60 mL), dried over Na2SO4, filtered, concentrated in vacuum to give a crude product, which was purified with flash column (EtOAc in PE=0-35%) to give AG3 (0.9 g) as a solid.
$^1$H NMR (400 MHz, CDCl$_3$) δ 2.60-2.41 (m, 1H), 2.24-2.18 (m, 1H), 1.91-1.72 (m, 6H), 1.70-1.60 (m, 3H), 1.60-1.49 (m, 4H), 1.49-1.39 (m, 3H), 1.39-1.12 (m, 5H), 1.12-1.08 (m, 3H), 1.08-1.02 (m, 1H), 0.99-0.94 (m, 1H), 0.94-0.80 (m, 4H).

Step 4

To suspension of Ph$_3$PEtBr (1.82 g, 4.92 mmol) in THF (20 mL) under nitrogen was added t-BuOK (552 mg, 4.92 mmol). The mixture became deep orange and stirred at 15° C. for 30 min. After that, AG3 (500 mg, 1.64 mmol) was added. The resulting mixture was stirred at 45° C. for 3 hrs. After cooling, the mixture was treated with NH$_4$Cl (200 mL), extracted with EtOAc (2×200 mL). The organic phase was washed with brine (100 mL), dried over Na$_2$SO$_4$, filtered and concentrated in vacuum to give crude product, which was purified by a silica gel column (PE/EtOAc=0-10%) to give AG4 (300 mg, impure) as a solid.
$^1$H NMR (400 MHz, CDCl$_3$) δ 5.18-5.10 (m, 1H), 2.60-2.49 (m, 1H), 2.30-2.20 (m, 1H), 2.00 (s, 1H), 1.90-1.72 (m, 4H), 1.72-1.63 (m, 4H), 1.63-1.54 (m, 2H), 1.54-1.50 (m, 1H), 1.50-1.38 (m, 5H), 1.38-1.20 (m, 6H), 1.20-1.02 (m, 4H), 1.02-0.98 (m, 3H), 0.87 (s, 3H).

Step 5

To a solution of AG4 (300 mg, 0.947 mmol) in THF (10 mL) was added dropwise BH$_3$-Me$_2$S (2.84 mL, 2.84 mmol) at 0° C. The solution was stirred at 20° C. for 2 hrs. After cooling to 0° C., a solution of NaOH solution (1.81 mL, 5 M) was added very slowly. After addition, H$_2$O$_2$ (1.07 mL, 10.8 mmol, 30% in water) was added slowly and the inner temperature was maintained below 10° C. The resulting solution was stirred at 20° C. for 1 h. The mixture was extracted with EtOAc (3×20 mL). The combined organic layer was washed with saturated aqueous Na$_2$S$_2$O$_3$ (2×10 mL), brine (50 mL), dried over Na$_2$SO$_4$ and concentrated in vacuum to give crude product AG5 (210 mg, crude) as a solid.
$^1$H NMR (400 MHz, CDCl$_3$) δ 2.94-1.98 (m, 1H), 1.98-1.71 (m, 4H), 1.71-1.50 (m, 7H), 1.50-1.33 (m, 6H), 1.33-1.19 (m, 10H), 1.19-0.58 (m, 10H).

Step 1

To a solution of Y1 (5 g, 17.2 mmol) in DCM (100 mL) was added diethyloxalate (2.99 g, 20.5 mmol) at 20° C. After cooling to 0° C., MeONa (1.39 g, 25.7 mmol) was added. The mixture was stirred at 20° C. for 18 hours and treated with NaHCO$_3$ (1.8 g, solid). The mixture was stirred at 20°

Step 6

To a solution of AG5 (600 mg, crude) in DCM (25 mL) was added silica gel (1.65 g) and PCC (773 mg, 3.58 mmol) at 25° C. The reaction mixture was stirred for 1 h and diluted with PE (10 mL). The resulting mixture was filtered though a pad of silica gel. The silica was washed with PE/DCM (50/50 mL), filtered and concentrated in vacuum. The residue was purified by flash column (0-25% of EtOAc in PE) to give AG6 (520 mg, impure) as a solid.

$^1$H NMR (400 MHz, CDCl$_3$) δ 2.70-2.57 (m, 1H), 2.20-2.05 (m, 4H), 1.98-1.75 (m, 4H), 1.75-1.51 (m, 4H), 1.51-1.20 (m, 9H), 1.20-1.00 (m, 5H), 1.00-0.89 (m, 6H), 0.63 (s, 3H).

Step 7

To a solution of AG6 (520 mg, 1.56 mmol) in MeOH (10 mL) was added MeONa (421 mg, 7.8 mmol). After stirring at 40° C. for 18 hrs, the reaction was quenched water (5 mL). To the mixture was added water (5 mL) and EtOAc (5 mL). The mixture was extracted with EtOAc (2×10 mL). The combined organic layer was washed with brine (10 mL), dried over Na$_2$SO$_4$, filtered and concentrated. The residue was purified by flash column (0-10% of EtOAc in PE) to give Compound 94 (340 mg, impure) as a solid. The impure Compound 94 (340 mg, impure) was re-crystallized from MeCN to give Compound 94 (166 mg, 49%) as a solid.

$^1$H NMR (400 MHz, CDCl$_3$) δ 2.70-2.57 (m, 1H), 2.18-2.05 (m, 4H), 1.98-1.90 (m, 1H), 1.90-1.75 (m, 3H), 1.75-1.58 (m, 3H), 1.52-1.32 (m, 9H), 1.32-1.18 (m, 6H), 1.16-0.98 (m, 3H), 0.98-0.90 (m, 3H), 0.63 (s, 3H).

LCMS Rt=1.057 min in 2 min chromatography, 30-90AB_2MIN_E, purity 100%, MS ESI calcd. for C$_{22}$H$_{35}$O [M+H−H$_2$O]$^+$ 315, found 315.

The stereochemistry at C16 of Compound 94 was confirmed by NOE.)

Step 8

To a solution of Compound 94 (140 mg, 0.421 mmol) in MeOH (4 ml) was added HBr (17 mg, 0.0842 mmol, 40% in water) and Br$_2$ (73.9 mg, 0.463 mmol) in MeOH (2 mL) at 20° C. The mixture was stirred at 20° C. for 2.5 hrs. The mixture was quenched by sat·aq NaHCO$_3$ (10 mL), treated with water (10 mL), some solid was formed. The suspension was filtered to give AG7 (150 mg, crude) as a solid.

$^1$H NMR (400 MHz, CDCl$_3$) δ 3.95-3.80 (m, 1H), 3.54-3.48 (m, 1H), 2.77-2.60 (m, 1H), 1.90-1.75 (m, 4H), 1.75-1.62 (m, 1H), 1.62-1.49 (m, 4H), 1.49-1.20 (m, 13H), 1.19-0.90 (m, 7H), 0.66 (s, 3H).

Step 9

To a solution of AG7 (150 mg, 0.377 mmol) in acetone (2 mL) was added 1H-pyrazole-4-carbonitrile (38.5 mg, 0.414 mmol) and K$_2$CO$_3$ (104 mg, 0.754 mmol). After stirring at 20° C. for 16 hrs, the reaction mixture was quenched with water (5 mL). The resulting mixture was extracted with EtOAc (2×10 mL). The combined organic layer was washed with brine (5 mL). The organic layer was dried over Na$_2$SO$_4$, filtered and concentrated. The residue was purified by flash column (0-30% of EtOAc in PE) give Compound 95 (49 mg, 31%) as a solid.

$^1$H NMR (400 MHz, CDCl$_3$) δ 7.90-7.95 (m, 2H), 5.02-4.80 (m, 2H), 2.80-2.63 (m, 1H), 2.24-2.18 (m, 1H), 2.05-1.93 (m, 1H), 1.89-1.71 (m, 4H), 1.69-1.51 (m, 5H), 1.51-1.23 (m, 12H), 1.20-1.02 (m, 3H), 1.02-0.91 (m, 3H), 0.69 (s, 3H).

LCMS Rt=1.042 min in 2 min chromatography, 30-90AB_2MIN_E, purity 100%, MS ESI calcd. for C$_{26}$H$_{36}$N$_3$O [M+H−H$_2$O]$^+$ 406,

TABLE 2

| TBPS Data | | |
|---|---|---|
| Compound structure | Compound number | TBPS IC$_{50}$ (nM) |
| [steroid structure with nitrile and HO] | 1 | E |
| [steroid structure with nitrile and HO] | 2 | E |

TABLE 2-continued

TBPS Data

| Compound structure | Compound number | TBPS IC$_{50}$ (nM) |
|---|---|---|
| 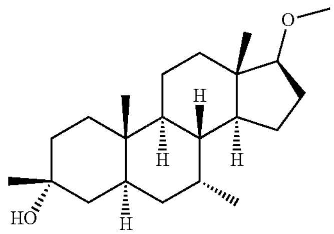 | 3 | E |
| 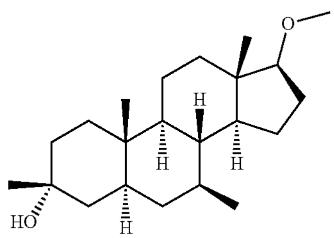 | 4 | E |
| 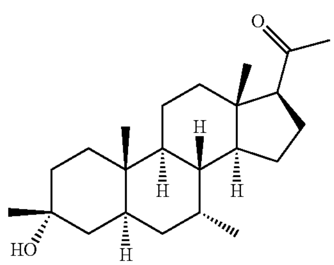 | 5 | E |
| 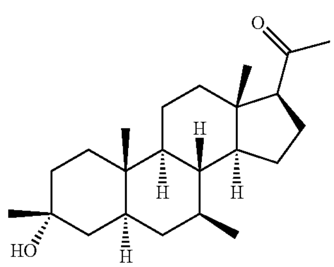 | 6 | E |
| 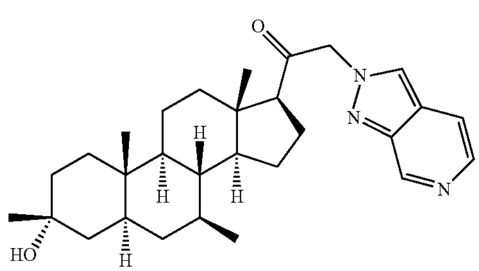 | 7 | E |
| 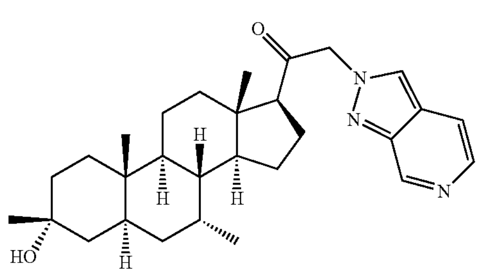 | 8 | E |

TABLE 2-continued

TBPS Data

| Compound structure | Compound number | TBPS IC$_{50}$ (nM) |
|---|---|---|
| (structure) | 9 | D |
| (structure) | 10 | E |
| (structure) | 11 | E |
| (structure) | 12 | E |
| (structure) | 13 | E |

TABLE 2-continued
TBPS Data
| Compound structure | Compound number | TBPS IC$_{50}$ (nM) |
|---|---|---|
| 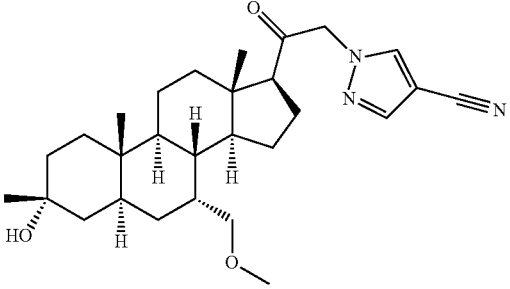 | 14 | E |
| 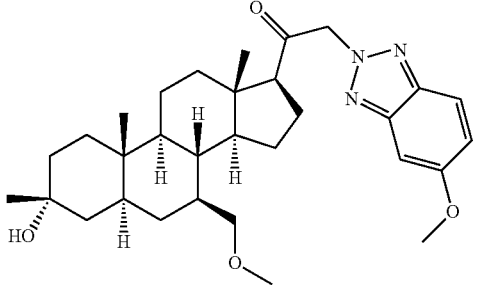 | 15 | E |
| 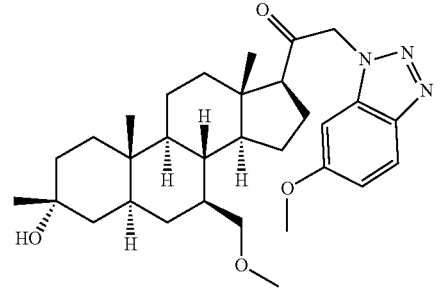 | 16 | E |
| 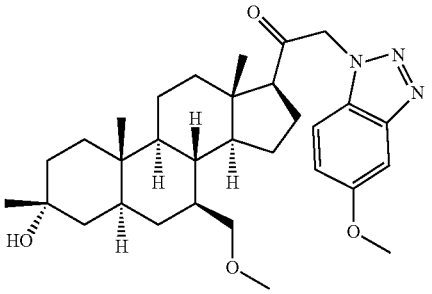 | 17 | E |
| 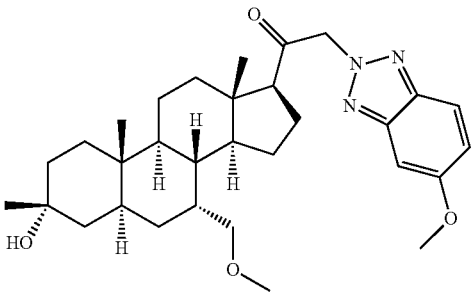 | 18 | E |

TABLE 2-continued

TBPS Data

| Compound structure | Compound number | TBPS IC$_{50}$ (nM) |
|---|---|---|
| 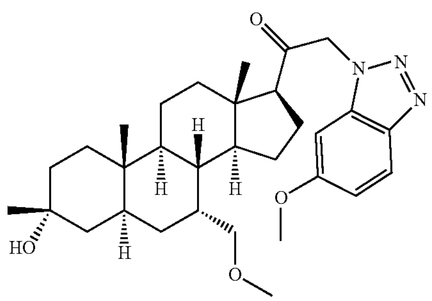 | 19 | E |
| 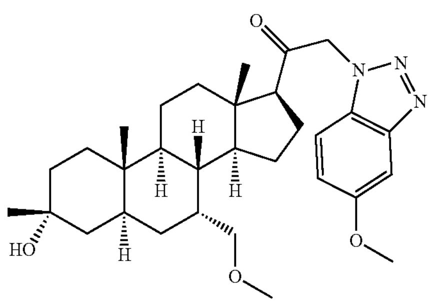 | 20 | E |
| 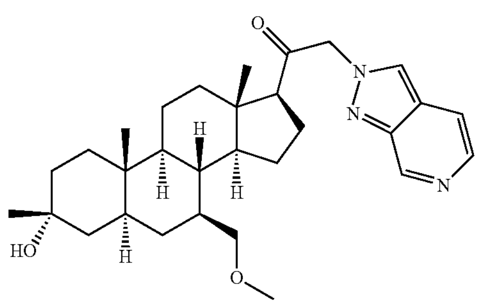 | 21 | E |
| 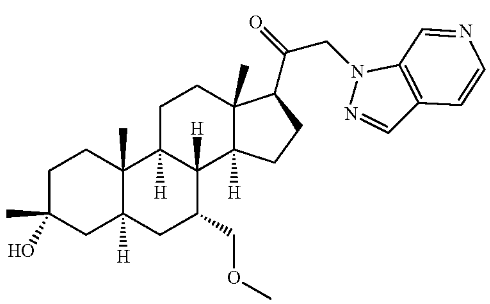 | 23 | E |
| 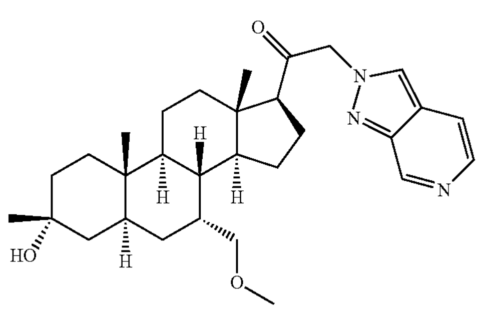 | 24 | E |

TABLE 2-continued

TBPS Data

| Compound structure | Compound number | TBPS IC$_{50}$ (nM) |
|---|---|---|
| 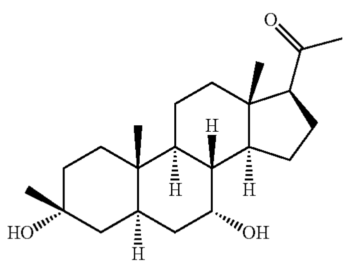 | 25 | E |
| 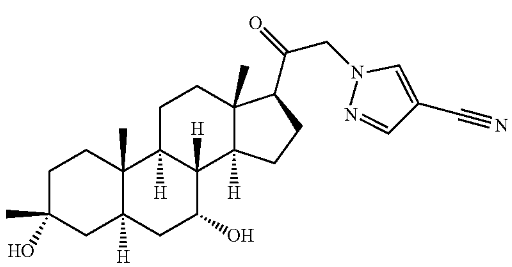 | 26 | E |
| 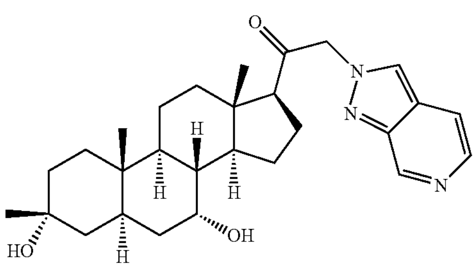 | 27 | E |
| 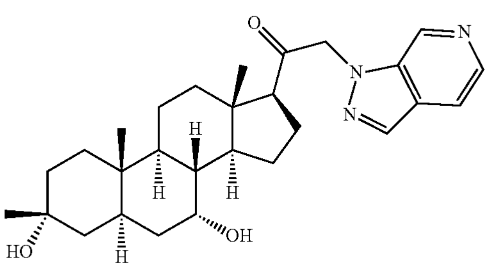 | 28 | E |
| 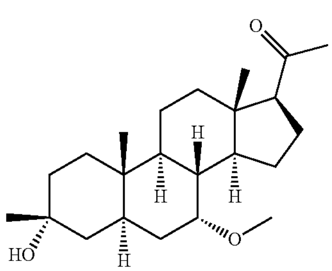 | 29 | E |

TABLE 2-continued
TBPS Data
| Compound structure | Compound number | TBPS IC$_{50}$ (nM) |
|---|---|---|
| 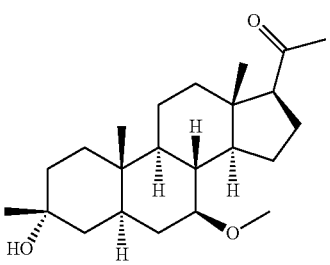 | 30 | E |
| 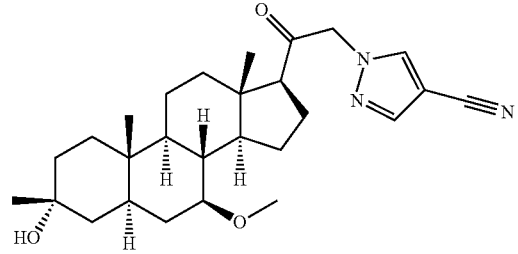 | 31 | E |
| 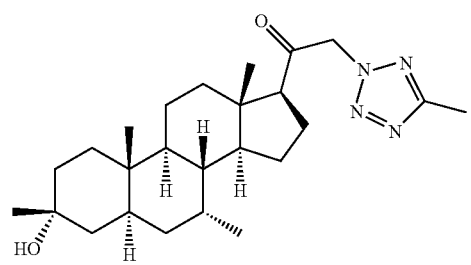 | 34 | E |
| 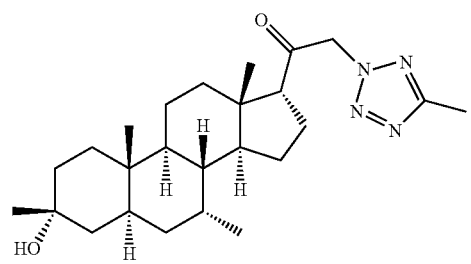 | 35 | E |
| 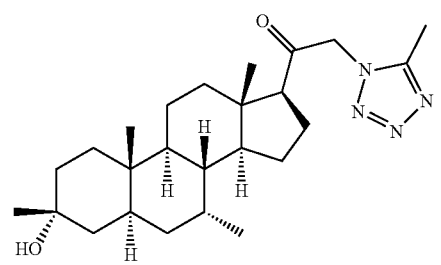 | 36 | E |

TABLE 2-continued

TBPS Data

| Compound structure | Compound number | TBPS IC$_{50}$ (nM) |
|---|---|---|
| 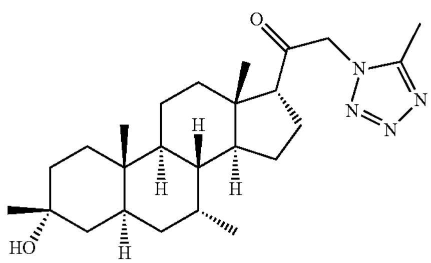 | 37 | E |
| 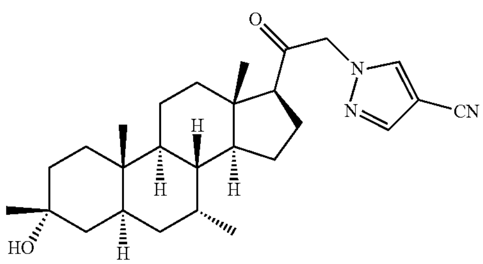 | 38 | D |
| 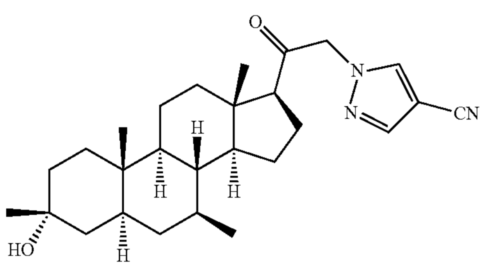 | 39 | D |
| 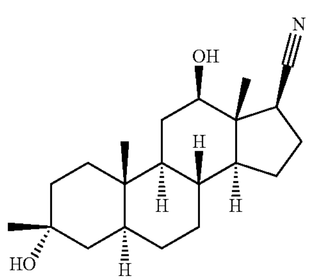 | 40 | E |
| 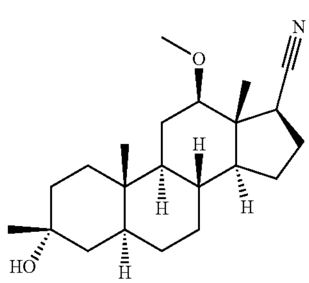 | 41 | D |

TABLE 2-continued

TBPS Data

| Compound structure | Compound number | TBPS IC$_{50}$ (nM) |
|---|---|---|
| 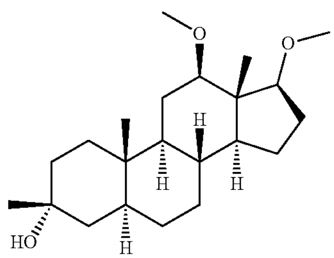 | 42 | D |
| 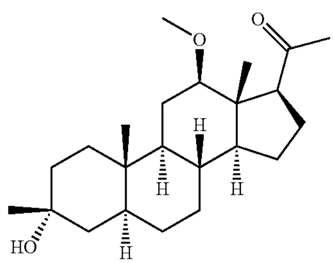 | 43 | D |
| 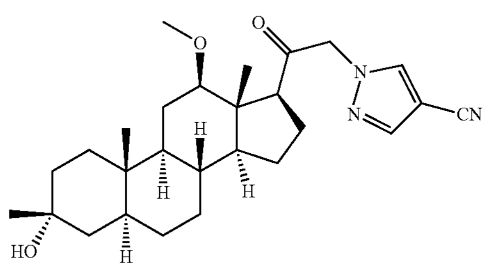 | 44 | B |
| 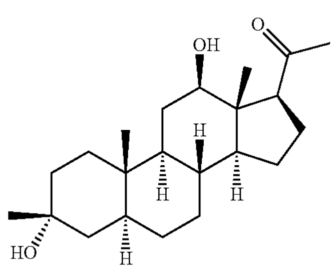 | 45 | E |
| 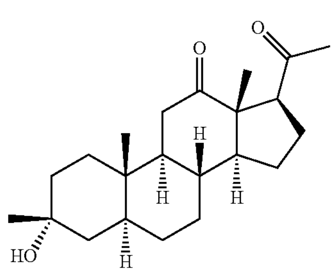 | 46 | E |

TABLE 2-continued

TBPS Data

| Compound structure | Compound number | TBPS IC$_{50}$ (nM) |
|---|---|---|
| 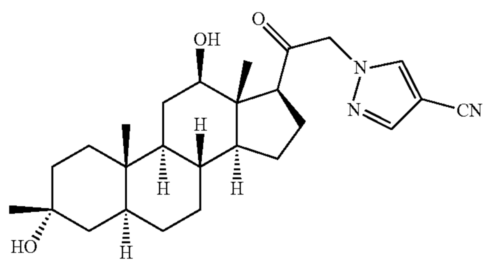 | 47 | E |
| 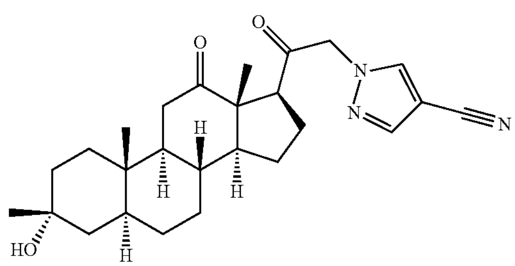 | 48 | E |
| 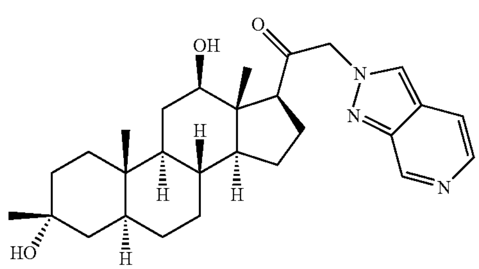 | 49 | D |
| 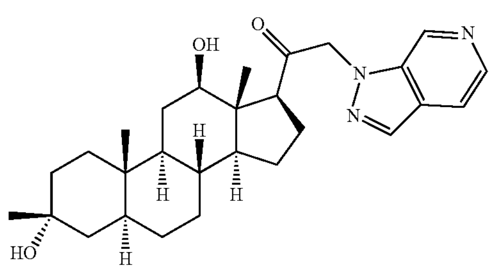 | 50 | E |
| 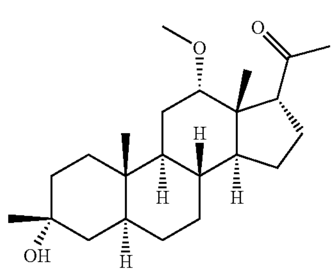 | 51 | E |

TABLE 2-continued

| TBPS Data | | |
|---|---|---|
| Compound structure | Compound number | TBPS IC$_{50}$ (nM) |
| | 52 | E |
| | 53 | E |
| | 54 | E |
| | 55 | E |
| | 56 | C |

TABLE 2-continued

TBPS Data

| Compound structure | Compound number | TBPS IC$_{50}$ (nM) |
|---|---|---|
| 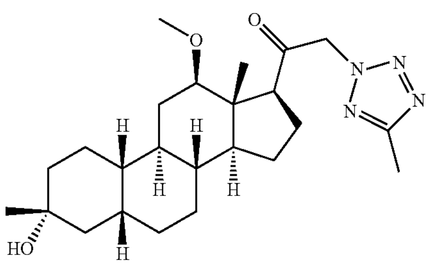 | 58 | C |
| 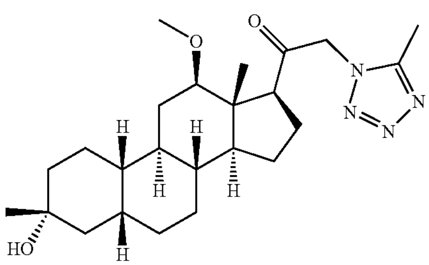 | 59 | D |
| 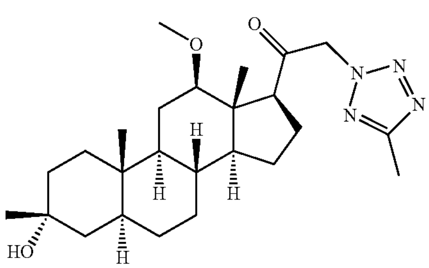 | 60 | D |
| 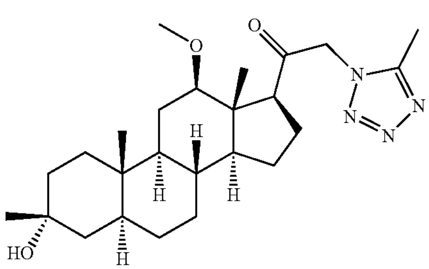 | 61 | D |
| 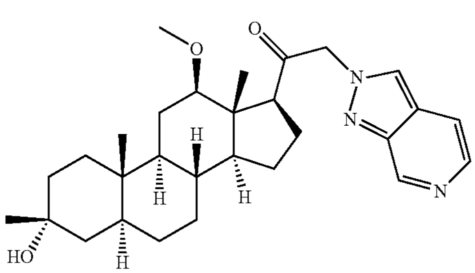 | 62 | B |

TABLE 2-continued
TBPS Data
| Compound structure | Compound number | TBPS IC$_{50}$ (nM) |
|---|---|---|
| 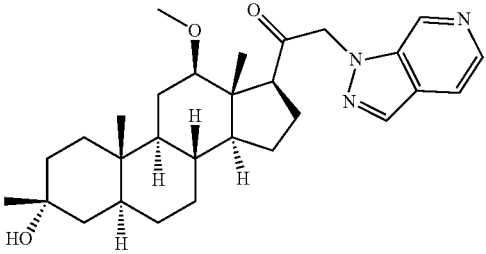 | 63 | D |
| 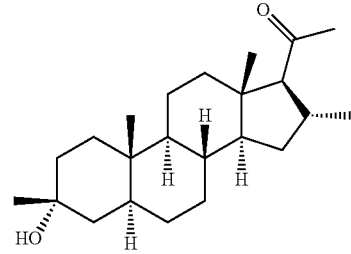 | 64 | D |
| 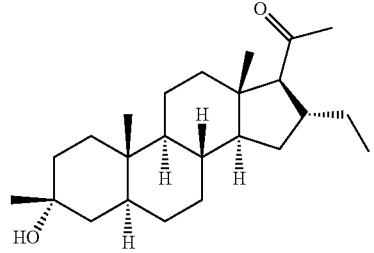 | 65 | E |
| 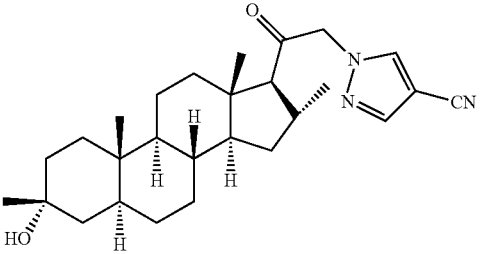 | 66 | B |
| 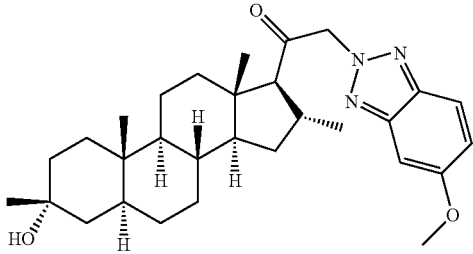 | 67 | B |

TABLE 2-continued
| | TBPS Data | |
|---|---|---|
| Compound structure | Compound number | TBPS IC$_{50}$ (nM) |
| 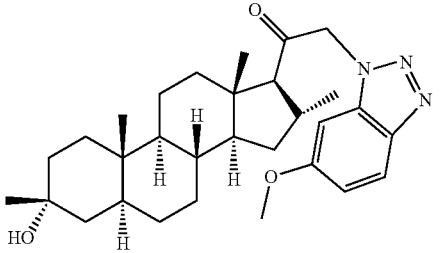 | 68 | B |
| 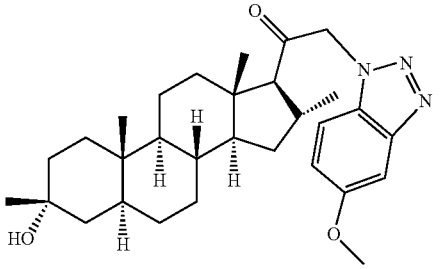 | 69 | B |
| 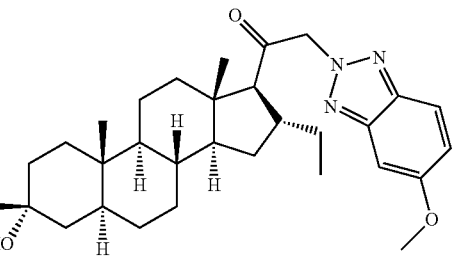 | 70 | E |
| 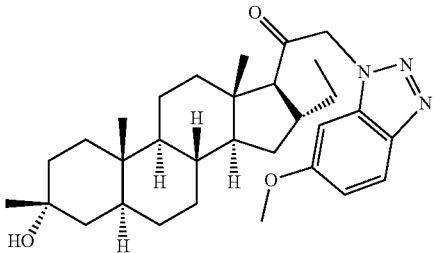 | 71 | E |
| 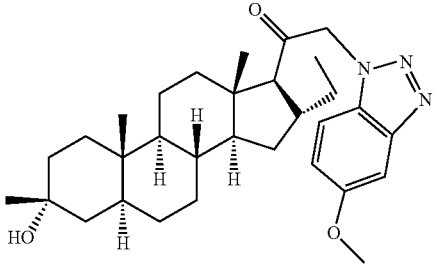 | 72 | E |

TABLE 2-continued
| | TBPS Data | |
|---|---|---|
| Compound structure | Compound number | TBPS IC$_{50}$ (nM) |
| 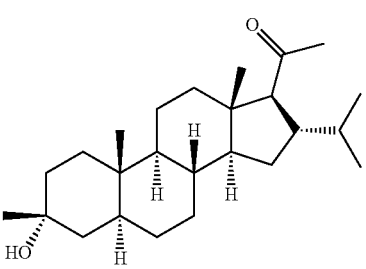 | 73 | E |
| 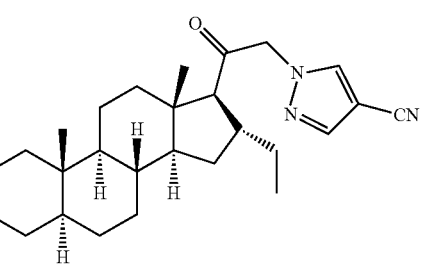 | 74 | E |
| 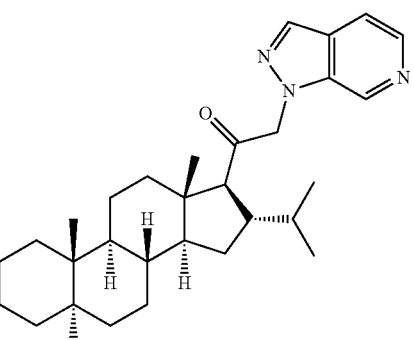 | 75 | E |
| 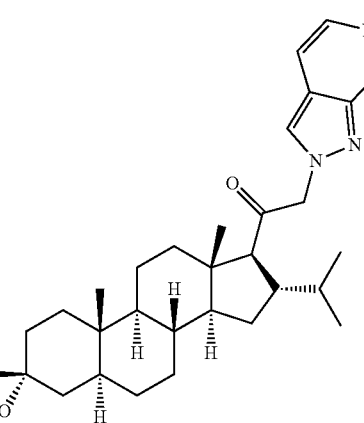 | 76 | E |

TABLE 2-continued
TBPS Data
| Compound structure | Compound number | TBPS IC$_{50}$ (nM) |
|---|---|---|
| 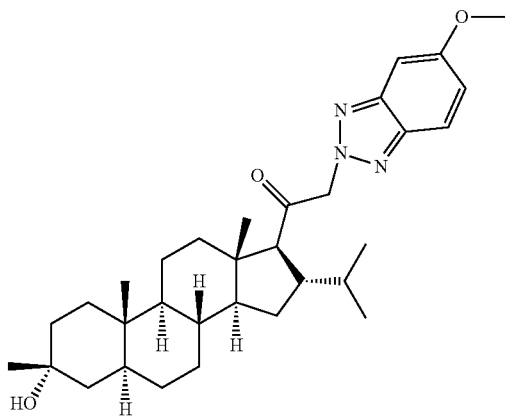 | 77 | E |
| 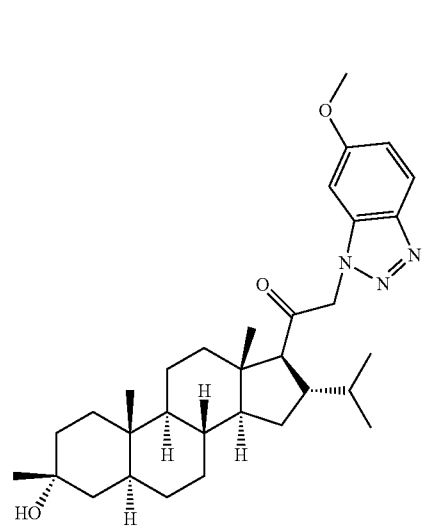 | 78 | E |
| 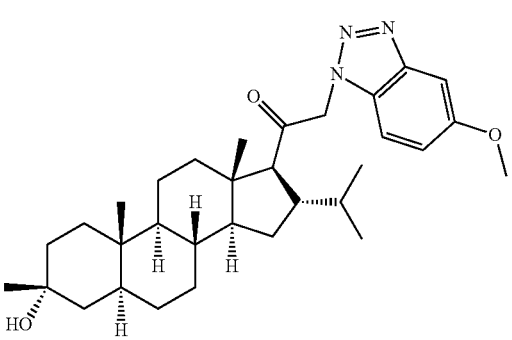 | 79 | E |

TABLE 2-continued

TBPS Data

| Compound structure | Compound number | TBPS IC$_{50}$ (nM) |
|---|---|---|
| 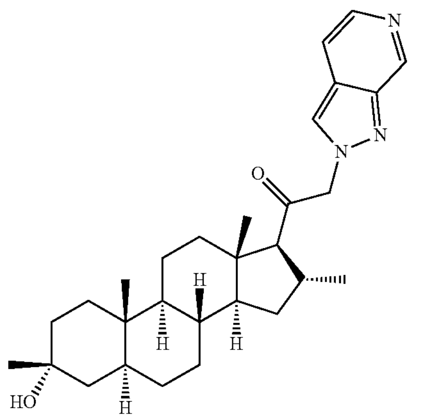 | 80 | D |
| 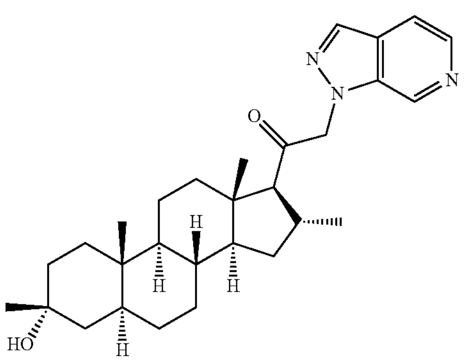 | 81 | C |
| 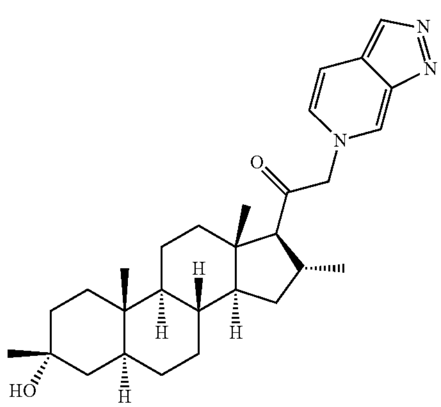 | 82 | E |
| 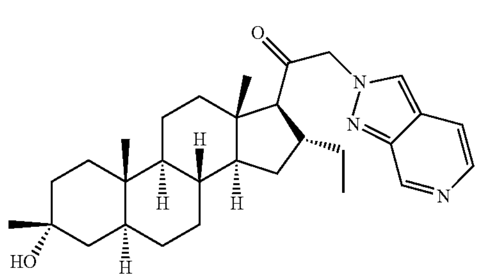 | 83 | E |

TABLE 2-continued

TBPS Data

| Compound structure | Compound number | TBPS IC$_{50}$ (nM) |
|---|---|---|
| 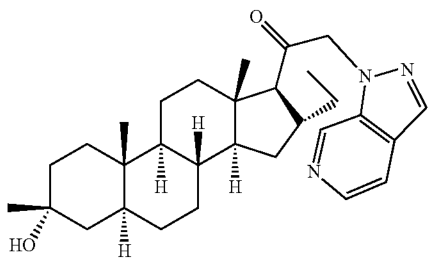 | 84 | E |
| 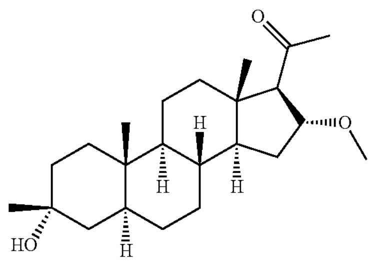 | 85 | E |
| 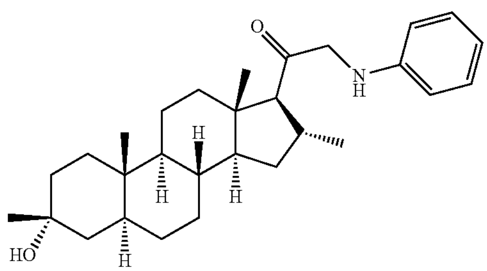 | 86 | D |
| 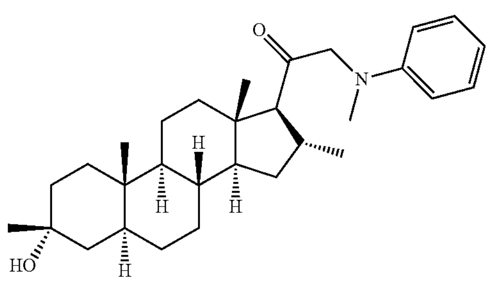 | 87 | D |
| 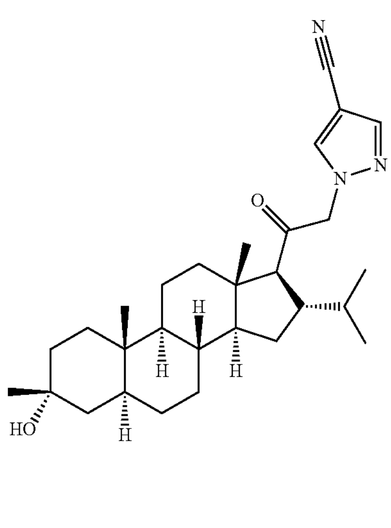 | 88 | E |

TABLE 2-continued

TBPS Data

| Compound structure | Compound number | TBPS IC$_{50}$ (nM) |
|---|---|---|
| (structure) | 89 | B |
| (structure) | 90 | D |
| (structure) | 91 | B |
| (structure) | 92 | B |

For Table 2: TBPS: A" indicates an IC$_{50}$<10 nM, "B" indicates an IC$_{50}$ 10 to <50 nM, "C" indicates an IC$_{50}$ 50 nM to <100 nM, "D" indicates an IC$_{50}$ 100 nM to <500 nM, and "E" indicates IC$_{50}$ greater than or equal to 500 nM.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (IX):

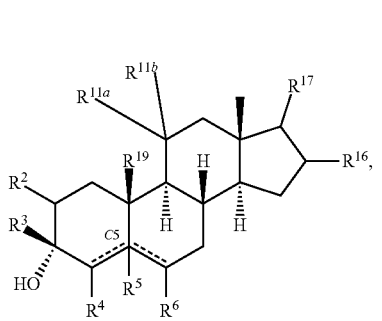

(IX)

or a pharmaceutically acceptable salt thereof, wherein
======= represents a single or double bond as valency permits;
each of $R^2$, $R^4$, $R^6$, $R^{11a}$ and $R^{11b}$ is independently hydrogen;
$R^3$ is $C_1$-$C_6$ alkyl;
$R^5$ is absent or hydrogen; and ====== represents a single or double bond, wherein when one of ====== a double bond, the other ====== is a single bond; when both of ====== are single bonds, then $R^5$ is hydrogen; and when one of the ====== is a double bond, $R^5$ is absent;
$R^{17}$ is alkoxy, cyano, nitro, aryl, heteroaryl, —C(O)$R^{B1}$, —C(O)CH$_2$$R^{B1}$, or —C(O)CH$_2$CH$_2$$R^{B1}$, wherein $R^{B1}$ is hydrogen, —OH, —N($R^{41}$)$_2$, alkoxy, aryl, or heteroaryl, and each $R^{41}$ is independently hydrogen, $C_1$-$C_6$ alkyl, carbocyclyl, aryl, or heteroaryl;
$R^{19}$ is hydrogen or alkyl; and
$R^{16}$ or $OR^{41}$.
2. The compound or pharmaceutically acceptable salt of claim 1, wherein the compound of Formula (IX) is a compound of Formula (IX-a) or (IX-b):

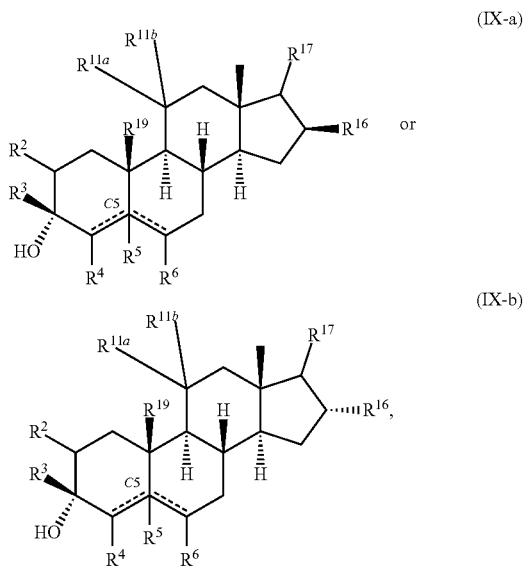

or a pharmaceutically acceptable salt thereof.
3. The compound or pharmaceutically acceptable salt of claim 2, wherein the compound of Formula (IX) is a compound of Formula (X-c) or (X-d):

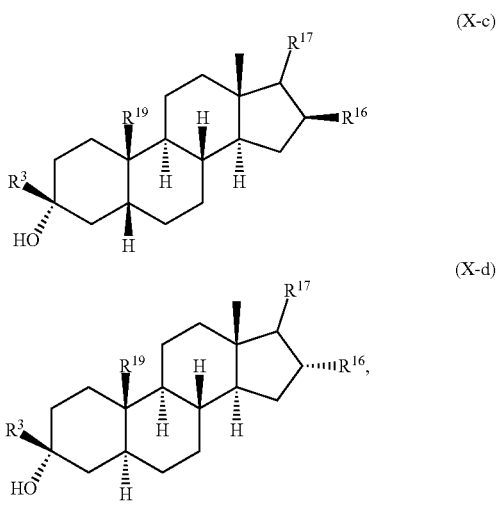

or a pharmaceutically acceptable salt thereof.
4. The compound or pharmaceutically acceptable salt of claim 3, wherein $R^{17}$ is —CH$_3$.
5. The compound or pharmaceutically acceptable salt of claim 3, wherein $R^{17}$ is —OCH$_3$, —CN, or —C(O)CH$_3$.
6. The compound or pharmaceutically acceptable salt of claim 3, wherein $R^{17}$ is —C(O)CH$_2$$R^{B1}$.
7. The compound or pharmaceutically acceptable salt of claim 3, wherein $R^{17}$ is alkoxy, cyano, or —C(O)$R^{B1}$.

8. The compound or pharmaceutically acceptable salt of claim 3, wherein $R^{B1}$ is pyrazolyl.

9. The compound or pharmaceutically acceptable salt of claim 3, wherein $R^{B1}$ is tetrazolyl.

10. The compound or pharmaceutically acceptable salt of claim 3, wherein $R^{B1}$ is a bicyclic heteroaryl.

11. The compound or pharmaceutically acceptable salt of claim 3, wherein $R^{B1}$ is

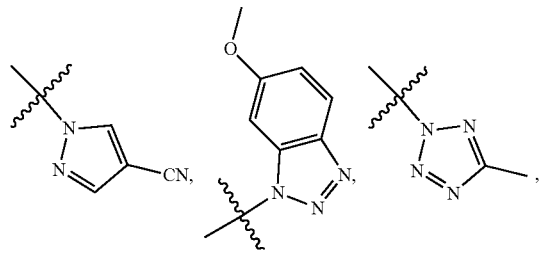

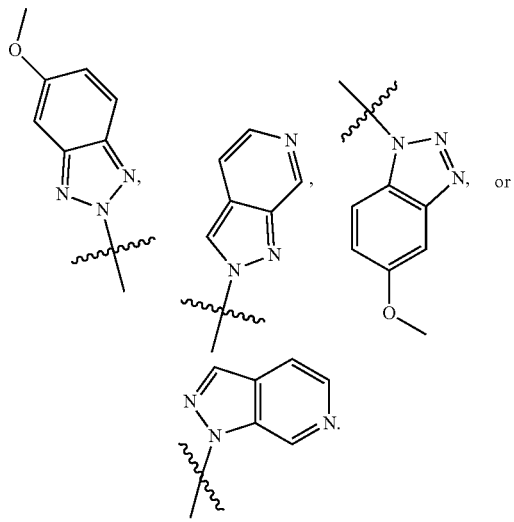

12. The compound or pharmaceutically acceptable salt of claim 3, wherein $R^{B1}$ is

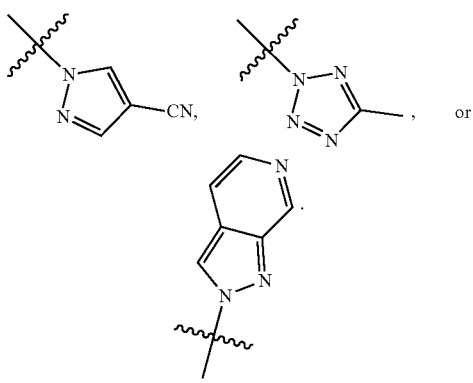

13. The compound or pharmaceutically acceptable salt of claim 1, wherein $R^{17}$ is $C_1$-$C_6$ alkoxy, cyano, or nitro.

14. The compound or pharmaceutically acceptable salt of claim 1, wherein $R^{19}$ is hydrogen or unsubstituted $C_1$-$C_6$ alkyl.

15. The compound or pharmaceutically acceptable salt of claim 1, wherein the compound of Formula (IX) is a compound of Formula (X-a1) or (X-b1):

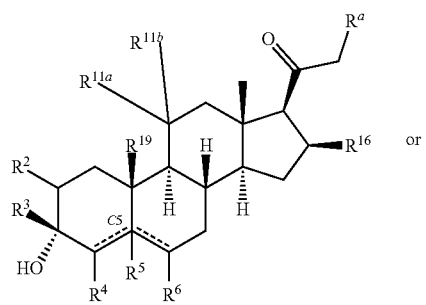

(X-a1)

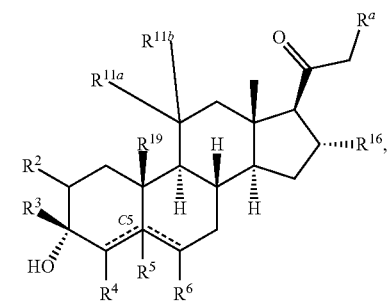

(X-b1)

or a pharmaceutically acceptable salt thereof, wherein IV is hydrogen, methyl, or —OH.

16. The compound or pharmaceutically acceptable salt of claim 1, wherein the compound of Formula (IX) is a compound of Formula (XI-a) or (XI-b):

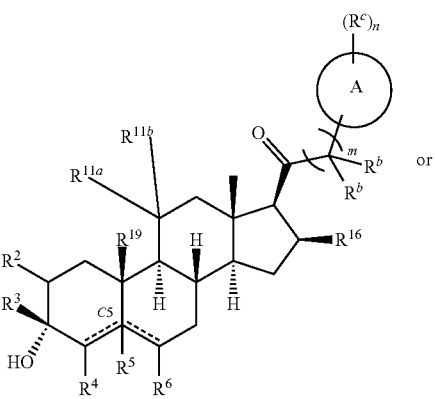

(XI-a)

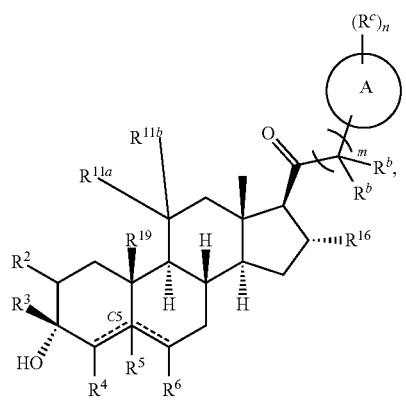

(XI-b)

or a pharmaceutically acceptable salt thereof, wherein m is 0, 1, or 2, n is 0, 1, or 2, each $R^b$ is hydrogen, halogen, A is a 5-10 membered heteroaryl ring, and each $R^c$ is independently halogen, $C_1$-$C_6$ alkyl, $C_1$-$C_6$ alkoxy, cyano, or —OH.
17. A compound selected from the group consisting of:
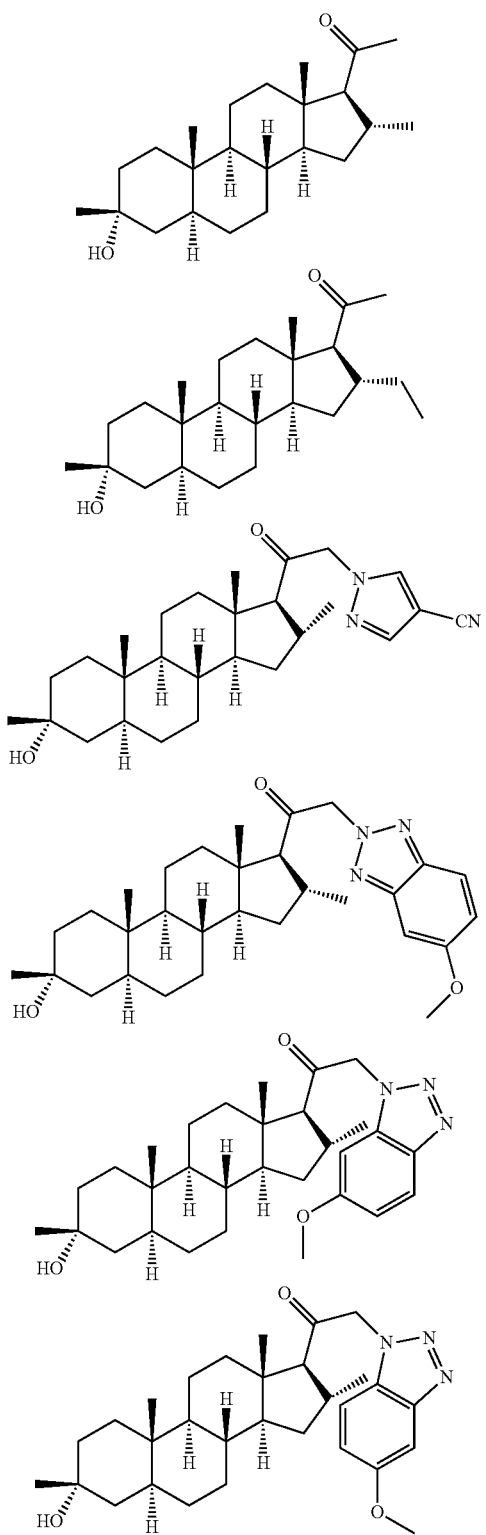
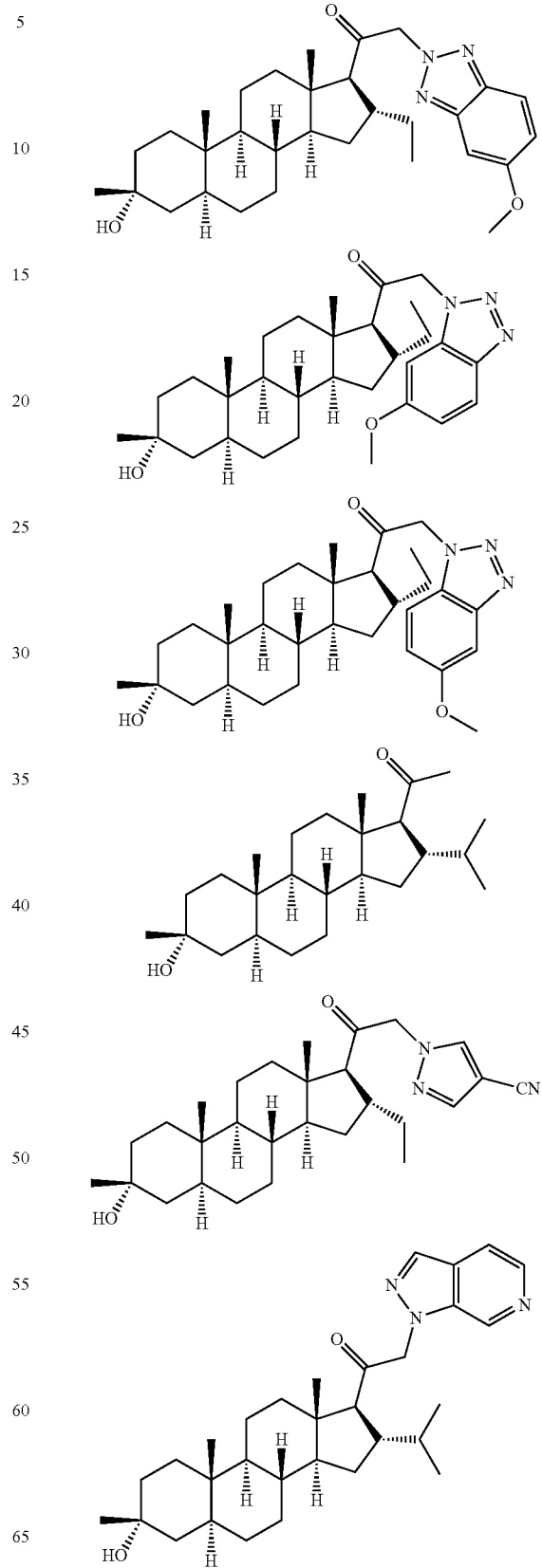

243
-continued
244
-continued
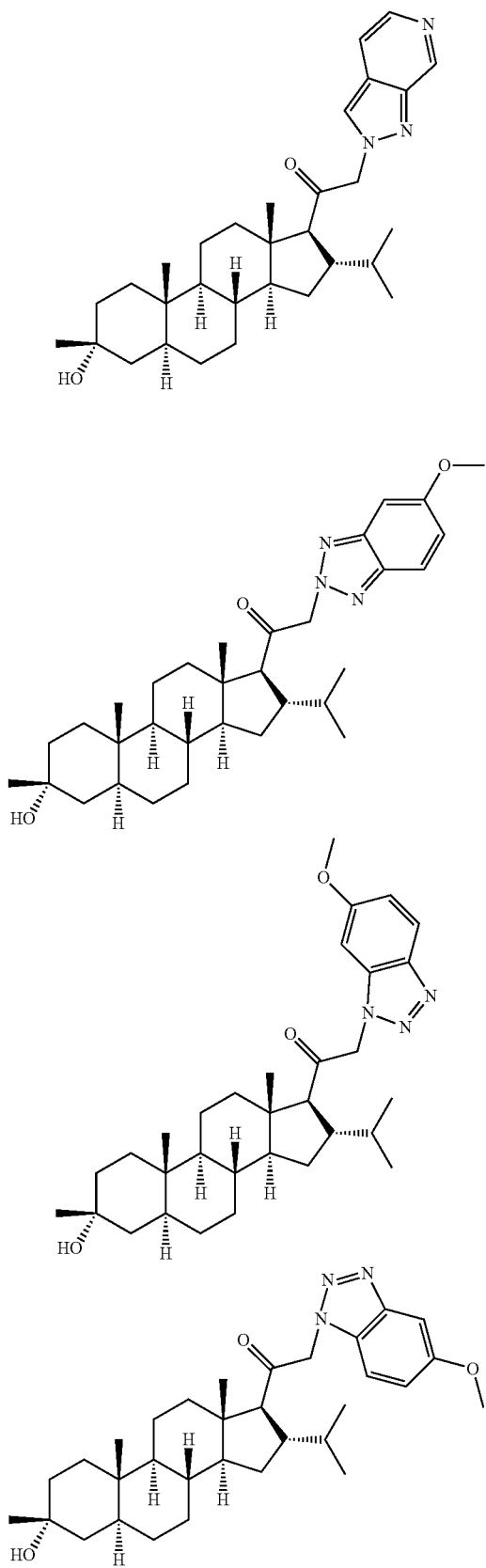
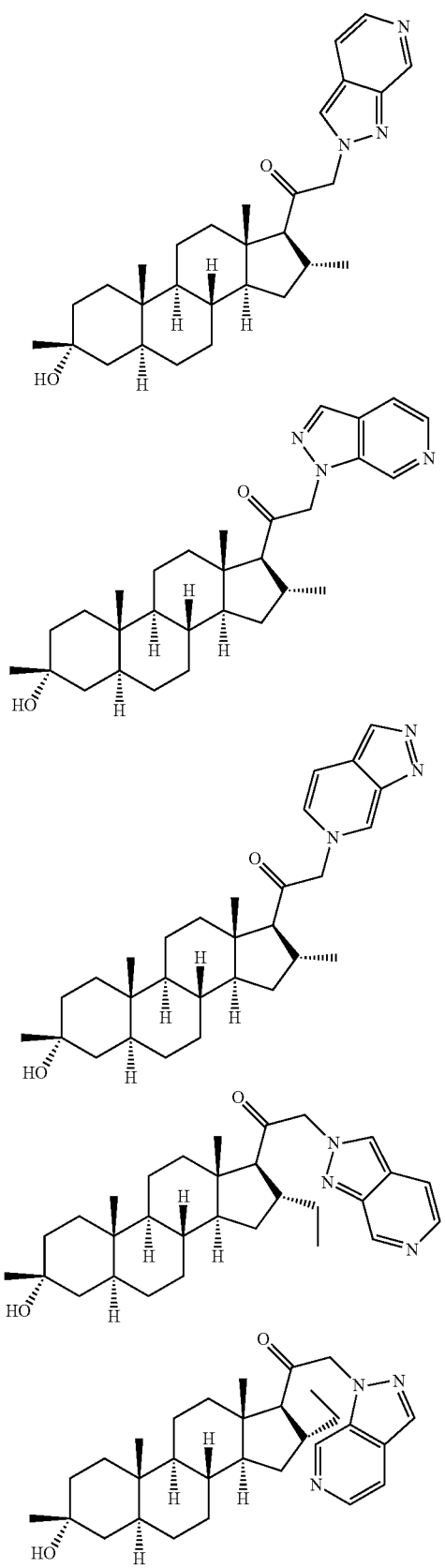

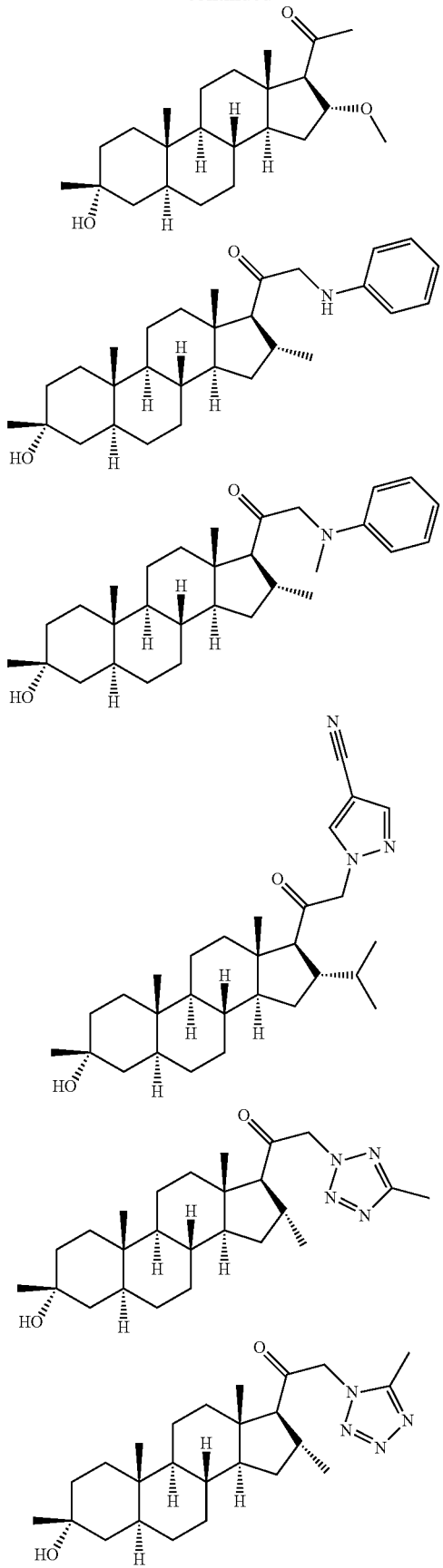
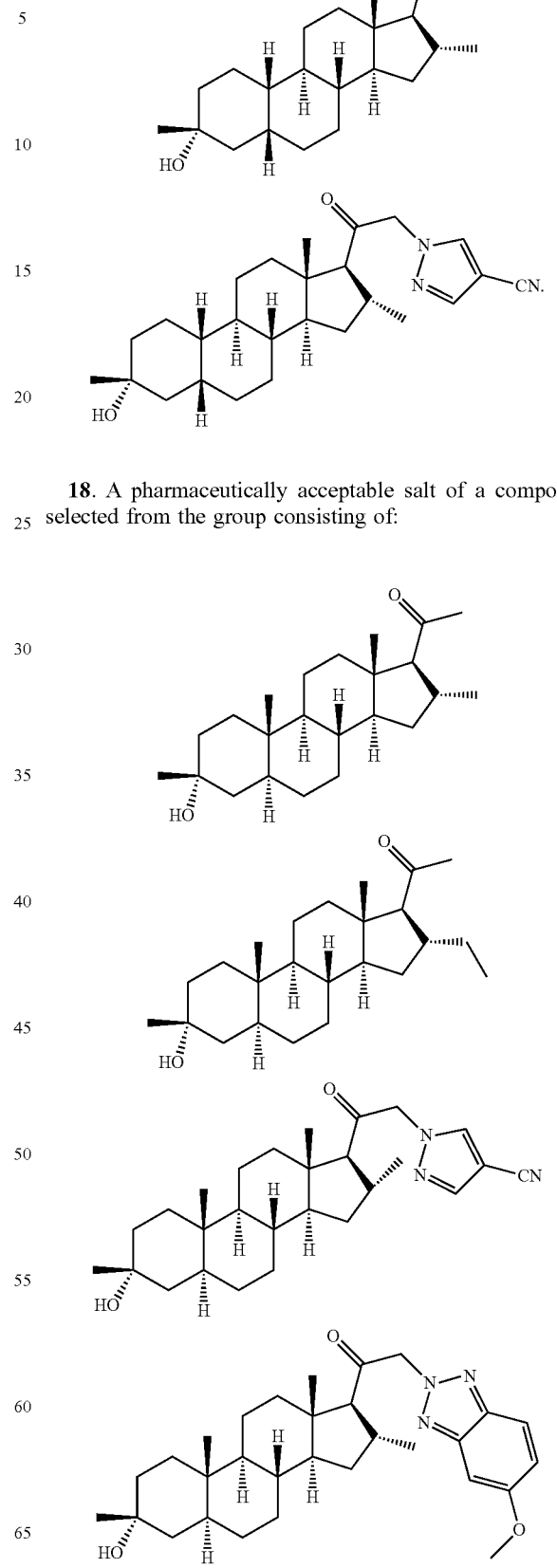
18. A pharmaceutically acceptable salt of a compound selected from the group consisting of:

247
-continued
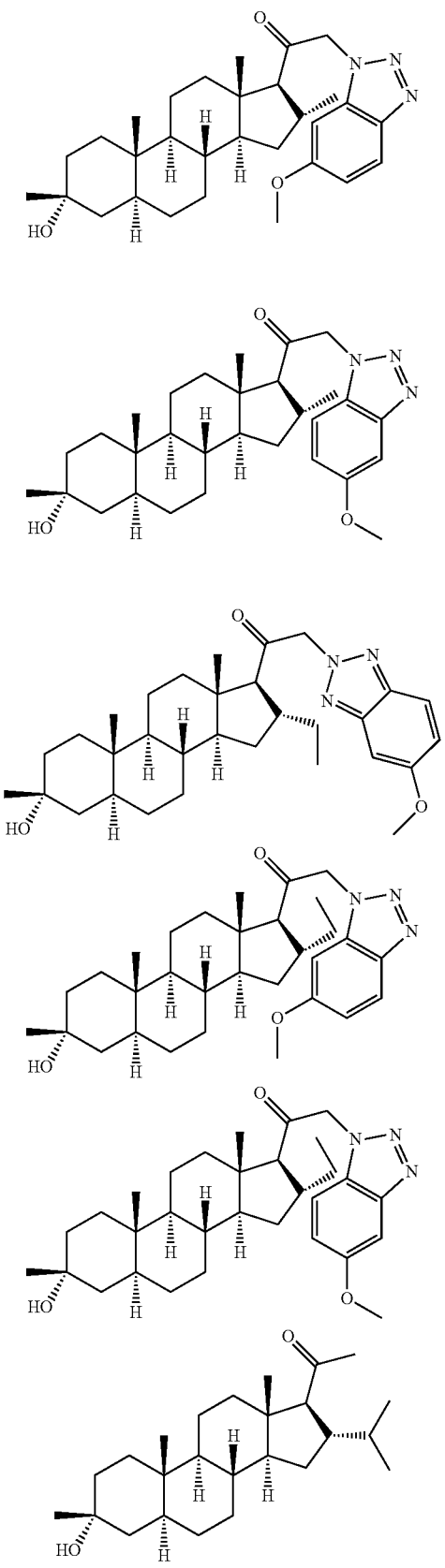
248
-continued
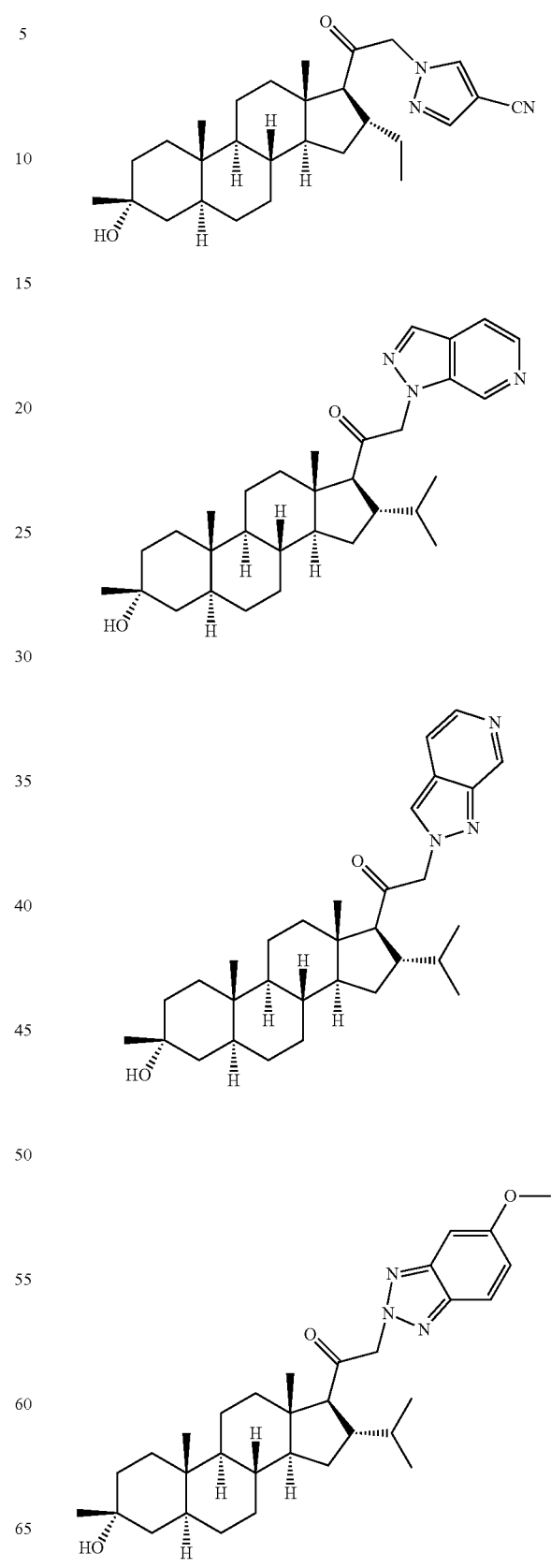

249
-continued
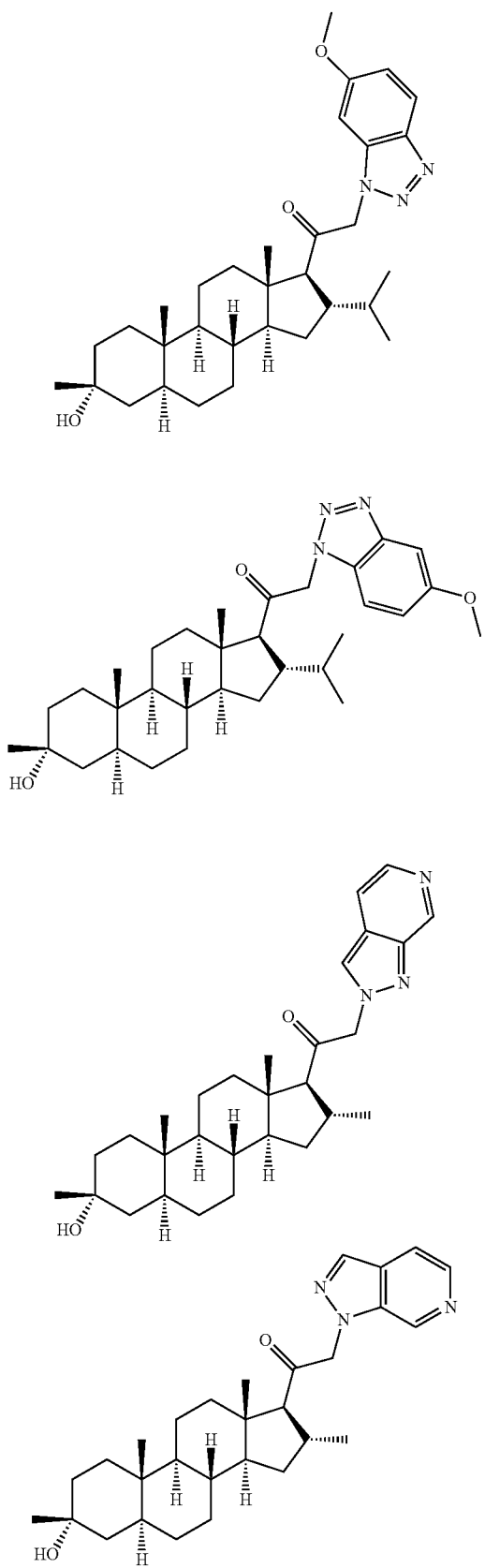
250
-continued
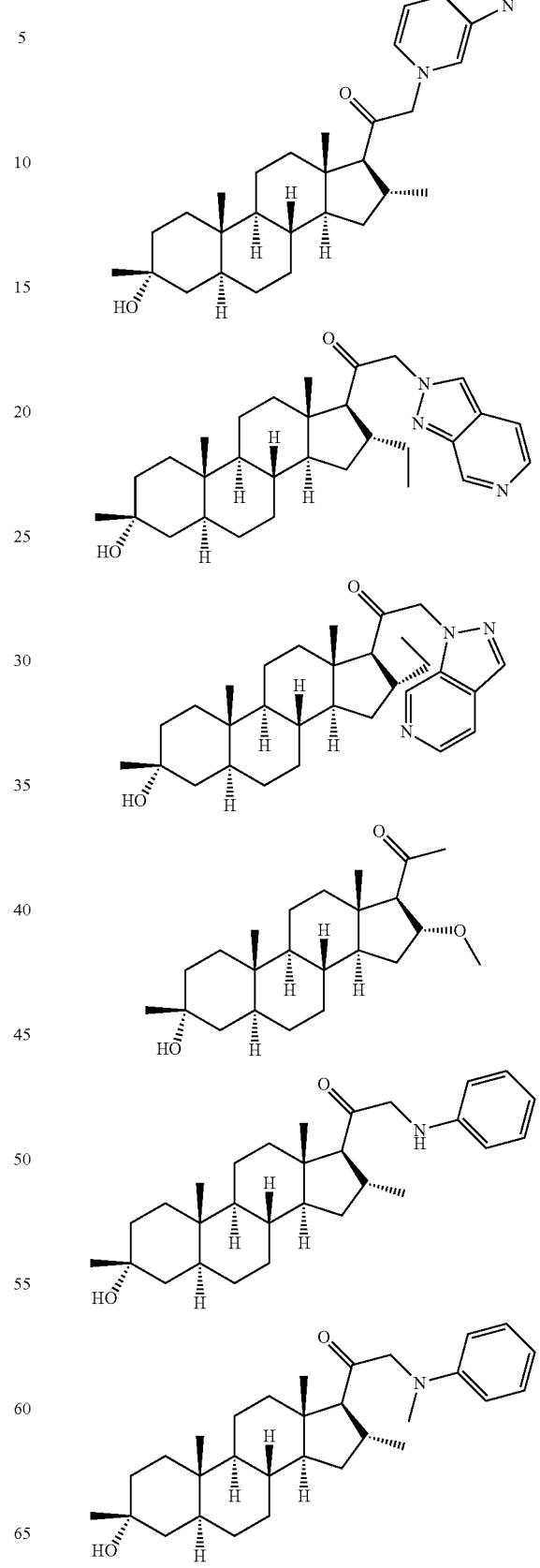

-continued

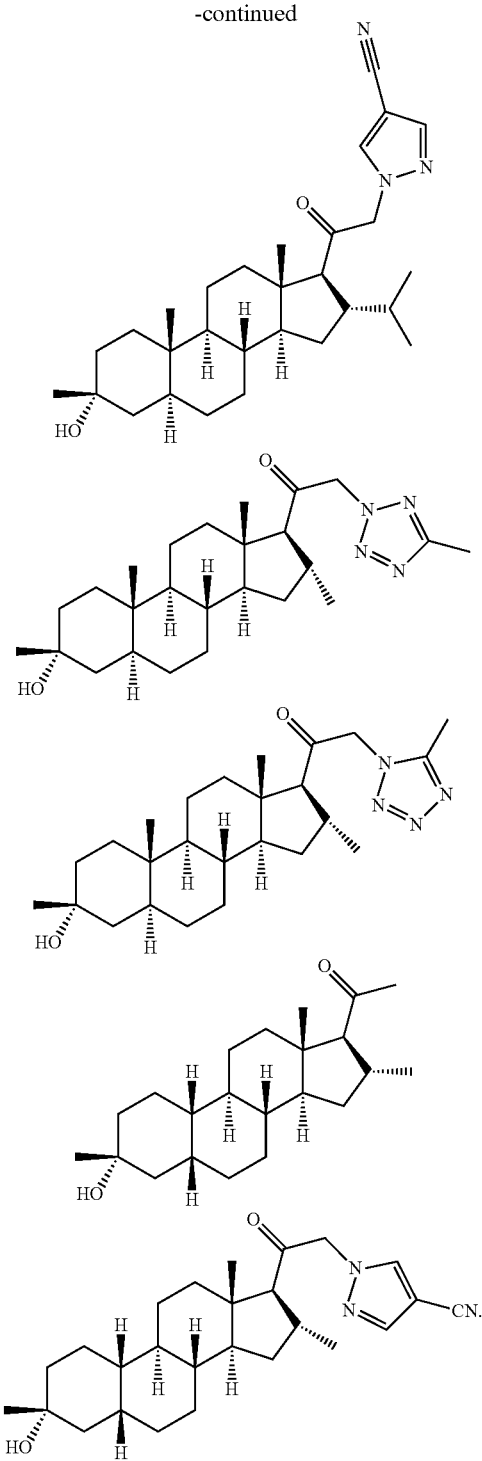

19. A pharmaceutical composition comprising a compound or a pharmaceutically acceptable salt of claim 1, and a pharmaceutically acceptable excipient.

20. A kit comprising a solid composition comprising a compound or pharmaceutically acceptable salt of claim 1 and a sterile diluent.

21. A method of inducing sedation and/or anesthesia in a subject, comprising administering to the subject an effective amount of a compound or pharmaceutically acceptable salt of claim 1.

22. The method of claim 21, wherein the subject experiences sedation and/or anesthesia within two hours of administration.

23. The method of claim 21, wherein the subject experiences sedation and/or anesthesia within one hour of administration.

24. The method of claim 21, wherein the subject experiences sedation and/or anesthesia instantaneously.

25. The method of claim 21, wherein the compound or pharmaceutically acceptable salt is administered by intravenous, oral, or intramuscular administration.

26. The method of claim 21, wherein the compound or pharmaceutically acceptable salt is administered chronically.

27. The method of claim 21, wherein the subject is a mammal.

28. The method of claim 21, wherein the subject is a human.

29. The method of claim 21, wherein the compound or pharmaceutically acceptable salt is administered in combination with another therapeutic agent.

30. A method of treating seizure in a subject, comprising administering to the subject an effective amount of a compound or pharmaceutically acceptable salt of claim 1.

31. A method of treating epilepsy or status epilepticus in a subject, comprising administering to the subject an effective amount of a compound or pharmaceutically acceptable salt of claim 1.

32. A method of treating a neuroendocrine disorder or dysfunction in a subject, comprising administering to the subject an effective amount of a compound or pharmaceutically acceptable salt of claim 1.

33. A method of treating a neurodegenerative disease or disorder in a subject, comprising administering to the subject an effective amount of a compound or pharmaceutically acceptable salt of claim 1.

34. A method of treating a movement disorder or tremor in a subject, comprising administering to the subject an effective amount of a compound or pharmaceutically acceptable salt of claim 1.

35. A method of treating a mood disorder or anxiety disorder in a subject, comprising administering to the subject an effective amount of a compound or pharmaceutically acceptable salt of claim 1.

36. A method of treating disorders related to GABA function in a subject in need thereof, comprising administering to the subject a therapeutically effective amount of a compound or pharmaceutically acceptable salt of claim 1.

37. A method of treating a CNS-related disorder in a subject in need thereof, comprising administering to the subject an effective amount of a compound or pharmaceutically acceptable salt of claim 1.

38. The method of claim 37, wherein the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus.

39. The method of claim 37, wherein the subject is a subject with Rett syndrome, Fragile X syndrome, or Angelman syndrome.

* * * * *